(12) United States Patent
Jones et al.

(10) Patent No.: US 9,108,969 B2
(45) Date of Patent: *Aug. 18, 2015

(54) SUBSTITUTED TRICYCLIC ACID DERIVATIVES AS S1P1 RECEPTOR AGONISTS USEFUL IN THE TREATMENT OF AUTOIMMUNE AND INFLAMMATORY DISORDERS

(71) Applicant: Arena Pharmaceuticals, Inc., San Diego, CA (US)

(72) Inventors: Robert M. Jones, San Diego, CA (US); Daniel J. Buzard, San Diego, CA (US); Andrew M. Kawasaki, San Diego, CA (US); Sun Hee Kim, San Diego, CA (US); Lars Thoresen, Venice, CA (US); Juerg Lehmann, San Diego, CA (US); Xiuwen Zhu, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/787,233

(22) Filed: Mar. 6, 2013

(65) Prior Publication Data

US 2013/0184307 A1    Jul. 18, 2013

Related U.S. Application Data

(63) Continuation of application No. 13/060,477, filed as application No. PCT/US2009/004851 on Aug. 26, 2009, now Pat. No. 8,415,484.

(60) Provisional application No. 61/190,311, filed on Aug. 27, 2008, provisional application No. 61/269,519, filed on Jun. 24, 2009.

(51) Int. Cl.
| | |
|---|---|
| *C07D 487/16* | (2006.01) |
| *A61K 31/403* | (2006.01) |
| *C07D 487/04* | (2006.01) |
| *C07D 471/04* | (2006.01) |

(52) U.S. Cl.
CPC ............ *C07D 487/04* (2013.01); *C07D 471/04* (2013.01)

(58) Field of Classification Search
USPC .......................................................... 548/428
See application file for complete search history.

(56) References Cited

U.S. PATENT DOCUMENTS

| | | | |
|---|---|---|---|
| 3,206,470 A | 9/1965 | William et al. | |
| 4,057,559 A | 11/1977 | Asselin et al. | |
| 4,782,076 A | 11/1988 | Mobilio et al. | |
| 4,810,699 A | 3/1989 | Sabatucci et al. | |
| 5,221,678 A | 6/1993 | Atkinson et al. | |
| 5,776,967 A | 7/1998 | Kreft et al. | |
| 5,830,911 A | 11/1998 | Failli et al. | |
| 6,410,583 B1 | 6/2002 | Labelle et al. | |
| 6,960,692 B2 | 11/2005 | Kohno et al. | |
| 7,250,441 B2 | 7/2007 | Gopalsamy et al. | |
| 8,415,484 B2 * | 4/2013 | Jones et al. ................. | 548/302.4 |
| 2003/0083269 A1 | 5/2003 | Brouillette et al. | |

(Continued)

FOREIGN PATENT DOCUMENTS

| | | |
|---|---|---|
| EP | 0468785 | 1/1992 |
| EP | 1650186 | 4/2006 |

(Continued)

OTHER PUBLICATIONS

Actelion, Clinical Trials.gov, "Multicenter, Randomized, Double-blind, Placebo-controlled, Phase IIa Study to Evaluate the Efficacy, Safety, and Tolerability of Act-128800, an S1P1 Receptor Agonist, Administered for 6 Weeks to Subjects With Moderate to Severe Chronic Plaque Psoriasis" http://clinicaltrials.gov/ct2/show/NCT00852670, 2009.

(Continued)

*Primary Examiner* — Nymeemah A Grazier
(74) *Attorney, Agent, or Firm* — Fish & Richardson P.C.; Lyle W. Spruce

(57) ABSTRACT

The present invention relates to certain substituted tricyclic acid derivatives of Formula (I) and pharmaceutically acceptable salts thereof, which exhibit useful pharmacological properties, for example, as agonists of the S1P1 receptor.

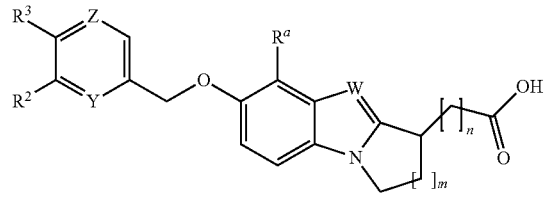

Also provided by the present invention are pharmaceutical compositions containing compounds of the invention, and methods of using the compounds and compositions of the invention in the treatment of S1P1-associated disorders, for example, psoriasis, rheumatoid arthritis, Crohn's disease, transplant rejection, multiple sclerosis, systemic lupus erythematosus, ulcerative colitis, type I diabetes, acne, myocardial ischemia-reperfusion injury, hypertensive nephropathy, glomerulosclerosis, gastritis, polymyositis, thyroiditis, vitiligo, hepatitis, biliary cirrhosis, microbial infections and associated diseases, viral infections and associated diseases, diseases and disorders mediated by lymphocytes, auto immune diseases, inflammatory diseases, and cancer.

33 Claims, 14 Drawing Sheets

(56) References Cited

U.S. PATENT DOCUMENTS

| | | |
|---|---|---|
| 2003/0211421 A1 | 11/2003 | Hanabata et al. |
| 2004/0224941 A1 | 11/2004 | Seko et al. |
| 2004/0254222 A1 | 12/2004 | Kohno et al. |
| 2005/0004114 A1 | 1/2005 | Whitehouse et al. |
| 2005/0009786 A1 | 1/2005 | Pan et al. |
| 2005/0014724 A1 | 1/2005 | Marsilje et al. |
| 2005/0014725 A1 | 1/2005 | Mi et al. |
| 2005/0014728 A1 | 1/2005 | Pan et al. |
| 2005/0033055 A1 | 2/2005 | Bugianesi et al. |
| 2005/0239899 A1 | 10/2005 | Fecke et al. |
| 2006/0004010 A1 | 1/2006 | Habashita et al. |
| 2006/0063821 A1 | 3/2006 | Gopalsamy et al. |
| 2006/0079542 A1 | 4/2006 | Nestor |
| 2006/0122222 A1 | 6/2006 | Whitehouse et al. |
| 2006/0160771 A1 | 7/2006 | Kohno et al. |
| 2006/0211656 A1 | 9/2006 | Albert et al. |
| 2006/0223866 A1 | 10/2006 | Evindar et al. |
| 2007/0010494 A1 | 1/2007 | Ehrhardt et al. |
| 2007/0043014 A1 | 2/2007 | Doherty et al. |
| 2007/0060573 A1 | 3/2007 | Wortmann et al. |
| 2007/0149595 A1 | 6/2007 | Tanaka et al. |
| 2007/0149597 A1 | 6/2007 | Nishi et al. |
| 2007/0167425 A1 | 7/2007 | Nakade et al. |
| 2007/0173487 A1 | 7/2007 | Saha et al. |
| 2007/0173507 A1 | 7/2007 | Hirata |
| 2007/0191313 A1 | 8/2007 | Beard et al. |
| 2007/0191371 A1 | 8/2007 | Bennett et al. |
| 2007/0191468 A1 | 8/2007 | Nishi et al. |
| 2007/0244155 A1 | 10/2007 | Sharma et al. |
| 2007/0254886 A1 | 11/2007 | Habashita et al. |
| 2008/0051418 A1 | 2/2008 | Maekawa et al. |
| 2008/0153882 A1 | 6/2008 | Nishi et al. |
| 2008/0200535 A1 | 8/2008 | Ohmori et al. |
| 2008/0207584 A1 | 8/2008 | Habashita et al. |
| 2008/0319077 A1 | 12/2008 | Suzuki et al. |
| 2009/0012093 A1 | 1/2009 | Fukatsu et al. |
| 2009/0076070 A1 | 3/2009 | Harada et al. |
| 2009/0131438 A1 | 5/2009 | Ono et al. |
| 2009/0137685 A1 | 5/2009 | Kojima et al. |
| 2009/0325907 A1 | 12/2009 | Kohno et al. |
| 2010/0267778 A1 | 10/2010 | Kusuda et al. |
| 2010/0273806 A1 | 10/2010 | Jones et al. |
| 2010/0292233 A1 | 11/2010 | Jones et al. |
| 2011/0130409 A1 | 6/2011 | Jones et al. |
| 2012/0064060 A1 | 3/2012 | Habashita et al. |
| 2012/0295947 A1 | 11/2012 | Montalban et al. |
| 2012/0329848 A1* | 12/2012 | Jones et al. .................. 514/411 |

FOREIGN PATENT DOCUMENTS

| | | |
|---|---|---|
| EP | 1826197 | 8/2007 |
| EP | 2003132 | 12/2008 |
| EP | 1772145 | 3/2011 |
| EP | 2017263 | 11/2011 |
| GB | 1436893 | 5/1976 |
| JP | 2007262009 | 10/2007 |
| WO | WO 91/06537 | 5/1991 |
| WO | WO 97/14674 | 4/1997 |
| WO | WO 00/64888 | 11/2000 |
| WO | WO 02/39987 | 5/2002 |
| WO | WO 02/064616 | 8/2002 |
| WO | WO 02/092068 | 11/2002 |
| WO | WO 03/029205 | 4/2003 |
| WO | WO 03/062252 | 7/2003 |
| WO | WO 03/061567 | 12/2003 |
| WO | WO 03/105771 | 12/2003 |
| WO | WO 03/074008 | 2/2004 |
| WO | WO 03/073986 | 5/2004 |
| WO | WO 2004/058149 | 9/2004 |
| WO | WO 2004/074297 | 9/2004 |
| WO | WO 2004/010949 | 10/2004 |
| WO | WO 2004/071442 | 10/2004 |
| WO | WO 2004/096752 | 11/2004 |
| WO | WO 2004/103309 | 12/2004 |
| WO | WO 2004/104205 | 12/2004 |
| WO | WO 2004/096757 | 1/2005 |
| WO | WO 2005/000833 | 1/2005 |
| WO | WO 2004/110979 | 2/2005 |
| WO | WO 2004/103306 | 3/2005 |
| WO | WO 2005/021503 | 3/2005 |
| WO | WO 2005/020882 | 4/2005 |
| WO | WO 2005/032465 | 4/2005 |
| WO | WO 2004/103279 | 5/2005 |
| WO | WO 2005/041899 | 5/2005 |
| WO | WO 2005/044780 | 5/2005 |
| WO | WO 2005/058848 | 6/2005 |
| WO | WO 2005/070886 | 8/2005 |
| WO | WO 2005/079788 | 9/2005 |
| WO | WO 2005/082089 | 9/2005 |
| WO | WO 2005/082841 | 9/2005 |
| WO | WO 2005/085179 | 9/2005 |
| WO | WO 2005/097745 | 10/2005 |
| WO | WO 2005/058295 | 11/2005 |
| WO | WO 2005/123677 | 12/2005 |
| WO | WO 2006/001463 | 1/2006 |
| WO | WO 2006/009092 | 1/2006 |
| WO | WO 2006/010379 | 2/2006 |
| WO | WO 2006/011554 | 2/2006 |
| WO | WO 2006/013948 | 2/2006 |
| WO | WO 2006/020951 | 2/2006 |
| WO | WO 2004/113330 | 3/2006 |
| WO | WO 2006/010544 | 3/2006 |
| WO | WO 2006/034337 | 3/2006 |
| WO | WO 2006/043149 | 4/2006 |
| WO | WO 2006/047195 | 5/2006 |
| WO | WO 2006/064757 | 6/2006 |
| WO | WO 2006/079406 | 8/2006 |
| WO | WO 2006/088944 | 8/2006 |
| WO | WO 2006/100631 | 9/2006 |
| WO | WO 2006/100633 | 9/2006 |
| WO | WO 2006/100635 | 9/2006 |
| WO | WO 2006/063033 | 11/2006 |
| WO | WO 2006/131336 | 12/2006 |
| WO | WO 2006/137019 | 12/2006 |
| WO | WO 2006/137509 | 12/2006 |
| WO | WO 2007/024922 | 3/2007 |
| WO | WO 2007/037196 | 4/2007 |
| WO | WO 2007/060626 | 5/2007 |
| WO | WO 2007/080542 | 7/2007 |
| WO | WO 2007/083089 | 7/2007 |
| WO | WO 2007/085451 | 8/2007 |
| WO | WO 2007/086001 | 8/2007 |
| WO | WO 2007/091396 | 8/2007 |
| WO | WO 2007/091501 | 8/2007 |
| WO | WO 2007/092638 | 8/2007 |
| WO | WO 2007/098474 | 8/2007 |
| WO | WO 2007/100617 | 9/2007 |
| WO | WO 2007/109330 | 9/2007 |
| WO | WO 2007/109334 | 9/2007 |
| WO | WO 2007/095561 | 10/2007 |
| WO | WO 2007/115820 | 10/2007 |
| WO | WO 2007/116866 | 10/2007 |
| WO | WO 2007/061458 | 11/2007 |
| WO | WO 2007/092190 | 11/2007 |
| WO | WO 2007/129473 | 11/2007 |
| WO | WO 2007/129745 | 11/2007 |
| WO | WO 2007/132307 | 11/2007 |
| WO | WO 2008/016674 | 2/2008 |
| WO | WO 2008/018427 | 2/2008 |
| WO | WO 2008/019090 | 2/2008 |
| WO | WO 2008/023783 | 2/2008 |
| WO | WO 2008/024196 | 2/2008 |
| WO | WO 2008/016692 | 3/2008 |
| WO | WO 2008/028937 | 3/2008 |
| WO | WO 2008/029371 | 3/2008 |
| WO | WO 2008/030843 | 3/2008 |
| WO | WO 2008/035239 | 3/2008 |
| WO | WO 2008/029306 | 5/2008 |
| WO | WO 2008/074820 | 6/2008 |
| WO | WO 2008/074821 | 6/2008 |
| WO | WO 2008/076356 | 6/2008 |
| WO | WO 2008/079382 | 7/2008 |
| WO | WO 2008/089015 | 7/2008 |

(56) References Cited

FOREIGN PATENT DOCUMENTS

| | | |
|---|---|---|
| WO | WO 2008/091967 | 7/2008 |
| WO | WO 2008/114157 | 9/2008 |
| WO | WO 2008/128951 | 10/2008 |
| WO | WO 2008/097819 | 11/2008 |
| WO | WO 2008/152149 | 12/2008 |
| WO | WO 2009/019167 | 2/2009 |
| WO | WO 2009/019506 | 2/2009 |
| WO | WO 2009/011850 | 3/2009 |
| WO | WO 2009/064250 | 5/2009 |
| WO | WO 2009/078983 | 6/2009 |
| WO | WO 2009/094157 | 7/2009 |
| WO | WO 2009/103552 | 8/2009 |
| WO | WO 2009/151529 | 12/2009 |
| WO | WO 2009/151621 | 12/2009 |
| WO | WO 2009/151626 | 12/2009 |
| WO | WO 2010/011316 | 1/2010 |
| WO | WO 2010/027431 | 3/2010 |
| WO | WO 2010/093704 | 8/2010 |
| WO | WO 2011/005290 | 1/2011 |
| WO | WO 2011/005295 | 1/2011 |
| WO | WO 2011/059784 | 5/2011 |
| WO | WO 2011/094008 | 8/2011 |
| WO | WO 2011/109471 | 9/2011 |
| WO | WO 2012/015758 | 2/2012 |

OTHER PUBLICATIONS

Arbiser, "Why targeted therapy hasn't worked in advanced cancer," J Clinical Invest., 117(10):2762-2765.

Avoiding Fatal Responses to Flu Infection, ScienceDaily, http://www.sciencedaily.com/releases/2011/09/110915134410.htm, Sep. 15, 2011, 2 pages.

Balatoni et al., "FTY720 sustains and restores neuronal function in the DA rat model of MOG-induced experimental autoimmunue encephalomyelitis," Brain Res. Bull., 2007, 74:307-316.

Bar-Haim et al., "Interrelationship between Dendritic Cell Trafficking and Francisella tularensis Dissemination following Airway Infection," PLoS Pathog., 2008, 4(11):e1000211, 15 pages.

Baumruker et al., "FTY720, an immunomodulatory sphingolipid mimetic: translation of a novel mechanism into clinical benefit in multiple sclerosis," Expert Opin. Investig. Drugs, 2007, 16(3):283-289.

Berge et al., "Pharmaceutical Salts," J Pharma Sci., 1977, 66(1):1-19.

Biopharmatiques, "Merging Pharma and Biotech", http://www.biopharmaceutiques.com/fr/tables/clinical_studies_709.html, 2009.

Bioreversible Carriers in Drug Design, ed. Edward B. Roche, American Pharmaceutical Association and Pergamon Press 1987 *too voluminous.

Boismenu et al., "Insights from mouse models of colitis," K. Leukoc Biol, 67:267-278, 2000.

Bolic et al., "Sphingosine-l-Phosphate Prevents Tumor Necrosis Factor-alpha-Mediated Monocyte Adhesion to Aortic Endothelium in Mice," Arterioscler. Thromb. Vasc. Biol., 2005, 25:976-981.

Brinkman, "Sphingosine 1-phosphate receptors in health and disease: Mechanistic insights from gene deletion studies and reverse pharmacology," Pharmacol. Ther., 2007, 115:84-105.

Brinkmann et al., "FTY720 Alters Lymphocyte Homing and Protects Allografts Without Inducing General Immunosuppression," Transplantation Proc., 2001, 33:530-531.

Brinkmann et al., "FTY720: Altered Lymphocyte Traffic Results in Allograft Protection," Transplantation, Sep. 2001, 72(5):764-769.

Brinkmann et al., "The Immune Modulator FTY720 Targets Sphingosine 1-Phosphate Receptors," J Biol. Chem., 2002, 277(24):21453-21457.

Brinkmann, "FTY720 (fingolimod) in Multiple Sclerosis: therapeutic effects in the immune and the central nervous system", British Journal of Pharmacology, 158: 1173-1182, 2009.

Budde et al., "First Human Trial of FTY720, a Novel Immunomodulator, in Stable Renal Transplant Patients," J Am Soc. Nephrol., 2002, 13:1073-1083.

Buzard, Daniel J. et al, "Recent Progress in the Development of Selective S1P1 Receptor Agonists for the Treatment of Inflammatory and Autoimmune Disorders", Expert Opinion, 1141-1159, 2008.

Buzard et al., "Discovery and Characterization of Potent and Selective 4-Oxo-4-(5-(5-phenyl-1,2,4-oxadiazol-3-yl)indolin-1-yl)butanoic acids as S1P1 Agonists", Biorganic Med. Chem. Lett., 2011, 6013-6018.

Buzard, Daniel J. et al., "Discovery and Characterization of Potent and Selective 4-Oxo-4-(5-(5phenyl-1,2,4-oxadiazol-3-yl)indolin-l-yl)butanoic acids as S1P1 Receptor Agonists", Arena Pharmaceuticals, Inc., MEDI099, ACS, Mar. 2011.

Chawla et al., Challenges in Polymorphism of Pharmaceuticals, CRIPS, Jan.-Mar. 2004, vol. 5, No. 1, 4 pages.

Chiba et al., "Role of Sphingosine 1-Phosphate Receptor Type 1 in Lumphocyte Egress from Secondary Lymphoid Tissues and Thymus," Cell Mole Immunol., Feb. 2006, 3(1):11-19.

Chiba, "FTY720, a new class of immunomodulator, inhibits lymphocyte egress from secondary lymphoid tissues and thymus by agonistic activity at sphingosine 1-phosphate receptors," Pharmacol. Ther., 2005, 108:308-319.

Chun et al., "International Union of Pharmacology. XXXIV. Lysophospholipid Receptor Nomenclature," Pharmacol. Rev., 2002, 54(2):256-269.

Coelho et al., "The Immunomodulator FTY720 has a direct cytoprotective effect in oligodendrocyte Progenitors," J Pharmacol. Exp. Ther., 2007, 323:626-635.

Collier et al, "Radiosynthesis and In-vivo Evaluation of the Psuedopeptide 8-pioid Antagonist [$^{125}$I]—ITIPP(Ψ)," J. Labelled Compd. Radiopharm., 1999, 42, S264-S266.

Coste et al., "Antinociceptive activity of the S1P-receptor agonist FTY720," J Cell Moll Med., 2008, 12(3):995-1004.

Daniel et al., "FTY720 Ameliorates Th1-Mediated Colitis in Mice by Directly Affecting the Functional Activity of DC4+CD25+ Regulatory T Celli," J Immunol, 2007, 178:2458-2468.

Deguchi et al., "The S1P receptor modulator FTY720 prevents the development of experimental colitis in mice," Oncol. Rep., 2006, 16:699-703.

Dev et al., "Brain sphingosine-1-phosphate receptors: Implication for FTY720 in the treatment of multiple sclerosis," Pharmacol Ther., 2008, 117:77-93.

Fischer et al., "Targeting receptor tyrosine kinase signalling in small cell lung cancer (SCLC): What have we learned so far?" Cancer Treatment Revs., 2007, 33:391-406.

Fu et al., "Long-term islet graft survival in streptozotocin- and autoimmune-induced diabetes models by immunosuppressive and potential insulinotropic agent FTY720," Transplantation, May 2002, 73(9):1425-1430.

Fujii et al., "FTY720 suppresses CD4+CD44highCD62L—effector memory T cell-mediated colitis," Am J Physiol Gastrointest Liver Physiol., 2006, 291:G267-G274.

Fujino et al., "Amerlioration of Experimental Autoimmune Encephalomyelitis in Lewis Rats by FTY720 Treatment," J Pharmacol. Exp. Ther., 2003, 305(1):70-77.

Fujishiro et al., "Change from Cyclosporine to Combination Therapy of Mycophenolic Acid with the New Sphinogosine-l-phosphate Receptor Agonist, KRP-203, Prevents Host Nephrotoxicity and Transplant Vasculopathy in Rats," J Heart Lung Transplant, 2006, 25:825-833.

Gabriel et al, ASSAY and Drug Development Technologies, 1:291-303, 2003.

Golub et al., "Molecular Classification of Cancer: Class Discovery and Class Prediction by Gene Expression Monitoring," Science, 1999, 286:531-537.

Gottlieb, et al., "NMR Chemical Shifts of Common Laboratory Solvents as trace Impurities," J. Org. Chem. 1997, 62, 7512-7515.

Greene, T.W. and Wuts, P.G.M., Protecting Groups in Organic Synthesis, 3$^{rd}$ Edition, 1999 [Wiley] * (too voluminous).

Griesser, "The Importance of Solvates" in *Polymorphism in the Pharmaceutical Industry*, 211-233 (Rolf Hilfiker, ed., 2006).

Groeneveld, "Vascular pharmacology of acute lung injury and acute respiratory distress syndrome," Vascular Pharmacol., 2003, 39:247-256.

(56) References Cited

OTHER PUBLICATIONS

Guillory, "Generation of Polymorphs, Hydrates, Solvates, and Amorphous Solids," in:Polymorphism in Pharmaceutical Solids, ed. Harry G.Brittan, vol. 95, Marcel Dekker, Inc. New York, 1999, pp. 202-209.

Hale et al., "Potent S1P receptor agonists replicate the pharmacologic actions of the novel immune modulator FTY720," Bioorganic Med Chem. Lett., 2004, 14:3351-335.

Han, Sangdon et al., "Discovery of 2-(7-(5-phenyl-1,2,4-oxadiazol-3-yl)-1,2,3,4-tetrahydrocyclopenta[b]indol-3-yl)acetic acids: Potent and Selective Sphingosine-1-phosphate (S1P1) Receptor Agonists", Arena Pharmaceuticals, Inc., MEDI098, ACS Poster, Mar. 2011.

Herzinger et al., "Sphingosine-1-Phosphate Signaling and the Skin," Am J Clin Dermatol., 2007, 8(6):329-336.

Higuchi and Stella, Pro-drugs as Novel Delivery Systems vol. 14 of the A.C.S. Symposium Series, 1975, 129 pages.

Hwang et al., "FTY720, a New Immunosuppressant, Promotes Long-Term Graft Survival and Inhibits the Progression of Graft Coronary Artery Disease in a Murine Model of Cardiac Transplantation," Circulation, 1999, 100:1322-1329.

Idzko et al., "Local application of FTY720 to the lung abrogates experimental asthma by altering dendritic cell function," J Clinc Invest., Nov. 2006, 116(11):2935- 2944.

Ishii et al., "Sphingosine-1-phosphate mobilizes osteoclast precursors and regulates bone homeostasis," Nature, Mar. 2009, 458(7237):524-528.

Jones, Robert M., "Discovery of Potent and Selective Sphingosine-1-Phosphate 1 (S1P1) Receptor Agonists", CHI 6th Annual Drug Discovery Chemistry, San Diego, CA, Apr. 12, 2011.

Jones, Robert M., "Discovery of Potent and Selective Sphingosine-1-Phosphate 1(S1P1) Receptor Agonists", CHI 6th Annual Discovery on Target, Boston, MA, Nov. 3, 2011.

Jung et al., "Functional Consequences of S1P Receptor Modulation in Rat Oligodendroglial Lineage Cells," Glia, 2007, 55:1656-1667.

Kaneider et al., "The immune modulator FTY720 targets sphingosine-kinase-dependent migration of human monocytes in response to amyloid beta-protein and its precursor," FASEB J, 2004, 18:309-311.

Kappos et al., "Oral Fingolimod (FTY720) for Relapsing Multiple Sclerosis," N. Engl J Med., 2006, 355:1124-1140.

Kataoka et al., "FTY720, Sphingosine 1-Phosphate Receptor Modulator, Ameliorates Experimental Autoimmune Encephalomyelitis by Inhibition of T Cell Infiltration," Cell Mol. Immunol., Dec. 2005, 2(6):439-448.

Kaudel et al., "FTY720 for Treatment of Ischemia-Reperfusion Injury Following Complete Renal Ischemia; Impact on Long-Term Survival and T-Lymphocyte Tissue Infiltration," Transplantation Proc., 2007, 39:499-502.

Kawasaki, Andrew et al., "Discovery and Characterization of 2-(7-(5-phenyl-1,2,4-oxadiazol-3-yl)- 2,3-dihydro-1H-pyrrolo[1,2-a]indol-1-yl)acetic acid Derivatives as Potent & Selective Human S1P1 Receptor Agonists", Arena Pharmaceuticals, Inc., MEDI254, ACS, Mar. 2011.

Keul et al., "The Sphinogosine-1-Phosphate Analogue FTY720 Reduces Atherosclerosis in Apolipoprotein E-Deficient Mice," Arterioscler Thromb Vasc Biol., 2007, 27:607-613.

Kim et al., "Sphingosine-1-phosphate inhibits human keratinocyte proliferation via Akt/protein kinase B inactivation," Cell Signal, 2004, 16:89-95.

Kimura et al., "Essential Roles of Sphingosine 1-Phosphate/S1P1 Receptor Axis in the Migration of Neural Stem Cells Toward a Site of Spinal Cord Injury," Stem Cells, 2007, 25:115-124.

Kitabayashi et al., "FTY720 Prevents Development of Experimental Autoimmune Myocarditis Through Reduction of Circulating Lymphocytes," J Cardiovasc. Pharmacol. 2000, 35:410-416.

Kohno et al., "A Novel Immunomodulator, FTY720, Prevents Development of Experimental Autoimmune Myasthenia Gravis in C57BL/6 Mice," Biol Pharma Bull., 2005, 28(4):736-739.

Kohno et al., "A Novel Immunomodulator, FTY720, Prevents Spontaneous Dermatitis in NC/Nga Mice," BIol. Pharm. Bull., 2004, 27(9):1392-1396.

Koreck et al., "The Role of Innate Immunity in the Pathogensis of Acne," Dermatol., 2003, 206:96-105.

Kurose et al., "Effects of FTY720, a novel immunosuppressant, on experimental autoimmune uveoretinitis in rats," Exp. Eye Res., 2000, 70:7-15.

Lala et al., "Role of nitric oxide in tumor progression: Lessons from experimental tumors," Cancer Metastasis Rev., 1998, 17:91-106.

LaMontagne et al., "Antagonism of Sphingosine-1-Phosphate Receptors by FTY720 Inhibits Angiogenesis and Tumor Vascularization," Cancer Res., 2006, 66:221-231.

Le Bas, et al, "Radioiodinated Analogs of EP 00652218 for the Exploration of the Tachykinin NK1 Receptor by Spect," J. Labelled Compl. Radiopharm. 2001, 44, S280-S282.

Lee et al., "FTY720: A Promising Agent for Treatment of Metastatic Hepatocellular Carcinoma," Clin. Cancer Res., 2005, 11:8458-8466.

Lima et al., "FTY720 Treatment Prolongs Skin Graft Survival in a Completely Incompatible Strain Combination," Transplant Proc., 2004, 36:1015-1017.

Liu et al., "Long-Term Effect of FTY720 on Lymphocyte Count and Islet Allograft Survival in Mice," Microsurgery, 2007, 27:300-304.

Madhusudan et al., "Tyrosine kinase inhibitors in cancer therapy," Clinical Biochem., 2004, 37:618-635.

Maki et al., "Prevention and Cure of Autoimmune Diabetes in Nonobese Diabetic Mice by Continuous Administration of FTY720," Transplantation, 2005, 79:1051-1055.

Maki et al., "Prevention of autoimmune diabetes by FTY720 in Nonobese diabetic mice," Transplantation, Dec. 2002, 74(12):1684-1686.

Martini et al., "Current perspectives on FTY720," Expert Opin. Investig. Drugs, 2007, 16:505-518.

Martini et al., "S1P modulator FTY720 limits matrix expansion in acute anti-thy1 mesangioproliferative glomerulonephritis," Am J Physiol Renal Physiol., 2007, 292:F1761-F1770.

Matloubian et al., "Lymphocyte egress from thymus and peripheral lymphoid organs in dependent on SIP receptor 1," Nature, Jan. 2004, 427:355-360.

Matsuura et al., "Effect of FTY720, a novel immunosuppressant, on adjuvant- and collagen-induced arthritis in rats," Int. J Immunopharmacol. 2000, 22:323-331.

Matsuura et al., "Effect of FTY720, a novel immunosuppressant, on adjuvant-induced arthritis in rats," Inflamm. Res. 2000, 49:404-410.

Miron et al., "FTY720 Modulates Human Oligodendrocyte Progenitor Process Extension and Survival," Ann Neurol, 2008, 63:61-71.

Miyamoto et al., "Therapeutic Effects of FTY720, a New Immunosuppressive Agent, in a Murine Model of Acute Viral Myocarditis," J Am Coll Cardiol., 2001, 37(6):1713-1718.

Mizushima et al., "Therapeutic Effects of a New Lymphocyte Homing Reagent FTY720 in Interleukin-10 Gene-deficient Mice with Colitis," Inflamm Bowel Dis., May 2004, 10(3):182-192.

Morissette, et al., "High-Throughput Crystallization: Polymorphs, Salts, Co-Crystals and Solvates", Adv. Drug Delivery Rev., 56:275-300 (2004).

Nakashima et al., "Impaired Initiation of Contact Hypersensitivity by FTY720," J Invest Dermatol., 2008, 128:2833-2841.

Neurath et al., "Antibodies to Interleukin 12 Abrogate Established Experimental Colitis in Mice," J. Exp. Med, 182:1281-1290, 1995.

Newman et al., "Solid-state analysis of active pharmaceutical ingredient in drug products," DDT, Oct. 2003, 8(19):898-905.

Nofer et al., "FTY720, a Synthetic Sphingosine 1 Phosphate Analogue, Inhibits Development of Atherosclerosis in Low-Density Lipoprotein Receptor Deficient Mice," Circulation, 2007, 115:501-508.

Ogawa et al., "A novel sphingosine-1-phosphate receptor agonist KRP-203 attenuates rate autoimmune myocarditis," Biochem. Biophys. Res. Commun., 2007, 361:621-628.

Okayasu et al, "A Novel Method in the Induction of Reliable Experimental Acute and Chronic Ulcerative Colitis in Mice," Gastroenterology, 98:694-702, 1990.

Okazaki et al., "Effects of FTY720 in MRL-Ipr/Ipr mice: therapeutic potential in systemic lupus erythematosus," J Rheumatol., 2002, 29:707-716.

(56) References Cited

OTHER PUBLICATIONS

Oo et al, "Immunosuppressive and Anti-angiogenic Sphingosine 1-Phosphate Receptor-1 Agonists Induce Ubiquitinylation and Proteasomal Degradation of the Receptor," J Biol Chem., 2007, 282(12):9082-9089.
Pan et al., "A Monoselective Sphingosine-1-Phosphate Receptor-1 Agonist Prevents Allograft Rejection in a Stringent Rat Heart Transplantation Model," Chem. Biol., 2006, 13:1227-1234.
Pheilschifter et al., "Treatment with immunomodulator FTY720 does not promote spontaneous bacterial infections after experimental stroke mice," Experimental Translational Stroke Med., 2011, 3, 6 pages.
Premenko-Lanier et al., "Transient FTY720 treatment promotes immune-mediated clearance of a chronic viral infection," Nature, Aug. 2008, 454:894-899.
Rausch et al., "Predictiability of FTY720 Efficacy in Experimental Autoimmune Encephalomyelitis by In Vivo Macrophage Tracking: Clinical Implications for Ultrasmall Superparamagnetic Iron Oxide-Enhanced Magnetic Resonance Imaging," 2004, J Magn. Reson. Imaging, 2004, 20:16-24.
Raveney et al., "Fingolimod (FTY720) as an Acute Rescue Therapy for Intraocular Inflammatory Disease," Arch Ophthalmol, 2008, 126(10):1390-1395.
Remington, The Science and Practice of Pharmacy, 20$^{th}$ Edition, 2000, Lippincott Williams & Wilkins, (Editors: Gennaro et al) * (too voluminous).
Rheumatoid Arthritis Health Center—Most Common Types of Arthritis, WebMD, http://www.webmd.com/rheumatoid-arthritis/guide/most-common-arthritis-types, 2012, 2 pages.
Ronald Hoffman, M.D., "Crohns disease and ulcerative colitis," Sep. 1995, http://www.drhoffman.com/page.cfm/171, 5 pages.
Rosen et al., "Egress: a receptor-regulated step in lymphocyte trafficking," Immunol Rev. 2003, 195:160-177.
Sakagawa et al., "Rejection following donor or recipient preoperative treatment with FTY720 in rat small bowel transplantation," Transpl. Immunol., 2004, 13:161-168.
Sanchez et al., "Phosphorylation and Action of the Immunomodulator FTY720 Inhibits Vascular Endothelial Cell Growth Factor-induced Vascular Permeability," J Biol Chem., 2003, 278(47):47281-47290.
Sanna et al., "Enhancement of cappillary leakage and restoration of lymphocyte egress by a chiral S1P1 antagonist in vivo," Nature Chem Biol., Aug. 2006, 2(8):434-441.
Sanna et al., "Sphingosine 1-Phosphate (S1P) Receptor Subtypes S1P1 and S1P3, Respectively, Regulate Lymphocyte Recirculation and Heart Rate," J. Biol Chem., 2004, 279(14):13839-13848.
Sauer et al., "Involvement of Smad Signlaing in Sphingosine 1-Phosphate-mediated Biological Responses of Keratinocytes," J Biol. Chem., 2004, 279:38471-38479.
Sawicka et al, "Inhibition of Th1- and Th2-Mediated Airway Inflammation by the Sphingosine 1-Phosphate Receptor Agonist FTY720," J Immunol., 2003, 171:6206-6214.
Schmid et al., "The Immunosuppressant FTY720 inhibits tumor Angiogenesis via the Sphingosine 1-Phosphate Receptor 1," J Cell Biochem., 2007, 101:259-270.
Schwab and Cyster, "Finding a way out: lymphocyte egress from lymphoid organs," Nature Immunol., Dec. 2007, 8(12):1295-1301.
Shimizu et al., "KRP-203, a Novel Synthetic Immunosuppressant, Prolongs Graft Survival and Attenuates Chronic Rejection in Rat Skin and Heart Allografts," Circulation, 2005, 111:222-229.
Stahly, "Diversity in Single- and Multiple-Component Crystals. The Search for and Prevalence of Polymorphs and Cocrystals," Crystal Growth & Design (2007), 7(6), 1007-1026.
Storey, et al., "Automation of Solid Form Screening Procedures in the Pharmaceutical Industry-How to Avoid the Bottlenecks", *Crystallography Reviews*, 10(1):45-46 (2004).

Sturino et al: "Discovery of a potent and selective prostaglandin D2 receptor antagonist, [(3R)-4-(4-chloro-benzyl)-7-Fluoro-5-(methylsulfony1)-1,2,3,4-tetrahydrocyclopenta[b]indol-3-yl]-acetic acid (MK-0524)", Journal of Medicinal Chemistry, Feb. 22, 2007, pp. 794-806.
Suzuki et al., "Efficacy of Mycophenolic Acid Combined with KRP-203, a Novel Immunomodulator, in a Rat Heart Transplantation Model," J Heart Lung Transplant, 2006, 25:302-309.
Suzuki et al, "Immunosuppressive effect of a new drug, FTY720, on lymphocyte responses in vitro and cardiac allograft survival in rats," Transplant Immunol., 1996, 4:252-255.
Taylor et al., "Insights into the mechanism of FTY720 and compatibility with regulatory T cells for the inhibition of graft-versus-host disease (GVHD)," Blood, 2007, 110:3480-3488.
Truong et al., "Human Islet Function is not Impaired by the Sphingosine-1-Phosphate Receptor Modulator FTY720," Am J Transplantation, 2007, 7:2031-2038.
Vachal et al., "Highly selective and potent agonists of sphinogosin-1-phosphate 1 (S1P1) receptor," Bioorganic Med Chem Lett., Jul. 2006, 16(14):3684-3687.
Villullas et al, "Characterisation of a Sphingosine 1-Phosphate-Activated Ca2+ Signalling Pathway in Human Neuroblastoma Cells," J. Neurosci. Res, 73:215-226, 2003.
Vippagunta, et al., "Crystalline Solids," *Adv. Drug Delivery Rev.*, 48:3-26 (2001).
Webb et al., "Sphingosine 1-phosphate receptors agonists attenuate relapsing—remitting experimental autoimmune encephalitis in SJL mice," J Neuroimmunol., 2004, 153:108-121.
Webster, "The Pathophysiology of Acne," Cutis, 2005, 76(suppl. 2):4-7.
Whetzel et al., "Sphingosine-1 Phosphate Prevents Monocyte/Endothelial Interactions in Type 1 Diabetic NOD Mice Through Activation of the S1P1 Receptor," Circ. Res., 2006, 99:731-739.
Yan et al., "Discovery of 3-arylpropionic acids as potent agonists of sphingosine-1-phosphate receptor-1 (S1P1) with high selectivity against all other known S1P receptor subtypes," Bioorg. Med. Chem. Lett., 2006, 16:3679-3683.
Yanagawa et al., "FTY720, a Novel Immunosuppressant, Induces Sequestration of Circulating Mature Lymphocytes by Acceleration of Lymphocyte Homing in Rats. II. FTY720 Prolongs Skin Allograft Survival by Decreasing T Cell Infiltration into Grafts But not cytokine production in vivo," J Immunol., 1998, 160:5493-5499.
Yang et al., "The immune modulator FYT720 prevents autoimmune diabetes in nonobese diabetic mice," Clin. Immunol., 2003, 107:30-35.
Zhang et al., "FTY720 attenuates accumulation of EMAP-II+ and MHC-II+ monocytes in early lesions of rat traumatic brain injury," J Cell Mol Med., 2007, 11(2):307-314.
Zhang et al., "FTY720: A Most Promising Immunosuppressant Modulating Immune Cell Functions," Mini Rev. Med Chem., 2007, 7:845-850.
Zhu et al, "Synthesis and Mode of Action of 125I-and 3H- Labeled Thieno[2,3-c]pyridine Antagonists of Cell Adhesion Molecule Expression," J. Org. Chem., 2002, 67, 943-948.
Schafiee et al., "An efficent enzyme-catalyzed kinetic resolution: large-scale preparation of an enantiomerically pure indole-ethyl ester derivative, a key component for the synthesis of a prostaglandin D2 receptor antagonist, an anti-allergic rhinitis drug candidate," *Tetrahedron: Asymmetry*, 2005, 16:3094-3098.
Truppo et al., "Optimization and Scale-Up of a Lipase-Catalyzed Enzymatic Resolution of an Indole Ester Intermediate for a Prostaglandin D2 (DP) Receptor Antagonist Targeting Allergic Rhinitis," Organic Process Research and Development, Feb. 2006, 10(3):592-598.

\* cited by examiner

SUBSTITUTED TRICYCLIC ACID DERIVATIVES AS S1P1 RECEPTOR AGONISTS USEFUL IN THE TREATMENT OF AUTOIMMUNE AND INFLAMMATORY DISORDERS

This application is a continuation of U.S. application Ser. No. 13/060,477, filed Feb. 24, 2011, which is a §371 National Stage Application of International Application PCT/US2009/004851, filed Aug. 26, 2009, which claims benefit of priority of U.S. Provisional Application Nos. 61/269,519, filed June 24, 2009 and 61/190,311, filed Aug. 27, 2008, each of which is incorporated herein by reference in its entirety.

FIELD OF THE INVENTION

The present invention relates to certain substituted tricyclic acid derivatives of Formula (I) and pharmaceutically acceptable salts thereof, which exhibit useful pharmacological properties, for example, as agonists of the S1P1 receptor.

Also provided by the present invention are pharmaceutical compositions containing compounds of the invention, and methods of using the compounds and compositions of the invention in the treatment of S1P1-associated disorders, for example, psoriasis, rheumatoid arthritis, Crohn's disease, transplant rejection, multiple sclerosis, systemic lupus erythematosus, ulcerative colitis, type I diabetes, acne, myocardial ischemia-reperfusion injury, hypertensive nephropathy, glomerulosclerosis, gastritis, polymyositis, thyroiditis, vitiligo, hepatitis, biliary cirrhosis, microbial infections and associated diseases, viral infections and associated diseases, diseases and disorders mediated by lymphocytes, auto immune diseases, inflammatory diseases, and cancer.

BACKGROUND OF THE INVENTION

The present invention relates to compounds that are S1P1 receptor agonists having at least immunosuppressive, anti-inflammatory, and/or hemostatic activities, e.g. by virtue of modulating leukocyte trafficking, sequestering lymphocytes in secondary lymphoid tissues, and/or enhancing vascular integrity.

The present application is in part focused on addressing an unmet need for immunosuppressive agents such as may be orally available which have therapeutic efficacy for at least autoimmune diseases and disorders, inflammatory diseases and disorders (e.g., acute and chronic inflammatory conditions), transplant rejection, cancer, and/or conditions that have an underlying defect in vascular integrity or that are associated with angiogenesis such as may be pathologic (e.g., as may occur in inflammation, tumor development, and atherosclerosis) with fewer side effects such as the impairment of immune responses to systemic infection.

The sphingosine-1-phosphate (S1P) receptors 1-5 constitute a family of G protein-coupled receptors with a seven-transmembrane domain. These receptors, referred to as S1P1 to S1P5 (formerly termed endothelial differentiation gene (EDG) receptor-1, -5, -3, -6, and -8, respectively; Chun et al., *Pharmacological Reviews*, 54:265-269, 2002), are activated via binding by sphingosine-1-phosphate, which is produced by the sphingosine kinase-catalyzed phosphorylation of sphingosine. S1P1, S1P4, and S1P5 receptors activate Gi but not Gq, whereas S1P2 and S1P3 receptors activate both Gi and Gq. The S1P3 receptor, but not the S1P1 receptor, responds to an agonist with an increase in intracellular calcium.

S1P receptor agonists having agonist activity on the S1P1 receptor have been shown to rapidly and reversibly induce lymphopenia (also referred to as peripheral lymphocyte lowering (PLL); Hale et al., *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al., *Nature Immunol.*, 8:1295-1301, 2007). This lymphocyte sequestration, for example in lymph nodes, is thought to be a consequence of concurrent agonist-driven functional antagonism of the S1P1 receptor on T-cells (whereby the ability of S1P to mobilize T-cell egress from lymph nodes is reduced) and persistent agonism of the S1P1 receptor on lymph node endothelium (such that barrier function opposing transmigration of lymphocytes is increased) (Matloubian et al., *Nature*, 427:355-360, 2004; Baumruker et al., *Expert Opin. Investig. Drugs*, 16:283-289, 2007). It has been reported that agonism of the S1P1 receptor alone is sufficient to achieve lymphocyte sequestration (Sanna et al., *J. Biol. Chem.*, 279:13839-13848, 2004) and that this occurs without impairment of immune responses to systemic infection (Brinkmann et al, *Transplantation*, 72:764-769, 2001; Brinkmann et al., *Transplant Proc.*, 33:530-531, 2001).

That agonism of endothelial S1P1 receptors has a broader role in promoting vascular integrity is supported by work implicating the S1P1 receptor in capillary integrity in mouse skin and lung (Sanna et al., *Nat Chem. Biol.*, 2:434-441, 2006). Vascular integrity can be compromised by inflammatory processes, for example as may derive from sepsis, major trauma and surgery so as to lead to acute lung injury or respiratory distress syndrome (Johan Groeneveld, *Vascul. Pharmacol.*, 39:247-256, 2003).

An exemplary S1P receptor agonist having agonist activity on the S1P1 receptor is FTY720 (fingolimod), an immunosuppressive agent currently in clinical trials (Martini et al, *Expert Opin. Investig. Drugs*, 16:505-518, 2007). FTY720 acts as a prodrug which is phosphorylated in vivo; the phosphorylated derivative is an agonist for S1P1, S1P3, S1P4, and S1P5 receptors (but not the S1P2 receptor) (Chiba, *Pharmacology & Therapeutics*, 108:308-319, 2005). FTY720 has been shown to rapidly and reversibly induce lymphopenia (also referred to as peripheral lymphocyte lowering (PLL); Hale et al, *Bioorg. Med. Chem. Lett.*, 14:3351-3355, 2004). This is attended by clinically useful immunosuppression by virtue of sequestering T- and B-cells in secondary lymphoid tissue (lymph nodes and Peyer's patches) and thus apart from sites of inflammation and organ grafts (Rosen et al., *Immunol. Rev.*, 195:160-177, 2003; Schwab et al, *Nature Immunol.*, 8:1295-1301, 2007).

In clinical trials, FTY720 elicited an adverse event (i.e., transient asymptomatic bradycardia) due to its agonism of the S1P3 receptor (Budde et al., *J. Am. Soc. Nephrol.*, 13:1073-1083, 2002; Sanna et al., *J. Biol. Chem.*, 279:13839-13848, 2004; Ogawa et al., *BBRC*, 361:621-628, 2007).

FTY720 has been reported to have therapeutic efficacy in at least: a rat model for autoimmune myocarditis and a mouse model for acute viral myocarditis (Kiyabayashi et al., *J. Cardiovasc. Pharmacol.*, 35:410-416, 2000; Miyamoto et al., *J. Am. Coll. Cardiol.*, 37:1713-1718, 2001); mouse models for inflammatory bowel disease including colitis (Mizushima et al., *Inflamm. Bowel Dis.*, 10:182-192, 2004; Deguchi et al., *Oncology Reports*, 16:699-703, 2006; Fujii et al., *Am. J. Physiol. Gastrointest. Liver Physiol.*, 291:G267-G274, 2006; Daniel et al., *J. Immunol.*, 178:2458-2468, 2007); a rat model for progressive mesangioproliferative glomerulonephritis (Martini et al., *Am. J. Physiol. Renal Physiol.*, 292:F1761-F1770, 2007); a mouse model for asthma, suggested to be primarily through the S1P1 receptor on the basis of work using the S1P1 receptor agonist SEW2871 (Idzko et al, J. Clin. Invest., 116:2935-2944, 2006); a mouse model for airway inflammation and induction of bronchial hyperresponsiveness (Sawicka et al., J. Immunol., 171; 6206-6214, 2003); a mouse model for atopic dermatitis (Kohno et al., Biol. Pharm. Bull., 27:1392-1396, 2004); a mouse model for ischemia-reperfusion injury (Kaudel et al., Transplant. Proc, 39:499-502, 2007); a mouse model for systemic lupus erythematosus (SLE) (Okazaki et al., J. Rheumatol., 29:707-716, 2002; Herzinger et al, Am. J. Clin. Dermatol., 8:329-336, 2007); rat models for rheumatoid arthritis (Matsuura et al., Int. J. Immunopharmacol., 22:323-331, 2000; Matsuura et al., Inflamm. Res., 49:404-410, 2000); a rat model for autoimmune uveitis (Kurose et al., Exp. Eye Res., 70:7-15, 2000); mouse models for type I diabetes (Fu et al, Transplantation, 73:1425-1430, 2002; Maki et al., Transplantation, 74:1684-1686, 2002; Yang et al., Clinical Immunology, 107:30-35, 2003; Maki et al., Transplantation, 79:1051-1055, 2005); mouse models for atherosclerosis (Nofer et al., Circulation, 115:501-508, 2007; Keul et al., Arterioscler. Thromb. Vasc. Biol., 27:607-613, 2007); a rat model for brain inflammatory reaction following traumatic brain injury (TBI) (Zhang et al., J. Cell. Mol. Med., 11:307-314, 2007); and mouse models for graft coronary artery disease and graft-versus-host disease (GVHD) (Hwang et al., Circulation, 100:1322-1329, 1999; Taylor et al., Blood, 110:3480-3488, 2007). In vitro results suggest that FTY720 may have therapeutic efficacy for β-amyloid-related inflammatory diseases including Alzheimer's disease (Kaneider et al., FASEB J., 18:309-311, 2004). KRP-203, an S1P receptor agonist having agonist activity on the S1P1 receptor, has been reported to have therapeutic efficacy in a rat model for autoimmune myocarditis (Ogawa et al., BBRC, 361:621-628, 2007). Using the S1P1 receptor agonist SEW2871, it has been shown that agonism of endothelial S1P1 receptors prevents proinflammatory monocyte/endothelial interactions in type I diabetic vascular endothelium (Whetzel et al., Circ. Res., 99:731-739, 2006) and protects the vasculature against TNFα-mediated monocyte/endothelial interactions (Bolick et al., Arterioscler. Thromb. Vasc. Biol., 25:976-981, 2005).

Additionally, FTY720 has been reported to have therapeutic efficacy in experimental autoimmune encephalomyelitis (EAE) in rats and mice, a model for human multiple sclerosis (Brinkmann et al., J. Biol. Chem., 277:21453-21457, 2002; Fujino et al., J. Pharmacol. Exp. Ther., 305:70-77, 2003; Webb et al., J. Neuroimmunol., 153:108-121, 2004; Rausch et al., J. Magn. Reson. Imaging, 20:16-24, 2004; Kataoka et al., Cellular & Molecular Immunology, 2:439-448, 2005; Brinkmann et al., Pharmacology & Therapeutics, 115:84-105, 2007; Baumruker et al., Expert Opin. Investig. Drugs, 16:283-289, 2007; Balatoni et al., Brain Research Bulletin, 74:307-316, 2007). Furthermore, FTY720 has been found to have therapeutic efficacy for multiple sclerosis in clinical trials. In Phase II clinical trials for relapsing-remitting multiple sclerosis, FTY720 was found to reduce the number of lesions detected by magnetic resonance imaging (MRI) and clinical disease activity in patients with multiple sclerosis (Kappos et al., N Engl. J. Med., 355:1124-1140, 2006; Martini et al., Expert Opin. Investig. Drugs, 16:505-518, 2007; Zhang et al., Mini-Reviews in Medicinal Chemistry, 7:845-850, 2007; Brinkmann, Pharmacology & Therapeutics, 115: 84-105, 2007). FTY720 is currently in Phase III studies of remitting-relapsing multiple sclerosis (Brinkmann, Pharmacology & Therapeutics, 115:84-105, 2007; Baumruker et al., Expert. Opin. Investig. Drugs, 16:283-289, 2007; Dev et al., Pharmacology and Therapeutics, 117:77-93, 2008).

Recently, FTY720 has been reported to have anti-viral activity. Specific data has been presented in the lymphocytic choriomeningitis virus (LCMV) mouse model, wherein the mice were infected with either the Armstrong or the clone 13 strain of LCMV (Premenko-Lanier et al., Nature, 454, 894, 2008).

FTY720 has been reported to impair migration of dendritic cells infected with Francisella tularensis to the mediastinal lymph node, thereby reducing the bacterial colonization of it. *Francisella tularensis* is associated with tularemia, ulceroglandular infection, respiratory infection and a typhoidal disease (E. Bar-Haim et al, PLoS Pathogens, 4(11): e1000211. doi:10.1371/journal.ppat.1000211, 2008).

It has also been recently reported that a short-term high dose of FTY720 rapidly reduced ocular infiltrates in experimental autoimmune uveoretinitis. When given in the early stages of ocular inflammation, FTY720 rapidly prevented retinal damage. It was reported to not only prevent infiltration of target organs, but also reduce existing infiltration (Raveney et al., Arch. Ophthalmol. 126(10), 1390, 2008).

It has been reported that treatment with FTY720 relieved ovariectomy-induced osteoporosis in mice by reducing the number of mature osteoclasts attached to the bone surface. The data provided evidence that S1P controled the migratory behaviour of osteoclast precursors, dynamically regulating bone mineral homeostasis (Ishii et al., Nature, advance online publication, 8 Feb. 2009, doi:10.1038/nature07713).

Agonism of the S1P1 receptor has been implicated in enhancement of survival of oligodendrocyte progenitor cells. Survival of oligodendrocyte progenitor cells is a required component of the remyelination process. Remyelination of multiple sclerosis lesions is considered to promote recovery from clinical relapses. (Miron et al., *Ann. Neurol.,* 63:61-71, 2008; Coelho et al., *J. Pharmacol. Exp. Ther.,* 323:626-635, 2007; Dev et al., *Pharmacology and Therapeutics,* 117:77-93, 2008). It also has been shown that the S1P1 receptor plays a role in platelet-derived growth factor (PDGF)-induced oligodendrocyte progenitor cell mitogenesis (Jung et al., *Glia,* 55:1656-1667, 2007).

Agonism of the S1P1 receptor has also been reported to mediate migration of neural stem cells toward injured areas of the central nervous system (CNS), including in a rat model of spinal cord injury (Kimura et al., *Stem Cells,* 25:115-124, 2007).

Agonism of the S1P1 receptor has been implicated in the inhibition of keratinocyte proliferation (Sauer et al., *J. Biol. Chem.,* 279:38471-38479, 2004), consistent with reports that S1P inhibits keratinocyte proliferation (Kim et al., *Cell Signal,* 16:89-95, 2004). The hyperproliferation of keratinocytes at the entrance to the hair follicle, which can then become blocked, and an associated inflammation are significant pathogenetic factors of acne (Koreck et al., *Dermatology,* 206:96-105, 2003; Webster, *Cutis,* 76:4-7, 2005).

FTY720 has been reported to have therapeutic efficacy in inhibiting pathologic angiogenesis, such as that as may occur in tumor development. Inhibition of angiogenesis by FTY720 is thought to involve agonism of the S1P1 receptor (Oo et al., *J. Biol. Chem.,* 282; 9082-9089, 2007; Schmid et al., *J. Cell Biochem.,* 101:259-270, 2007). FTY720 has been reported to have therapeutic efficacy for inhibiting primary and metastatic tumor growth in a mouse model of melanoma (LaMontagne et al., *Cancer Res.,* 66:221-231, 2006). FTY720 has been reported to have therapeutic efficacy in a mouse model for metastatic hepatocellular carcinoma (Lee et al., *Clin. Cancer Res.,* 11:84588466, 2005).

It has been reported that oral administration of FTY720 to mice potently blocked VEGF-induced vascular permeability, an important process associated with angiogenesis, inflammation, and pathological conditions such as sepsis, hypoxia, and solid tumor growth (T Sanchez et al, J. Biol. Chem., 278(47), 47281-47290, 2003).

Cyclosporin A and FK506 (calcineurin inhibitors) are drugs used to prevent rejection of transplanted organs. Although they are effective in delaying or suppressing transplant rejection, classical immunosuppressants such as cyclosporin A and FK506 are known to cause several undesirable side effects including nephrotoxicity, neurotoxicity, β-cell toxicity and gastrointestinal discomfort. There is an unmet need in organ transplantation for an immunosuppressant without these side effects which is effective as a monotherapy or in combination with a classical immunosuppressant for inhibiting migration of, e.g., alloantigen-reactive T-cells to the grafted tissue, thereby prolonging graft survival.

FTY720 has been shown to have therapeutic efficacy in transplant rejection both as a monotherapy and in synergistic combination with a classical immunosuppressant, including cyclosporin A, FK506 and RAD (an mTOR inhibitor). It has been shown that, unlike the classical immunosuppressants cyclosporin A, FK506 and RAD, FTY720 has efficacy for prolonging graft survival without inducing general immunosuppression, and this difference in drug action is believed to be relevant to the synergism observed for the combination (Brinkmann et al., *Transplant Proc.*, 33:530-531, 2001; Brinkmann et al., *Transplantation*, 72:764-769, 2001).

Agonism of the S1P1 receptor has been reported to have therapeutic efficacy for prolonging allograft survival in mouse and rat skin allograft models (Lima et al., *Transplant Proc.*, 36:1015-1017, 2004; Yan et al., *Bioorg. & Med. Chem. Lett.*, 16:3679-3683, 2006). FTY720 has been reported to have therapeutic efficacy for prolonging allograft survival in a rat cardiac allograft model (Suzuki et al., *Transpl. Immunol.*, 4:252-255, 1996). FTY720 has been reported to act synergistically with cyclosporin A to prolong rat skin allograft survival (Yanagawa et al., *J. Immunol.*, 160:5493-5499, 1998), to act synergistically with cyclosporin A and with FK506 to prolong rat cardiac allograft survival, and to act synergistically with cyclosporin A to prolong canine renal allograft survival and monkey renal allograft survival (Chiba et al., *Cell Mol Biol.*, 3:11-19, 2006). KRP-203, an S1P receptor agonist has been reported to have therapeutic efficacy for prolonging allograft survival in a rat skin allograft model and both as monotherapy and in synergistic combination with cyclosporin A in a rat cardiac allograft model (Shimizu et al., *Circulation*, 111:222-229, 2005). KRP-203 also has been reported to have therapeutic efficacy in combination with mycophenolate mofetil (MMF; a prodrug for which the active metabolite is mycophenolic acid, an inhibitor of purine biosynthesis) for prolonging allograft survival both in a rat renal allograft model and in a rat cardiac allograft model (Suzuki et al., *J Heart Lung Transplant*, 25:302-209, 2006; Fujishiro et al., *J. Heart Lung Transplant*, 25:825-833, 2006). It has been reported that an agonist of the S1P1 receptor, AUY954, in combination with a subtherapeutic dose of RAD001 (Certican/Everolimus, an mTOR inhibitor) can prolong rat cardiac allograft survival (Pan et al., *Chemistry & Biology*, 13:1227-1234, 2006). In a rat small bowel allograft model, FTY720 has been reported to act synergistically with cyclosporin A to prolong small bowel allograft survival (Sakagawa et al., *Transpl. Immunol.*, 13:161-168, 2004). FTY720 has been reported to have therapeutic efficacy in a mouse islet graft model (Fu et al., *Transplantation*, 73:1425-1430, 2002; Liu et al., *Microsurgery*, 27:300-304; 2007) and in a study using human islet cells to evidence no detrimental effects on human islet function (Truong et al., *American Journal of Transplantation*, 7:2031-2038, 2007).

FTY720 has been reported to reduce the nociceptive behavior in the spared nerve injury model for neuropathic pain which does not depend on prostaglandin synthesis (O. Costu et al, Journal of Cellular and Molecular Medicine 12(3), 995-1004, 2008).

FTY720 has been reported to impair initiation of murine contact hypersensitivity (CHS). Adoptive transfer of immunized lymph node cells from mice treated with FTY720 during the sensitization phase was virtually incapable of inducing CHS response in recipients (D. Nakashima et al., J. Investigative Dermatology (128(12), 2833-2841, 2008).

It has been reported that prophylactic oral administration of FTY720 (1 mg/kg, three times a week), completely prevented the development of experimental autoimmune myasthenia gravis (EAMG) in C57BL/6 mice (T. Kohono et al, Biological & Pharmaceutical Bulletin, 28(4), 736-739, 2005).

In one embodiment, the present invention encompasses compounds which are agonists of the S1P1 receptor having selectivity over the S1P3 receptor. The S1P3 receptor, and not the S1P1 receptor, has been directly implicated in bradycardia (Sanna et al., *J. Biol. Chem.*, 279:13839-13848, 2004). An S1P1 receptor agonist selective over at least the S1P3 receptor has advantages over current therapies by virtue of an enhanced therapeutic window, allowing better tolerability with higher dosing and thus improving efficacy as therapy. The present invention encompasses compounds which are agonists of the S1P1 receptor and which exhibit no or substantially no activity for bradycardia.

S1P1 receptor agonists are useful to treat or prevent conditions where suppression of the immune system or agonism of the S1P1 receptor is in order, such as diseases and disorders mediated by lymphocytes, transplant rejection, autoimmune diseases and disorders, inflammatory diseases and disorders, and conditions that have an underlying defect in vascular integrity or that relate to angiogenesis such as may be pathologic.

In one embodiment, the present invention encompasses compounds which are agonists of the S1P1 receptor having good overall physical properties and biological activities and having an effectiveness that is substantially at least that of prior compounds with activity at the S1P1 receptor.

Citation of any reference throughout this application is not to be construed as an admission that such reference is prior art to the present application.

SUMMARY OF THE INVENTION

The present invention encompasses compounds of Formula (I) and pharmaceutically acceptable salts, solvates, and hydrates thereof:

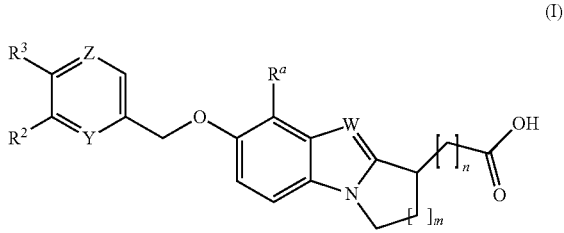

wherein:
m is 1 or 2;
n is 1 or 2;
Y is N or $CR^1$;
Z is N or $CR^4$;
W is N or $CR^5$;
$R^a$ is H or $C_1$-$C_6$ alkyl;
$R^1$, $R^2$, $R^3$, and $R^4$ are each independently selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl, and heterocyclyl, wherein the $C_1$-$C_6$ alkyl and $C_1$-$C_6$ alkoxy are each optionally substituted with one $C_3$-$C_7$ cycloalkyl group; and
$R^5$ is selected from the group consisting of H, $C_1$-$C_6$ alkyl, $C_1$-$C_6$ alkylsulfonyl, cyano, $C_3$-$C_7$ cycloalkyl, $C_1$-$C_6$ haloalkyl, halogen, heteroaryl, and heterocyclyl.

One aspect of the present invention pertains to compounds of Formula (Ia) and pharmaceutically acceptable salts, solvates, and hydrates thereof:

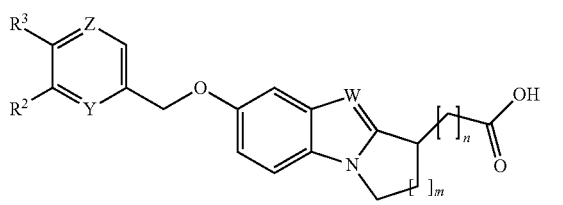

(Ia)

wherein:
m is 1 or 2;
n is 1 or 2;
Y is N or $CR^1$;
Z is N or $CR^4$;
W is N or $CR^5$;
$R^1$, $R^2$, $R^3$, and $R^4$ are each independently selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl, and heterocyclyl, wherein the $C_1$-$C_6$ alkyl and $C_1$-$C_6$ alkoxy are each optionally substituted with one $C_3$-$C_7$ cycloalkyl group; and
$R^5$ is selected from the group consisting of H, $C_1$-$C_6$ alkyl, cyano, $C_3$-$C_7$ cycloalkyl, $C_1$-$C_6$ haloalkyl, halogen, and heterocyclyl.

The present invention encompasses compounds which are S1P1 receptor agonists having at least immunosuppressive, anti-inflammatory and/or hemostatic activities, e.g. by virtue of modulating leukocyte trafficking, sequestering lymphocytes in secondary lymphoid tissues, and/or enhancing vascular integrity.

S1P1 receptor agonists are useful to treat or prevent conditions where suppression of the immune system or agonism of the S1P1 receptor is in order, such as diseases and disorders mediated by lymphocytes, transplant rejection, autoimmune diseases and disorders, inflammatory diseases and disorders (e.g., acute and chronic inflammatory conditions), cancer, and conditions that have an underlying defect in vascular integrity or that are associated with angiogenesis such as may be pathologic (e.g., as may occur in inflammation, tumor development and atherosclerosis). Such conditions where suppression of the immune system or agonism of the S1P1 receptor is in order include diseases and disorders mediated by lymphocytes, conditions that have an underlying defect in vascular integrity, autoimmune diseases and disorders, inflammatory diseases and disorders (e.g., acute and chronic inflammatory conditions), acute or chronic rejection of cells, tissue or solid organ grafts, arthritis including psoriatic arthritis and rheumatoid arthritis, diabetes including type I diabetes, demyelinating disease including multiple sclerosis, ischemia-reperfusion injury including renal and cardiac ischemia-reperfusion injury, inflammatory skin disease including psoriasis, atopic dermatitis and acne, hyperproliferative skin disease including acne, inflammatory bowel disease including Crohn's disease and ulcerative colitis, systemic lupus erythematosis, asthma, uveitis, myocarditis, allergy, atherosclerosis, brain inflammation including Alzheimer's disease and brain inflammatory reaction following traumatic brain injury, central nervous system disease including spinal cord injury or cerebral infarction, pathologic angiogenesis including as may occur in primary and metastatic tumor growth, rheumatoid arthritis, diabetic retinopathy and atherosclerosis, cancer, chronic pulmonary disease, acute lung injury, acute respiratory disease syndrome, sepsis, and the like.

One aspect of the present invention pertains to pharmaceutical compositions comprising a compound of the present invention and a pharmaceutically acceptable carrier.

One aspect of the present invention pertains to methods for treating a disorder associated with the S1P1 receptor in an individual comprising administering to the individual in need thereof a therapeutically effective amount of a compound of the present invention or a pharmaceutical composition thereof.

One aspect of the present invention pertains to methods for treating an S1P1 receptor-associated disorder in an individual comprising administering to the individual in need thereof a therapeutically effective amount of a compound of the present invention or a pharmaceutical composition thereof.

One aspect of the present invention pertains to methods for treating a disease or disorder mediated by lymphocytes in an individual comprising administering to the individual in need thereof a therapeutically effective amount of a compound of the present invention or a pharmaceutical composition thereof.

One aspect of the present invention pertains to methods for treating an autoimmune disease or disorder in an individual comprising administering to the individual in need thereof a therapeutically effective amount of a compound of the present invention or a pharmaceutical composition thereof.

One aspect of the present invention pertains to methods for treating an inflammatory disease or disorder in an individual comprising administering to the individual in need thereof a therapeutically effective amount of a compound of the present invention or a pharmaceutical composition thereof.

One aspect of the present invention pertains to methods for treating a microbial or viral infection or disease in an individual comprising administering to the individual in need thereof a therapeutically effective amount of a compound of the present invention or a pharmaceutical composition thereof.

One aspect of the present invention pertains to methods for treating cancer in an individual comprising administering to the individual in need thereof a therapeutically effective amount of a compound of the present invention or a pharmaceutical composition thereof.

One aspect of the present invention pertains to methods for treating an S1P1 receptor-associated disorder in an individual comprising administering to the individual in need thereof a therapeutically effective amount of a compound of the present invention or a pharmaceutical composition thereof, wherein the disorder is selected from the group consisting of psoriasis, rheumatoid arthritis, Crohn's disease, transplant rejection, multiple sclerosis, systemic lupus erythematosus, ulcerative colitis, type I diabetes, hypertensive nephropathy, glomerulosclerosis, myocardial ischemia-reperfusion injury, and acne.

One aspect of the present invention pertains to methods for treating a disorder in an individual comprising administering to the individual in need thereof a therapeutically effective amount of a compound of the present invention or a pharmaceutical composition thereof, wherein the disorder is selected from the group consisting of psoriasis, rheumatoid arthritis, Crohn's disease, transplant rejection, multiple sclerosis, systemic lupus erythematosus, ulcerative colitis, type I diabetes, and acne.

One aspect of the present invention pertains to methods for treating psoriasis in an individual comprising administering to the individual in need thereof a therapeutically effective amount of a compound of the present invention or a pharmaceutical composition thereof.

One aspect of the present invention pertains to methods for treating rheumatoid arthritis in an individual comprising administering to the individual in need thereof a therapeutically effective amount of a compound of the present invention or a pharmaceutical composition thereof.

One aspect of the present invention pertains to methods for treating Crohn's disease in an individual comprising administering to the individual in need thereof a therapeutically effective amount of a compound of the present invention or a pharmaceutical composition thereof.

One aspect of the present invention pertains to methods for treating transplant rejection in an individual comprising administering to the individual in need thereof a therapeutically effective amount of a compound of the present invention or a pharmaceutical composition thereof.

One aspect of the present invention pertains to methods for treating multiple sclerosis in an individual comprising administering to the individual in need thereof a therapeutically effective amount of a compound of the present invention or a pharmaceutical composition thereof.

One aspect of the present invention pertains to methods for treating systemic lupus erythematosus in an individual comprising administering to the individual in need thereof a therapeutically effective amount of a compound of the present invention or a pharmaceutical composition thereof.

One aspect of the present invention pertains to methods for treating ulcerative colitis in an individual comprising administering to the individual in need thereof a therapeutically effective amount of a compound of the present invention or a pharmaceutical composition thereof.

One aspect of the present invention pertains to methods for treating type I diabetes in an individual comprising administering to the individual in need thereof a therapeutically effective amount of a compound of the present invention or a pharmaceutical composition thereof.

One aspect of the present invention pertains to methods for treating hypertensive nephropathy in an individual comprising administering to the individual in need thereof a therapeutically effective amount of a compound of the present invention or a pharmaceutical composition thereof.

One aspect of the present invention pertains to methods for treating glomerulosclerosis in an individual comprising administering to the individual in need thereof a therapeutically effective amount of a compound of the present invention or a pharmaceutical composition thereof.

One aspect of the present invention pertains to methods for treating myocardial ischemia-reperfusion injury in an individual comprising administering to the individual in need thereof a therapeutically effective amount of a compound of the present invention or a pharmaceutical composition thereof.

One aspect of the present invention pertains to methods for treating acne in an individual comprising administering to the individual in need thereof a therapeutically effective amount of a compound of the present invention or a pharmaceutical composition thereof.

One aspect of the present invention pertains to the use of compounds of the present invention in the manufacture of a medicament for the treatment of an S1P1 receptor-associated disorder.

One aspect of the present invention pertains to the use of compounds of the present invention in the manufacture of a medicament for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes, hypertensive nephropathy, glomerulosclerosis, myocardial ischemia-reperfusion injury, and acne.

One aspect of the present invention pertains to the use of compounds of the present invention in the manufacture of a medicament for the treatment of a disease or disorder mediated by lymphocytes.

One aspect of the present invention pertains to the use of compounds of the present invention in the manufacture of a medicament for the treatment of an autoimmune disease or disorder.

One aspect of the present invention pertains to the use of compounds of the present invention in the manufacture of a medicament for the treatment of an inflammatory disease or disorder.

One aspect of the present invention pertains to the use of compounds of the present invention in the manufacture of a medicament for the treatment of a microbial or viral infection or disease.

One aspect of the present invention pertains to the use of compounds of the present invention in the manufacture of a medicament for the treatment of cancer.

One aspect of the present invention pertains to the use of compounds of the present invention in the manufacture of a medicament for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes, and acne.

One aspect of the present invention pertains to the use of compounds of the present invention in the manufacture of a medicament for the treatment of psoriasis.

One aspect of the present invention pertains to the use of compounds of the present invention in the manufacture of a medicament for the treatment of rheumatoid arthritis.

One aspect of the present invention pertains to the use of compounds of the present invention in the manufacture of a medicament for the treatment of Crohn's disease.

One aspect of the present invention pertains to the use of compounds of the present invention in the manufacture of a medicament for the treatment of transplant rejection.

One aspect of the present invention pertains to the use of compounds of the present invention in the manufacture of a medicament for the treatment of multiple sclerosis.

One aspect of the present invention pertains to the use of compounds of the present invention in the manufacture of a medicament for the treatment of systemic lupus erythematosus.

One aspect of the present invention pertains to the use of compounds of the present invention in the manufacture of a medicament for the treatment of ulcerative colitis.

One aspect of the present invention pertains to the use of compounds of the present invention in the manufacture of a medicament for the treatment of type I diabetes.

One aspect of the present invention pertains to the use of compounds of the present invention in the manufacture of a medicament for the treatment of hypertensive nephropathy.

One aspect of the present invention pertains to the use of compounds of the present invention in the manufacture of a medicament for the treatment of glomerulosclerosis.

One aspect of the present invention pertains to the use of compounds of the present invention in the manufacture of a medicament for the treatment of myocardial ischemia-reperfusion injury.

One aspect of the present invention pertains to the use of compounds of the present invention in the manufacture of a medicament for the treatment of acne.

One aspect of the present invention pertains to compounds of the present invention for use in a method for the treatment of the human or animal body by therapy.

One aspect of the present invention pertains to compounds of the present invention for use in a method for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes, hypertensive nephropathy, glomerulosclerosis, myocardial ischemia-reperfusion injury, and acne.

One aspect of the present invention pertains to compounds of the present invention for use in a method for the treatment of an S1P1 receptor-associated disorder.

One aspect of the present invention pertains to compounds of the present invention for use in a method for the treatment of a disease or disorder mediated by lymphocytes.

One aspect of the present invention pertains to compounds of the present invention for use in a method for the treatment of an autoimmune disease or disorder.

One aspect of the present invention pertains to compounds of the present invention for use in a method for the treatment of an inflammatory disease or disorder.

One aspect of the present invention pertains to compounds of the present invention for use in a method for the treatment of a microbial or viral infection or disease.

One aspect of the present invention pertains to compounds of the present invention for use in a method for the treatment of cancer.

One aspect of the present invention pertains to compounds of the present invention for use in a method for the treatment of an S1P1 receptor-associated disorder selected from the group consisting of psoriasis, rheumatoid arthritis, Crohn's disease, transplant rejection, multiple sclerosis, systemic lupus erythematosus, ulcerative colitis, type I diabetes, and acne.

One aspect of the present invention pertains to compounds of the present invention for use in a method for the treatment of psoriasis.

One aspect of the present invention pertains to compounds of the present invention for use in a method for the treatment of rheumatoid arthritis.

One aspect of the present invention pertains to compounds of the present invention for use in a method for the treatment of Crohn's disease.

One aspect of the present invention pertains to compounds of the present invention for use in a method for the treatment of transplant rejection.

One aspect of the present invention pertains to compounds of the present invention for use in a method for the treatment of multiple sclerosis.

One aspect of the present invention pertains to compounds of the present invention for use in a method for the treatment of systemic lupus erythematosus.

One aspect of the present invention pertains to compounds of the present invention for use in a method for the treatment of ulcerative colitis.

One aspect of the present invention pertains to compounds of the present invention for use in a method for the treatment of type I diabetes.

One aspect of the present invention pertains to compounds of the present invention for use in a method for the treatment of hypertensive nephropathy.

One aspect of the present invention pertains to compounds of the present invention for use in a method for the treatment of glomerulosclerosis.

One aspect of the present invention pertains to compounds of the present invention for use in a method for the treatment of myocardial ischemia-reperfusion injury.

One aspect of the present invention pertains to compounds of the present invention for use in a method for the treatment of acne.

One aspect of the present invention pertains to processes for preparing a composition comprising admixing a compound of the present invention and a pharmaceutically acceptable carrier.

These and other aspects of the invention disclosed herein will be set forth in greater detail as the patent disclosure proceeds.

DETAILED DESCRIPTION OF THE INVENTION

Definitions

Figure 1:
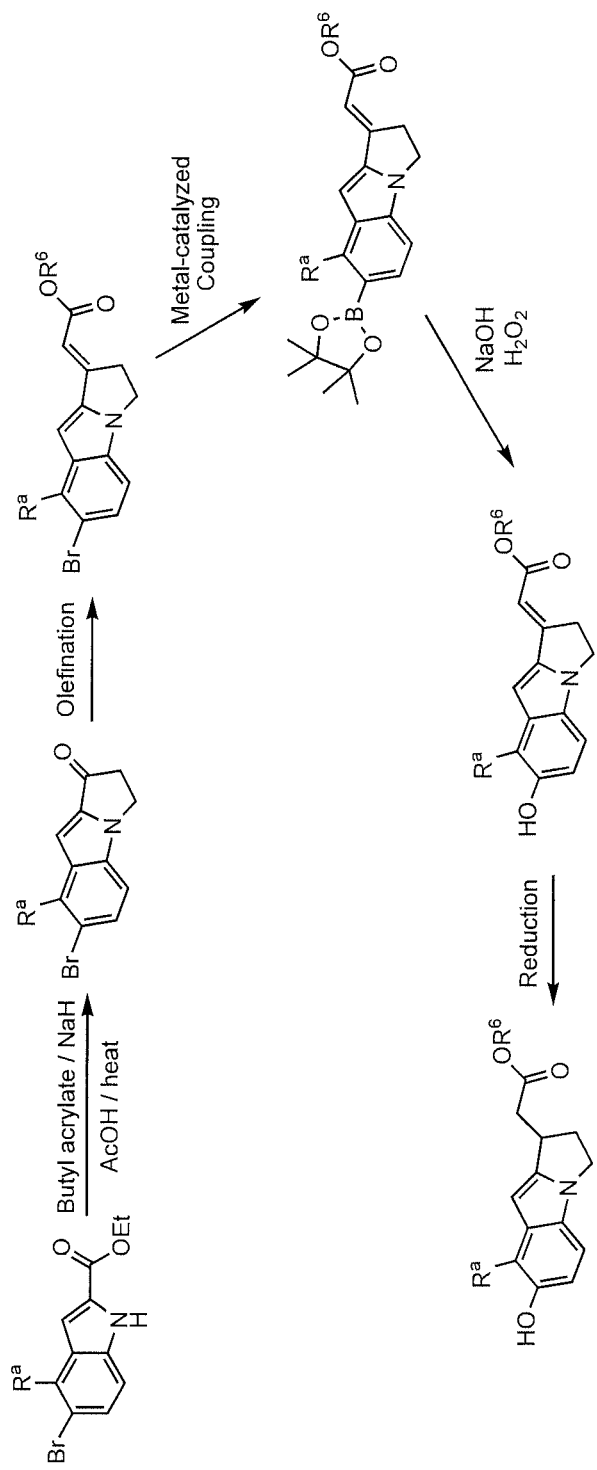
FIG. 1 shows a general synthetic scheme for the preparation of 2-(7-hydroxy-2,3-dihydro-1H-pyrrolo[1,2-a]indol-1-yl)acetate derivatives, as intermediates useful in the preparation of compounds of Formula (I), by treatment of ethyl 5-bromo-1H-indole-2-carboxylate with butyl acrylate and subsequent decarboxylation, followed by olefination, conversion of the bromo group to a hydroxyl group and reduction of the double bond.
Figure 2:
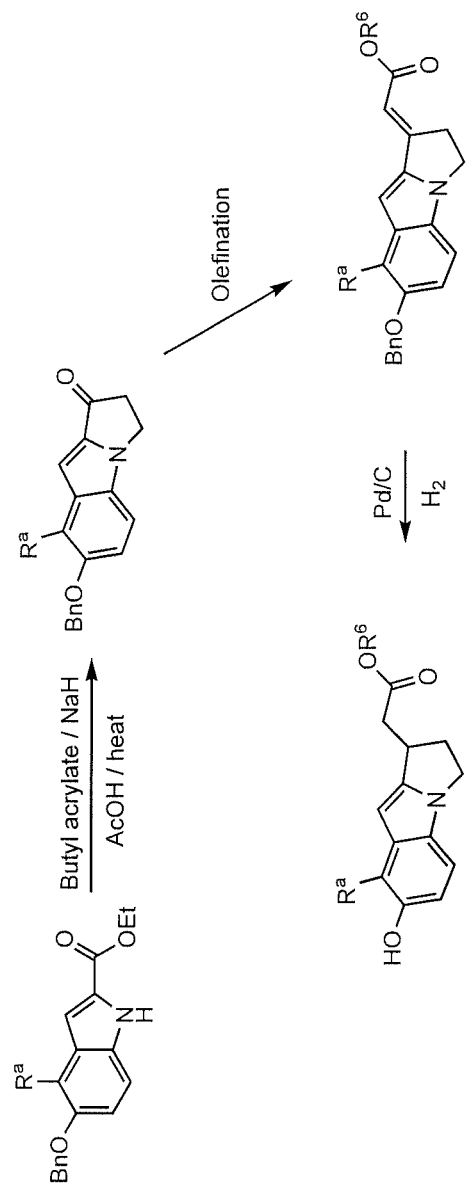
FIG. 2 shows a general synthetic scheme for the preparation of 2-(7-hydroxy-2,3-dihydro-1H-pyrrolo[1,2-a]indol-1-yl)acetate derivatives, as intermediates useful in the preparation of compounds of Formula (I), by treatment of ethyl 5-(benzyloxy)-1H-indole-2-carboxylate with butyl acrylate and subsequent decarboxylation, followed by olefination and reduction/deprotection.
Figure 3:
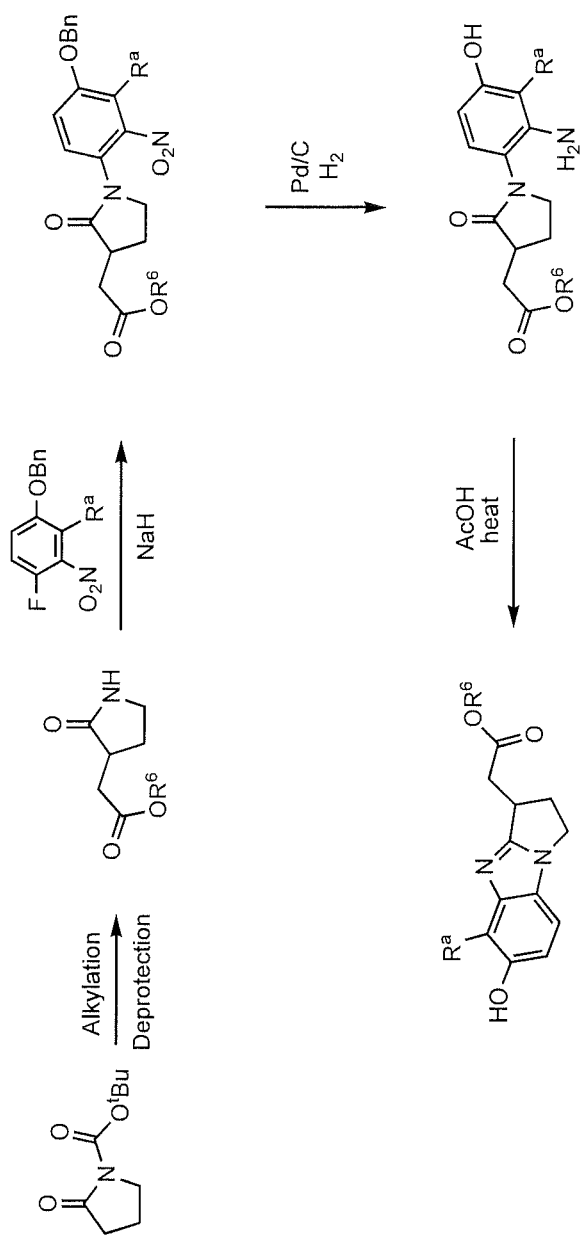
FIG. 3 shows a general synthetic scheme for the preparation of 2-(6-hydroxy-2,3-dihydro-1H-benzo[d]pyrrolo[1,2-a]imidazol-3-yl)acetate derivatives, as intermediates useful in the preparation of compounds of Formula (I), by alkylation of tert-butyl 2-oxopyrrolidine-1-carboxylate, followed by N-arylation, reduction/deprotection and cyclization.
Figure 4:
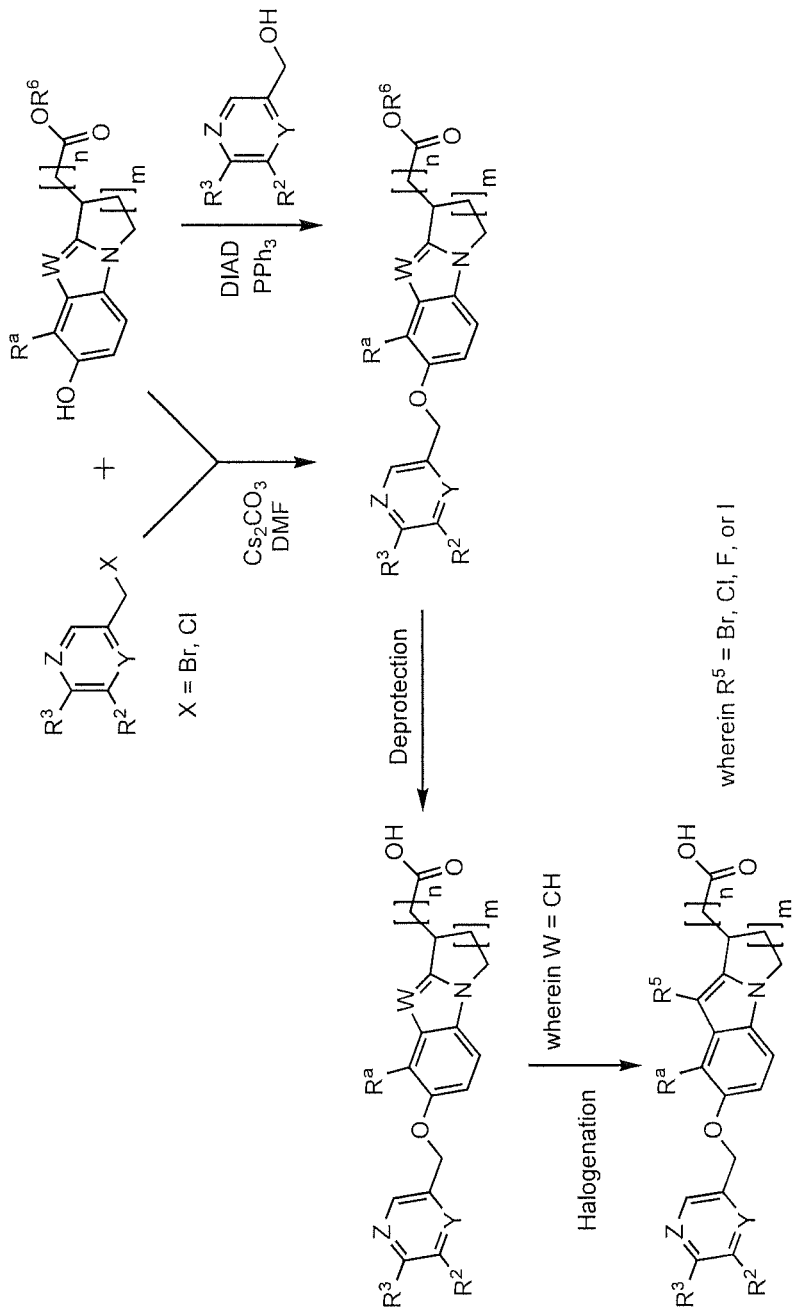
FIG. 4 shows a general synthetic scheme for the preparation of tricyclic acid derivatives, via coupling of the aryl methyl halides or alcohols with 2,3-dihydro-1H-pyrrolo acetate derivatives. Subsequent deprotection and/or halogenation afford compounds of Formula (I).
Figure 5:
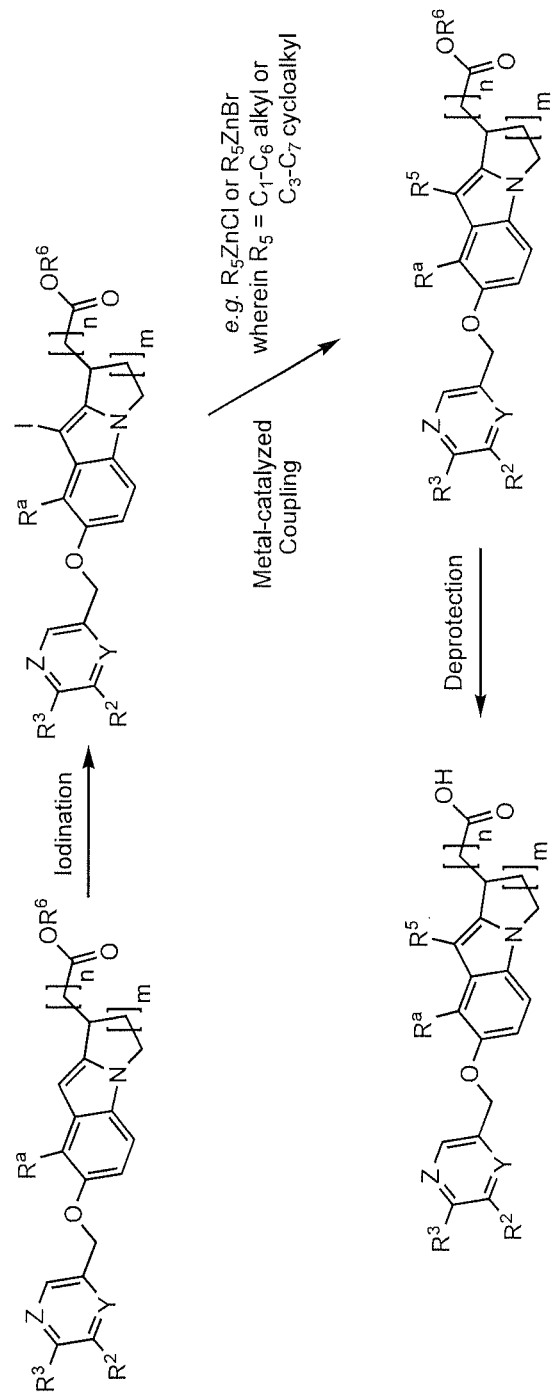
FIG. 5 shows a general synthetic scheme for the preparation of tricyclic acid derivatives, via iodination of tricyclic ester derivatives. Subsequent metal-catalyzed coupling reaction and deprotection afford compounds of Formula (I).
Figure 6:
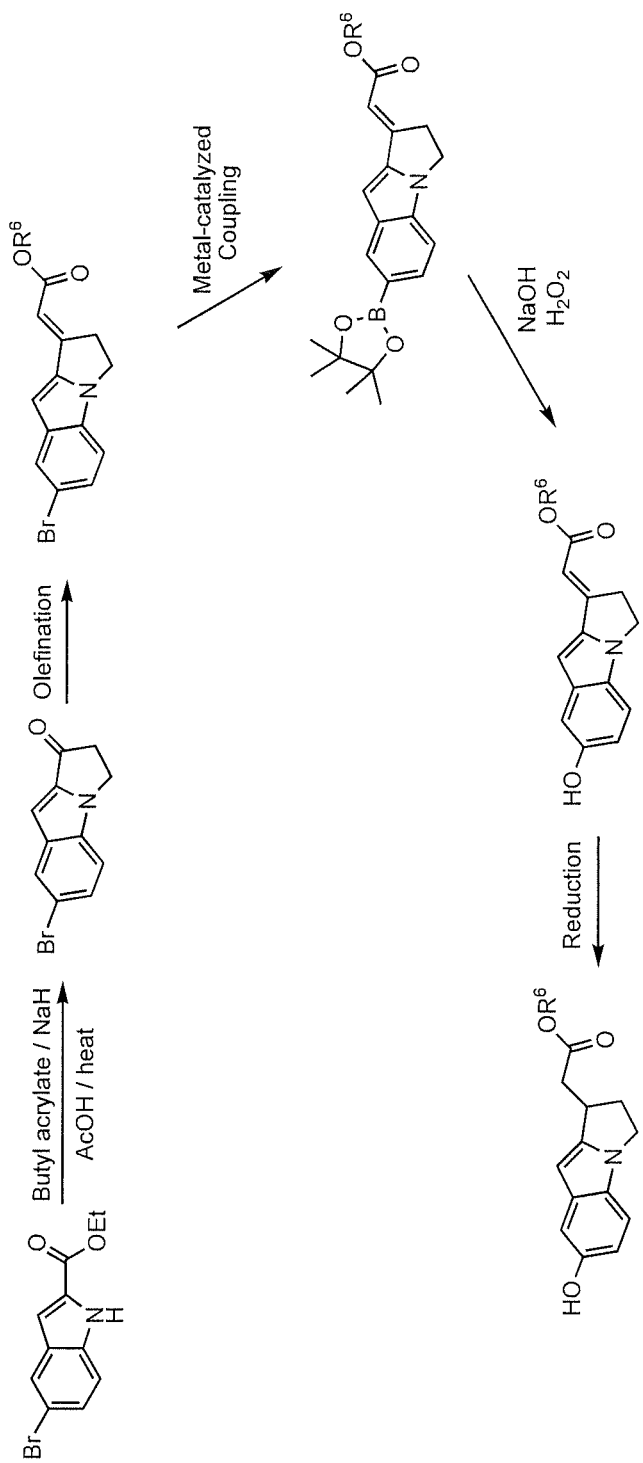
FIG. 6 shows a general synthetic scheme for the preparation of 2-(7-hydroxy-2,3-dihydro-1H-pyrrolo[1,2-a]indol-1-yl)acetate derivatives, as intermediates useful in the preparation of compounds of Formula (Ia), by treatment of ethyl 5-bromo-1H-indole-2-carboxylate with butyl acrylate and subsequent decarboxylation, followed by olefination, conversion of the bromo group to a hydroxyl group and reduction of the double bond.
Figure 7:
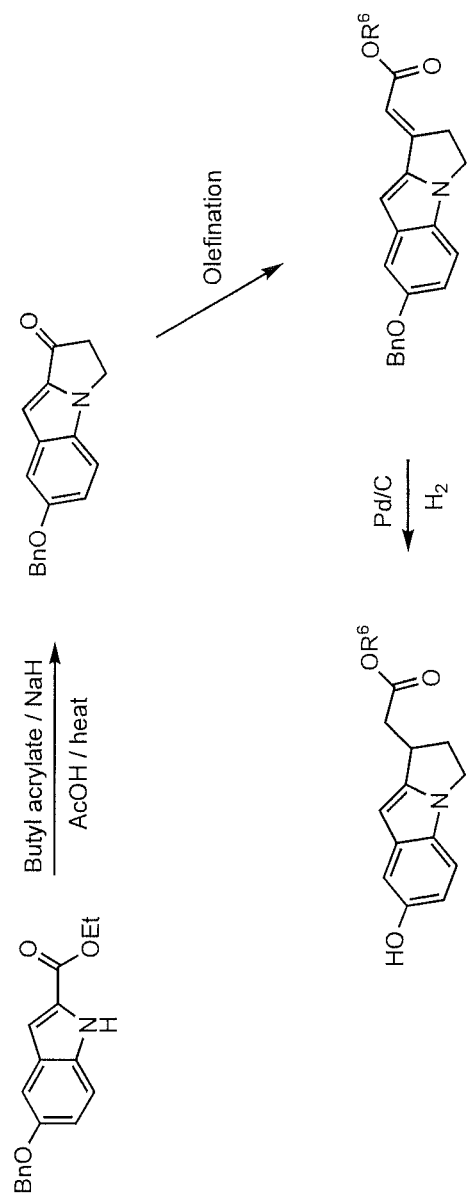
FIG. 7 shows a general synthetic scheme for the preparation of 2-(7-hydroxy-2,3-dihydro-1H-pyrrolo[1,2-a]indol-1-yl)acetate derivatives, as intermediates useful in the preparation of compounds of Formula (Ia), by treatment of ethyl 5-(benzyloxy)-1H-indole-2-carboxylate with butyl acrylate and subsequent decarboxylation, followed by olefination and reduction/deprotection.
Figure 8:
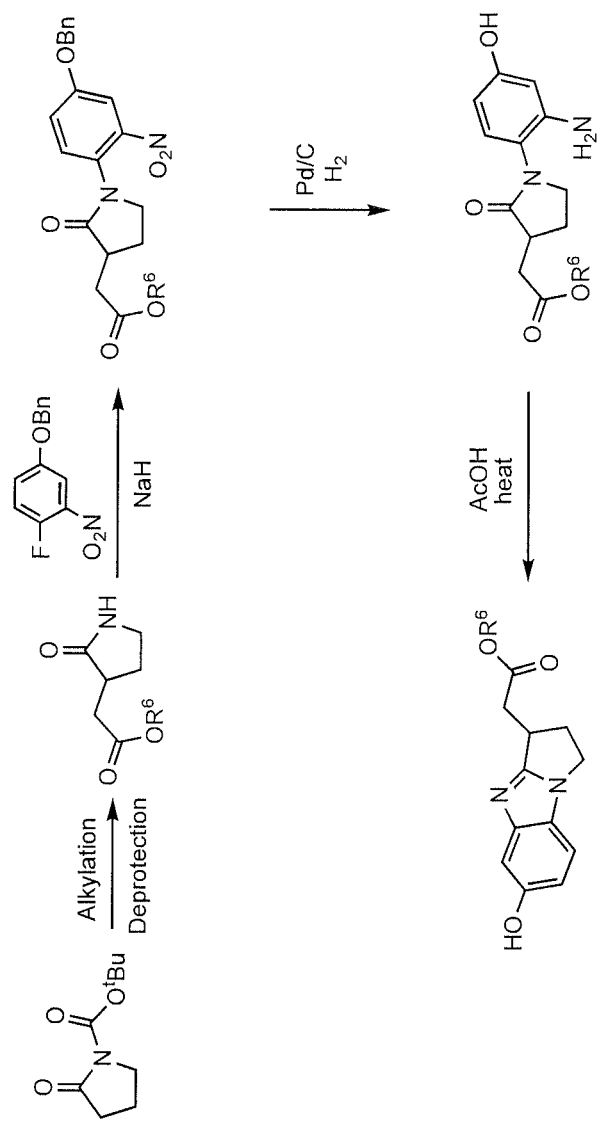
FIG. 8 shows a general synthetic scheme for the preparation of 2-(6-hydroxy-2,3-dihydro-1H-benzo[d]pyrrolo[1,2-a]imidazol-3-yl)acetate derivatives, as intermediates useful in the preparation of compounds of Formula (Ia), by alkylation of tert-butyl 2-oxopyrrolidine-1-carboxylate, followed by N-arylation, reduction/deprotection and cyclization.
Figure 9:
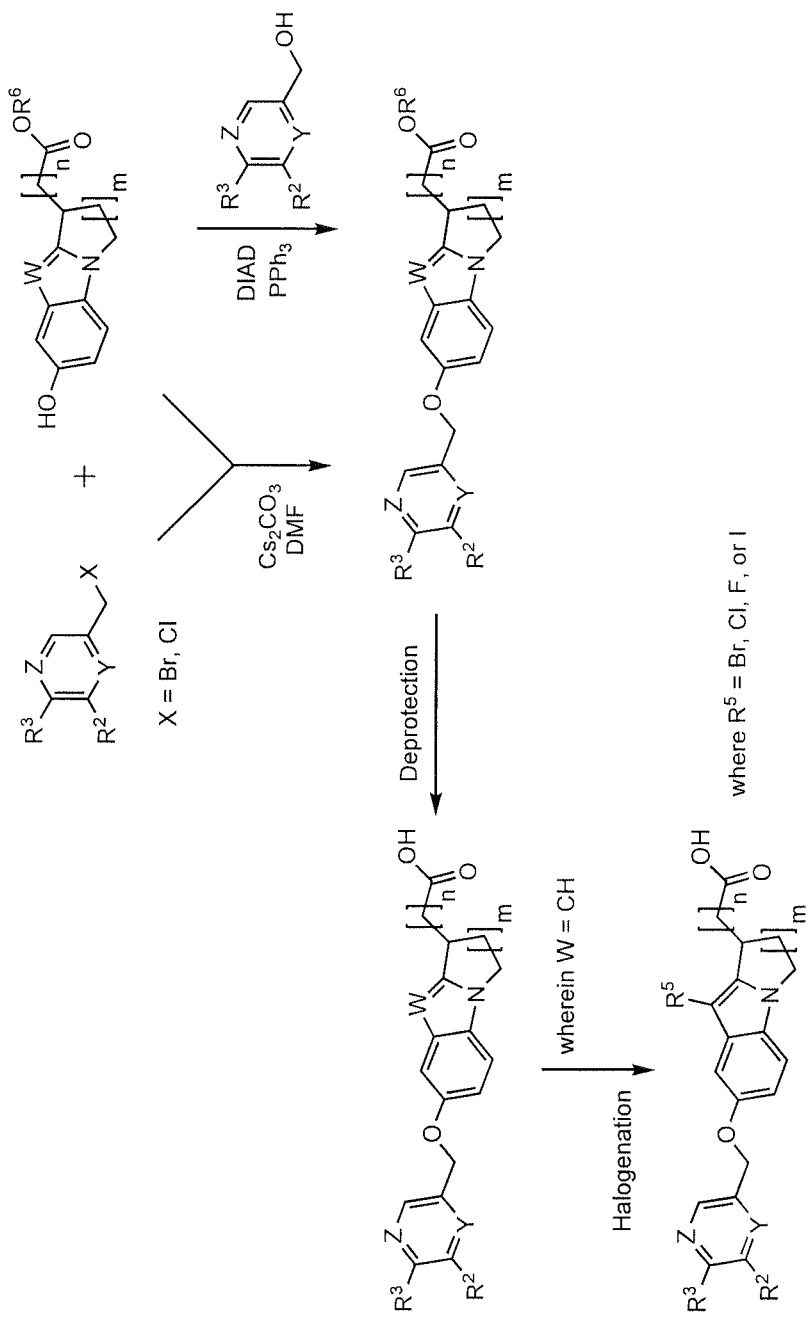
FIG. 9 shows a general synthetic scheme for the preparation of tricyclic acid derivatives, via coupling of the aryl methyl halides or alcohols with 2,3-dihydro-1H-pyrrolo acetate derivatives. Subsequent deprotection and/or halogenation afford compounds of Formula (Ia).
Figure 10:
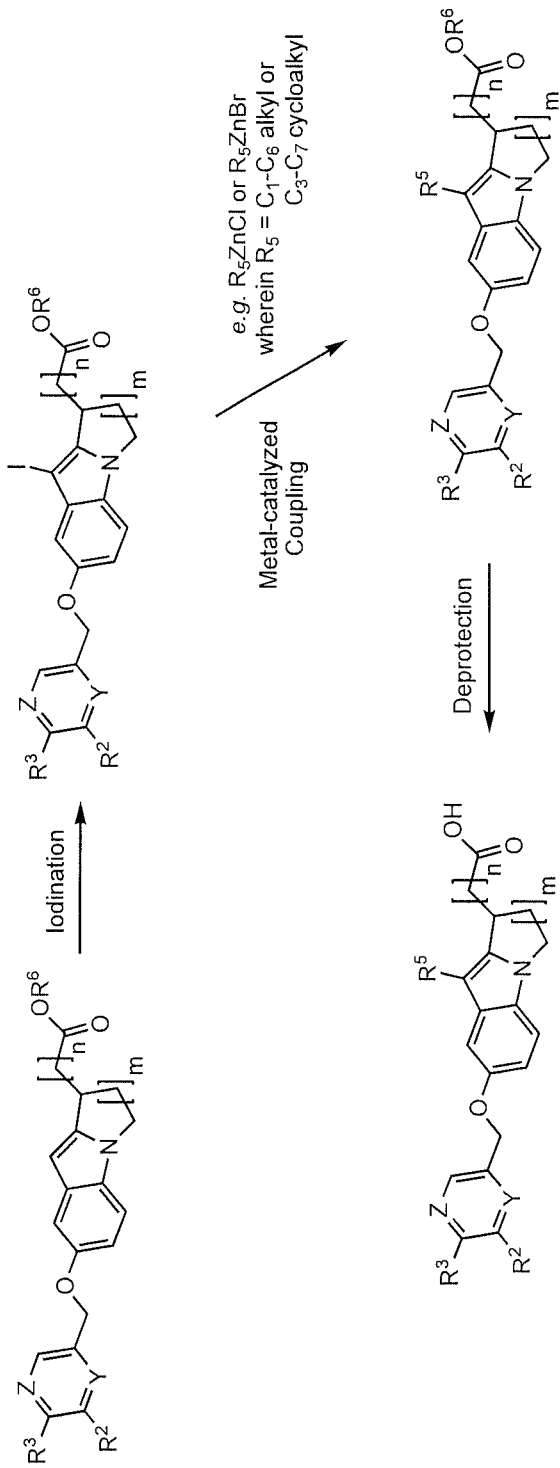
FIG. 10 shows a general synthetic scheme for the preparation of tricyclic acid derivatives, via iodination of tricyclic ester derivatives. Subsequent metal-catalyzed coupling reaction and deprotection afford compounds of Formula (Ia).

For clarity and consistency, the following definitions will be used throughout this patent document.

The term "agonist" is intended to mean a moiety that interacts with and activates a G-protein-coupled receptor, such as the S1P1 receptor, such as can thereby initiate a physiological or pharmacological response characteristic of that receptor. For example, an agonist activites an intracellular response upon binding to the receptor, or enhances GTP binding to a membrane. In certain embodiments, an agonist of the invention is an S1P1 receptor agonist that is capable of facilitating sustained S1P1 receptor internalization (see e.g., Matloubian et al., Nature, 427, 355, 2004).

The term "antagonist" is intended to mean a moietiy that competitively binds to the receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist.

The term "hydrate" as used herein means a compound of the invention or a salt thereof, that further includes a stoichiometric or non-stoichiometric amount of water bound by non-covalent intermolecular forces.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" is intended to mean any animal, including mammals, preferably mice, rats, other rodents, rabbits, dogs, cats, swine, cattle, sheep, horses, or primates and most preferably humans.

The term "inverse agonist" is intended to mean a moiety that binds to the endogenous form of the receptor or to the constitutively activated form of the receptor and which inhibits the baseline intracellular response initiated by the active form of the receptor below the normal base level of activity which is observed in the absence of an agonist or partial agonist, or decreases GTP binding to a membrane. In some embodiments, the baseline intracellular response is inhibited in the presence of the inverse agonist by at least 30%. In some embodiments, the baseline intracellular response is inhibited in the presence of the inverse agonist by at least 50%. In some embodiments, the baseline intracellular response is inhibited in the presence of the inverse agonist by at least 75%, as compared with the baseline response in the absence of the inverse agonist.

The term "modulate or modulating" is intended to mean an increase or decrease in the amount, quality, response or effect of a particular activity, function or molecule.

The term "pharmaceutical composition" is intended to mean a composition comprising at least one active ingredient; including but not limited to, salts, solvates, and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" is intended to mean the amount of active compound or pharmaceutical agent that elicits the biological or medicinal response in a tissue, system, animal, individual or human that is being sought by a researcher, veterinarian, medical doctor or other clinician, caregiver or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

Chemical Group, Moiety or Radical

The term "$C_1$-$C_6$ alkoxy" is intended to mean a $C_1$-$C_6$ alkyl radical, as defined herein, attached directly to an oxygen atom. Some embodiments are 1 to 5 carbons, some embodiments are 1 to 4 carbons, some embodiments are 1 to 3 carbons and some embodiments are 1 or 2 carbons. Examples include methoxy, ethoxy, n-propoxy, isopropoxy, n-butoxy, tert-butoxy, isobutoxy, sec-butoxy, and the like.

The term "$C_1$-$C_6$ alkyl" is intended to mean a straight or branched carbon radical containing 1 to 6 carbons. Some embodiments are 1 to 5 carbons, some embodiments are 1 to 4 carbons, some embodiments are 1 to 3 carbons and some embodiments are 1 or 2 carbons.

Examples of an alkyl include, but are not limited to, methyl, ethyl, n-propyl, isopropyl, n-butyl, sec-butyl, isobutyl, tert-butyl, pentyl, isopentyl, tert-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl, and the like.

The term "$C_1$-$C_6$ alkylamino" is intended to mean one alkyl radical attached to an —NH-radical wherein the alkyl radical has the same meaning as described herein. Some examples include, but are not limited to, methylamino, ethylamino, n-propylamino, isopropylamino, n-butylamino, sec-butylamino, isobutylamino, tert-butylamino, and the like.

The term "$C_1$-$C_6$ alkylsulfonyl" is intended to mean a $C_1$-$C_6$ alkyl radical attached to the sulfur of a sulfone radical having the formula: —S(O)$_2$— wherein the alkyl radical has the same definition as described herein. Examples include, but are not limited to, methylsulfonyl, ethylsulfonyl, n-propylsulfonyl, isopropylsulfonyl, n-butylsulfonyl, sec-butylsulfonyl, isobutylsulfonyl, tert-butylsulfonyl, and the like.

The term "$C_1$-$C_6$ alkylthio" is intended to mean a $C_1$-$C_6$ alkyl radical attached to a sulfur atom (i.e., —S—) wherein the alkyl radical has the same definition as described herein. Examples include, but are not limited to, methylsulfanyl (i.e., CH$_3$S—), ethylsulfanyl, n-propylsulfanyl, isopropylsulfanyl, n-butylsulfanyl, sec-butylsulfanyl, isobutylsulfanyl, t-butylsulfanyl, and the like.

The term "carboxamide" is intended to mean the group —CONH$_2$.

The term "cyano" is intended to mean the group —CN.

The term "$C_3$-$C_7$ cycloalkoxy" is intended to mean a saturated ring radical containing 3 to 7 carbons directly bonded to an oxygen atom. Some examples include cyclopropyl-O—, cyclobutyl-O—, cyclopentyl-O—, cyclohexyl-O—, and the like.

The term "$C_3$-$C_7$ cycloalkyl" is intended to mean a saturated ring radical containing 3 to 7 carbons. Some embodiments contain 3 to 6 carbons. Some embodiments contain 3 to 5 carbons. Some embodiments contain 5 to 7 carbons. Some embodiments contain 3 to 4 carbons. Examples include cyclopropyl, cyclobutyl, cyclopentyl, cyclohexyl, cycloheptyl, and the like.

The term "$C_1$-$C_6$ haloalkoxy" is intended to mean a $C_1$-$C_6$ haloalkyl, as defined herein, which is directly attached to an oxygen atom. Examples include, but are not limited to, difluoromethoxy, trifluoromethoxy, 2,2,2-trifluoroethoxy, pentafluoroethoxy, and the like.

The term "$C_1$-$C_6$ haloalkyl" is intended to mean an $C_1$-$C_6$ alkyl group, defined herein, wherein the alkyl is substituted with between one halogen up to fully substituted wherein a fully substituted $C_1$-$C_6$ haloalkyl can be represented by the formula $C_zL_{2z+1}$ wherein L is a halogen and "z" is 1, 2, 3, 4, 5 or 6. When more than one halogen is present, the halogens may be the same or different and selected from the group consisting of fluoro, chloro, bromo or iodo, preferably fluoro. Some embodiments are 1 to 5 carbons, some embodiments are 1 to 4 carbons, some embodiments are 1 to 3 carbons and some embodiments are 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl, and the like.

The term "halogen" or "halo" is intended to mean a fluoro, chloro, bromo or iodo group.

The term "heteroaryl" is intended to mean an aromatic ring system containing 5 to 14 aromatic ring atoms that may be a single ring, two fused rings or three fused rings, wherein at least one aromatic ring atom is a heteroatom selected from, for example, but not limited to, the group consisting of O, S, and N wherein the N can be optionally substituted with H, acyl or $C_1$-$C_4$ alkyl. Some embodiments contain 5 to 6 ring atoms, for example, furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl, and the like. Some embodiments contain 8 to 14 ring atoms, for example, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl, phenazinyl, phenothiazinyl, phenoxazinyl, benzoxazolyl, benzothiazolyl, 1H-benzimidazolyl, imidazopyridinyl, benzothienyl, benzofuranyl, isobenzofuran, and the like.

The term "heterocyclic" or "heterocyclyl" is intended to mean a non-aromatic ring containing 3 to 8 ring atoms wherein one, two or three ring atoms are heteroatoms selected from, for example, the group consisting of O, S, S(=O), S(=O)$_2$, and NH, wherein the N is optionally substituted as described herein. In some embodiments, the nitrogen is optionally substituted with $C_1$-$C_4$ acyl or $C_1$-$C_4$ alkyl. In some embodiments, ring carbon atoms are optionally substituted with oxo thus forming a carbonyl group. In some embodiments, ring sulfur atoms are optionally substituted with oxo atoms thus forming a thiocarbonyl group. The heterocyclic group can be attached/bonded to any available ring atom, for example, ring carbon, ring nitrogen, and the like. In some embodiments the heterocyclic group is a 3-, 4-, 5-, 6- or 7-membered ring. Examples of a heterocyclic group include, but are not limited to, aziridin-1-yl, aziridin-2-yl, azetidin-1-yl, azetidin-2-yl, azetidin-3-yl, piperidin-1-yl, piperidin-2-yl, piperidin-3-yl, piperidin-4-yl, morpholin-2-yl, morpholin-3-yl, morpholin-4-yl, piperzin-1-yl, piperzin-2-yl, piperzin-3-yl, piperzin-4-yl, pyrrolidin-1-yl, pyrrolidin-2-yl, pyrrolidin-3-yl, [1,3]-dioxolan-2-yl, thiomorpholin-4-yl, [1,4] oxazepan-4-yl, 1,1-dioxothiomorpholin-4-yl, azepan-1-yl, azepan-2-yl, azepan-3-yl, azepan-4-yl, tetrahydrofuran-2-yl, tetrahydrofuran-3-yl, and the like.

Compounds of the Invention

One aspect of the present invention pertains to certain compounds of Formula (I) and pharmaceutically acceptable salts, solvates, and hydrates thereof:

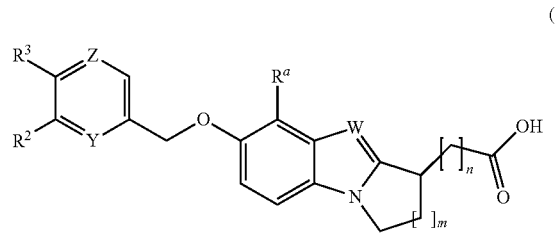

(I)

wherein:
m, n, $R^a$, $R^2$, $R^3$, W, Y, and Z have the same definitions as described herein, supra and infra.

One aspect of the present invention pertains to compounds of Formula (Ia) and pharmaceutically acceptable salts, solvates, and hydrates thereof:

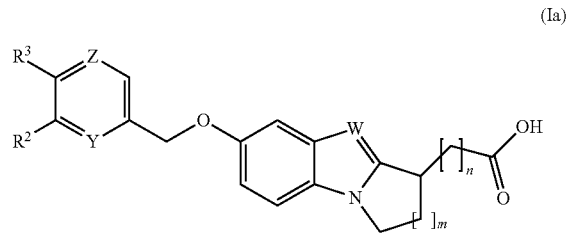

(Ia)

wherein:
m is 1 or 2;
n is 1 or 2;
Y is N or $CR^1$;
Z is N or $CR^4$;
W is N or $CR^5$;
$R^1$, $R^2$, $R^3$, and $R^4$ are each independently selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl, and heterocyclyl, wherein the $C_1$-$C_6$ alkyl and $C_1$-$C_6$ alkoxy are each optionally substituted with one $C_3$-$C_7$ cycloalkyl group; and
$R^5$ is selected from the group consisting of H, $C_1$-$C_6$ alkyl, cyano, $C_3$-$C_7$ cycloalkyl, $C_1$-$C_6$ haloalkyl, halogen, and heterocyclyl.

It is understood that the present invention embraces compounds, solvates and/or hydrates of compounds, pharmaceutically acceptable salts of compounds, and solvates and/or hydrates of pharmaceutically acceptable salts of compounds, wherein the compounds are as described herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g. m, n, $R^a$, $R^1$, $R^2$, $R^3$, $R^4$, $R^5$, $R^6$, W, Y, Z, etc.) contained within the generic chemical formulae described herein, for example, (e.g. I, Ia, Ic, Ie, Ig, Ii, Ij, Ik, Im, IIa, IIb, IIc, IId, IIe, IIf, IIg, IIh, IIi, etc.) are specifically embraced by the present invention just as if each and every combination was individually explicitly recited, to the extent that such combinations embrace stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group. The non-hydrogen substituent or group can be monovalent or divalent. When the substituent or group is divalent, then it is understood that this group is further substituted with another substituent or group. When a chemical group herein is "substituted" it may have up to the full valence of substitution, for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one substituent, the substituents can be identical or they can be different.

Compounds of the invention also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

Compounds of the invention also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of Formula (I) and (Ia), and formulae related thereto, may have one or more chiral centers and therefore can exist as enantiomers and/or diastereomers. The invention is understood to extend to and embrace all such enantiomers, diastereomers and mixtures thereof, including but not limited to racemates. It is understood that Formula (I) and (Ia), and formulae used throughout this disclosure, are intended to represent all individual enantiomers and mixtures thereof, unless stated or shown otherwise.

The Variable "n"

In some embodiments, n is 1.

In some embodiments, compounds of the present invention are represented by Formula (Ic) as illustrated below:

(Ic)

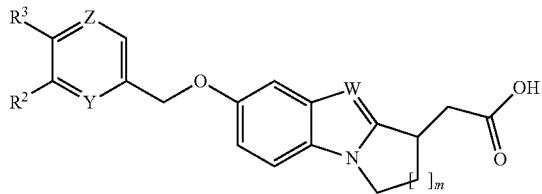

wherein each variable in Formula (Ic) has the same meaning as described herein, supra and infra.

In some embodiments, n is 2.

In some embodiments, compounds of the present invention are represented by Formula (Ie) as illustrated below:

(Ie)

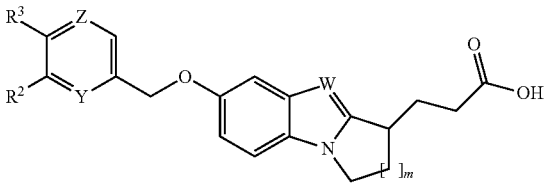

wherein each variable in Formula (Ie) has the same meaning as described herein, supra and infra.

The Variable "m"

In some embodiments, m is 1.

In some embodiments, compounds of the present invention are represented by Formula (Ig) as illustrated below:

(Ig)

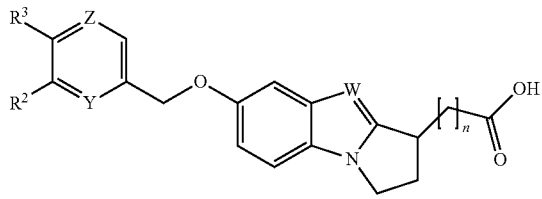

wherein each variable in Formula (Ig) has the same meaning as described herein, supra and infra.

In some embodiments, m is 2.

In some embodiments, compounds of the present invention are represented by Formula (Ii) as illustrated below:

(Ii)

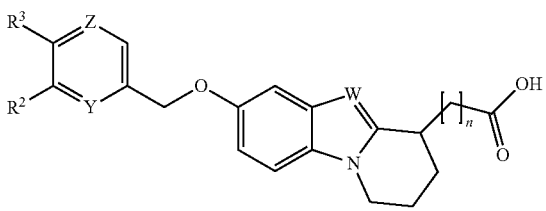

wherein each variable in Formula (Ii) has the same meaning as described herein, supra and infra.

The Variables Y, Z and W

In some embodiments, Y is N or $CR^1$, Z is N or $CR^4$, and W is N or $CR^5$.

In some embodiments, Y is N, Z is N, and W is N.
In some embodiments, Y is N, Z is N, and W is $CR^5$.
In some embodiments, Y is N, Z is $CR^4$, and W is N.
In some embodiments, Y is $CR^1$, Z is N, and W is N.
In some embodiments, Y is N, Z is $CR^4$, and W is $CR^5$.
In some embodiments, Y is $CR^1$, Z is N, and W is $CR^5$.
In some embodiments, Y is $CR^1$, Z is $CR^4$, and W is N.
In some embodiments, Y is $CR^1$, Z is $CR^4$, and W is $CR^5$.
In some embodiments, Y is N.
In some embodiments, Y is $CR^1$.
In some embodiments, Z is N.
In some embodiments, Z is $CR^4$.
In some embodiments, W is N.
In some embodiments, W is $CR^5$.

The Group $R^a$

In some embodiments, $R^a$ is H or $C_1$-$C_6$ alkyl.
In some embodiments, $R^a$ is H or methyl.
In some embodiments, $R^a$ is H.

The Group $R^1$

In some embodiments, $R^1$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl, and heterocyclyl, wherein the $C_1$-$C_6$ alkyl and $C_1$-$C_6$ alkoxy are each optionally substituted with one $C_3$-$C_7$ cycloalkyl group.

In some embodiments, $R^1$ is H or $C_1$-$C_6$ haloalkyl.
In some embodiments, $R^1$ is H or trifluoromethyl.
In some embodiments, $R^1$ is H.
In some embodiments, $R^1$ is trifluoromethyl.

The Group $R^2$

In some embodiments, $R^2$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl, and heterocyclyl, wherein the $C_1$-$C_6$ alkyl and $C_1$-$C_6$ alkoxy are each optionally substituted with one $C_3$-$C_7$ cycloalkyl group.

In some embodiments, $R^2$ is selected from the group consisting of H, $C_1$-$C_6$ alkoxy, cyano, $C_1$-$C_6$ haloalkoxy, $C_1$-$C_6$ haloalkyl, $C_1$-$C_6$ haloalkyl, and halogen.

In some embodiments, $R^2$ is selected from the group consisting of cyano, $C_1$-$C_6$ haloalkoxy, and $C_1$-$C_6$ haloalkyl.

In some embodiments, $R^2$ is selected from the group consisting of H, chloro, cyano, ethoxy, trifluoromethoxy, and trifluoromethyl.

In some embodiments, $R^2$ is selected from the group consisting of cyano, trifluoromethoxy, and trifluoromethyl.

In some embodiments, $R^2$ is cyano.
In some embodiments, $R^2$ is trifluoromethoxy.
In some embodiments, $R^2$ is trifluoromethyl.
In some embodiments, $R^2$ is chloro.
In some embodiments, $R^2$ is ethoxy.

The Group $R^3$

In some embodiments, $R^3$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl, and heterocyclyl, wherein the $C_1$-$C_6$ alkyl and $C_1$-$C_6$ alkoxy are each optionally substituted with one $C_3$-$C_7$ cycloalkyl group.

In some embodiments, $R^3$ is selected from the group consisting of H, $C_1$-$C_6$ alkoxy, $C_1$-$C_6$ alkyl, $C_1$-$C_6$ alkylsulfonyl, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, and heteroaryl, wherein the $C_1$-$C_6$ alkyl and $C_1$-$C_6$ alkoxy are each optionally substituted with one $C_3$-$C_7$ cycloalkyl group.

In some embodiments, $R^3$ is selected from the group consisting of H, $C_1$-$C_6$ alkoxy, $C_1$-$C_6$ alkyl, $C_1$-$C_6$ alkylsulfonyl, carboxamide, cyano, $C_3$-$C_7$ cycloalkoxy, $C_3$-$C_7$ cycloalkyl, $C_1$-$C_6$ haloalkoxy, and halogen, wherein the $C_1$-$C_6$ alkyl and $C_1$-$C_6$ alkoxy are each optionally substituted with one $C_3$-$C_7$ cycloalkyl group.

In some embodiments, $R^3$ is selected from the group consisting of H, $C_1$-$C_6$ alkoxy, $C_1$-$C_6$ alkyl, and $C_3$-$C_7$ cycloalkyl.

In some embodiments, $R^3$ is selected from the group consisting of H, chloro, carboxamide, cyano, cyclohexyl, cyclohexylmethyl, cyclopentyloxy, cyclopentyl, cyclopropylmethoxy, 1,3-difluoropropan-2-yloxy, ethoxy, fluoromethoxy, isobutyl, isopropoxy, methoxy, methylsulfonyl, pyrazolyl, and trifluoromethyl.

In some embodiments, $R^3$ is selected from the group consisting of H, chloro, carboxamide, cyano, cyclohexyl, cyclohexylmethyl, cyclopentyloxy, cyclopentyl, cyclopropylmethoxy, 1,3-difluoropropan-2-yloxy, ethoxy, fluoromethoxy, isobutyl, isopropoxy, methoxy, and methylsulfonyl.

In some embodiments, $R^3$ is selected from the group consisting of H, cyclohexyl, cyclopentyl, isobutyl, and isopropoxy.

In some embodiments, $R^3$ is H.
In some embodiments, $R^3$ is chloro.
In some embodiments, $R^3$ is carboxamide.
In some embodiments, $R^3$ is cyano.
In some embodiments, $R^3$ is cyclohexyl.
In some embodiments, $R^3$ is cyclohexylmethyl.
In some embodiments, $R^3$ is cyclopentyloxy.
In some embodiments, $R^3$ is cyclopentyl.
In some embodiments, $R^3$ is cyclopropylmethoxy.
In some embodiments, $R^3$ is 1,3-difluoropropan-2-yloxy.
In some embodiments, $R^3$ is ethoxy.
In some embodiments, $R^3$ is fluoromethoxy.
In some embodiments, $R^3$ is isobutyl.
In some embodiments, $R^3$ is isopropoxy.
In some embodiments, $R^3$ is methoxy.
In some embodiments, $R^3$ is methylsulfonyl.
In some embodiments, $R^3$ is trifluoromethyl.
In some embodiments, $R^3$ is pyrazolyl.

The Group $R^4$

In some embodiments, $R^4$ is selected from the group consisting of H, $C_1$-$C_6$ alkoxy, $C_1$-$C_6$ alkyl, $C_1$-$C_6$ alkylamino, $C_1$-$C_6$ alkylsulfonyl, $C_1$-$C_6$ alkylthio, carboxamide, cyano, $C_3$-$C_7$ cycloalkoxy, $C_3$-$C_7$ cycloalkyl, $C_1$-$C_6$ haloalkoxy, $C_1$-$C_6$ haloalkyl, halogen, heteroaryl, and heterocyclyl, wherein the $C_1$-$C_6$ alkyl and $C_1$-$C_6$ alkoxy are each optionally substituted with one $C_3$-$C_7$ cycloalkyl group.

In some embodiments, $R^4$ is selected from the group consisting of H, cyano, $C_1$-$C_6$ haloalkyl, and $C_1$-$C_6$ haloalkoxy.

In some embodiments, $R^4$ is selected from the group consisting of H, cyano, trifluoromethoxy, and trifluoromethyl.

In some embodiments, $R^4$ is H or cyano.
In some embodiments, $R^4$ is H.
In some embodiments, $R^4$ is cyano.

The Group $R^5$

In some embodiments, $R^5$ is selected from the group consisting of H, $C_1$-$C_6$ alkyl, cyano, $C_3$-$C_7$ cycloalkyl, $C_1$-$C_6$ haloalkyl, halogen, heteroaryl, and heterocyclyl.

In some embodiments, $R^5$ is selected from the group consisting of H, $C_1$-$C_6$ alkyl, cyano, $C_3$-$C_7$ cycloalkyl, $C_1$-$C_6$ haloalkyl, halogen, heteroaryl, and heterocyclyl.

In some embodiments, $R^5$ is selected from the group consisting of H, $C_1$-$C_6$ alkyl, $C_1$-$C_6$ alkylsulfonyl, $C_3$-$C_7$ cycloalkyl, halogen, and heteroaryl.

In some embodiments, $R^5$ is selected from the group consisting of H, $C_1$-$C_6$ alkyl, $C_3$-$C_7$ cycloalkyl, and halogen.

In some embodiments, $R^5$ is selected from the group consisting of H, bromo, chloro, cyclobutyl, cyclopropyl, ethyl, fluoro, iodo, methyl, methylsulfonyl, and pyridin-2-yl.

In some embodiments, $R^5$ is selected from the group consisting of H, bromo, chloro, cyclobutyl, cyclopropyl, fluoro, iodo, and methyl.

In some embodiments, $R^5$ is H.
In some embodiments, $R^5$ is bromo.
In some embodiments, $R^5$ is chloro.
In some embodiments, $R^5$ is cyclobutyl.
In some embodiments, $R^5$ is cyclopropyl.
In some embodiments, $R^5$ is ethyl.
In some embodiments, $R^5$ is fluoro.
In some embodiments, $R^5$ is iodo.
In some embodiments, $R^5$ is methyl.
In some embodiments, $R^5$ is methylsulfonyl.
In some embodiments, $R^5$ is pyridin-2-yl.

Certain Combinations

Some embodiments of the present invention pertain to compounds selected from compounds of Formula (Ia) and pharmaceutically acceptable salts, solvates, and hydrates thereof, wherein:

m is 1 or 2;
n is 1 or 2;
Y is N or $CR^1$;
Z is N or $CR^4$;
W is N or $CR^5$;
$R^1$ is H;
$R^2$ is selected from the group consisting of cyano, $C_1$-$C_6$ haloalkoxy, and $C_1$-$C_6$ haloalkyl;
$R^3$ is selected from the group consisting of H, $C_1$-$C_6$ alkoxy, $C_1$-$C_6$ alkyl, and $C_3$-$C_7$ cycloalkyl;
$R^4$ is H or cyano; and
$R^5$ is selected from the group consisting of H, $C_1$-$C_6$ alkyl, $C_3$-$C_7$ cycloalkyl, and halogen.

Some embodiments of the present invention pertain to compounds selected from compounds of Formula (Ia) and pharmaceutically acceptable salts, solvates, and hydrates thereof, wherein:

m is 1 or 2;
n is 1 or 2;
Y is N or $CR^1$;
Z is N or $CR^4$;
W is N or $CR^5$;
$R^1$ is H;
$R^2$ is selected from the group consisting of cyano, trifluoromethoxy, and trifluoromethyl;
$R^3$ is selected from the group consisting of H, cyclohexyl, cyclopentyl, isobutyl, and isopropoxy;
$R^4$ is H or cyano; and
$R^5$ is selected from the group consisting of H, bromo, chloro, cyclobutyl, cyclopropyl, fluoro, iodo, and methyl.

Some embodiments of the present invention pertain to compounds selected from compounds of Formula (Ij) and pharmaceutically acceptable salts, solvates, and hydrates thereof:

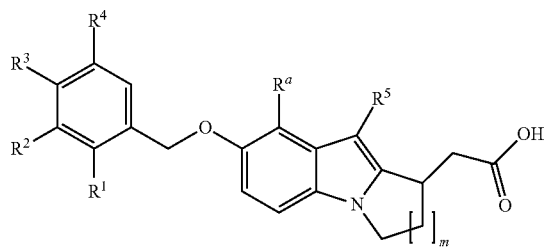

wherein:
m is 1 or 2;
$R^1$ is H or $C_1$-$C_6$ haloalkyl;
$R^2$ is selected from the group consisting of H, $C_1$-$C_6$ alkoxy, cyano, $C_1$-$C_6$ haloalkoxy, $C_1$-$C_6$ haloalkyl, $C_1$-$C_6$ haloalkyl, and halogen;
$R^3$ is selected from the group consisting of H, $C_1$-$C_6$ alkoxy, $C_1$-$C_6$ alkyl, $C_1$-$C_6$ alkylsulfonyl, carboxamide, cyano, $C_3$-$C_7$ cycloalkoxy, $C_3$-$C_7$ cycloalkyl, $C_1$-$C_6$ haloalkoxy, and halogen, wherein the $C_1$-$C_6$ alkyl and $C_1$-$C_6$ alkoxy are each optionally substituted with one $C_3$-$C_7$ cycloalkyl group;
$R^4$ is selected from the group consisting of H, cyano, $C_1$-$C_6$ haloalkyl, and $C_1$-$C_6$ haloalkoxy; and
$R^5$ is selected from the group consisting of H, $C_1$-$C_6$ alkyl, $C_1$-$C_6$ alkylsulfonyl, $C_3$-$C_7$ cycloalkyl, halogen, and heteroaryl.

Some embodiments of the present invention pertain to compounds selected from compounds of Formula (Ij) and pharmaceutically acceptable salts, solvates, and hydrates thereof:

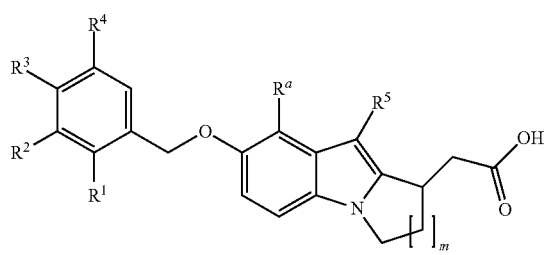

wherein:
m is 1 or 2;
$R^1$ is H or trifluoromethyl;
$R^2$ is selected from the group consisting of H, chloro, cyano, ethoxy, trifluoromethoxy, and trifluoromethyl;
$R^3$ is selected from the group consisting of H, chloro, carboxamide, cyano, cyclohexyl, cyclohexylmethyl, cyclopentyloxy, cyclopentyl, cyclopropylmethoxy, 1,3-difluoropropan-2-yloxy, ethoxy, fluoromethoxy, isobutyl, isopropoxy, methoxy, and methylsulfonyl;
$R^4$ is selected from the group consisting of H, cyano, trifluoromethoxy, and trifluoromethyl; and
$R^5$ is selected from the group consisting of H, bromo, chloro, cyclobutyl, cyclopropyl, ethyl, fluoro, iodo, methyl, methylsulfonyl, and pyridin-2-yl.

Some embodiments of the present invention pertain to compounds selected from compounds of Formula (Ik) and pharmaceutically acceptable salts, solvates, and hydrates thereof:

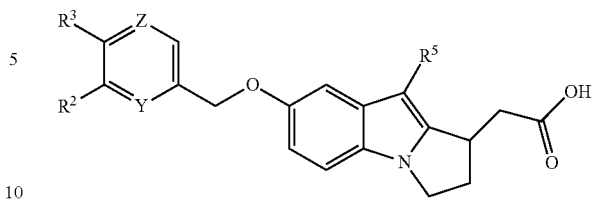

wherein:
Y is N or $CR^1$;
Z is N or $CR^4$;
$R^1$ is H;
$R^2$ is selected from the group consisting of cyano, $C_1$-$C_6$ haloalkoxy, and $C_1$-$C_6$ haloalkyl;
$R^3$ is selected from the group consisting of H, $C_1$-$C_6$ alkoxy, $C_1$-$C_6$ alkyl, and $C_3$-$C_7$ cycloalkyl;
$R^4$ is H or cyano; and
$R^5$ is selected from the group consisting of H, $C_1$-$C_6$ alkyl, $C_3$-$C_7$ cycloalkyl, and halogen.

Some embodiments of the present invention pertain to compounds selected from compounds of Formula (Ik) and pharmaceutically acceptable salts, solvates, and hydrates thereof, wherein:
Y is N or $CR^1$;
Z is N or $CR^4$;
$R^1$ is H;
$R^2$ is selected from the group consisting of cyano, trifluoromethoxy, and trifluoromethyl;
$R^3$ is selected from the group consisting of H, cyclohexyl, cyclopentyl, isobutyl, and isopropoxy;
$R^4$ is H or cyano; and
$R^5$ is selected from the group consisting of H, bromo, chloro, cyclobutyl, cyclopropyl, fluoro, iodo, and methyl.

Some embodiments of the present invention pertain to compounds selected from compounds of Formula (Im) and pharmaceutically acceptable salts, solvates, and hydrates thereof:

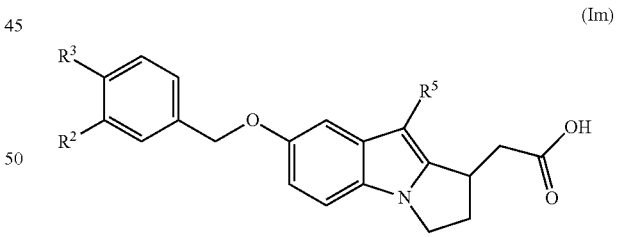

wherein:
$R^2$ is selected from the group consisting of cyano, $C_1$-$C_6$ haloalkoxy, and $C_1$-$C_6$ haloalkyl;
$R^3$ is selected from the group consisting of H, $C_1$-$C_6$ alkoxy, $C_1$-$C_6$ alkyl, and $C_3$-$C_7$ cycloalkyl; and
$R^5$ is selected from the group consisting of H, $C_1$-$C_6$ alkyl, $C_3$-$C_7$ cycloalkyl, and halogen.

Some embodiments of the present invention pertain to compounds selected from compounds of Formula (Im) and pharmaceutically acceptable salts, solvates, and hydrates thereof, wherein:
$R^2$ is selected from the group consisting of cyano, trifluoromethoxy, and trifluoromethyl;

R³ is selected from the group consisting of H, cyclohexyl, cyclopentyl, isobutyl, and isopropoxy; and R⁵ is selected from the group consisting of H, bromo, chloro, cyclobutyl, cyclopropyl, fluoro, iodo, and methyl.

Esters and Prodrugs

One aspect of the present invention pertains to compounds of Formula (II) as synthetic intermediates useful in the preparation of compounds of Formula (I) and/or prodrugs useful for the delivery of compounds of Formula (I):

(II)

$$\text{structure}$$

wherein:

m, n, R$^a$, R$^2$, R$^3$, Y, Z, and W have the same definitions as described herein, supra and infra, and R$^6$ is C$_1$-C$_6$ alkyl.

One aspect of the present invention pertains to compounds of Formula (IIa) as synthetic intermediates useful in the preparation of compounds of Formula (Ia) and/or prodrugs useful for the delivery of compounds of Formula (Ia):

(IIa)

$$\text{structure}$$

wherein:

m, n, R², R³, Y, Z, and W have the same definitions as described herein, supra and infra, and R⁶ is C$_1$-C$_6$ alkyl.

It is appreciated that all of the embodiments described herein, supra and infra, that relate to the common variables shared between Compounds of Formula (I) and (II) namely, m, n, R$^a$, R², R³, Y, Z, and W, apply to Compounds of Formula (II) just as if they were each individually disclosed herewith specific reference to Formula (II).

One aspect of the present invention pertains to compounds of Formula (II).

One aspect of the present invention pertains to compounds of Formula (IIa).

In some embodiments, R⁶ is ethyl.

In some embodiments, R⁶ is tert-butyl.

It is appreciated that all of the embodiments described herein, supra and infra, that relate to the common variables shared between Compounds of Formula (Ia) and (IIa) namely, m, n, R², R³, Y, Z, and W, apply to Compounds of Formula (IIa) just as if they were each individually disclosed herewith specific reference to Formula (IIa).

One aspect of the present invention pertains to compounds of Formula (II) as synthetic intermediates useful in the preparation of compounds of Formula (I).

One aspect of the present invention pertains to compounds of Formula (IIa) as synthetic intermediates useful in the preparation of compounds of Formula (Ia).

One aspect of the present invention pertains to compounds of Formula (II) as esters of compounds, described and shown herein, such as compounds in Table A, where R⁶ is ethyl.

One aspect of the present invention pertains to compounds of Formula (IIa) as esters of compounds, described and shown herein, such as compounds in Table A, where R⁶ is ethyl.

One aspect of the present invention pertains to compounds of Formula (II) as prodrugs useful for the delivery of compounds of Formula (I).

One aspect of the present invention pertains to compounds of Formula (IIa) as prodrugs useful for the delivery of compounds of Formula (Ia).

One aspect of the present invention pertains to compounds of Formula (II) useful as prodrugs of compounds of Formula (I).

One aspect of the present invention pertains to compounds of Formula (IIa) useful as prodrugs of compounds of Formula (Ia).

Some embodiments of the present invention include every combination of one or more compounds selected from the following group shown in Table A.

TABLE A

| Cmpd No. | Chemical Structure | Chemical Name |
|---|---|---|
| 1 | 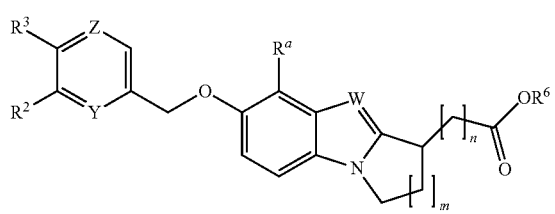 | 2-(7-(4-cyclopentyl-3-(trifluoromethyl)benzyloxy)-9-methyl-2,3-dihydro-1H-pyrrolo[1,2-a]indol-1-yl)acetic acid |
| 2 | 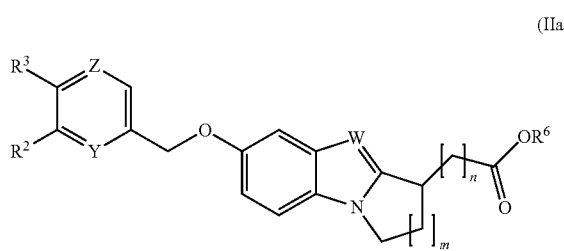 | 2-(7-(3-cyano-5-(trifluoromethoxy)benzyloxy)-2,3-dihydro-1H-pyrrolo[1,2-a]indol-1-yl)acetic acid |

TABLE A-continued

| Cmpd No. | Chemical Structure | Chemical Name |
|---|---|---|
| 3 | 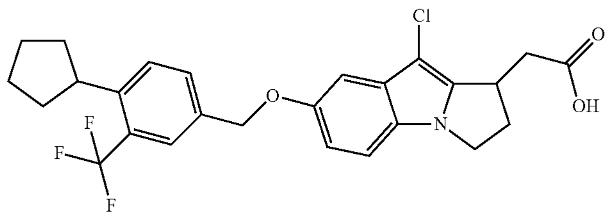 [SMILES: O=C(O)CC1CCn2c1c(Cl)c1cc(OCc3ccc(C4CCCC4)c(C(F)(F)F)c3)ccc12] | 2-(9-chloro-7-(4-cyclopentyl-3-(trifluoromethyl)benzyloxy)-2,3-dihydro-1H-pyrrolo[1,2-a]indol-1-yl)acetic acid |
| 4 | 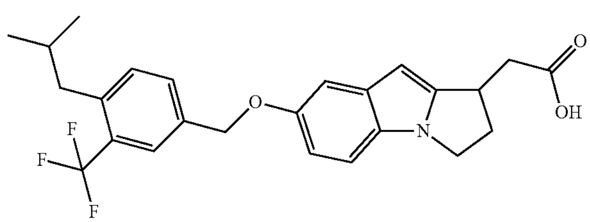 [SMILES: CC(C)Cc1ccc(COc2ccc3c(c2)cc2n3CCC2CC(=O)O)cc1C(F)(F)F] | 2-(7-(4-isobutyl-3-(trifluoromethyl)benzyloxy)-2,3-dihydro-1H-pyrrolo[1,2-a]indol-1-yl)acetic acid |
| 5 | 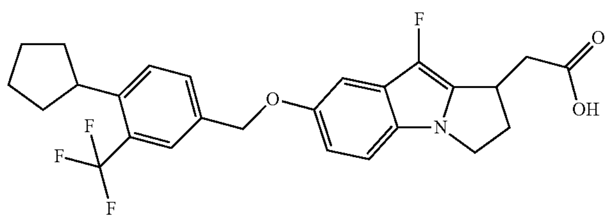 [SMILES: O=C(O)CC1CCn2c1c(F)c1cc(OCc3ccc(C4CCCC4)c(C(F)(F)F)c3)ccc12] | 2-(7-(4-cyclopentyl-3-(trifluoromethyl)benzyloxy)-9-fluoro-2,3-dihydro-1H-pyrrolo[1,2-a]indol-1-yl)acetic acid |
| 6 | 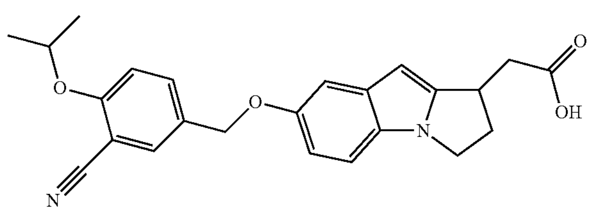 [SMILES: CC(C)Oc1ccc(COc2ccc3c(c2)cc2n3CCC2CC(=O)O)cc1C#N] | 2-(7-(3-cyano-4-isopropoxybenzyloxy)-2,3-dihydro-1H-pyrrolo[1,2-a]indol-1-yl)acetic acid |
| 7 | 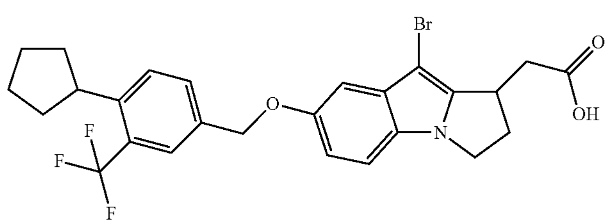 | 2-(9-bromo-7-(4-cyclopentyl-3-(trifluoromethyl)benzyloxy)-2,3-dihydro-1H-pyrrolo[1,2-a]indol-1-yl)acetic acid |
| 8 | 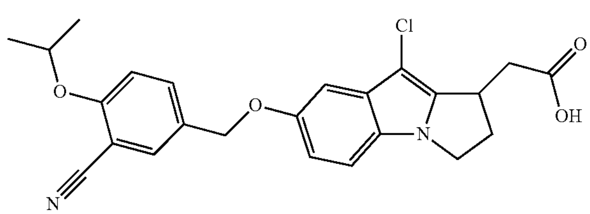 [SMILES: CC(C)Oc1ccc(COc2ccc3c(c2)c(Cl)c2n3CCC2CC(=O)O)cc1C#N] | 2-(9-chloro-7-(3-cyano-4-isopropoxybenzyloxy)-2,3-dihydro-1H-pyrrolo[1,2-a]indol-1-yl)acetic acid |
| 9 | 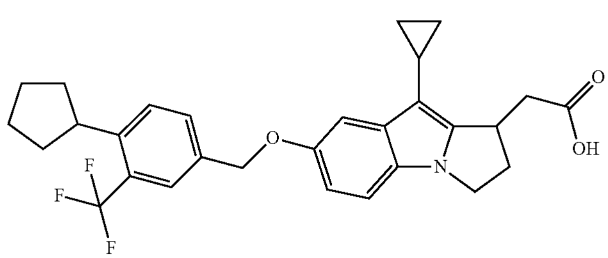 [SMILES: O=C(O)CC1CCn2c1c(C1CC1)c1cc(OCc3ccc(C4CCCC4)c(C(F)(F)F)c3)ccc12] | 2-(7-(4-cyclopentyl-3-(trifluoromethyl)benzyloxy)-9-cyclopropyl-2,3-dihydro-1H-pyrrolo[1,2-a]indol-1-yl)acetic acid |

TABLE A-continued

| Cmpd No. | Chemical Structure | Chemical Name |
|---|---|---|
| 10 | 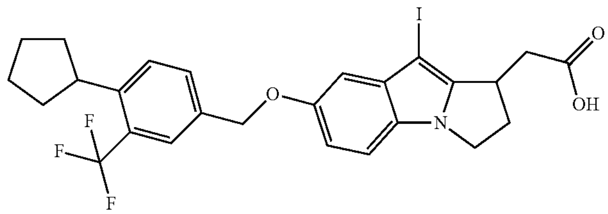 | 2-(7-(4-cyclopentyl-3-(trifluoromethyl)benzyloxy)-9-iodo-2,3-dihydro-1H-pyrrolo[1,2-a]indol-1-yl)acetic acid |
| 11 | 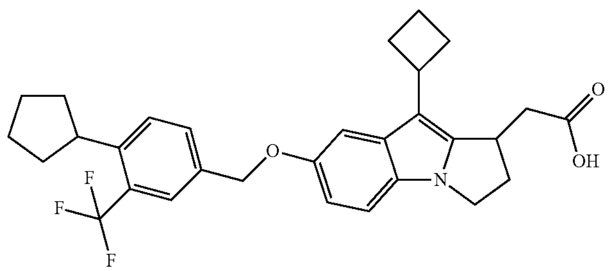 [SMILES: O=C(O)CC1CCn2c1c(C1CCC1)c1cc(OCc3ccc(C4CCCC4)c(C(F)(F)F)c3)ccc12] | 2-(9-cyclobutyl-7-(4-cyclopentyl-3-(trifluoromethyl)benzyloxy)-2,3-dihydro-1H-pyrrolo[1,2-a]indol-1-yl)acetic acid |
| 12 | 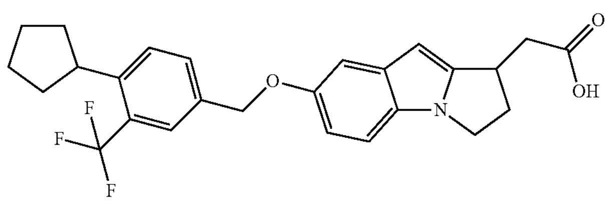 [SMILES: O=C(O)CC1CCn2c1cc1cc(OCc3ccc(C4CCCC4)c(C(F)(F)F)c3)ccc12] | 2-(7-(4-cyclopentyl-3-(trifluoromethyl)benzyloxy)-2,3-dihydro-1H-pyrrolo[1,2-a]indol-1-yl)acetic acid |
| 13 | 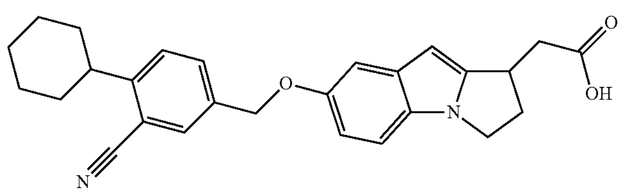 [SMILES: N#Cc1cc(COc2ccc3c(c2)cc2n3CCC2CC(=O)O)ccc1C1CCCCC1] | 2-(7-(3-cyano-4-cyclohexylbenzyloxy)-2,3-dihydro-1H-pyrrolo[1,2-a]indol-1-yl)acetic acid |
| 14 | 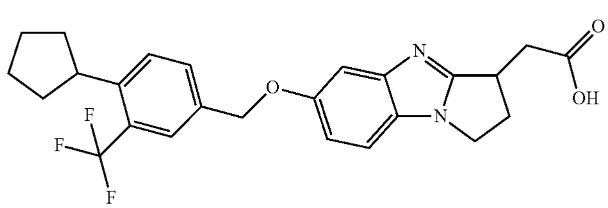 [SMILES: O=C(O)CC1CCn2c1nc1cc(OCc3ccc(C4CCCC4)c(C(F)(F)F)c3)ccc12] | 2-(6-(4-cyclopentyl-3-(trifluoromethyl)benzyloxy)-2,3-dihydro-1H-benzo[d]pyrrolo[1,2-a]imidazol-3-yl)acetic acid |
| 15 | 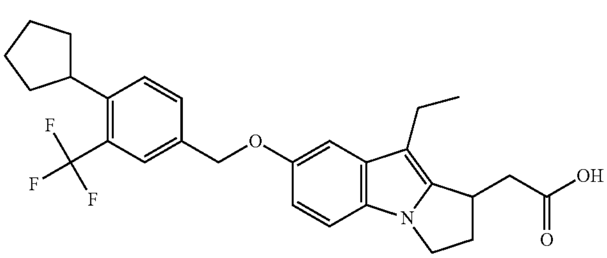 [SMILES: CCc1c2n(c3ccc(OCc4ccc(C5CCCC5)c(C(F)(F)F)c4)cc13)CCC2CC(=O)O] | 2-(7-(4-cyclopentyl-3-(trifluoromethyl)benzyloxy)-9-ethyl-2,3-dihydro-1H-pyrrolo[1,2-a]indol-1-yl)acetic acid |

TABLE A-continued

| Cmpd No. | Chemical Structure | Chemical Name |
|---|---|---|
| 16 | 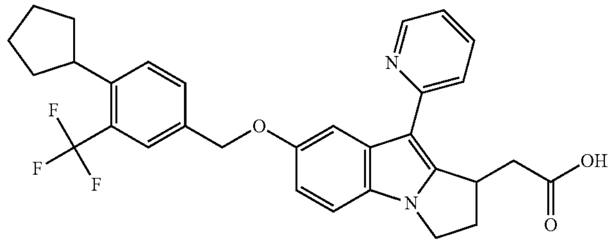 [SMILES: O=C(O)CC1CCn2c1c(-c1ccccn1)c1cc(OCc3ccc(C4CCCC4)c(C(F)(F)F)c3)ccc12] | 2-(7-(4-cyclopentyl-3-(trifluoromethyl)benzyloxy)-9-(pyridin-2-yl)-2,3-dihydro-1H-pyrrolo[1,2-a]indol-1-yl)acetic acid |
| 17 | 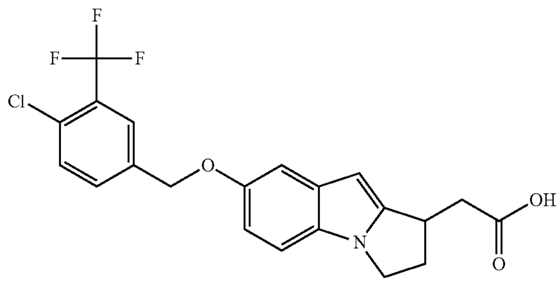 [SMILES: O=C(O)CC1CCn2c1cc1cc(OCc3ccc(Cl)c(C(F)(F)F)c3)ccc12] | 2-(7-(4-chloro-3-(trifluoromethyl)benzyloxy)-2,3-dihydro-1H-pyrrolo[1,2-a]indol-1-yl)acetic acid |
| 18 | 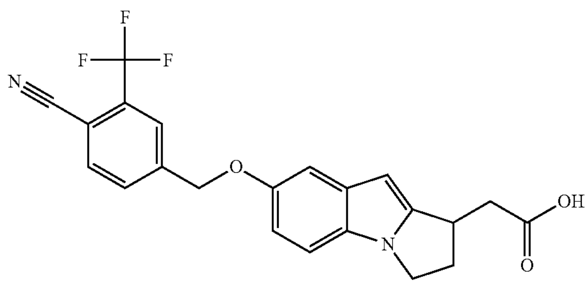 [SMILES: N#Cc1ccc(COc2ccc3c(c2)cc2n3CCC2CC(=O)O)cc1C(F)(F)F] | 2-(7-(4-cyano-3-(trifluoromethyl)benzyloxy)-2,3-dihydro-1H-pyrrolo[1,2-a]indol-1-yl)acetic acid |
| 19 | 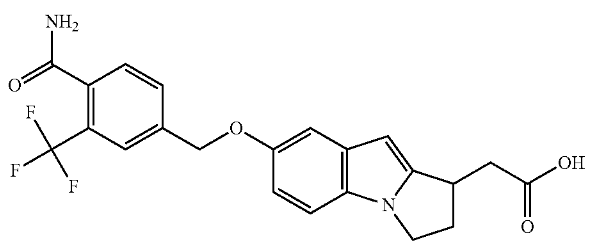 [SMILES: NC(=O)c1ccc(COc2ccc3c(c2)cc2n3CCC2CC(=O)O)cc1C(F)(F)F] | 2-(7-(4-carbamoyl-3-(trifluoromethyl)benzyloxy)-2,3-dihydro-1H-pyrrolo[1,2-a]indol-1-yl)acetic acid |
| 20 | 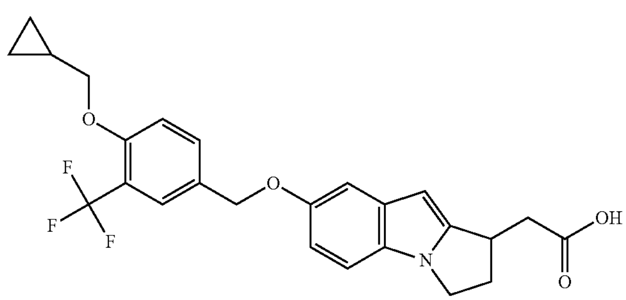 [SMILES: O=C(O)CC1CCn2c1cc1cc(OCc3ccc(OCC4CC4)c(C(F)(F)F)c3)ccc12] | 2-(7-(4-(cyclopropylmethoxy)-3-(trifluoromethyl)benzyloxy)-2,3-dihydro-1H-pyrrolo[1,2-a]indol-1-yl)acetic acid |

TABLE A-continued

| Cmpd No. | Chemical Structure | Chemical Name |
|---|---|---|
| 21 | 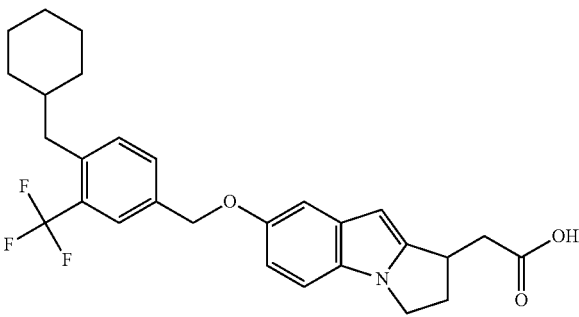 [SMILES: O=C(O)CC1CCn2c1cc1cc(OCc3ccc(CC4CCCCC4)c(C(F)(F)F)c3)ccc12] | 2-(7-(4-(cyclohexylmethyl)-3-(trifluoromethyl)benzyloxy)-2,3-dihydro-1H-pyrrolo[1,2-a]indol-1-yl)acetic acid |
| 22 | 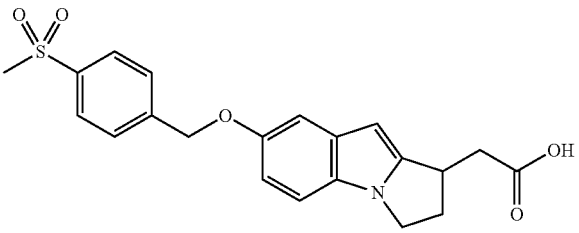 [SMILES: CS(=O)(=O)c1ccc(COc2ccc3c(c2)cc2n3CCC2CC(=O)O)cc1] | 2-(7-(4-(methylsulfonyl)benzyloxy)-2,3-dihydro-1H-pyrrolo[1,2-a]indol-1-yl)acetic acid |
| 23 | 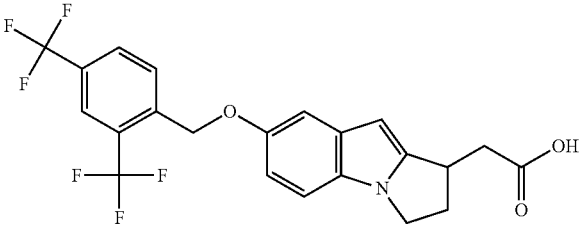 [SMILES: O=C(O)CC1CCn2c1cc1cc(OCc3ccc(C(F)(F)F)cc3C(F)(F)F)ccc12] | 2-(7-(2,4-bis(trifluoromethyl)benzyloxy)-2,3-dihydro-1H-pyrrolo[1,2-a]indol-1-yl)acetic acid |
| 24 | 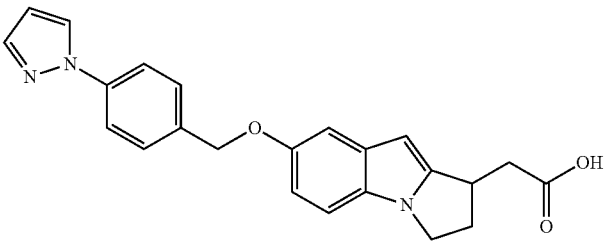 [SMILES: O=C(O)CC1CCn2c1cc1cc(OCc3ccc(-n4cccn4)cc3)ccc12] | 2-(7-(4-(1H-pyrazol-1-yl)benzyloxy)-2,3-dihydro-1H-pyrrolo[1,2-a]indol-1-yl)acetic acid |
| 25 | 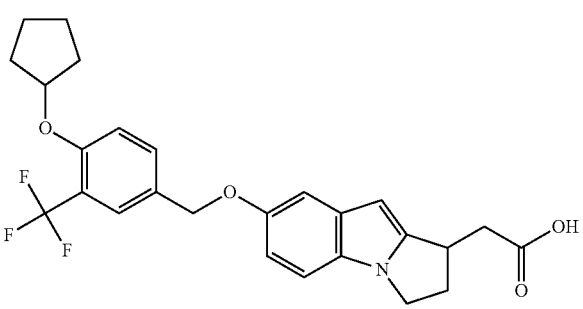 [SMILES: O=C(O)CC1CCn2c1cc1cc(OCc3ccc(OC4CCCC4)c(C(F)(F)F)c3)ccc12] | 2-(7-(4-(cyclopentyloxy)-3-(trifluoromethyl)benzyloxy)-2,3-dihydro-1H-pyrrolo[1,2-a]indol-1-yl)acetic acid |

TABLE A-continued

| Cmpd No. | Chemical Structure | Chemical Name |
|---|---|---|
| 26 | 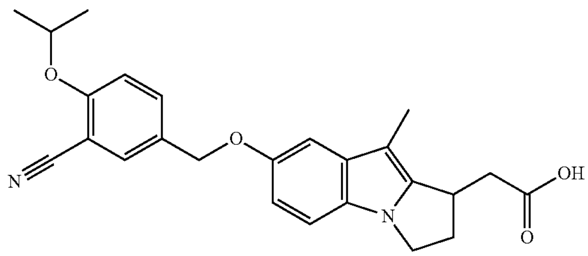 [SMILES: Cc1c2n(c3ccc(OCc4ccc(OC(C)C)c(C#N)c4)cc13)CCC2CC(=O)O] | 2-(7-(3-cyano-4-isopropoxybenzyloxy)-9-methyl-2,3-dihydro-1H-pyrrolo[1,2-a]indol-1-yl)acetic acid |
| 27 | 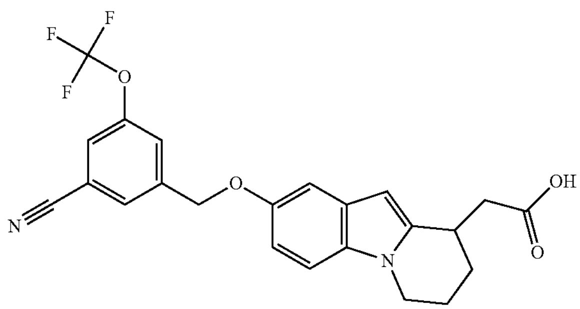 [SMILES: N#Cc1cc(COc2ccc3c(c2)cc2n3CCCC2CC(=O)O)cc(OC(F)(F)F)c1] | 2-(2-(3-cyano-5-(trifluoromethoxy)benzyloxy)-6,7,8,9-tetrahydropyrido[1,2-a]indol-9-yl)acetic acid |
| 28 | 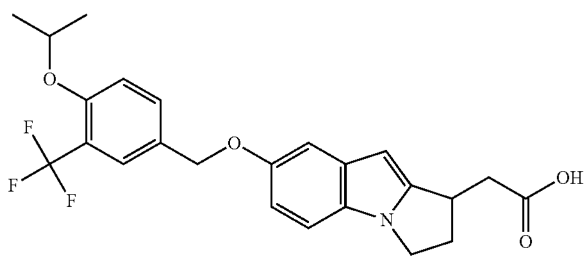 [SMILES: CC(C)Oc1ccc(COc2ccc3c(c2)cc2n3CCC2CC(=O)O)cc1C(F)(F)F] | 2-(7-(4-isopropoxy-3-(trifluoromethyl)benzyloxy)-2,3-dihydro-1H-pyrrolo[1,2-a]indol-1-yl)acetic acid |
| 29 | 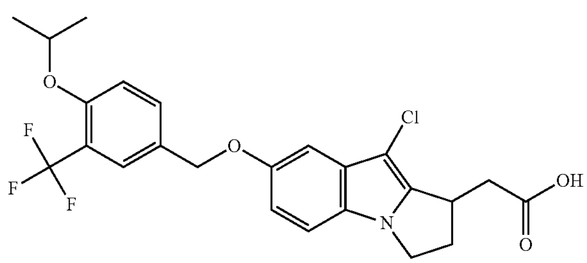 [SMILES: CC(C)Oc1ccc(COc2ccc3c(c2)c(Cl)c2n3CCC2CC(=O)O)cc1C(F)(F)F] | 2-(9-chloro-7-(4-isopropoxy-3-(trifluoromethyl)benzyloxy)-2,3-1H-pyrrolo[1,2-a]indol-1-yl)acetic acid |
| 30 | 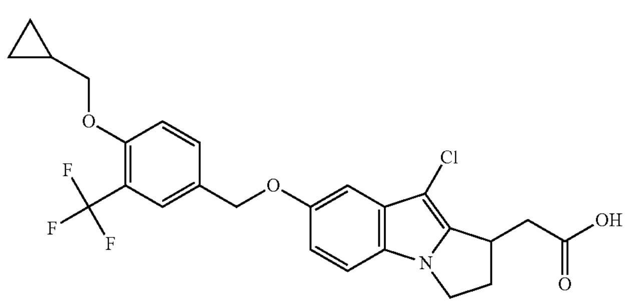 [SMILES: O=C(O)CC1CCn2c1c(Cl)c1cc(OCc3ccc(OCC4CC4)c(C(F)(F)F)c3)ccc12] | 2-(9-chloro-7-(4-(cyclopropylmethoxy)-3-(trifluoromethyl)benzyloxy)-2,3-dihydro-1H-pyrrolo[1,2-a]indol-1-yl)acetic acid |
| 31 | 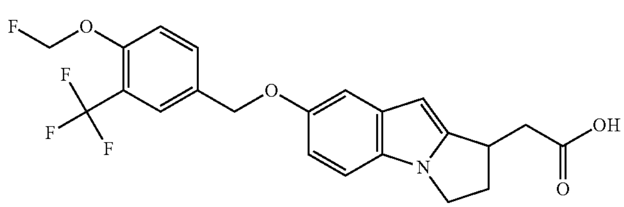 [SMILES: O=C(O)CC1CCn2c1cc1cc(OCc3ccc(OCF)c(C(F)(F)F)c3)ccc12] | 2-(7-(4-(fluoromethoxy)-3-(trifluoromethyl)benzyloxy)-2,3-dihydro-1H-pyrrolo[1,2-a]indol-1-yl)acetic acid |

TABLE A-continued

| Cmpd No. | Chemical Structure | Chemical Name |
|---|---|---|
| 32 | 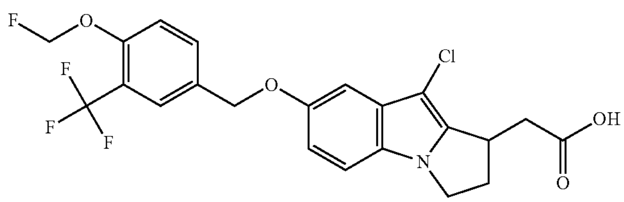 [SMILES: O=C(O)CC1CCn2c1c(Cl)c1cc(OCc3ccc(OCF)c(C(F)(F)F)c3)ccc12] | 2-(9-chloro-7-(4-(fluoromethoxy)-3-(trifluoromethyl)benzyloxy)-2,3-dihydro-1H-pyrrolo[1,2-a]indol-1-yl)acetic acid |
| 33 | 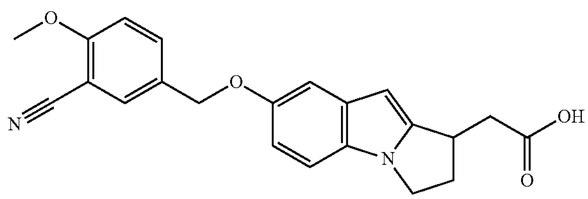 [SMILES: COc1ccc(COc2ccc3c(c2)cc2n3CCC2CC(=O)O)cc1C#N] | 2-(7-(3-cyano-4-methoxybenzyloxy)-2,3-dihydro-1H-pyrrolo[1,2-a]indol-1-yl)acetic acid |
| 34 | 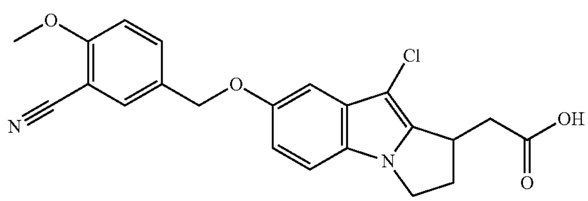 [SMILES: COc1ccc(COc2ccc3c(c2)c(Cl)c2n3CCC2CC(=O)O)cc1C#N] | 2-(9-chloro-7-(3-cyano-4-methoxybenzyloxy)-2,3-dihydro-1H-pyrrolo[1,2-a]indol-1-yl)acetic acid |
| 35 | 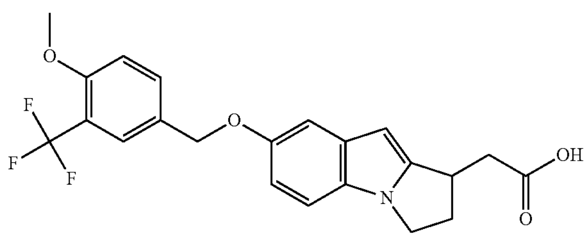 [SMILES: COc1ccc(COc2ccc3c(c2)cc2n3CCC2CC(=O)O)cc1C(F)(F)F] | 2-(7-(4-methoxy-3-(trifluoromethyl)benzyloxy)-2,3-dihydro-1H-pyrrolo[1,2-a]indol-1-yl)acetic acid |
| 36 | 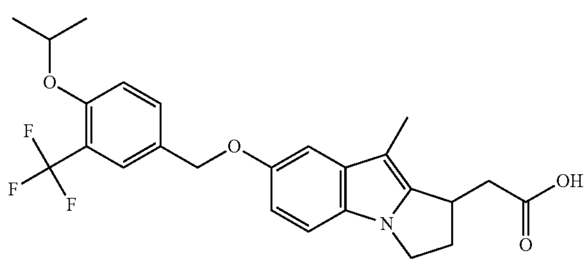 [SMILES: Cc1c2n(c3ccc(OCc4ccc(OC(C)C)c(C(F)(F)F)c4)cc13)CCC2CC(=O)O] | 2-(7-(4-isopropoxy-3-(trifluoromethyl)benzyloxy)-9-methyl-2,3-dihydro-1H-pyrrolo[1,2-a]indol-1-yl)acetic acid |
| 37 | 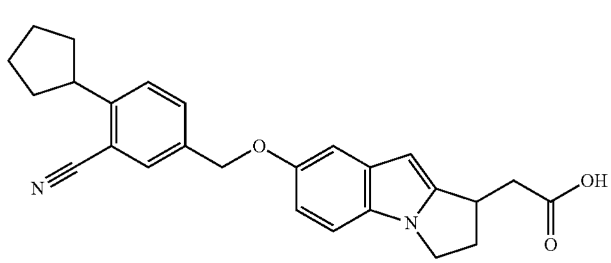 [SMILES: N#Cc1cc(COc2ccc3c(c2)cc2n3CCC2CC(=O)O)ccc1C1CCCC1] | 2-(7-(3-cyano-4-cyclopentylbenzyloxy)-2,3-dihydro-1H-pyrrolo[1,2-a]indol-1-yl)acetic acid |

TABLE A-continued

| Cmpd No. | Chemical Structure | Chemical Name |
|---|---|---|
| 38 | 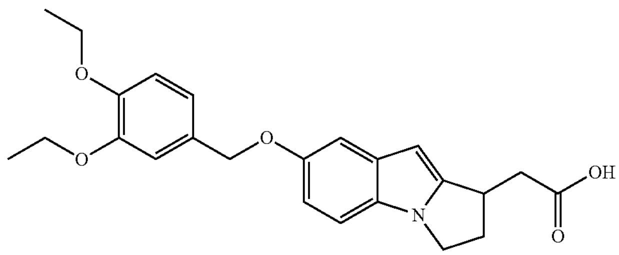 [SMILES: CCOc1ccc(COc2ccc3c(c2)cc2n3CCC2CC(=O)O)cc1OCC] | 2-(7-(3,4-diethoxybenzyloxy)-2,3-dihydro-1H-pyrrolo[1,2-a]indol-1-yl)acetic acid |
| 39 | 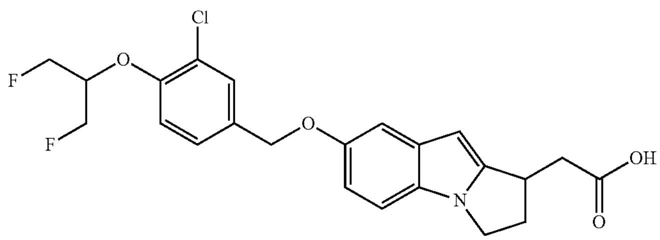 [SMILES: O=C(O)CC1CCn2c1cc1cc(OCc3ccc(OC(CF)CF)c(Cl)c3)ccc12] | 2-(7-(3-chloro-4-(1,3-difluoropropan-2-yloxy)benzyloxy)-2,3-dihydro-1H-pyrrolo[1,2-a]indol-1-yl)acetic acid |
| 40 | 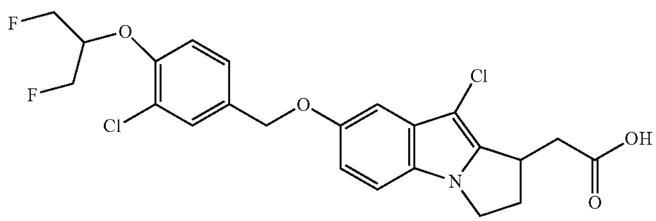 [SMILES: O=C(O)CC1CCn2c1c(Cl)c1cc(OCc3ccc(OC(CF)CF)c(Cl)c3)ccc12] | 2-(9-chloro-7-(3-chloro-4-(1,3-difluoropropan-2-yloxy)benzyloxy)-2,3-dihydro-1H-pyrrolo[1,2-a]indol-1-yl)acetic acid |
| 41 | 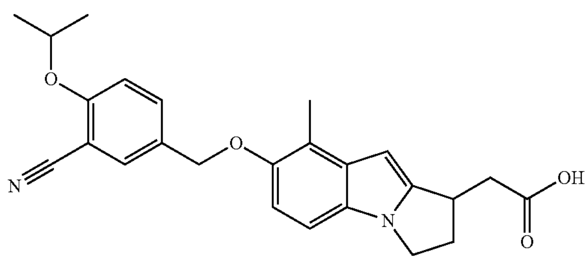 [SMILES: Cc1c(OCc2ccc(OC(C)C)c(C#N)c2)ccc2c1cc1n2CCC1CC(=O)O] | 2-(7-(3-cyano-4-isopropoxybenzyloxy)-8-methyl-2,3-dihydro-1H-pyrrolo[1,2-a]indol-1-yl)acetic acid |
| 42 | 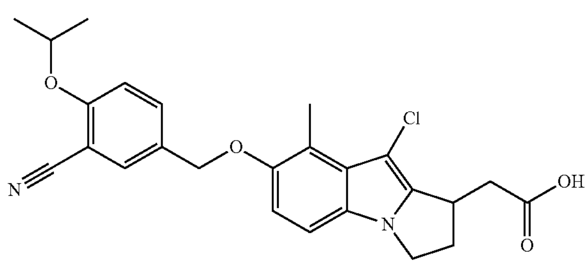 [SMILES: Cc1c(OCc2ccc(OC(C)C)c(C#N)c2)ccc2c1c(Cl)c1n2CCC1CC(=O)O] | 2-(9-chloro-7-(3-cyano-4-isopropoxybenzyloxy)-8-methyl-2,3-dihydro-1H-pyrrolo[1,2-a]indol-1-yl)acetic acid |
| 43 | 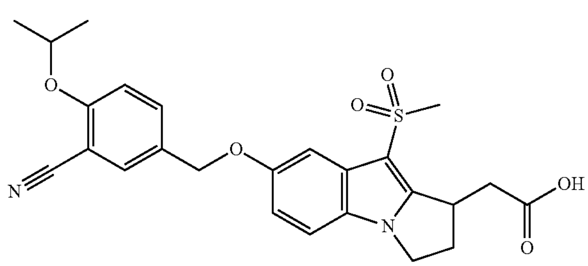 [SMILES: CC(C)Oc1ccc(COc2ccc3c(c2)c(S(C)(=O)=O)c2n3CCC2CC(=O)O)cc1C#N] | 2-(7-(3-cyano-4-isopropoxybenzyloxy)-9-(methylsulfonyl)-2,3-dihydro-1H-pyrrolo[1,2-a]indol-1-yl)acetic acid |

TABLE A-continued

| Cmpd No. | Chemical Structure | Chemical Name |
|---|---|---|
| 44 | 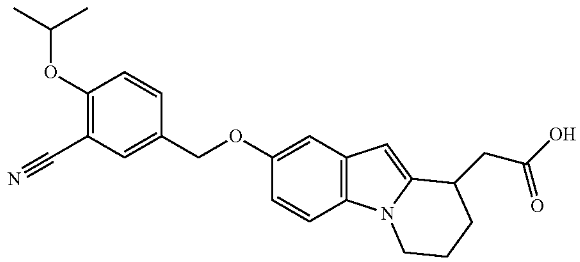 [SMILES: CC(C)Oc1ccc(COc2ccc3c(c2)cc2n3CCCC2CC(=O)O)cc1C#N] | 2-(2-(3-cyano-4-isopropoxybenzyloxy)-6,7,8,9-tetrahydropyrido[1,2-a]indol-9-yl)acetic acid |
| 45 | 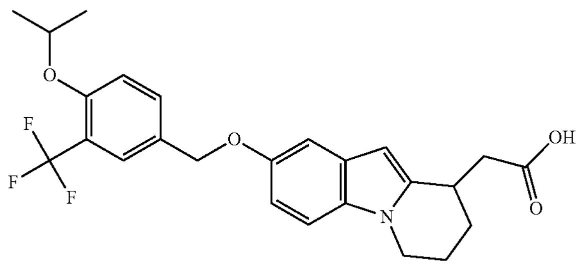 [SMILES: CC(C)Oc1ccc(COc2ccc3c(c2)cc2n3CCCC2CC(=O)O)cc1C(F)(F)F] | 2-(2-(4-isopropoxy-3-(trifluoromethyl)benzyloxy)-6,7,8,9-tetrahydropyrido[1,2-a]indol-9-yl)acetic acid |
| 46 | 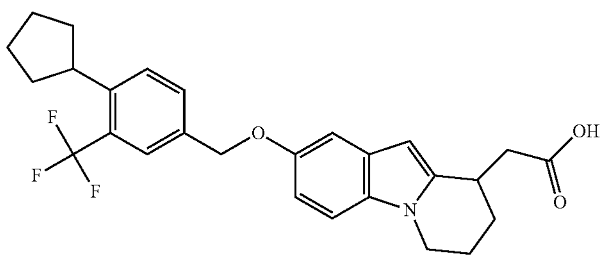 [SMILES: O=C(O)CC1CCCn2c1cc1cc(OCc3ccc(C4CCCC4)c(C(F)(F)F)c3)ccc12] | 2-(2-(4-cyclopentyl-3-(trifluoromethyl)benzyloxy)-6,7,8,9-tetrahydropyrido[1,2-a]indol-9-yl)acetic acid |
| 47 | 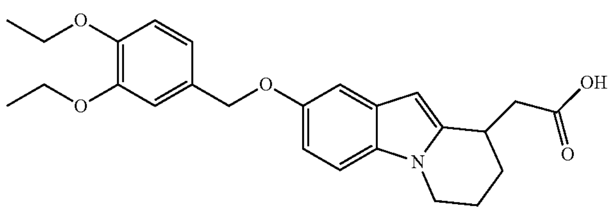 [SMILES: CCOc1ccc(COc2ccc3c(c2)cc2n3CCCC2CC(=O)O)cc1OCC] | 2-(2-(3,4-diethoxybenzyloxy)-6,7,8,9-tetrahydropyrido[1,2-a]indol-9-yl)acetic acid |
| 48 | 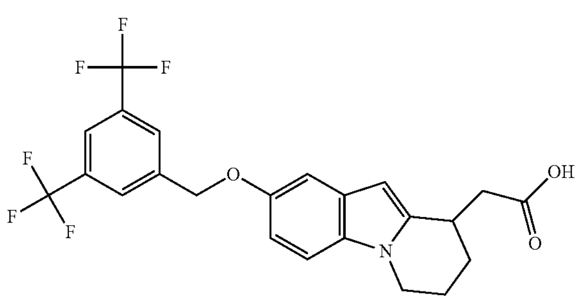 [SMILES: O=C(O)CC1CCCn2c1cc1cc(OCc3cc(C(F)(F)F)cc(C(F)(F)F)c3)ccc12] | 2-(2-(3,5-bis(trifluoromethyl)benzyloxy)-6,7,8,9-trahydropyrido[1,2-a]indol-9-yl)acetic acid |

C(1) Ring Carbon Stereochemistry

Compounds of the present invention contain a fused tricyclic system. Present on one of the rings is either a —CH$_2$CO$_2$H group (n=1) or a —CH$_2$CH$_2$CO$_2$H group (n=2). The ring carbon to which the —CH$_2$CO$_2$H or the —CH$_2$CH$_2$CO$_2$H group is bonded, is referred to herein the C(1) ring carbon. It is understood that the stereochemistry for the C(1) ring carbon contained in the fused tricyclic ring system can be either R or S.

A. C(1) Ring Carbon "R" Stereochemistry

In some embodiments, the stereochemistry for the C(1) ring carbon is R.

Some embodiments of the present invention pertain to compounds of Formula (IIb) and pharmaceutically acceptable salts, solvates, and hydrates thereof:

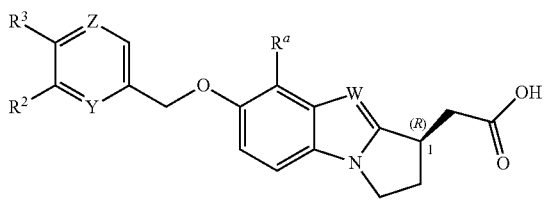

(IIb)

wherein each variable in Formula (IIb) has the same meaning as described herein, supra and infra.

Some embodiments of the present invention pertain to compounds of Formula (IIc) and pharmaceutically acceptable salts, solvates, and hydrates thereof:

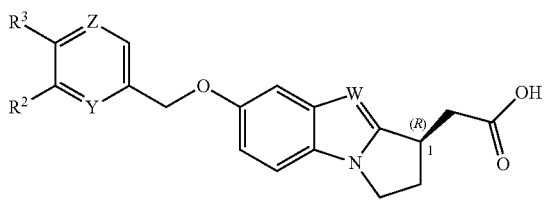

(IIc)

wherein each variable in Formula (IIc) has the same meaning as described herein, supra and infra.

Some embodiments of the present invention pertain to compounds of Formula (IId) and pharmaceutically acceptable salts, solvates, and hydrates thereof:

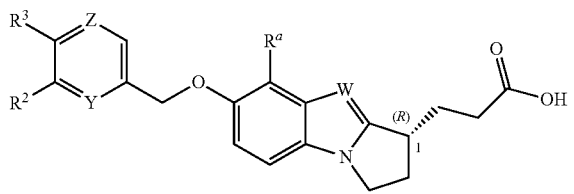

(IId)

wherein each variable in Formula (IId) has the same meaning as described herein, supra and infra.

Some embodiments of the present invention pertain to compounds of Formula (IIe) and pharmaceutically acceptable salts, solvates, and hydrates thereof:

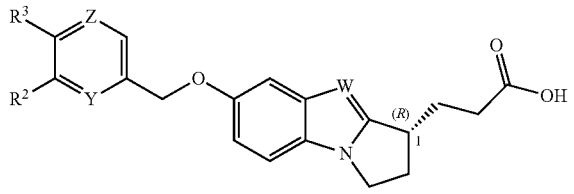

(IIe)

wherein each variable in Formula (IIe) has the same meaning as described herein, supra and infra.

Some embodiments of the present invention include every combination of one or more compounds selected from the following group: (R)-2-(7-(4-cyclopentyl-3-(trifluoromethyl) benzyloxy)-9-methyl-2,3-dihydro-1H-pyrrolo[1,2-a] indol-1-yl)acetic acid; (R)-2-(7-(3-cyano-5-(trifluoromethoxy)benzyloxy)-2,3-dihydro-1H-pyrrolo[1,2-a] indol-1-yl)acetic acid; (R)-2-(9-chloro-7-(4-cyclopentyl-3-(trifluoromethyl)benzyloxy)-2,3-dihydro-1H-pyrrolo[1,2-a] indol-1-yl)acetic acid; (R)-2-(7-(4-isobutyl-3-(trifluoromethyl)benzyloxy)-2,3-dihydro-1H-pyrrolo[1,2-a] indol-1-yl)acetic acid; (R)-2-(7-(4-cyclopentyl-3-(trifluoromethyl)benzyloxy)-9-fluoro-2,3-dihydro-1H-pyrrolo[1,2-a]indol-1-yl)acetic acid; (R)-2-(7-(3-cyano-4-isopropoxybenzyloxy)-2,3-dihydro-1H-pyrrolo[1,2-a]indol-1-yl)acetic acid; (R)-2-(9-bromo-7-(4-cyclopentyl-3-(trifluoromethyl)benzyloxy)-2,3-dihydro-1H-pyrrolo[1,2-a] indol-1-yl)acetic acid; (R)-2-(9-chloro-7-(3-cyano-4-isopropoxybenzyloxy)-2,3-dihydro-1H-pyrrolo[1,2-a]indol-1-yl)acetic acid; (R)-2-(7-(4-cyclopentyl-3-(trifluoromethyl) benzyloxy)-9-cyclopropyl-2,3-dihydro-1H-pyrrolo[1,2-a] indol-1-yl)acetic acid; (R)-2-(7-(4-cyclopentyl-3-(trifluoromethyl)benzyloxy)-9-iodo-2,3-dihydro-1H-pyrrolo[1,2-a]indol-1-yl)acetic acid; (R)-2-(9-cyclobutyl-7-(4-cyclopentyl-3-(trifluoromethyl)benzyloxy)-2,3-dihydro-1H-pyrrolo[1,2-a]indol-1-yl)acetic acid; (R)-2-(7-(4-cyclopentyl-3-(trifluoromethyl)benzyloxy)-2,3-dihydro-1H-pyrrolo[1,2-a]indol-1-yl)acetic acid; (R)-2-(7-(3-cyano-4-cyclohexylbenzyloxy)-2,3-dihydro-1H-pyrrolo[1,2-a]indol-1-yl)acetic acid; and (R)-2-(6-(4-cyclopentyl-3-(trifluoromethyl)benzyloxy)-2,3-dihydro-1H-benzo[d] pyrrolo[1,2-a]imidazol-3-yl)acetic acid.

Some embodiments of the present invention include every combination of one or more compounds selected from the following group: (R)-2-(7-(4-cyclopentyl-3-(trifluoromethyl)benzyloxy)-9-ethyl-2,3-dihydro-1H-pyrrolo[1,2-a]indol-1-yl)acetic acid; (R)-2-(7-(4-cyclopentyl-3-(trifluoromethyl)benzyloxy)-9-(pyridin-2-yl)-2,3-dihydro-1H-pyrrolo [1,2-a]indol-1-yl)acetic acid; (R)-2-(7-(4-chloro-3-(trifluoromethyl)benzyloxy)-2,3-dihydro-1H-pyrrolo[1,2-a] indol-1-yl)acetic acid; (R)-2-(7-(4-cyano-3-(trifluoromethyl)benzyloxy)-2,3-dihydro-1H-pyrrolo[1,2-a] indol-1-yl)acetic acid; (R)-2-(7-(4-carbamoyl-3-(trifluoromethyl)benzyloxy)-2,3-dihydro-1H-pyrrolo[1,2-a] indol-1-yl)acetic acid; (R)-2-(7-(4-(cyclopropylmethoxy)-3-(trifluoromethyl)benzyloxy)-2,3-dihydro-1H-pyrrolo[1,2-a] indol-1-yl)acetic acid; (R)-2-(7-(4-(cyclohexylmethyl)-3-(trifluoromethyl)benzyloxy)-2,3-dihydro-1H-pyrrolo[1,2-a] indol-1-yl)acetic acid; (R)-2-(7-(4-(methylsulfonyl) benzyloxy)-2,3-dihydro-1H-pyrrolo[1,2-a]indol-1-yl)acetic acid; (R)-2-(7-(2,4-bis(trifluoromethyl)benzyloxy)-2,3-dihydro-1H-pyrrolo[1,2-a]indol-1-yl)acetic acid; (R)-2-(7-(4-(1H-pyrazol-1-yl)benzyloxy)-2,3-dihydro-1H-pyrrolo[1,2-a]indol-1-yl)acetic acid; (R)-2-(7-(4-(cyclopentyloxy)-3-(trifluoromethyl)benzyloxy)-2,3-dihydro-1H-pyrrolo[1,2-a] indol-1-yl)acetic acid; (R)-2-(7-(3-cyano-4-isopropoxybenzyloxy)-9-methyl-2,3-dihydro-1H-pyrrolo[1, 2-a]indol-1-yl)acetic acid; (R)-2-(7-(4-isopropoxy-3-(trifluoromethyl)benzyloxy)-2,3-dihydro-1H-pyrrolo[1,2-a] indol-1-yl)acetic acid; (R)-2-(9-chloro-7-(4-isopropoxy-3-(trifluoromethyl)benzyloxy)-2,3-dihydro-1H-pyrrolo[1,2-a] indol-1-yl)acetic acid; (R)-2-(9-chloro-7-(4-(cyclopropylmethoxy)-3-(trifluoromethyl)benzyloxy)-2,3-dihydro-1H-pyrrolo[1,2-a]indol-1-yl)acetic acid; (R)-2-(7-(4-(fluoromethoxy)-3-(trifluoromethyl)benzyloxy)-2,3-dihydro-1H-pyrrolo[1,2-a]indol-1-yl)acetic acid; (R)-2-(9- chloro-7-(4-(fluoromethoxy)-3-(trifluoromethyl)benzyloxy)-2,3-dihydro-1H-pyrrolo[1,2-a]indol-1-yl)acetic acid; (R)-2-(7-(3-cyano-4-methoxybenzyloxy)-2,3-dihydro-1H-pyrrolo[1,2-a]indol-1-yl)acetic acid; (R)-2-(9-chloro-7-(3-cyano-4-methoxybenzyloxy)-2,3-dihydro-1H-pyrrolo[1,2-a]indol-1-yl)acetic acid; (R)-2-(7-(4-methoxy-3-(trifluoromethyl)benzyloxy)-2,3-dihydro-1H-pyrrolo[1,2-a]indol-1-yl)acetic acid; (R)-2-(7-(4-isopropoxy-3-(trifluoromethyl)benzyloxy)-9-methyl-2,3-dihydro-1H-pyrrolo[1,2-a]indol-1-yl)acetic acid; (R)-2-(7-(3-cyano-4-cyclopentylbenzyloxy)-2,3-dihydro-1H-pyrrolo[1,2-a]indol-1-yl)acetic acid; (R)-2-(7-(3,4-diethoxybenzyloxy)-2,3-dihydro-1H-pyrrolo[1,2-a]indol-1-yl)acetic acid; (R)-2-(7-(3-chloro-4-(1,3-difluoropropan-2-yloxy)benzyloxy)-2,3-dihydro-1H-pyrrolo[1,2-a]indol-1-yl)acetic acid; (R)-2-(9-chloro-7-(3-chloro-4-(1,3-difluoropropan-2-yloxy)benzyloxy)-2,3-dihydro-1H-pyrrolo[1,2-a]indol-1-yl)acetic acid; (R)-2-(7-(3-cyano-4-isopropoxybenzyloxy)-8-methyl-2,3-dihydro-1H-pyrrolo[1,2-a]indol-1-yl)acetic acid; (R)-2-(9-chloro-7-(3-cyano-4-isopropoxybenzyloxy)-8-methyl-2,3-dihydro-1H-pyrrolo[1,2-a]indol-1-yl)acetic acid; (R)-2-(7-(3-cyano-4-isopropoxybenzyloxy)-9-(methylsulfonyl)-2,3-dihydro-1H-pyrrolo[1,2-a]indol-1-yl)acetic acid; (R)-2-(2-(3-cyano-4-isopropoxybenzyloxy)-6,7,8,9-tetrahydropyrido[1,2-a]indol-9-yl)acetic acid; (R)-2-(2-(4-isopropoxy-3-(trifluoromethyl)benzyloxy)-6,7,8,9-tetrahydropyrido[1,2-a]indol-9-yl)acetic acid; (R)-2-(2-(4-cyclopentyl-3-(trifluoromethyl)benzyloxy)-6,7,8,9-tetrahydropyrido[1,2-a]indol-9-yl)acetic acid; (R)-2-(2-(3,4-diethoxybenzyloxy)-6,7,8,9-tetrahydropyrido[1,2-a]indol-9-yl)acetic acid; (R)-2-(2-(3,5-bis(trifluoromethyl)benzyloxy)-6,7,8,9-tetrahydropyrido[1,2-a]indol-9-yl)acetic acid; and (R)-2-(2-(3-cyano-5-(trifluoromethoxy)benzyloxy)-6,7,8,9-tetrahydropyrido[1,2-a]indol-9-yl)acetic acid.

B. C(1) Ring Carbon "S" Stereochemistry

In some embodiments, the stereochemistry for the C(1) ring carbon is S.

Some embodiments of the present invention pertain to compounds of Formula (IIf) and pharmaceutically acceptable salts, solvates, and hydrates thereof:

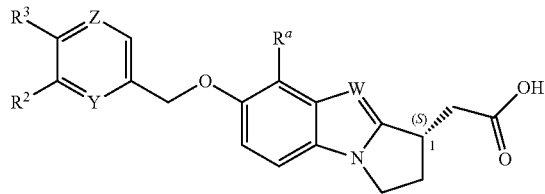

(IIf)

wherein each variable in Formula (IIf) has the same meaning as described herein, supra and infra.

Some embodiments of the present invention pertain to compounds of Formula (IIg) and pharmaceutically acceptable salts, solvates, and hydrates thereof:

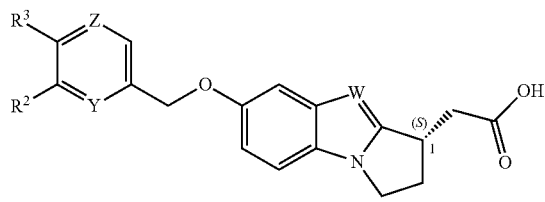

(IIg)

wherein each variable in Formula (IIg) has the same meaning as described herein, supra and infra.

Some embodiments of the present invention pertain to compounds of Formula (IIh) and pharmaceutically acceptable salts, solvates, and hydrates thereof:

(IIh)

wherein each variable in Formula (IIh) has the same meaning as described herein, supra and infra.

Some embodiments of the present invention pertain to compounds of Formula (IIi) and pharmaceutically acceptable salts, solvates, and hydrates thereof:

(IIi)

wherein each variable in Formula (IIi) has the same meaning as described herein, supra and infra.

Some embodiments of the present invention include every combination of one or more compounds selected from the following group: (S)-2-(7-(4-cyclopentyl-3-(trifluoromethyl)benzyloxy)-9-methyl-2,3-dihydro-1H-pyrrolo[1,2-a]indol-1-yl)acetic acid; (S)-2-(7-(3-cyano-5-(trifluoromethoxy)benzyloxy)-2,3-dihydro-1H-pyrrolo[1,2-a]indol-1-yl)acetic acid; (S)-2-(9-chloro-7-(4-cyclopentyl-3-(trifluoromethyl)benzyloxy)-2,3-dihydro-1H-pyrrolo[1,2-a]indol-1-yl)acetic acid; (S)-2-(7-(4-isobutyl-3-(trifluoromethyl)benzyloxy)-2,3-dihydro-1H-pyrrolo[1,2-a]indol-1-yl)acetic acid; (S)-2-(7-(4-cyclopentyl-3-(trifluoromethyl)benzyloxy)-9-fluoro-2,3-dihydro-1H-pyrrolo[1,2-a]indol-1-yl)acetic acid; (S)-2-(7-(3-cyano-4-isopropoxybenzyloxy)-2,3-dihydro-1H-pyrrolo[1,2-a]indol-1-yl)acetic acid; (S)-2-(9-bromo-7-(4-cyclopentyl-3-(trifluoromethyl)benzyloxy)-2,3-dihydro-1H-pyrrolo[1,2-a]indol-1-yl)acetic acid; (S)-2-(9-chloro-7-(3-cyano-4-isopropoxybenzyloxy)-2,3-dihydro-1H-pyrrolo[1,2-a]indol-1-yl)acetic acid; (S)-2-(7-(4-cyclopentyl-3-(trifluoromethyl)benzyloxy)-9-cyclopropyl-2,3-dihydro-1H-pyrrolo[1,2-a]indol-1-yl)acetic acid; (S)-2-(7-(4-cyclopentyl-3-(trifluoromethyl)benzyloxy)-9-iodo-2,3-dihydro-1H-pyrrolo[1,2-a]indol-1-yl)acetic acid; (S)-2-(9-cyclobutyl-7-(4-cyclopentyl-3-(trifluoromethyl)benzyloxy)-2,3-dihydro-1H-pyrrolo[1,2-a]indol-1-yl)acetic acid; (S)-2-(7-(4-cyclopentyl-3-(trifluoromethyl)benzyloxy)-2,3-dihydro-1H-pyrrolo[1,2-a]indol-1-yl)acetic acid; (S)-2-(7-(3-cyano-4-cyclohexylbenzyloxy)-2,3-dihydro-1H-pyrrolo[1,2-a]indol-1-yl)acetic acid, and (S)-2-(6-(4-cyclopentyl-3-(trifluoromethyl)benzyloxy)-2,3-dihydro-1H-benzo[d]pyrrolo[1,2-a]imidazol-3-yl)acetic acid.

Some embodiments of the present invention include every combination of one or more compounds selected from the following group: (S)-2-(2-(7-(4-cyclopentyl-3-(trifluoromethyl)benzyloxy)-9-ethyl-2,3-dihydro-1H-pyrrolo[1,2-a]indol-1-yl)acetic acid; (S)-2-(7-(4-cyclopentyl-3-(trifluoromethyl)benzyloxy)-9-(pyridin-2-yl)-2,3-dihydro-1H-pyrrolo[1,2-a]indol-1-yl)acetic acid; (S)-2-(7-(4-chloro-3-(trifluoromethyl)benzyloxy)-2,3-dihydro-1H-pyrrolo[1,2-a]indol-1-yl)acetic acid; (S)-2-(7-(4-cyano-3-(trifluoromethyl)benzyloxy)-2,3-dihydro-1H-pyrrolo[1,2-a]indol-1-yl)acetic acid; (S)-2-(7-(4-carbamoyl-3-(trifluoromethyl)benzyloxy)-2,3-dihydro-1H-pyrrolo[1,2-a]indol-1-yl)acetic acid; (S)-2-(7-(4-(cyclopropylmethoxy)-3-(trifluoromethyl)benzyloxy)-2,3-dihydro-1H-pyrrolo[1,2-a]indol-1-yl)acetic acid; (S)-2-(7-(4-(cyclohexylmethyl)-3-(trifluoromethyl)benzyloxy)-2,3-dihydro-1H-pyrrolo[1,2-a]indol-1-yl)acetic acid; (S)-2-(7-(4-(methylsulfonyl)benzyloxy)-2,3-dihydro-1H-pyrrolo[1,2-a]indol-1-yl)acetic acid; (S)-2-(7-(2,4-bis(trifluoromethyl)benzyloxy)-2,3-dihydro-1H-pyrrolo[1,2-a]indol-1-yl)acetic acid; (S)-2-(7-(4-(1H-pyrazol-1-yl)benzyloxy)-2,3-dihydro-1H-pyrrolo[1,2-a]indol-1-yl)acetic acid; (S)-2-(7-(4-(cyclopentyloxy)-3-(trifluoromethyl)benzyloxy)-2,3-dihydro-1H-pyrrolo[1,2-a]indol-1-yl)acetic acid; (S)-2-(7-(3-cyano-4-isopropoxybenzyloxy)-9-methyl-2,3-dihydro-1H-pyrrolo[1,2-a]indol-1-yl)acetic acid; (S)-2-(7-(4-isopropoxy-3-(trifluoromethyl)benzyloxy)-2,3-dihydro-1H-pyrrolo[1,2-a]indol-1-yl)acetic acid; (S)-2-(9-chloro-7-(4-isopropoxy-3-(trifluoromethyl)benzyloxy)-2,3-dihydro-1H-pyrrolo[1,2-a]indol-1-yl)acetic acid; (S)-2-(9-chloro-7-(4-(cyclopropylmethoxy)-3-(trifluoromethyl)benzyloxy)-2,3-dihydro-1H-pyrrolo[1,2-a]indol-1-yl)acetic acid; (S)-2-(7-(4-(fluoromethoxy)-3-(trifluoromethyl)benzyloxy)-2,3-dihydro-1H-pyrrolo[1,2-a]indol-1-yl)acetic acid; (S)-2-(9-chloro-7-(4-(fluoromethoxy)-3-(trifluoromethyl)benzyloxy)-2,3-dihydro-1H-pyrrolo[1,2-a]indol-1-yl)acetic acid; (S)-2-(7-(3-cyano-4-methoxybenzyloxy)-2,3-dihydro-1H-pyrrolo[1,2-a]indol-1-yl)acetic acid; (S)-2-(9-chloro-7-(3-cyano-4-methoxybenzyloxy)-2,3-dihydro-1H-pyrrolo[1,2-a]indol-1-yl)acetic acid; (S)-2-(7-(4-methoxy-3-(trifluoromethyl)benzyloxy)-2,3-dihydro-1H-pyrrolo[1,2-a]indol-1-yl)acetic acid; (S)-2-(7-(4-isopropoxy-3-(trifluoromethyl)benzyloxy)-9-methyl-2,3-dihydro-1H-pyrrolo[1,2-a]indol-1-yl)acetic acid; (S)-2-(7-(3-cyano-4-cyclopentylbenzyloxy)-2,3-dihydro-1H-pyrrolo[1,2-a]indol-1-yl)acetic acid; (S)-2-(7-(3,4-diethoxybenzyloxy)-2,3-dihydro-1H-pyrrolo[1,2-a]indol-1-yl)acetic acid; (S)-2-(7-(3-chloro-4-(1,3-difluoropropan-2-yloxy)benzyloxy)-2,3-dihydro-1H-pyrrolo[1,2-a]indol-1-yl)acetic acid; (S)-2-(9-chloro-7-(3-chloro-4-(1,3-difluoropropan-2-yloxy)benzyloxy)-2,3-dihydro-1H-pyrrolo[1,2-a]indol-1-yl)acetic acid; (S)-2-(7-(3-cyano-4-isopropoxybenzyloxy)-8-methyl-2,3-dihydro-1H-pyrrolo[1,2-a]indol-1-yl)acetic acid; (S)-2-(9-chloro-7-(3-cyano-4-isopropoxybenzyloxy)-8-methyl-2,3-dihydro-1H-pyrrolo[1,2-a]indol-1-yl)acetic acid; (S)-2-(7-(3-cyano-4-isopropoxybenzyloxy)-9-(methylsulfonyl)-2,3-dihydro-1H-pyrrolo[1,2-a]indol-1-yl)acetic acid; (S)-2-(2-(3-cyano-4-isopropoxybenzyloxy)-6,7,8,9-tetrahydropyrido[1,2-a]indol-9-yl)acetic acid; (S)-2-(2-(4-isopropoxy-3-(trifluoromethyl)benzyloxy)-6,7,8,9-tetrahydropyrido[1,2-a]indol-9-yl)acetic acid; (S)-2-(2-(4-cyclopentyl-3-(trifluoromethyl)benzyloxy)-6,7,8,9-tetrahydropyrido[1,2-a]indol-9-yl)acetic acid; (S)-2-(2-(3,4-diethoxybenzyloxy)-6,7,8,9-tetrahydropyrido[1,2-a]indol-9-yl)acetic acid; (S)-2-(2-(3,5-bis(trifluoromethyl)benzyloxy)-6,7,8,9-tetrahydropyrido[1,2-a]indol-9-yl)acetic acid; and (S)-2-(2-(3-cyano-5-(trifluoromethoxy)benzyloxy)-6,7,8,9-tetrahydropyrido[1,2-a]indol-9-yl)acetic acid.

Additionally, individual compounds and chemical genera of the present invention, for example, those compounds found in Table A including diastereomers and enantiomers thereof, encompass all pharmaceutically acceptable salts, solvates, and hydrates, thereof.

It is understood that the present invention embraces each diastereomer, each enantiomer and mixtures thereof of each compound and generic formulae disclosed herein just as if they were each individually disclosed with the specific stereochemical designation for each chiral carbon. Separation of the individual isomers (such as, by chiral HPLC, recrystallization of diastereomeric mixtures, and the like) or selective synthesis (such as, by enantiomeric selective syntheses and the like) of the individual isomers is accomplished by application of various methods which are well known to practitioners in the art.

The compounds of the Formula (Ia) of the present invention may be prepared according to relevant published literature procedures that are used by one skilled in the art. Exemplary reagents and procedures for these reactions appear hereinafter in the working examples.

Protection and deprotection may be carried out by procedures generally known in the art (see, for example, Greene, T. W. and Wuts, P. G. M., *Protecting Groups in Organic Synthesis*, $3^{rd}$ Edition, 1999 [Wiley]; incorporated herein by reference in its entirety).

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically acceptable carriers, outside those mentioned herein, are known in the art; for example, see Remington, *The Science and Practice of Pharmacy*, $20^{th}$ Edition, 2000, Lippincott Williams & Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt, solvate, hydrate or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or suspensions, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a salt, solvate, hydrate or physiologically functional derivative thereof can be used as active ingredients in pharmaceutical compositions, specifically as S1P1 receptor modulators. The term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate by the patient's physician or caregiver it may be necessary to deviate upward or downward from the doses described herein.

The amount of active ingredient or an active salt, solvate or hydrate derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in one model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, whether an acute or chronic disease state is being treated or prophylaxis is conducted or whether further active compounds are administered in addition to the compounds of the present invention and as part of a drug combination. The dosage regimen for treating a disease condition with the compounds and/or compositions of this invention is selected in accordance with a variety factors including those cited above. Thus, the actual dosage regimen employed may vary widely and therefore may deviate from a preferred dosage regimen and one skilled in the art will recognize that dosage and dosage regimens outside these typical ranges can be tested and, where appropriate, may be used in the methods of this invention.

The desired dose may conveniently be presented in a single dose or as divided doses administered at appropriate intervals, for example, as 2, 3, 4 or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

For preparing pharmaceutical compositions from the compounds of the present invention, the suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or encapsulating materials.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may be from 0.5 to about 90 percent of the active compound. However, an artisan would know when amounts outside of this range are necessary. Suitable carriers for powders and tablets include magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein (e.g., by stirring). The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols (e.g., nasal aerosols, by inhalation), this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. Solutions or dispersions of the compounds of the present invention or a pharmaceutically acceptable salt, solvate, hydrate or derivative thereof in water, water/alcohol mixtures or suitable saline solutions, for example, can be employed using customary additives (e.g., benzyl alcohol or other suitable preservatives), absorption enhancers for increasing the bioavailability, solubilizers, dispersants and others and, if appropriate, customary propellants (e.g., carbon dioxide, CFCs, such as, dichlorodifluoromethane, trichlorofluoromethane, dichlorotetrafluoroethane and the like). The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder (e.g., a powder mix of the compound in a suitable powder base such as lactose, starch, starch derivatives such as hydroxypropylmethyl cellulose and polyvinylpyrrolidone (PVP)). Conveniently the powder carrier will form a gel in the nasal cavity. The powder composition may be presented in unit dose form (e.g., capsules, cartridges) as for gelatin or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

In some embodiments, the compositions are tablets or capsules for oral administration.

In some embodiments, the compositions are liquids for intravenous administration.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed by Berge et al., *Journal of Pharmaceutical Sciences*, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and that when administered into an individual undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when S1P1 receptor agonists are utilized as active ingredients in a pharmaceutical composition, these are not intended for use only in humans, but in other non-human mammals as well. Indeed, recent advances in the area of animal health-care mandate that consideration be given for the use of active agents, such as S1P1 receptor agonists, for the treatment of an S1P1 receptor-associated disease or disorder in companionship animals (e.g., cats, dogs, etc.) and in livestock animals (e.g., cows, chickens, fish, etc.). Those of ordinary skill in the art are readily credited with understanding the utility of such compounds in such settings.

Hydrates and Solvates

It is understood that when the phrase "pharmaceutically acceptable salts, solvates and hydrates" is used when referring to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula.

The compounds of the present invention can be administrated in a wide variety of oral and parenteral dosage forms. It will be apparent to those skilled in the art that the following dosage forms may comprise, as the active component, either a compound of the invention or a pharmaceutically acceptable salt or as a solvate or hydrate thereof. Moreover, various hydrates and solvates of the compounds of the invention and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: *Polymorphism in Pharmaceutical Solids*, ed. Harry G. Britton, Vol. 95, Marcel Dekker, Inc., New York, 1999, incorporated herein by reference in its entirety. Accordingly, one aspect of the present invention pertains to hydrates and solvates of compounds of Formula (I) and (Ia), or Formula (II) and (IIa) and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Other Utilities

Another object of the present invention relates to radiolabeled compounds of the present invention that are useful not only in radio-imaging but also in assays, both in vitro and in vivo, for localizing and quantitating the S1P1 receptor in tissue samples, including human and for identifying S1P1 receptor ligands by inhibition binding of a radiolabeled compound. It is a further object of this invention to develop novel S1P1 receptor assays which comprise such radiolabeled compounds.

The present invention embraces isotopically-labeled compounds of the present invention. Isotopically or radiolabeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include, but are not limited, to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{75}$Br, $^{76}$Br, $^{77}$Br, $^{82}$Br, $^{123}$I, $^{124}$I, $^{125}$I and $^{131}$I. The radionuclide that is incorporated in the instant radiolabeled compounds will depend on the specific application of that radiolabeled compound. For example, for in vitro S1P1 receptor labeling and competition assays, compounds that incorporate $^3$H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radiolabeled" or "labeled compound" is a compound as described herein, for example, a compound found in Formula (I), (Ia), (Ic), (Ie), (Ig), (Ii), (Ij), (Ik), (Im), (IIa), (IIb), (IIc), (IId), (IIe), (IIf), (IIg), (IIh), or (IIi), or compound of Table A, containing at least one radionuclide. In some embodiments the radionuclide is selected from the group consisting of $^3$H, $^{14}$C, $^{125}$I, $^{35}$S, and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in FIGS. 1 to 10 and examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or a scarcer radio-isotope or nonradioactive isotope.

Synthetic methods for incorporating radio-isotopes into organic compounds are applicable to compounds of the invention and are well known in the art. Certain synthetic methods, for example, for incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters, and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl [$^3$H] products by treating appropriate precursors with high specific activity methyl iodide [$^3$H]. This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in *J. Org. Chem.,* 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.,* 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled S1P1 receptor compound of Formula (I) or (Ia), or Formula (IIa) or (IIa) can be used in a screening assay to identify/evaluate compounds. In general terms, a newly synthesized or identified compound (i.e., test compound) can be evaluated for its ability to reduce binding of the "radiolabeled compound of Formula (I) or (Ia), or Formula (IIa) or (IIa)" to the S1P1 receptor. Accordingly, the ability of a test compound to compete with the "radiolabeled compound of Formula (I) or (Ia), or Formula (IIa) or (IIa)" for the binding to the S1P1 receptor directly correlates to its binding affinity.

The labeled compounds of the present invention bind to the S1P1 receptor. In one embodiment the labeled compound has an IC$_{50}$ less than about 500 μM, in another embodiment the labeled compound has an IC$_{50}$ less than about 100 μM, in yet another embodiment the labeled compound has an IC$_{50}$ less than about 10 μM, in yet another embodiment the labeled compound has an IC$_{50}$ less than about 1 μM and in still yet another embodiment the labeled inhibitor has an IC$_{50}$ less than about 0.1 μM.

Other uses of the disclosed receptors and methods will become apparent to those of skill in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1

Syntheses of Compounds of the Present Invention

Illustrated syntheses for compounds of the present invention are shown in FIGS. 1 through 10 where the variables have the same definitions as used throughout this disclosure.

The compounds of the invention and their syntheses are further illustrated by the following examples. The following examples are provided to further define the invention without, however, limiting the invention to the particulars of these examples. The compounds described herein, supra and infra, are named according to the AutoNom version 2.2, CS ChemDraw Ultra Version 9.0.7. In certain instances common names are used and it is understood that these common names would be recognized by those skilled in the art.

Chemistry: Proton nuclear magnetic resonance ($^1$H NMR) spectra were recorded on a Bruker Avance-400 equipped with a QNP (Quad Nucleus Probe) or a BBI (Broad Band Inverse) and z-gradient. Proton nuclear magnetic resonance ($^1$H NMR) spectra were also recorded on a Bruker Avance-500 equipped a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, t=triplet, q=quartet, m=multiplet, bs=broad singlet. Microwave irradiations were carried out using a Smith Synthesizer™ or an Emrys Optimizer™ (Biotage). Thin-layer chromatography (TLC) was performed on silica gel 60 $F_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a BUN rotary evaporator. Celite® 545 was used for filtration of palladium.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2. Resolution of Compound 6 by supercritical fluid chiral separation (Example 1.2): Chiral Technologies, Inc (USA).

Example 1.1

Preparation of 2-(7-(3-Cyano-5-(trifluoromethoxy) benzyloxy)-2,3-dihydro-1H-pyrrolo[1,2-a]indol-1-yl)acetic Acid (Compound 2)

Step A: Preparation of 7-Bromo-2,3-dihydro-1H-pyrrolo[1,2-a]indol-1-one

To a solution of ethyl 5-bromo-1H-indole-2-carboxylate (30 g, 112 mmol) in toluene (500 mL) was added portionwise sodium hydride (60% dispersion in mineral oil, 9.40 g, 235 mmol). Vigorous gas evolution was observed. The resulting white suspension was heated to 110° C. Butyl acrylate (35.1 mL, 246 mmol) was added dropwise (using a syring pump) over 24 h while stirring vigorously at an internal temperature of 110° C. Additional butyl acrylate (10 mL) was added in one portion and stirring was continued at 110° C. for 4 h followed by additional sodium hydride (60% dispersion in mineral oil, 5 g) and butyl acrylate (10 mL). 4 h later, butyl acrylate (6 mL) was added. Stirring was continued at 110° C. for a total of 48 h. The reaction was cooled in an ice-bath and 2 M HCl (400 mL) was added carefully. The layers were separated and the aqueous layer was extracted with dichloromethane (2×200 mL). The combined organic extracts were washed with brine, dried over MgSO$_4$, filtered and concentrated. The resulting orange residue was dissolved in acetic acid (900 mL) and water (100 mL). The orange solution was refluxed 16 h before the solvents were removed under vacuum. To the residue was added dichloromethane (300 mL). The resulting precipitate was collected by filtration and rinsed twice with dichloromethane to provide the title compound. LCMS m/z=250.2 [M+H]$^+$; $^1$H NMR (400 MHz, DMSO-d$_6$) δ ppm 3.20 (t, J=6.1 Hz, 2H), 4.46 (t, J=6.1 Hz, 2H), 6.92 (s, 1H), 7.46 (dd, J=8.8, 1.8 Hz, 1H), 7.63 (d, J=8.8 Hz, 1H), 7.98 (d, J=2.0 Hz, 1H).

Step B: Preparation of tert-Butyl 2-(7-Bromo-2,3-dihydro-1H-pyrrolo[1,2-a]indol-1-ylidene)acetate To a solution of 7-bromo-2,3-dihydro-1H-pyrrolo[1,2-a] indol-1-one (0.50 g, 1.999 mmol) in THF (10 mL) was added (tert-butoxycarbonylmethylene)triphenylphosphorane (1.881 g, 5.00 mmol). The mixture was stirred at 65° C. for 16 h and concentrated. The residue was purified by silica gel flash chromatography to provide the title compound (0.50 g). LCMS m/z=348 [M+H]$^+$.

Step C: Preparation of tert-Butyl 2-(7-(4,4,5,5-Tetramethyl-1,3,2-dioxaborolan-2-yl)-2,3-dihydro-1H-pyrrolo[1,2-a]indol-1-ylidene)acetate To a solution of tert-butyl 2-(7-bromo-2,3-dihydro-1H-pyrrolo[1,2-a]indol-1-ylidene)acetate (300 mg, 0.86 mmol) and potassium acetate (296 mg, 3.02 mmol) in dioxane (10 mL) was added 4,4,4',4',5,5,5',5'-octamethyl-2,2'-bi(1,3,2-dioxaborolane) (241 mg, 0.95 mmol). Nitrogen was bubbled through the mixture for 10 min. PdCl$_2$(dppf) (31.5 mg, 0.04 mmol) was added and the mixture was stirred under nitrogen at 90° C. for 1.5 h. The mixture was concentrated. The residue was purified by silica gel flash chromatography to provide the title compound as a yellow solid (340 mg). LCMS m/z=396.3 [M+H]$^+$.

Step D: Preparation of tert-Butyl 2-(7-Hydroxy-2,3-dihydro-1H-pyrrolo[1,2-a]indol-1-ylidene)acetate To a solution of tert-butyl 2-(7-(4,4,5,5-tetramethyl-1,3,2-dioxaborolan-2-yl)-2,3-dihydro-1H-pyrrolo[1,2-a]indol-1-ylidene)acetate (330 mg, 0.835 mmol) in THF (10 mL) was added a 2.0 M aqueous solution of sodium hydroxide (4.17 mL, 8.35 mmol). Then was added dropwise hydrogen peroxide (30 wt % aqueous solution, 0.853 mL, 8.35 mmol). The mixture was stirred at 23° C. for 25 min before 0.5 M HCl (50 mL) was added. The resulting mixture was extracted with dichloromethane (2×35 mL). The combined organic extracts were dried over MgSO$_4$, filtered and concentrated under vacuum. The residue was purified by silica gel flash chromatography to provide the title compound as a pale yellow solid (186 mg). LCMS m/z=286.3 [M+H]$^+$.

Step E: Preparation of tert-Butyl 2-(7-Hydroxy-2,3-dihydro-1H-pyrrolo[1,2-a]indol-1-yl)acetate tert-Butyl 2-(7-hydroxy-2,3-dihydro-1H-pyrrolo[1,2-a] indol-1-ylidene)acetate (230 mg, 0.806 mmol) was dissolved in ethyl acetate (5 mL). Degussa wet (50 wt % water) 10% Pd/C (223 mg, 0.105 mmol) was added and the mixture was stirred in a hydrogenation reactor under 95 psi hydrogen for 3 h. The mixture was filtered through Celite®. The filtrate was concentrated and purified by silica gel flash chromatography to provide the title compound as a white solid (131 mg). LCMS m/z=288.3 [M+H]$^+$.

Step F: Preparation of tert-Butyl 2-(7-(3-Cyano-5-(trifluoromethoxy)benzyloxy)-2,3-dihydro-1H-pyrrolo[1,2-a]indol-1-yl)acetate To an ice-cooled solution of tert-butyl 2-(7-hydroxy-2,3-dihydro-1H-pyrrolo[1,2-a]indol-1-yl)acetate (131 mg, 0.456 mmol), 3-(hydroxymethyl)-5-(trifluoromethoxy)benzonitrile (114 mg, 0.524 mmol) and triphenylphosphine (179 mg, 0.684 mmol) in THF (3 mL) was added diisopropyl diazene-1,2-dicarboxylate (0.135 mL, 0.684 mmol) dropwise. After stirring at 0° C. for 15 min, the cooling bath was removed and the mixture was stirred at 23° C. for 3 h and then concentrated. The residue was purified by preparative TLC to provide the title compound as a yellow solid (50 mg). LCMS m/z=487.4 [M+H]$^+$.

Step G: Preparation of 2-(7-(3-Cyano-5-(trifluoromethoxy)benzyloxy)-2,3-dihydro-1H-pyrrolo[1,2-a]indol-1-yl)acetic Acid To a solution of tert-butyl 2-(7-(3-cyano-5-(trifluoromethoxy)benzyloxy)-2,3-dihydro-1H-pyrrolo[1,2-a]indol-1-yl)acetate (50 mg, 0.103 mmol) and thioanisole (0.121 mL, 1.028 mmol) in dichloromethane (1 mL) was added trifluoroacetic acid (0.305 mL, 4.11 mmol). The solution was stirred at 23° C. for 3 h. The reaction mixture was concentrated. The residue was triturated with hexanes and purified by HPLC to provide the title compound as a white solid (19 mg). LCMS m/z=431.2 [M+H]$^+$; $^1$H NMR (400 MHz, CDCl$_3$) δ ppm 2.27-2.36 (m, 1H), 2.68 (dd, J=16.6, 8.2 Hz, 1H), 2.87-2.96 (m, 2H), 3.76 (quintet, J=7.5 Hz, 1H), 3.99-4.05 (m, 1H), 4.11-4.17 (m, 1H), 5.11 (s, 2H), 6.13 (s, 1H), 6.86 (dd, J=8.7, 2.4 Hz, 1H), 7.05 (d, J=2.4 Hz, 1H), 7.16 (d, J=8.7 Hz, 1H), 7.43 (s, 1H), 7.57 (s, 1H), 7.68 (s, 1H).

Example 1.2

Preparation of 2-(7-(3-Cyano-4-isopropoxybenzyloxy)-2,3-dihydro-1H-pyrrolo[1,2-a]indol-1-yl)acetic Acid (Compound 6)

Step A: Preparation of 7-(Benzyloxy)-2,3-dihydro-1H-pyrrolo[1,2-a]indol-1-one Ethyl 5-(benzyloxy)-1H-indole-2-carboxylate (25 g, 85 mmol) was dissolved in toluene (125 mL) and 60% sodium hydride in mineral oil (7.79 g, 195 mmol) was added portionwise. The reaction was stirred for 50 min and butyl acrylate (26.6 mL, 186 mmol) was added. The reaction was stirred at room temperature for 1.5 h and additional butyl acrylate (20 mL) was added. After stirring for 30 min, the solution was warmed to 70° C. and stirred for 1 h. The reaction was cooled to room temperature and sodium hydride (4.0 g) was added. The reaction was warmed to 70° C. causing the reaction to reflux. The heat source was removed and butyl acrylate (15 mL) was added and heating at 70° C. was resumed. After 30 min, the heat source was removed and the reaction was left to stir for 16 h. Water (25 mL) was added followed by 1.0 M HCL (250 mL) and 12 M HCL (50 mL). The aqueous layer was removed and the toluene was washed two times with water (100 mL). The toluene layer was concentrated under reduced pressure and the concentrate was taken up in acetic acid (120 mL) and water (12 mL). The reaction mixture was heated under reflux and stirred for 24 h. The reaction mixture was cooled to room temperature and water (200 mL) was added. The aqueous mixture was diluted with ethyl acetate and washed with water and brine. The ethyl acetate layer was filtered through a pad of Celite® and the filtrate was concentrated under reduced pressure. The residue was purified by crystallization from methanol to provide the title compound (8.0 g). LCMS m/z=278.2 [M+H]$^+$; $^1$H NMR (400 MHz, DMSO-d$_6$) δ ppm 3.20 (t, J=6.6 Hz, 2H), 4.41 (t, J=6.2 Hz, 2H), 5.11 (s, 2H), 6.91 (s, 1H), 7.13 (dd, J=9.0, 2.4 Hz, 1H), 7.19 (d, J=2.4 Hz, 1H), 7.30-7.42 (m, 4H), 7.44-7.49 (m, 2H).

Step B: Preparation of tert-Butyl 2-(7-(benzyloxy)-2,3-dihydro-1H-pyrrolo[1,2-a]indol-1-ylidene)acetate 7-(Benzyloxy)-2,3-dihydro-1H-pyrrolo[1,2-a]indol-1-one (3.6 g, 12.98 mmol) and (tert-butoxycarbonylmethylene)triphenylphosphorane (5.86 g, 15.58 mmol) were dissolved in toluene (40 mL) and the reaction mixture was heated under reflux and stirred for 24 h. The solution was cooled to room temperature. The precipitate was collected by filtration. The filtrate was concentrated under reduced pressure to yield additional white solid. The process was repeated to provide the title compound (1.391 g). LCMS m/z=376.4 [M+H]$^+$.

Step C: Preparation of tert-Butyl 2-(7-Hydroxy-2,3-dihydro-1H-pyrrolo[1,2-a]indol-1-yl)acetate tert-Butyl-2-(7-(benzyloxy)-2,3-dihydro-1H-pyrrolo[1,2-a]indol-1-ylidene)acetate (1.391 g, 3.70 mmol) was dissolved in THF (25 mL) and 10% palladium on carbon (50% in water, 217 mg) was added. The reaction mixture was placed under 225 psi of hydrogen in a hydrogenation reactor for 24 h. The mixture was filtered and the filtrate was concentrated under reduced pressure to provide tert-butyl 2-(7-(benzyloxy)-2,3-dihydro-1H-pyrrolo[1,2-a]indol-1-yl)acetate. The above material was taken up in a mixture of THF (20 mL) and EtOH (20 mL) and Pd(OH)$_2$/C (250 mg) was added. The reaction mixture was placed under 200 psi of hydrogen in a hydrogenation reactor for 2 days. Additional Pd(OH)$_2$/C (250 mg) was added and the reaction mixture was placed under 300 psi of hydrogen in a hydrogenation reactor for 24 h. Pd(OH)$_2$/C (250 mg) was again added and the vessel placed under 500 psi of hydrogen in a hydrogenation reactor for 24 h. The hydrogenation reactor was warmed to 50° C. for 8 h. The reaction mixture was cooled to room temperature and AcOH (5 mL) was added. The reaction mixture was placed under 500 psi of hydrogen for 16 h. The reaction mixture was filtered through Celite® and the filtrate was concentrated under reduced pressure to provide a mixture of the title compound and tert-butyl 2-(7-hydroxy-2,3,9,9a-tetrahydro-1H-pyrrolo[1,2-a]indol-1-yl)acetate. The title compound (150 mg) was isolated by silica gel column chromatography. tert-Butyl 2-(7-hydroxy-2,3,9,9a-tetrahydro-1H-pyrrolo[1,2-a]indol-1-yl)acetate (600 mg) was dissolved in toluene (100 mL) and Pd/C (1.0 g) was added. The reaction mixture was warmed to 80° C. and stirred for 2 days. The reaction mixture was filtered through Celite® and the title compound (250 mg) was isolated as a white solid resulting from precipitation during concentration of the filtrate. LCMS m/z=288.3 [M+H]$^+$.

Step D: Preparation of tert-Butyl 2-(7-(3-cyano-4-isopropoxybenzyloxy)-2,3-dihydro-1H-pyrrolo[1,2-a]indol-1-yl)acetate tert-Butyl 2-(7-hydroxy-2,3-dihydro-1H-pyrrolo[1,2-a]indol-1-yl)acetate (461 mg, 1.60 mmol) was dissolved in DMF (3.0 mL) and 5-(chloromethyl)-2-isopropoxybenzonitrile (337 mg, 1.60 mmol) and cesium carbonate (533 mg, 1.60 mmol) were added. The reaction mixture was stirred at room temperature for 2 days and partitioned between ethyl acetate and water. The organics were removed and the aqueous mixture was extracted two times with ethyl acetate. The combined extracts were dried over $Na_2SO_4$, filtered and concentrated under reduced pressure. The residual oil was dissolved in methanol (10 mL) and cooled to 0° C. The precipitate was collected by filtration and triturated with 10% ethyl acetate/hexanes to provide the title compound (462 mg). LCMS m/z=461.5 [M+H]$^+$; $^1$H NMR (400 MHz, DMSO-d$_6$) δ ppm 1.31 (d, J=6.1 Hz, 6H), 1.44 (s, 9H), 2.15-2.25 (m, 1H), 2.51-2.68 (m, 2H), 2.71-2.81 (m, 1H), 3.53-3.61 (m, 1H), 3.91-3.99 (m, 1H), 4.04-4.13 (m, 1H), 4.78 (septet, J=6.1 Hz, 1H), 5.02 (s, 2H), 5.99 (s, 1H), 6.74 (dd, J=8.7, 2.4 Hz, 1H), 7.06 (d, J=2.4 Hz, 1H), 7.18 (d, J=8.7 Hz, 1H), 7.27 (d, J=9.0 Hz, 1H), 7.70 (dd, J=8.7, 2.3 Hz, 1H), 7.76 (d, J=2.1 Hz, 1H).

Step E: Preparation of 2-(7-(3-Cyano-4-isopropoxybenzyloxy)-2,3-dihydro-1H-pyrrolo[1,2-a]indol-1-yl)acetic Acid tert-Butyl 2-(7-(3-cyano-4-isopropoxybenzyloxy)-2,3-dihydro-1H-pyrrolo[1,2-a]indol-1-yl)acetate (452 mg, 0.981 mmol) was added to a solution of 2-amino-3-mercaptopropanoic acid (214 mg, 1.767 mmol) in TFA (5 mL) and was stirred at room temperature for 15 min. The reaction mixture was poured into ice water. The white precipitate was collected by filtration to provide the title compound (342 mg). LCMS m/z=405.5 [M+H]$^+$; $^1$H NMR (400 MHz, CDCl$_3$) δ ppm 1.40 (d, J=6.1 Hz, 6H), 2.26-2.36 (m, 1H), 2.66 (dd, J=16.4, 8.5 Hz, 1H), 2.85-2.97 (m, 2H), 3.72-3.80 (m, 1H), 3.98-4.06 (m, 1H), 4.10-4.17 (m, 1H), 4.65 (septet, J=6.1 Hz, 1H), 5.00 (s, 2H), 6.12 (s, 1H), 6.84 (dd, J=8.8, 2.4 Hz, 1H), 6.96 (d, J=8.7 Hz, 1H), 7.06 (d, J=2.4 Hz, 1H), 7.14 (d, J=8.7 Hz, 1H), 7.58 (dd, J=8.8, 2.4 Hz, 1H), 7.64 (d, J=2.1 Hz, 1H).
Resolution of Compound 6 by Chiral HPLC.
Column: normal phase preparative ChiralPak AD-H column, 5×25 cm ID
Eluent: 65% CO$_2$/35% IPA
Pressure: 270 bars (inlet) and 100 bars (back)
Gradient: Isocratic
Flow: 400 mL/min
Temperature: 25° C.
Detector: 230 nm
Retention Times: 1$^{st}$ enantiomer: 6.7 min; 2$^{nd}$ enantiomer: 9.2 min.

Example 1.3

Preparation of 2-(7-(4-Cyclopentyl-3-(trifluoromethyl)benzyloxy)-2,3-dihydro-1H-pyrrolo[1,2-a]indol-1-yl)acetic Acid (Compound 12)

Step A: Preparation of tert-Butyl 2-(7-(4-Cyclopentyl-3-(trifluoromethyl)benzyloxy)-2,3-dihydro-1H-pyrrolo[1,2-a]indol-1-yl)acetate tert-Butyl 2-(7-hydroxy-2,3-dihydro-1H-pyrrolo[1,2-a]indol-1-yl)acetate (0.563 g, 1.960 mmol), 4-(chloromethyl)-1-cyclopentyl-2-(trifluoromethyl)benzene (0.515 g, 1.960 mmol) and cesium carbonate (0.703 g, 2.156 mmol) in DMF (4 mL) were heated to 50° C. for 16 h in a 20 mL sealed scintillation vial. The reaction mixture was filtered by vacuum filtration through Celite® and washed with EtOAc (3×10 mL). The filtrate was concentrated under reduced pressure. The residue was taken up in EtOAc (25 mL), washed with water (2×25 mL), saturated NaCl (20 mL), dried over MgSO$_4$ and filtered. The filtrate was concentrated under reduced pressure and the residue was purified by silica gel column chromatography to give a yellow sticky oil. A precipitate, formed by addition of hexanes to the oil, was collected by filtration, was washed with hexanes (3×20 mL) and dried (vacuum oven) to provide the title compound as a white solid (0.6273 g). LCMS m/z=514.4 [M+H]$^+$; $^1$H NMR (400 MHz, DMSO-d$_6$) δ ppm 1.44 (s, 9H), 1.57-1.72 (m, 4H), 1.81-1.87 (m, 2H), 1.95-2.04 (m, 2H), 2.15-2.24 (m, 1H), 2.53-2.67 (m, 2H), 2.71-2.81 (m, 1H), 3.20-3.27 (m, 1H), 3.57 (quintet, J=7.75 Hz, 1H), 3.91-3.99 (m, 1H), 4.06-4.13 (m, 1H), 5.13 (s, 2H), 5.99 (s, 1H), 6.77 (dd, J=8.65, 2.08 Hz, 1H), 7.07 (d, J=2.27 Hz, 1H), 7.19 (d, J=8.72 Hz, 1H), 7.62 (d, J=8.72 Hz, 1H) 7.68-7.70 (m, 2H).

Step B: Preparation of 2-(7-(4-Cyclopentyl-3-(trifluoromethyl)benzyloxy)-2,3-dihydro-1H-pyrrolo[1,2-a]indol-1-yl)acetic Acid tert-Butyl 2-(7-(4-cyclopentyl-3-(trifluoromethyl)benzyloxy)-2,3-dihydro-1H-pyrrolo[1,2-a]indol-1-yl)acetate (0.800 g, 1.558 mmol) was added to a solution of 2-amino-3-mercaptopropanoic acid (0.189 g, 1.558 mmol) in TFA (10 mL). The reaction mixture was stirred at 23° C. for 15 min in a 20 mL sealed scintillation vial. After 15 min the reaction mixture was poured into ice water and a precipitate formed. The precipitate was collected by filtration, washed with hexanes (3×20 mL) and dried (vacuum oven) to provide the title compound as a white solid (0.595 g). LCMS m/z=458.4 [M+H]$^+$; $^1$H NMR (400 MHz, DMSO-d$_6$) δ ppm 1.53-1.74 (m, 4H), 1.79-1.89 (m, 2H), 1.94-2.04 (m, 2H), 2.15-2.26 (m, 1H), 2.51-2.69 (m, 2H), 2.72-2.83 (m, 1H), 3.23-3.27 (m, 1H), 3.58 (quintet, J=7.20 Hz, 1H), 3.91-4.00 (m, 1H), 4.05-4.14 (m, 1H), 5.13 (s, 2H), 6.01 (s, 1H), 6.77 (dd, J=8.72, 2.40 Hz, 1H), 7.07 (d, J=2.27 Hz, 1H), 7.19 (d, J=8.84 Hz, 1H), 7.62 (d, J=8.08 Hz, 1H), 7.68-7.71 (m, 2H), 12.27 (s, 1H).
Resolution of Compound 12 by Chiral HPLC.
Column: normal phase preparative ChiralPak AD-H column, 20×250 mm ID, 5 μm particle size
Eluent: Acetonitrile 100%
Gradient: Isocratic
Flow: 7 mL/min
Detector: 280 nm
Retention Times: 1$^{st}$ enantiomer: 15 min; 2$^{nd}$ enantiomer: 18 min.

Example 1.4

Preparation of 2-(9-Chloro-7-(4-cyclopentyl-3-(trifluoromethyl)benzyloxy)-2,3-dihydro-1H-pyrrolo[1,2-a]indol-1-yl)acetic Acid (Compound 3)

To a solution of 2-(7-(4-cyclopentyl-3-(trifluoromethyl)benzyloxy)-2,3-dihydro-1H-pyrrolo[1,2-a]indol-1-yl)acetic acid (34 mg, 0.074 mmol) dissolved in DCM (0.500 mL) and cooled to 0° C. was added NCS (9.92 mg, 0.074 mmol). The reaction was stirred at 0° C. for 15 min in a 20 mL sealed scintillation vial. After 15 min, the reaction mixture was diluted with DCM and washed with water (2×10 mL), washed with sodium thiolsulfate pentahydrate (aq.) (2×10 mL), dried over MgSO$_4$ and filtered. The filtrate was concentrated under reduced pressure to give the title compound as a light yellow solid (32 mg). LCMS m/z=492.3 [M+H]$^+$; $^1$H NMR (400 MHz, DMSO-d$_6$) δ ppm 1.54-1.73 (m, 4H), 1.80-1.89 (m, 2H), 1.95-2.05 (m, 2H), 2.24-2.35 (m, 1H), 2.52-2.58 (m, 1H), 2.77-2.87 (m, 1H), 2.94 (dd, J=16.36, 4.11 Hz, 1H), 3.21-3.29 (m, 1H), 3.64-3.72 (m, 1H), 3.95-4.05 (m, 1H), 4.11-4.19 (m, 1H), 5.18 (s, 2H), 6.87 (dd, J=8.78, 2.46 Hz, 1H), 6.98 (d, J=2.27 Hz, 1H), 7.29 (d, J=8.84 Hz, 1H), 7.63 (d, J=7.96 Hz 1H), 7.69-7.76 (m, 2H), 12.35 (bs, 1H).

Example 1.5

Preparation of 2-(9-Bromo-7-(4-cyclopentyl-3-(trifluoromethyl)benzyloxy)-2,3-dihydro-1H-pyrrolo indol-1-yl)acetic Acid (Compound 7)

From 2-(7-(4-cyclopentyl-3-(trifluoromethyl)benzyloxy)-2,3-dihydro-1H-pyrrolo[1,2-a]indol-1-yl)acetic acid and NBS, in a similar manner to the one described in Example 1.4, the title compound was obtained as a light yellow solid. LCMS m/z=536.6 [M+H]$^+$; $^1$H NMR (400 MHz, DMSO-d$_6$) δ ppm 1.55-1.71 (m, 4H), 1.80-1.89 (m, 2H), 1.95-2.04 (m, 2H), 2.25-2.36 (m, 1H), 2.51-2.57 (m, 1H), 2.78-2.88 (m, 1H), 2.98 (dd, J=16.42, 3.66 Hz, 1H), 3.22-3.28 (m, 1H), 3.58-3.67 (m, 1H), 3.98-4.06 (m, 1H), 4.13-4.20 (m, 1H), 5.18 (s, 2H), 6.88 (dd, J=8.84, 2.40 Hz, 1H), 6.91 (d, J=2.15 Hz, 1H), 7.29 (d, J=8.72 Hz, 1H), 7.63 (d, J=8.21 Hz, 1H), 7.70-7.76 (m, 2H), 12.33 (bs, 1H).

Example 1.6

Preparation of 2-(6-(4-Cyclopentyl-3-(trifluoromethyl)benzyloxy)-2,3-dihydro-1H-benzo[d]pyrrolo[1,2-a]imidazol-3-yl)acetic Acid (Compound 14)

Step A: Preparation of Ethyl 2-(2-oxopyrrolidin-3-yl)Acetate tert-Butyl 2-oxopyrrolidine-1-carboxylate (10 g, 54.0 mmol) was dissolved in THF (75 mL) and cooled to −78° C. LDA (1.8 M in THF/heptane, 30.0 mL, 54.0 mmol) was added and the solution was stirred for 1 h. Ethyl 2-bromoacetate (9.02 g, 54.0 mmol) was added and the mixture was stirred for 1 h and allowed to warm to room temperature and stirred for 16 h. The reaction mixture was partitioned between water and EtOAc. The aqueous layer was extracted two times with EtOAc and the combined extracts were dried (sodium sulfate), filtered and concentrated under reduced pressure. The residue was purified by column chromatography to provide partially purified tert-butyl 3-(2-ethoxy-2-oxoethyl)-2-oxopyrrolidine-1-carboxylate. tert-Butyl 3-(2-ethoxy-2-oxoethyl)-2-oxopyrrolidine-1-carboxylate (4.72 g, 17.40 mmol) was dissolved in EtOH (30 mL) and TFA (10 mL). The reaction was stirred at room temperature for 2 h and 20 mL of TFA was added. After stirring for an additional 2 h, the reaction mixture was concentrated under reduced pressure and purified by column chromatography to provide the title compound (1.77 g). $^1$H NMR (400 MHz, CDCl$_3$) δ ppm 1.26 (t, J=7.2 Hz, 3H), 1.81-1.93 (m, 1H), 2.35-2.49 (m, 2H), 2.75-2.85 (m, 1H), 2.88 (dd, J=16.4, 3.9 Hz, 1H), 3.31-3.40 (m, 2H), 4.09-4.21 (m, 2H), 5.96 (bs, 1H).

Step B: Preparation of Ethyl 2-(1-(4-(Benzyloxy)-2-nitrophenyl)-2-oxopyrrolidin-3-yl)acetate Ethyl 2-(2-oxopyn-olidin-3-yl)acetate (1.77 g, 10.34 mmol) was dissolved in DMF (20 mL) and cooled to 0° C. Sodium hydride (60% in mineral oil, 0.414 g, 10.34 mmol) was added. After stirring for several min, the reaction was allowed to warm to room temperature and stirred for 10 min. 4-(Benzyloxy)-1-fluoro-2-nitrobenzene (2.56 g, 10.34 mmol) was added and the mixture was stirred at room temperature for 21 h. The reaction was poured into water and acidified to pH 5 with 1.0 M HCL. The aqueous mixture was extracted three times with EtOAc and the combined extracts were dried over sodium sulfate, filtered and concentrated under reduced pressure. The residue was purified by column chromatography to provide the title compound (1.09 g). LCMS m/z=399.4 [M+H]$^+$; $^1$H NMR (400 MHz, CDCl$_3$) δ ppm 1.27 (t, J=7.2 Hz, 3H), 1.97-2.01 (m, 1H), 2.46-2.59 (m, 2H), 2.95 (dd, J=12.9, 3.8 Hz, 1H), 2.96-3.06 (m, 1H), 3.69-3.76 (m, 1H), 3.79-3.88 (m, 1H), 4.17 (q, J=7.1 Hz, 2H), 5.13 (s, 2H), 6.90 (d, J=2.5 Hz, 1H), 6.94 (dd, J=9.0, 2.7 Hz, 1H), 7.37-7.42 (m, 5H), 8.04 (d, J=9.1 Hz, 1H).

Step C: Preparation of Ethyl 2-(1-(2-Amino-4-hydroxyphenyl)-2-oxopyrrolidin-3-yl)acetate Ethyl 2-(1-(4-(benzyloxy)-2-nitrophenyl)-2-oxopyrrolidin-3-yl)acetate (1.09 g, 2.73 mmol) was taken up in EtOH and THF (1:1 mixture, 40 mL) and Pd/C (500 mg) was added. The reaction was pressurized with hydrogen (500 psi) in a bomb reactor and stirred at room temperature for 1 h. The reaction mixture was filtered through a pad of Celite® and the filtrate was concentrated under reduced pressure to provide the title compound (752 mg). LCMS m/z=279.3 [M+H]$^+$; $^1$H NMR (400 MHz, CDCl$_3$) δ ppm 1.27 (t, J=7.1 Hz, 3H), 1.96-2.08 (m, 1H), 2.38-2.48 (m, 1H), 2.70 (dd, J=16.9, 7.7 Hz, 1H), 2.86 (dd, J=17.0, 4.0 Hz, 1H), 2.95-3.05 (m, 1H), 3.63-3.79 (m, 2H), 4.18 (q, J=7.2 Hz, 2H), 6.53 (d, J=2.7 Hz, 1H), 6.59 (dd, J=8.6, 2.6 Hz, 1H), 6.66 (d, J=8.6 Hz, 1H).

Step D: Preparation of Ethyl 2-(6-Hydroxy-2,3-dihydro-1H-benzo[d]pyrrolo[1,2-a]imidazol-3-yl)acetate Ethyl 2-(1-(2-amino-4-hydroxyphenyl)-2-oxopyrrolidin-3-yl)acetate (0.740 g, 2.66 mmol) was dissolved in AcOH (50 mL) and was warmed to 75° C. and stirred for 8 h. The reaction mixture was concentrated under reduced pressure and the residue was taken up in toluene and concentrated again. The black concentrate was filtered through a plug of silica eluting with 10% MeOH in DCM. The filtrate was concentrated to provide the title compound (666 mg). LCMS m/z=261.2 [M+H]$^+$; $^1$H NMR (400 MHz, CDCl$_3$) δ ppm 1.19 (t, J=7.1 Hz, 3H), 2.25-2.36 (m, 1H), 2.63 (dd, J=16.4, 8.8 Hz, 1H), 2.79-2.89 (m, 2H), 3.48-3.56 (m, 1H), 3.90-3.98 (m, 1H), 4.02-4.14 (m, 2H), 6.61 (dd, J=8.6, 2.3 Hz, 1H), 6.73 (d, J=2.0 Hz, 1H), 7.30 (d, J=8.6 Hz, 1H), 9.11 (bs, 1H).

Step E: Preparation of Ethyl 2-(6-(4-Cyclopentyl-3-(trifluoromethyl)benzyloxy)-2,3-dihydro-1H-benzo[d]pyrrolo[1,2-a]imidazol-3-yl)acetate Ethyl 2-(6-hydroxy-2,3-dihydro-1H-benzo[d]pyrrolo[1,2-a]imidazol-3-yl)acetate (0.1 g, 0.384 mmol) was dissolved in DMF (1.0 mL) and cesium carbonate (0.150 g, 0.461 mmol) and 4-(chloromethyl)-1-cyclopentyl-2-(trifluoromethyl)benzene (0.111 g, 0.423 mmol) were added. The reaction mixture was stirred at room temperature for 1.5 h and then warmed to 40° C. After stirring for 1 h, the reaction mixture was diluted with water and extracted three times with EtOAc. The combined extracts were dried over sodium sulfate, filtered and concentrated under reduced pressure. The residue was purified by column chromatography to provide the title compound (126 mg). LCMS m/z=487.4 [M+H]$^+$; $^1$H NMR (400 MHz, CDCl$_3$) δ ppm 1.26 (t, J=7.2 Hz, 3H), 1.55-1.65 (m, 2H), 1.67-1.78 (m, 2H), 1.81-1.91 (m, 2H), 2.04-2.14 (m, 2H), 2.36-2.47 (m, 1H), 2.62 (dd, J=16.4, 9.7 Hz, 1H), 2.97-3.07 (m, 1H), 3.16 (dd, J=16.8, 3.8 Hz, 1H), 3.33-3.43 (m, 1H), 3.64-3.74 (m, 1H), 3.97-4.05 (m, 1H), 4.09-4.21 (m, 3H), 5.09 (s, 2H), 6.87 (d, J=2.4 Hz, 1H), 6.93 (dd, J=8.6, 2.4 Hz, 1H), 7.49 (d, J=8.3 Hz, 1H), 7.56-7.61 (m, 2H), 7.68 (s, 1H).

Step F: Preparation of 2-(6-(4-Cyclopentyl-3-(trifluoromethyl)benzyloxy)-2,3-dihydro-1H-benzo[d]pyrrolo[1,2-a]imidazol-3-yl)acetic Acid Ethyl 2-(6-(4-cyclopentyl-3-(trifluoromethyl)benzyloxy)-2,3-dihydro-1H-benzo[d]pyrrolo[1,2-a]imidazol-3-yl)acetate (0.109 g, 0.224 mmol) was dissolved in dioxane (2.5 mL) and 1.0 M aqueous lithium hydroxide (0.672 mL, 0.672 mmol) was added. The reaction mixture was stirred at room temperature for 1.5 h and then acidified (pH 2) with 1.0 M HCl. The reaction mixture was extracted three times with EtOAc and the combined extracts were dried over sodium sulfate, filtered and concentrated under reduced pressure to provide the title compound (103 mg). LCMS m/z=459.3 [M+H]$^+$; $^1$H NMR (400 MHz, DMSO-d$_6$) δ ppm 1.54-1.65 (m, 2H), 1.67-1.79 (m, 2H), 1.80-1.91 (m, 2H), 2.05-2.14 (m, 2H), 2.42-2.53 (m, 1H), 2.89 (d, J=7.1 Hz, 1H), 2.95-3.22 (m, 2H), 3.33-3.43 (m, 1H), 3.78-3.87 (m, 1H), 4.03-4.12 (m, 1H), 4.14-4.23 (m, 1H), 5.09 (s, 2H), 6.88 (d, J=2.4 Hz, 1H), 6.97 (dd, J=8.8, 2.5 Hz, 1H), 7.48 (d, J=8.2 Hz, 1H), 7.57 (d, J=8.1 Hz, 1H), 7.62 (d, J=8.8 Hz, 1H), 7.68 (s, 1H).

Example 1.7

Preparation of 2-(7-(4-Cyclopentyl-3-(trifluoromethyl)benzyloxy)-9-fluoro-2,3-dihydro-1H-pyrrolo[1,2-a]indol-1-yl)acetic Acid (Compound 5)

2-(7-(4-Cyclopentyl-3-(trifluoromethyl)benzyloxy)-2,3-dihydro-1H-pyrrolo[1,2-a]indol-1-yl)acetic Acid (0.051 g, 0.111 mmol) was dissolved in anhydrous DCM (2.0 mL). The reaction was cooled to 0° C. and N-fluoropyridinium triflate (0.029 g, 0.105 mmol) was added. The reaction was stirred at 0° C. for 1 h and then allowed to warm to 25° C. After 5 h at 25° C., the reaction was cooled to 0° C., additional N-fluoropyridinium triflate (4 mg, 0.01 mmol) was added and the reaction was allowed to warm to 25° C. After 5 h, the reaction was diluted with EtOAc (50 mL), washed with water (10 mL×2), brine (10 mL), dried over MgSO$_4$ and concentrated under vacuum. The oily residue was purified by silica gel flash column chromatography to give an oil (0.015 g). The oil was dissolved in DCM and co-evaporated with an excess of hexanes to give the title compound as a white solid. LCMS m/z=476.3 [M+H]$^+$; $^1$H NMR (400 MHz, DMSO-d$_6$) δ ppm 1.66 (d, J=6.69 Hz, 4H), 1.84 (d, J=2.53 Hz, 2H), 1.94-2.06 (m, 3H), 2.19-2.30 (m, 1H), 2.54-2.63 (m, 1H), 2.71-2.82 (m, 2H), 3.67-3.77 (m, 1H), 3.91-4.01 (m, 1H), 4.06-4.15 (m, 1H), 5.16 (s, 2H), 6.83 (dd, J=8.84, 2.40 Hz, 1H), 7.02 (d, J=2.27 Hz, 1H), 7.22 (dd, J=8.97, 2.27 Hz, 1H), 7.60-7.66 (m, 1H), 7.68-7.74 (m, 2H), 12.31 (bs, 1H).

Resolution Via Chiral HPLC

Column: normal phase preparative Chiralcel IC, 20×250 mm ID, 5 μm particle size

Eluent: 50:50 MTBE:Hexane with no trifluoroacetic acid

Gradient: Isocratic

Flow: 12 mL/minute

Detector: 280 nm

Retention Times: 1$^{st}$ enantiomer: 12 min; 2$^{nd}$ enantiomer: 16 min

Example 1.8

Preparation of 2-(7-(4-Cyclopentyl-3-(trifluoromethyl)benzyloxy)-9-iodo-2,3-dihydro-1H-pyrrolo[1,2-a]indol-1-yl)acetic Acid (Compound 10)

From 2-(7-(4-cyclopentyl-3-(trifluoromethyl)benzyloxy)-2,3-dihydro-1H-pyrrolo[1,2-a]indol-1-yl)acetic acid and 1-iodopyrrolidine-2,5-dione, in a similar manner to the one described in Example 1.4, the title compound was obtained as a brown solid. LCMS m/z=584.5 [M+H]$^+$; $^1$H NMR (400 MHz, DMSO-d$_6$) δ ppm 1.55-1.73 (m, 4H), 1.78-1.89 (m, 2H), 1.94-2.06 (m, 2H), 2.25-2.37 (m, 1H), 2.45-2.58 (m, 1H), 2.77-2.90 (m, 1H), 3.00 (dd, J=16.36, 3.35 Hz, 1H), 3.20-3.29 (m, 1H), 3.52-3.61 (m, 1H), 4.00-4.10 (m, 1H), 4.13-4.23 (m, 1H), 5.18 (s, 2H), 6.80 (d, J=2.40 Hz, 1H), 6.87 (dd, J=8.78, 2.34 Hz, 1H), 7.26 (d, J=8.72 Hz, 1H), 7.63 (d, J=8.08 Hz, 1H), 7.70-7.78 (m, 2H), 12.30 (bs, 1H).

Example 1.9

Preparation of 2-(7-(4-Cyclopentyl-3-(trifluoromethyl)benzyloxy)-9-methyl-2,3-dihydro-1H-pyrrolo[1,2-a]indol-1-yl)acetic Acid (Compound 1)

Step A: Preparation of tert-Butyl 2-(7-(4-Cyclopentyl-3-(trifluoromethyl)benzyloxy)-9-iodo-2,3-dihydro-1H-pyrrolo[1,2-a]indol-1-yl)acetate To a solution of tert-butyl 2-(7-(4-cyclopentyl-3-(trifluoromethyl)benzyloxy)-2,3-dihydro-1H-pyrrolo[1,2-a]indol-1-yl)acetate (100 mg, 0.195 mmol) in DCM (2 mL) was added 1-iodopyrrolidine-2,5-dione (43.8 mg, 0.195 mmol) at 0° C. and the reaction was allowed to continue at 0° C. for 30 min in a 20 mL sealed scintillation vial. After 30 min, the reaction mixture was diluted with DCM, washed with water (3×10 mL), sodium thiolsulfate pentahydrate (aq) (2×10 mL), dried over MgSO$_4$ and filtered. The filtrate was concentrated under reduced pressure to give the title compound as an off-white solid (118 mg). LCMS m/z=640.4 [M+H]$^+$; $^1$H NMR (400 MHz, DMSO-d$_6$) δ ppm 1.38 (s, 9H), 1.55-1.73 (m, 4H), 1.79-1.89 (m, 2H), 1.95-2.05 (m, 2H), 2.26-2.38 (m, 1H), 2.51-2.56 (m, 1H), 2.77-2.88 (m, 1H), 2.94 (dd, J=15.92, 3.41 Hz, 1H), 3.20-3.28 (m, 1H), 3.50-3.60 (m, 1H), 3.99-4.08 (m, 1H), 4.12-4.21 (m, 1H), 5.18 (s, 2H), 6.79 (d, J=2.27 Hz, 1H), 6.87 (dd, J=8.78, 2.46 Hz, 1H), 7.26 (d, J=8.84 Hz, 1H), 7.63 (d, J=8.59 Hz, 1H), 7.70-7.77 (m, 2H).

Step B: Preparation of tert-Butyl 2-(7-(4-Cyclopentyl-3-(trifluoromethyl)benzyloxy)-9-methyl-2,3-dihydro-1H-pyrrolo[1,2-a]indol-1-yl)acetate To a solution of tert-butyl 2-(7-(4-cyclopentyl-3-(trifluoromethyl)benzyloxy)-9-iodo-2,3-dihydro-1H-pyrrolo[1,2-a]indol-1-yl)acetate (50.0 mg, 0.078 mmol) in THF (1 mL) in a heavy-walled sealed microwave tube (0.5-2.0 mL) under N$_2$ was added methylzinc(II) chloride (2.0 M in THF, 0.055 mL, 0.109 mmol) and bis(tri-t-butylphosphine)palladium(0) (3.60 mg, 7.04 μmol). The reaction mixture was then heated to 70° C. for 2 h, quenched with saturated NaHCO$_3$ and filtered by vacuum filtration through a pad of Celite®. The pad of Celite® was washed with EtOAc (2×5 mL). The filtrate was extracted with EtOAc (3×5 mL). The organic layers were combined and washed with saturated NaCl (1×10 mL), dried over MgSO$_4$ and filtered by vacuum filtration. The filtrate was concentrated under reduced pressure. The residue was purified by preparative TLC to give the title compound as a colorless oil (21.1 mg). LCMS m/z=528.3 [M+H]⁺; ¹H NMR (400 MHz, CDCl₃) δ ppm 1.45 (s, 9H), 1.56-1.66 (m, 2H), 1.68-1.79 (m, 2H), 1.81-1.92 (m, 2H), 2.04-2.15 (m, 2H), 2.23 (s, 3H), 2.26-2.36 (m, 1H), 2.41 (dd, J=15.66, 10.11 Hz, 1H), 2.78-2.90 (m, 2H), 3.31-3.44 (m, 1H), 3.65-3.74 (m, 1H), 3.90-3.98 (m, 1H), 3.99-4.12 (m, 1H), 5.09 (s, 2H), 6.85 (dd, J=8.72, 2.40 Hz, 1H), 7.03 (d, J=2.15 Hz, 1H), 7.09 (d, J=8.72 Hz, 1H), 7.47 (d, J=8.08 Hz, 1H), 7.60 (d, J=8.21 Hz, 1H), 7.71 (d, J=1.39 Hz, 1H).

Step C: Preparation of 2-(7-(4-Cyclopentyl-3-(trifluoromethyl)benzyloxy)-9-methyl-2,3-dihydro-1H-pyrrolo [1,2-a] indol-1-yl)acetic Acid tert-Butyl 2-(7-(4-cyclopentyl-3-(trifluoromethyl)benzyloxy)-9-methyl-2,3-dihydro-1H-pyrrolo[1,2-a]indol-1-yl)acetate (17.5 mg, 0.033 mmol) was added to a solution of 2-amino-3-mercaptopropanoic acid (4.02 mg, 0.033 mmol) in TFA (1 mL) and were stirred at 23° C. for 15 min in a 20 mL sealed scintillation vial. After 15 min, the reaction mixture was poured into about 4 mL of ice water. A precipitate was formed and collected by vacuum filtration. The solid was washed with n-hexane (3×5 mL) and dried (vacuum oven) to give the title compound as a tan solid (13 mg). LCMS m/z=472.4 [M+H]⁺; ¹H NMR (400 MHz, DMSO-d₆) δ ppm 1.54-1.73 (m, 4H), 1.80-1.90 (m, 2H), 1.95-2.05 (m, 2H), 2.15 (s, 3H), 2.18-2.30 (m, 1H), 2.42-2.48 (m, 1H), 2.69-2.83 (m, 2H), 3.20-3.31 (m, 1H), 3.56-3.66 (m, 1H), 3.87-3.96 (m, 1H), 3.98-4.08 (m, 1H), 5.14 (s, 2H), 6.76 (dd, J=8.72, 2.40 Hz, 1H), 7.02 (d, J=2.27 Hz, 1H), 7.14 (d, J=8.72 Hz, 1H), 7.63 (d, J=7.96 Hz, 1H), 7.68-7.77 (m, 2H), 12.33 (bs, 1H).

Example 1.10

Preparation of 2-(7-(4-Cyclopentyl-3-(trifluoromethyl)benzyloxy)-9-cyclopropyl-2,3-dihydro-1H-pyrrolo[1,2-a]indol-1-yl)acetic Acid (Compound 9)

Step A: Preparation of tert-Butyl 2-(7-(4-Cyclopentyl-3-(trifluoromethyl)benzyloxy)-9-cyclopropyl-2,3-dihydro-1H-pyrrolo[1,2-a]indol-1-yl)acetate To a solution of tert-butyl 2-(7-(4-cyclopentyl-3-(trifluoromethyl)benzyloxy)-9-iodo-2,3-dihydro-1H-pyrrolo[1,2-a]indol-1-yl)acetate (50.0 mg, 0.078 mmol) in THF (1 mL) in a 2.0 mL heavy-walled sealed microwave tube under N₂ was added cyclopropylzinc(II) bromide (0.5 M solution in THF, 0.219 mL, 0.109 mmol) and bis(tri-t-butylphosphine)palladium(0) (3.60 mg, 7.04 μmol). The reaction mixture was heated to 70° C. for 2 h, quenched with saturated NaHCO₃ and filtered by vacuum filtration through Celite®. The Celite® was washed with EtOAc (2×5 mL). The filtrate was extracted with EtOAc (3×5 mL). The organic layers were combined and washed with saturated NaCl (10 mL), dried over MgSO₄, filtered by vacuum filtration. The filtrate was concentrated under reduced pressure. The residue was purified by preparative TLC to give the title compound as a amber oil (9.2 mg). LCMS m/z=554.6 [M+H]⁺.

Step B: Preparation of 2-(7-(4-Cyclopentyl-3-(trifluoromethyl)benzyloxy)-9-cyclopropyl-2,3-dihydro-1H-pyrrolo[1,2-a]indol-1-yl)acetic Acid tert-Butyl 2-(7-(4-cyclopentyl-3-(trifluoromethyl)benzyloxy)-9-cyclopropyl-2,3-dihydro-1H-pyrrolo[1,2-a]indol-1-yl)acetate (9.2 mg, 0.017 mmol) was added to a solution of 2-amino-3-mercaptopropanoic acid (2.013 mg, 0.017 mmol) in TFA (1 mL) and the resulting mixture was stirred at room temperature for 15 min in a 20 mL sealed scintillation vial. After 15 min, the reaction mixture was poured into approximately 4 mL of ice water. A precipitate formed and was collected by vacuum filtration. The solid was washed with n-hexane (3×5 mL) and dried (vacuum oven) to give the title compound as a off-white solid (5.5 mg). LCMS m/z=498.4 [M+H]⁺; ¹H NMR (400 MHz, DMSO-d₆) δ ppm 0.35-0.43 (m, 1H), 0.55-0.64 (m, 1H), 0.74-0.88 (m, 2H), 1.55-1.78 (m, 5H), 1.79-1.89 (m, 2H), 1.94-2.05 (m, 2H), 2.19-2.30 (m, 1H), 2.42-2.48 (m, 1H), 2.69-2.81 (m, 1H), 2.93 (dd, J=15.92, 3.79 Hz, 1H), 120-3.30 (m, 1H), 3.54-3.65 (m, 1H), 3.84-3.94 (m, 1H), 3.97-4.07 (m, 1H), 5.15 (s, 2H), 6.76 (dd, J=8.59, 2.27 Hz, 1H), 7.05 (d, J=2.27 Hz, 1H), 7.14 (d, J=8.59 Hz, 1H), 7.62 (d, J=8.33 Hz, 1H), 7.67-7.77 (m, 2H), 12.28 (bs, 1H).

Example 1.11

Preparation of an Enantiomer of 2-(9-Chloro-7-(3-cyano-4-isopropoxybenzyloxy)-2,3-dihydro-1H-pyrrolo[1,2-a]indol-1-yl)acetic Acid (Compound 8)

A solution of the 1ˢᵗ enantiomer obtained during the resolution of Compound 6 by chiral HPLC (described as the enantiomer isolated and having the retention time of 6.7 min per the conditions reported in Example 1.2) (20 mg, 0.049 mmol) in DCM (0.500 mL) was cooled to 0° C. NCS (6.60 mg, 0.049 mmol) was added and the reaction was allowed to continue at 0° C. for 15 min in a 20 mL sealed scintillation vial. After 15 min, the reaction mixture was diluted with DCM and washed with water (2×10 mL), then washed with sodium thiosulfate pentahydrate (aq) (2×10 mL), dried over MgSO₄ and filtered by vacuum filtration. The filtrate was concentrated under reduced pressure to give an enantiomer of Compound 8 as a yellow solid (16.7 mg). LCMS m/z=439.8 [M+H]⁺; ¹H NMR (400 MHz, DMSO-d₆) δ ppm 1.32 (d, J=5.94 Hz, 6H), 2.25-2.34 (m, 1H), 2.52-2.58 (m, 1H), 2.77-2.87 (m, 1H), 2.94 (dd, J=16.29, 4.17 Hz, 1H), 3.63-3.73 (m, 1H), 3.96-4.04 (m, 1H), 4.12-4.19 (m, 1H), 4.76-4.83 (m, 1H), 5.07 (s, 2H), 6.86 (dd, J=8.84, 2.40 Hz, 1H), 6.96 (d, J=2.40 Hz, 1H), 7.28 (d, J=3.66 Hz, 1H), 7.30 (d, J=3.66 Hz, 1H), 7.72 (dd, J=8.72, 2.27 Hz, 1H), 7.79 (d, J=2.15 Hz, 1H), 12.32 (bs, 1H).

Example 1.12

Preparation of an enantiomer of 2-(9-Chloro-7-(3-cyano-4-isopropoxybenzyloxy)-2,3-dihydro-1H-pyrrolo[1,2-a]indol-1-yl)acetic Acid (Compound 8)

From the 2ⁿᵈ enantiomer obtained during the resolution of Compound 6 by chiral HPLC (described as the enantiomer isolated and having the retention time of 9.2 min per the conditions reported in Example 1.2) (20 mg, 0.049 mmol) in a similar manner to the one described in Example 1.11, an enantiomer of Compound 8 was obtained as a yellow solid. LCMS m/z=439.4 [M+H]⁺; ¹H NMR (400 MHz, DMSO-d₆) δ ppm 1.32 (d, J=6.06 Hz, 6H), 2.24-2.36 (m, 1H), 2.52-2.58 (m, 1H), 2.77-2.87 (m, 1H), 2.94 (dd, J=16.36, 4.11 Hz, 1H), 3.64-3.73 (m, 1H), 3.95-4.06 (m, 1H), 4.11-4.19 (m, 1H), 4.75-4.83 (m, 1H), 5.07 (s, 2H), 6.86 (dd, J=8.84, 2.40 Hz, 1H), 6.96 (d, J=2.27 Hz, 1H), 7.28 (d, J=3.54 Hz, 1H), 7.30 (d, J=3.79 Hz, 1H), 7.72 (dd, J=8.78, 2.21 Hz, 1H), 7.79 (d, J=2.15 Hz, 1H), 12.32 (bs, 1H).

Example 1.13

Preparation of 2-(9-Cyclobutyl-7-(4-cyclopentyl-3-(trifluoromethyl)benzyloxy)-2,3-dihydro-1H-pyrrolo[1,2-a]indol-1-yl)acetic Acid (Compound 11)

Step A: Preparation of tert-Butyl 2-(9-Cyclobutyl-7-(4-cyclopentyl-3-(trifluoromethyl)benzyloxy)-2,3-dihydro-1H-pyrrolo[1,2-a]indol-1-yl)acetate tert-Butyl 2-(7-(4-cyclopentyl-3-(trifluoromethyl)benzyloxy)-9-iodo-2,3-dihydro-1H-pyrrolo[1,2-a]indol-1-yl)acetate (50 mg, 0.078 mmol) was dissolved in THF (1.0 mL) in a heavy walled sealed microwave tube (0.5-2.0 mL) under $N_2$. Cyclobutylzinc(II) bromide (0.156 mL, 0.078 mmol) and bis(tri-t-butylphosphine)palladium(0) (3.60 mg, 7.04 µmol) were added. The reaction mixture was heated to 70° C. for 2 h, quenched with saturated $NaHCO_3$ and filtered through Celite®. The filtrate was then extracted with EtOAc (3×5 mL). The organic layers were combined and washed with saturated NaCl (10 mL), dried over $MgSO_4$ and filtered. The filtrate was concentrated under reduced pressure. The residue was purified by preparative TLC to provide the title compound as an amber oil (17.3 mg). LCMS m/z=568.8 [M+H]$^+$.

Step B: Preparation of 2-(9-Cyclobutyl-7-(4-cyclopentyl-3-(trifluoromethyl)benzyloxy)-2,3-dihydro-1H-pyrrolo[1,2-a]indol-1-yl)acetic Acid tert-Butyl 2-(7-(4-cyclopentyl-3-(trifluoromethyl)benzyloxy)-9-cyclobutyl-2,3-dihydro-1H-pyrrolo[1,2-a]indol-1-yl)acetate (17.2 mg, 0.031 mmol) was added to a solution of 2-amino-3-mercaptopropanoic acid (3.76 mg, 0.031 mmol) in TFA (1 mL) and were stirred at 23° C. for 15 min in a 20 mL sealed scintillation vial. After 15 min, the reaction mixture was poured into about 4 mL of ice water. The product precipitated and was collected by vacuum filtration. The solid was washed with n-hexane (3×5 mL) and dried (vacuum oven) to give the title compound as an off-white solid (6.7 mg). LCMS m/z=512.5 [M+H]$^+$; $^1$H NMR (400 MHz, DMSO-d$_6$) δ ppm 1.53-1.72 (m, 4H), 1.80-1.91 (m, 3H), 1.93-2.04 (m, 3H), 2.17-2.36 (m, 5H), 2.39-2.48 (m, 1H), 2.63 (dd, J=15.98, 3.98 Hz, 1H), 2.69-2.78 (m, 1H), 3.19-3.28 (m, 1H), 3.57-3.69 (m, 2H), 3.90-4.02 (m, 2H), 5.16 (s, 2H), 6.76 (dd, J=8.72, 2.40 Hz, 1H), 7.07 (d, J=2.27 Hz, 1H), 7.14 (d, J=8.72 Hz, 1H), 7.62 (d, J=8.09 Hz, 1H), 7.67-7.76 (m, 2H), 12.26 (bs, 1H).

Example 1.14

Preparation of 2-(7-(3-Cyano-4-cyclohexylbenzyloxy)-2,3-dihydro-1H-pyrrolo[1,2-a]indol-1-yl)acetic Acid (Compound 13)

Step A: Preparation of tert-Butyl 2-(7-(3-Cyano-4-cyclohexylbenzyloxy)-2,3-dihydro-1H-pyrrolo[1,2-a]indol-1-yl)acetate To a solution of tert-butyl 2-(7-hydroxy-2,3-dihydro-1H-pyrrolo[1,2-a]indol-1-yl)acetate (40 mg, 0.139 mmol) and 5-(chloromethyl)-2-cyclohexylbenzonitrile (35.8 mg, 0.153 mmol) in N,N-dimethylformamide (3 mL) was added cesium carbonate (54.4 mg, 0.167 mmol). The mixture was stirred at 50° C. for 16 h. The mixture was cooled to room temperature, diluted with ethyl acetate and filtered through Celite®. The filtrate was concentrated under vacuum and purified by silica gel column chromatography to provide the title compound as an off-white foam (57.4 mg). LCMS m/z=485.4 [M+H]$^+$; $^1$H NMR (400 MHz, CDCl$_3$) α ppm 1.24-1.34 (m, 1H), 1.43-1.53 (m, 4H), 1.50 (s, 9H), 1.80 (dd, J=12.88, 1.26 Hz, 1H), 1.89 (t, J=10.86 Hz, 4H), 2.22-2.34 (m, 1H), 2.50 (dd, J=15.73, 8.40 Hz, 1H), 2.73 (dd, J=15.79, 6.44 Hz, 1H), 2.82-2.92 (m, 1H), 2.99 (t, J=3.09 Hz, 1H), 3.65-3.75 (m, 1H), 3.95-4.04 (m, 1H), 4.07-4.16 (m, 1H), 5.06 (s, 2H), 6.09 (s, 1H), 6.85 (dd, J=8.72, 2.40 Hz, 1H), 7.08 (d, J=2.27 Hz, 1H), 7.14 (d, J=8.72 Hz, 1H), 7.37 (d, J=8.08 Hz, 1H), 7.62 (dd, J=8.15, 1.71 Hz, 1H), 7.71 (d, J=1.52 Hz, 1H).

Step B: Preparation of 2-(7-(3-Cyano-4-cyclohexylbenzyloxy)-2,3-dihydro-1H-pyrrolo[1,2-a]indol-1-yl)acetic Acid To tert-butyl 2-(7-(3-cyano-4-cyclohexylbenzyloxy)-2,3-dihydro-1H-pyrrolo[1,2-a]indol-1-yl)acetate (51.4 mg, 0.106 mmol) was added a solution of DL-cysteine (19.87 mg, 0.159 mmol) in trifluoroacetic acid (1 mL). The mixture was stirred at room temperature for 15 min. The reaction mixture was poured into an ice water to form a solid. The solid was filtered and washed with water to provide the title compound as an off-white solid (41.8 mg). LCMS m/z=429.6 [M+H]$^+$; $^1$H NMR (400 MHz, DMSO-d$_6$) α ppm 1.19-1.31 (m, 1H), 1.32-1.55 (m, 4H), 1.69-1.75 (m, 1H), 1.75-1.85 (m, 4H), 2.14-2.25 (m, 1H), 2.56 (dd, J=12.00, 8.00 Hz, 1H), 2.67 (dd, J=12.00, 8.00 Hz, 1H), 2.71-2.78 (m, 1H), 2.79-2.90 (m, 1H), 3.57 (t, J=7.39 Hz, 1H), 3.87-3.99 (m, 1H), 4.02-4.16 (m, 1H), 5.08 (s, 2H), 6.00 (s, 1H), 6.76 (dd, J=8.72, 2.40 Hz, 1H), 7.05 (d, J=2.40 Hz, 1H), 7.18 (d, J=8.72 Hz, 1H), 7.51 (d, J=8.21 Hz, 1H), 7.72 (dd, J=8.21, 1.64 Hz, 1H), 7.81 (d, J=1.52 Hz, 1H), 12.26 (bs, 1H).

Example 1.15

Preparation of 2-(7-(4-Isobutyl-3-(trifluoromethyl)benzyloxy)-2,3-dihydro-1H-pyrrolo[1,2-a]indol-1-yl)acetic Acid (Compound 4)

Step A: Preparation of tert-Butyl 2-(7-(4-Isobutyl-3-(trifluoromethyl)benzyloxy)-2,3-dihydro-1H-pyrrolo[1,2-a]indol-1-yl)acetate tert-Butyl 2-(7-hydroxy-2,3-dihydro-1H-pyrrolo[1,2-a]indol-1-yl)acetate (0.04 g, 0.139 mmol) was dissolved in DMF (1.0 mL) and cesium carbonate (0.045 g, 0.139 mmol) and 4-(chloromethyl)-1-isobutyl-2-(trifluoromethyl)benzene (0.035 g, 0.139 mmol) was added. The reaction mixture was stirred at room temperature for 48 h and then filtered through Celite®. The filtrate was partitioned between EtOAc and water. The aqueous layer was extracted two additional times with EtOAc and the combined extracts were dried over sodium sulfate, filtered and concentrated under reduced pressure. The residue was purified by silica gel column chromatography to provide the title compound (58 mg). LCMS m/z=502.6 [M+H]$^+$.

Step B: Preparation of 2-(7-(4-Isobutyl-3-(trifluoromethyl)benzyloxy)-2,3-dihydro-1H-pyrrolo[1,2-a]indol-1-yl)acetic Acid A solution of 2-amino-3-mercaptopropanoic acid (0.042 g, 0.347 mmol) in TFA (600 µL, 7.79 mmol) was added to neat tert-butyl 2-(7-(4-isobutyl-3-(trifluoromethyl)benzyloxy)-2,3-dihydro-1H-pyrrolo[1,2-a]indol-1-yl)acetate (0.058 g, 0.116 mmol). The reaction mixture was stirred for 1 h at room temperature and then diluted with ice and water causing a tan solid to precipitate. The aqueous mixture was decanted off of the tan solid and the solid was rinsed with water. The solid was dried under vacuum to give the title compound (37 mg). LCMS m/z=446.7 [M+H]+; 1H NMR (400 MHz, CDCl3) δ ppm 0.89 (d, J=6.6 Hz, 6H), 1.87-1.98 (m, 1H), 2.16-2.26 (m, 1H), 2.53-2.82 (m, 5H), 3.53-3.62 (m, 1H), 3.92-4.00 (m, 1H), 4.06-4.14 (m, 1H), 5.13 (s, 2H), 6.01 (s, 1H), 6.77 (dd, J=8.7, 2.4 Hz, 1H), 7.07 (d, J=2.3 Hz, 1H), 7.19 (d, J=8.8 Hz, 1H), 7.47 (d, J=8.0 Hz, 1H), 7.67 (d, J=8.1 Hz, 1H), 7.75 (d, J=1.1 Hz, 1H).

Example 1.16

Preparation of 2-(7-(4-Chloro-3-(trifluoromethyl) benzyloxy)-2,3-dihydro-1H-pyrrolo[1,2-a]indol-1-yl)acetic Acid (Compound 17)

Step A: Preparation of tert-Butyl 2-(7-(4-Chloro-3-(trifluoromethyl)benzyloxy)-2,3-dihydro-1H-pyrrolo[1,2-a]indol-1-yl)acetate To a solution of tert-butyl 2-(7-hydroxy-2,3-dihydro-1H-pyrrolo[1,2-a]indol-1-yl)acetate (0.053 g, 0.183 mmol) in DMF (1 mL) was added Cs2CO3 (0.0.071 g, 0.219 mmol) followed by 4-(bromomethyl)-1-chloro-2-(trifluoromethyl) benzene (0.050 g, 0.183 mmol). The reaction was stirred at 60° C. for 16 h. The mixture was filtered. The filtrate was concentrated under vacuum and purified by silica gel column chromatography to give the title compound as a white solid (0.048 g). LCMS m/z=480.4 [M+H]+; 1H NMR (400 MHz, CDCl3) δ ppm 1.49 (s, 9H), 2.21-2.34 (On, 1H), 2.50 (dd, J=15.73, 8.40 Hz, 1H), 2.73 (dd, J=15.79, 6.32 Hz, 1H), 2.81-2.93 (m, 1H), 3.64-3.77 (m, 1H), 3.94-4.05 (m, 1H), 4.06-4.17 (On, 1H), 5.10 (s, 2H), 6.84 (dd, J=8.72, 2.40 Hz, 1H), 7.07 (d, J=2.40 Hz, 1H), 7.13 (d, J=8.72 Hz, 1H), 7.47-7.53 (m, 1H), 7.55-7.61 (m, 1H), 7.79 (s, 1H).

Step B: Preparation of 2-(7-(4-Chloro-3-(trifluoromethyl)benzyloxy)-2,3-dihydro-1H-pyrrolo[1,2-a]indol-1-yl)acetic Acid To a solution of D,L-cysteine (0.056 g, 0.460 mmol) in TFA (0.9 mL) was added tert-butyl 2-(7-(4-chloro-3-(trifluoromethyl)benzyloxy)-2,3-dihydro-1H-pyrrolo[1,2-a]indol-1-yl)acetate (0.079 g, 0.153 mmol). The reaction was stirred for 2 h and poured into ice water. The resulting precipitate was collected by vacuum filtration to give the title compound as a solid.
LCMS m/z=424.1 [M+H]+; 1H NMR (400 MHz, DMSO-d6) δ ppm 2.14-2.27 (m, 1H), 2.55 (dd, J=16.29, 7.96 Hz, 1H), 2.64-2.72 (m, 1H), 2.72-2.82 (m, 1H), 3.51-3.64 (m, 1H), 3.90-4.01 (m, 1H), 4.05-4.17 (m, 1H), 5.18 (s, 2H), 6.01 (s, 1H), 6.78 (dd, J=8.72, 2.40 Hz, 1H), 7.07 (d, J=2.40 Hz, 1H), 7.20 (d, J=8.72 Hz, 1H), 7.69-7.81 (m, 2H), 7.92 (s, 1H), 12.24 (bs, 1H).

Example 1.17

Preparation of 2-(7-(4-Cyano-3-(trifluoromethyl) benzyloxy)-2,3-dihydro-1H-pyrrolo[1,2-a]indol-1-yl)acetic Acid (Compound 18)

Step A: Preparation of tert-Butyl 2-(7-(4-Cyano-3-(trifluoromethyl)benzyloxy)-2,3-dihydro-1H-pyrrolo[1,2-a]indol-1-yl)acetate From 4-(chloromethyl)-2-(trifluoromethyl)benzonitrile, the title compound was prepared as a solid using a similar method to the one described in Example 1.16, Step A. LCMS m/z=471.2 [M+H]+; 1H NMR (400 MHz, CDCl3) δ ppm 1.49 (s, 9H), 2.22-2.34 (m, 1H), 2.50 (dd, J=15.73, 8.27 Hz, 1H), 2.73 (dd, J=15.79, 6.44 Hz, 1H), 2.80-2.93 (m, 1H), 3.65-3.77 (m, 1H), 3.95-4.05 (m, 1H), 4.07-4.17 (m, 1H), 5.20 (s, 2H), 6.85 (dd, J=8.59, 2.40 Hz, 1H), 7.06 (d, J=2.27 Hz, 1H), 7.15 (d, J=8.84 Hz, 1H), 7.74-7.81 (m, 1H), 7.82-7.87 (m, 1H), 7.91 (s, 1H).

Step B: Preparation of 2-(7-(4-Cyano-3-(trifluoromethyl)benzyloxy)-2,3-dihydro-1H-pyrrolo[1,2-a]indol-1-yl)acetic Acid From tert-Butyl 2-(7-(4-Cyano-3-(trifluoromethyl)benzyloxy)-2,3-dihydro-1H-pyrrolo[1,2-a]indol-1-yl)acetate, the title compound was prepared as a solid using a similar method to the one described in Example 1.16, Step B. LCMS m/z=415.4 [M+H]+; 1H NMR (400 MHz, DMSO-d6) δ ppm 2.15-2.27 (m, 1H), 2.55 (dd, J=16.17, 7.96 Hz, 1H), 2.64-2.72 (m, 1H), 2.72-2.83 (m, 1H), 3.53-3.63 (m, 1H), 3.91-4.01 (m, 1H), 4.06-4.15 (m, 1H), 5.30 (s, 2H), 6.02 (s, 1H), 6.81 (dd, J=8.72, 2.40 Hz, 1H), 7.08 (d, J=2.40 Hz, 1H), 7.21 (d, J=8.72 Hz, 1H), 7.96 (d, J=7.83 Hz, 1H), 8.06 (s, 1H), 8.19 (d, J=8.08 Hz, 1H), 12.27 (bs, 1H).

Example 1.18

Preparation of 2-(7-(4-Carbamoyl-3-(trifluoromethyl)benzyloxy)-2,3-dihydro-1H-pyrrolo[1,2-a]indol-1-yl)acetic Acid (Compound 19)

To a solution of 2-(7-(4-cyano-3-(trifluoromethyl)benzyloxy)-2,3-dihydro-1H-pyrrolo[1,2-a]indol-1-yl)acetic acid (15.0 mg, 0.036 mmol) in dioxane (1 mL) was added 1 M LiOH (aq) (3.0 mL). The reaction was stirred at 50° C. for 48 h. 1 M HCl (aq) was added until pH=3. The mixture was extracted with EtOAc. The organic extract was dried over MgSO4 and purified by preparative HPLC/MS to give the title compound as a solid (3.1 mg). LCMS m/z=433.4 [M+H]+; 1H NMR (400 MHz, DMSO-d6) δ ppm 2.14-2.27 (m, 1H), 2.55 (dd, J=16.23, 8.02 Hz, 1H), 2.63-2.72 (m, 1H), 2.72-2.83 (m, 1H), 3.52-3.63 (m, 1H), 3.90-4.00 (m, 1H), 4.04-4.15 (m, 1H), 5.21 (s, 2H), 6.01 (s, 1H), 6.78 (dd, J=8.72, 2.40 Hz, 1H), 7.07 (d, J=2.27 Hz, 1H), 7.20 (d, J=8.72 Hz, 1H), 7.49-7.60 (m, 2H), 7.75 (d, J=7.83 Hz, 1H), 7.82 (s, 1H), 7.91 (s, 1H), 12.28 (bs, 1H).

Example 1.19

Preparation of 2-(7-(4-(Cyclopropylmethoxy)-3-(trifluoromethyl)benzyloxy)-2,3-dihydro-1H-pyrrolo[1,2-a]indol-1-yl)acetic Acid (Compound 20)

Step A: Preparation of tert-Butyl 2-(7-(4-(cyclopropylmethoxy)-3-(trifluoromethyl)benzyloxy)-2,3-dihydro-1H-pyrrolo[1,2-a]indol-1-yl)acetate From 4-(chloromethyl)-1-(cyclopropylmethoxy)-2-(trifluoromethyl)benzene, the title compound was prepared as a solid using a similar method to the one described in Example 1.16,
Step A. LCMS m/z=516.3 [M+H]+; 1H NMR (400 MHz, DMSO-d6) δ ppm 0.31-0.38 (m, 2H), 0.52-0.60 (m, 2H), 1.15-1.30 (m, 1H), 1.44 (s, 9H), 2.13-2.26 (m, 1H), 2.53-2.59 (m, 1H), 2.59-2.68 (m, 1H), 2.69-2.82 (m, 1H), 3.51-3.63 (m, 1H), 3.90-4.02 (m, 3H), 4.04-4.14 (m, 1H), 5.06 (s, 2H), 5.99

(s, 1H), 6.75 (dd, J=8.72, 2.27 Hz, 1H), 7.06 (d, J=2.27 Hz, 1H), 7.18 (d, J=8.72 Hz, 1H), 7.23 (d, J=8.34 Hz, 1H), 7.61-7.70 (m, 2H).

Step B: Preparation of 2-(7-(4-(cyclopropylmethoxy)-3-(trifluoromethyl)benzyloxy)-2,3-dihydro-1H-pyrrolo[1,2-a]indol-1-yl)acetic acid To a solution of tert-butyl 2-(7-(4-(cyclopropylmethoxy)-3-(trifluoromethyl)benzyloxy)-2,3-dihydro-1H-pyrrolo[1,2-a]indol-1-yl)acetate (48.4 mg, 0.094 mmol) in DCM (1 mL) was added anisole (0.110 mL, 0.939 mmol) and TFA (0.209 mL, 2.82 mmol). The reaction mixture was stirred for 1 hour. The solvent was removed under vacuum. The residue was purified by preparative HPLC/MS to give the title compound as a solid (3.8 mg). LCMS m/z=460.4 [M+H]$^+$; $^1$H NMR (400 MHz, DMSO-d$_6$) δ ppm 0.29-0.38 (m, 2H), 0.50-0.61 (m, 2H), 1.14-1.28 (m, 1H), 2.14-2.26 (m, 1H), 2.53-2.61 (m, 1H), 2.63-2.72 (m, 1H), 2.72-2.83 (m, 1H), 3.52-3.61 (m, 1H), 3.89-4.03 (m, 3H), 4.04-4.16 (m, 1H), 5.06 (s, 2H), 6.01 (s, 1H), 6.75 (dd, J=8.72, 2.40 Hz, 1H), 7.06 (d, J=2.27 Hz, 1H), 7.18 (d, J=8.59 Hz, 1H), 7.24 (d, J=8.08 Hz, 1H), 7.61-7.72 (m, 2H), 12.27 (bs, 1H).
Resolution Via Chiral HPLC.
Column: normal phase ChiralPak IA column, 20 mm ID×250 mm L, 5 μm particle size
Eluent: 20% IPA/hexanes with 0.1% TFA
Gradient: Isocratic
Flow: 10 mL/min
Detector: 280 nm
Retention Times: 1$^{st}$ enantiomer: 17.1 min; 2$^{nd}$ enantiomer: 18.8 min

Example 1.20

Preparation of 2-(7-(4-(Cyclohexylmethyl)-3-(trifluoromethyl)benzyloxy)-2,3-dihydro-1H-pyrrolo[1,2-a]indol-1-yl)acetic Acid (Compound 21)

Step A: Preparation of Methyl 4-(Cyclohexylmethyl)-3-(trifluoromethyl)benzoate To a stirred solution of methyl 4-chloro-3-(trifluoromethyl)benzoate (238 mg, 1.0 mmol) and bis(tri-t-butylphosphine)palladium (0) (51 mg, 0.10 mmol) in THF (2 mL) was added (cyclohexylmethyl)zinc(II) bromide (6 mL, 3.00 mmol) at room temperature. The reaction mixture was heated at reflux for 2 h, quenched with saturated NaHCO$_3$ solution, and filtered through Celite®. The filtrate was extracted with ethyl acetate. The combined organics were dried and concentrated, and the residue was purified by silica gel column chromatography to give the title compound (280 mg) as a colorless oil. LCMS m/z=301.4. $^1$H NMR (400 MHz, CDCl$_3$) δ ppm 0.96-1.06 (m, 2H), 1.14-1.22 (m, 3H), 1.62-1.72 (m, 6H), 2.71 (d, J=6.7 Hz, 2H), 3.94 (s, 3H), 7.39 (d, J=8.1 Hz, 1H), 8.10 (dd, J=8.0, 1.5 Hz, 1H), 8.30 (d, J=1.4 Hz, 1H).

Step B: Preparation of (4-(Cyclohexylmethyl)-3-(trifluoromethyl)phenyl)methanol To a stirred solution of methyl 4-(cyclohexylmethyl)-3-(trifluoromethyl)benzoate (280 mg, 0.93 mmol) in dioxane (8 mL) was added 2 M lithium borohydride in THF solution (0.93 mL, 1.86 mmol). The reaction mixture was heated at 80° C. for 2 h, cooled down, poured into water, acidified with 1 M HCl aqueous solution to pH 4, extracted with ethyl acetate. The combined organics were washed with saturated NaHCO$_3$ solution and water, dried and concentrated. The residue was purified by silica gel column chromatography to give the title compound (190 mg) as colorless oil. $^1$H NMR (400 MHz, CDCl$_3$) δ ppm 0.96-1.06 (m, 2H), 1.14-1.22 (m, 3H), 1.62-1.72 (m, 6H), 2.67 (d, J=6.7 Hz, 2H), 4.71 (d, J=5.7 Hz, 2H), 7.29 (d, J=7.9 Hz, 1H), 7.45 (dd, J=8.0 and 1.6 Hz, 1H), 7.62 (d, J=1.6 Hz, 1H).

Step C: Preparation of 4-(Chloromethyl)-1-(cyclohexylmethyl)-2-(trifluoromethyl)benzene To a solution of (4-(cyclohexylmethyl)-3-(trifluoromethyl)phenyl)methanol (0.060 g, 0.220 mmol) in toluene (2 mL) was added thionyl chloride (1.32 mmol). The reaction was heated to 75° C. for 3 h and quenched with water at 0° C. The mixture was extracted with hexanes (twice). The combined organics were washed with saturated NaHCO$_3$(aq), dried over MgSO$_4$, and concentrated to give the title compound as an oil (0.220 mmol). $^1$H NMR (400 MHz, CDCl$_3$) δ ppm 0.91-1.06 (m, 2H), 1.12-1.23 (m, 3H), 1.61-1.74 (m, 6H), 2.66 (d, J=6.95 Hz, 2H), 4.59 (s, 2H), 7.30 (d, J=7.96 Hz, 1H), 7.47 (d, J=7.96 Hz, 1H), 7.63 (s, 1H).

Step D: Preparation of tert-Butyl 2-(7-(4-(Cyclohexylmethyl)-3-(trifluoromethyl)benzyloxy)-2,3-dihydro-1H-pyrrolo[1,2-a]indol-1-yl)acetate To a solution of tert-butyl 2-(7-hydroxy-2,3-dihydro-1H-pyrrolo[1,2-a]indol-1-yl)acetate (0.045 g, 0.157 mmol) in DMA (1 mL) was added Cs$_2$CO$_3$ (0.0.077 g, 0.235 mmol) followed by 4-(chloromethyl)-1-(cyclohexylmethyl)-2-(trifluoromethyl)benzene (0.050 g, 0.172 mmol). The reaction was stirred at 60° C. for 16 h. The mixture was filtered. The filtrate was concentrated under vacuum and purified by silica gel column chromatography to give the title compound as a white solid (0.053 g). LCMS m/z=542.5 [M+H]$^+$; $^1$H NMR (400 MHz, DMSO-d$_6$) δ ppm 0.90-1.03 (m, 2H), 1.09-1.19 (m, 3H), 1.44 (s, 9H), 1.53-1.69 (m, 6H), 2.14-2.26 (m, 1H), 2.51-2.58 (m, 1H), 2.59-2.67 (m, 3H), 2.71-2.81 (m, 1H), 3.53-3.63 (m, 1H), 3.91-3.99 (m, 1H), 4.05-4.14 (m, 1H), 5.12 (s, 2H), 5.99 (s, 1H), 6.77 (dd, J=8.72, 2.40 Hz, 1H), 7.07 (d, J=2.40 Hz, 1H), 7.19 (d, J=8.72 Hz, 1H), 7.44 (d, J=7.96 Hz, 1H), 7.65 (d, J=7.96 Hz, 1H), 7.73 (s, 1H).

Step E: Preparation of 2-(7-(4-(Cyclohexylmethyl)-3-(trifluoromethyl)benzyloxy)-2,3-dihydro-1H-pyrrolo[1,2-a]indol-1-yl)acetic Acid To a solution of tert-butyl 2-(7-(4-(cyclohexylmethyl)-3-(trifluoromethyl)benzyloxy)-2,3-dihydro-1H-pyrrolo[1,2-a]indol-1-yl)acetate (50 mg, 0.092 mmol) in DCM (1 mL) was added thioanisole (0.738 mmol) and TFA (1.85 mmol). The reaction mixture was stirred for 3 h. The solvent was removed under vacuum. The residue was purified by preparative HPLC/MS to give the title compound as a solid (26.1 mg). LCMS m/z=486.4 [M+H]$^+$; $^1$H NMR (400 MHz, DMSO-d$_6$) δ ppm 0.90-1.04 (m, 2H), 1.08-1.20 (m, 3H), 1.54-1.70 (m, 6H), 2.15-2.26 (m, 1H), 2.55 (dd, J=16.29, 8.08 Hz, 1H), 2.62 (d, J=6.44 Hz, 2H), 2.65-2.72 (m, 1H), 2.72-2.83 (m, 1H), 3.52-3.63 (m, 1H), 3.91-4.01 (m, 1H), 4.05-4.14 (m, 1H), 5.12 (s, 2H), 6.01 (s, 1H), 6.77 (dd, J=8.72, 2.40 Hz, 1H), 7.07 (d, J=2.40 Hz, 1H), 7.19 (d, J=8.59 Hz, 1H), 7.44 (d, J=8.08 Hz, 1H), 7.66 (d, J=7.71 Hz, 1H), 7.74 (s, 1H), 12.27 (bs, 1H).

Example 1.21

Preparation of 2-(7-(4-(Methylsulfonyl)benzyloxy)-2,3-dihydro-1H-pyrrolo[1,2-a]indol-1-yl)acetic Acid (Compound 22)

Step A: Preparation of tert-Butyl 2-(7-(4-(Methylsulfonyl)benzyloxy)-2,3-dihydro-1H-pyrrolo[1,2-a]indol-1-yl)acetate From 1-(bromomethyl)-4-(methylsulfonyl)benzene, the title compound was prepared as a solid using a similar method to the one described in Example 1.20, Step B. LCMS m/z=456.5 [M+H]$^+$; $^1$H NMR (400 MHz, DMSO-d$_6$) δ ppm 1.44 (s, 9H), 2.14-2.25 (m, 1H), 2.52-2.59 (m, 1H), 2.59-2.67 (m, 1H), 2.71-2.81 (m, 1H), 3.20 (s, 3H), 3.52-3.63 (m, 1H), 3.91-4.00 (m, 1H), 4.05-4.14 (m, 1H), 5.22 (s, 2H), 5.99 (s, 1H), 6.79 (dd, J=8.72, 2.40 Hz, 1H), 7.08 (d, J=2.40 Hz, 1H), 7.20 (d, J=8.72 Hz, 1H), 7.71 (d, J=8.21 Hz, 2H), 7.93 (d, J=8.34 Hz, 2H).

Step B: Preparation of 2-(7-(4-(Methylsulfonyl)benzyloxy)-2,3-dihydro-1H-pyrrolo[1,2-a]indol-1-yl)acetic Acid From tert-Butyl 2-(7-(4-(Methylsulfonyl)benzyloxy)-2,3-dihydro-1H-pyrrolo[1,2-a]indol-1-yl)acetate, the title compound was prepared as a solid using a similar method to the one described in Example 1.20, Step C. LCMS m/z=400.4 [M+H]$^+$; $^1$H NMR (400 MHz, DMSO-d$_6$) δ ppm 2.15-2.27 (m, 1H), 2.55 (dd, J=16.23, 8.02 Hz, 1H), 2.64-2.71 (m, 1H), 2.72-2.82 (m, 1H), 3.20 (s, 3H), 3.52-3.63 (m, 1H), 3.91-4.00 (m, 1H), 4.05-4.14 (m, 1H), 5.22 (s, 2H), 6.01 (s, 1H), 6.79 (dd, J=8.72, 2.40 Hz, 1H), 7.07 (d, J=2.40 Hz, 1H), 7.20 (d, J=8.72 Hz, 1H), 7.71 (d, J=8.34 Hz, 2H), 7.93 (d, J=8.46 Hz, 2H), 12.28 (bs, 1H).

Example 1.22

Preparation of 2-(7-(2,4-Bis(trifluoromethyl)benzyloxy)-2,3-dihydro-1H-pyrrolo[1,2-a]indol-1-yl)acetic Acid (Compound 23)

Step A: Preparation of tert-Butyl 2-(7-(2,4-Bis(trifluoromethyl)benzyloxy)-2,3-dihydro-1H-pyrrolo[1,2-a]indol-1-yl)acetate From 1-(bromomethyl)-2,4-bis(trifluoromethyl)benzene, the title compound was prepared as a solid using a similar method to the one described in Example 1.20, Step B. LCMS m/z=514.3 [M+H]$^+$; $^1$H NMR (400 MHz, DMSO-d$_6$) δ ppm 1.44 (s, 9H), 2.17-2.25 (m, 1H), 2.52-2.58 (m, 1H), 2.60-2.67 (m, 1H), 2.71-2.81 (m, 1H), 3.53-3.63 (m, 1H), 3.92-4.01 (m, 1H), 4.06-4.15 (m, 1H), 5.32 (s, 2H), 6.01 (s, 1H), 6.79 (dd, J=8.78, 2.34 Hz, 1H), 7.07 (d, J=2.27 Hz, 1H), 7.22 (d, J=8.72 Hz, 1H), 8.02-8.09 (m, 2H), 8.12 (d, 1H).

Step B: Preparation of 2-(7-(2,4-Bis(trifluoromethyl)benzyloxy)-2,3-dihydro-1H-pyrrolo[1,2-a]indol-1-yl)acetic Acid From tert-butyl 2-(7-(2,4-Bis(trifluoromethyl)benzyloxy)-2,3-dihydro-1H-pyrrolo[1,2-a]indol-1-yl)acetate, the title compound was prepared as a solid using a similar method to the one described in Example 1.20, Step C. LCMS m/z=458.3 [M+H]$^+$; $^1$H NMR (400 MHz, DMSO-d$_6$) δ ppm 2.16-2.27 (m, 1H), 2.52-2.59 (m, 1H), 2.64-2.72 (m, 1H), 2.72-2.82 (m, 1H), 3.53-3.63 (m, 1H), 3.92-4.01 (m, 1H), 4.07-4.15 (m, 1H), 5.32 (s, 2H), 6.03 (s, 1H), 6.79 (dd, J=8.72, 2.40 Hz, 1H), 7.06 (d, J=2.40 Hz, 1H), 7.22 (d, J=8.72 Hz, 1H), 8.02-8.09 (m, 2H), 8.10-8.14 (m, 1H), 12.28 (bs, 1H).

Example 1.23

Preparation of 2-(7-(4-(1H-Pyrazol-1-yl)benzyloxy)-2,3-dihydro-1H-pyrrolo[1,2-a]indol-1-yl)acetic Acid (Compound 24)

Step A: Preparation of tert-Butyl 2-(7-(4-(1H-Pyrazol-1-yl)benzyloxy)-2,3-dihydro-1H-pyrrolo[1,2-a]indol-1-yl)acetate From 1-(4-(bromomethyl)phenyl)-1H-pyrazole, the title compound was prepared as a solid using a similar method to the one described in Example 1.20, Step B. LCMS m/z=444.4 [M+H]$^+$; $^1$H NMR (400 MHz, CDCl$_3$) δ ppm 1.49 (s, 9H), 2.21-2.33 (m, 1H), 2.49 (dd, J=15.73, 8.40 Hz, 1H), 2.73 (dd, J=15.79, 6.32 Hz, 1H), 2.80-2.92 (m, 1H), 3.65-3.76 (m, 1H), 3.95-4.04 (m, 1H), 4.06-4.15 (m, 1H), 5.12 (s, 2H), 6.46-6.48 (m, 1H), 6.87 (dd, J=8.72, 2.40 Hz, 1H), 7.09-7.15 (m, 2H), 7.55 (d, J=8.46 Hz, 2H), 7.68-7.75 (m, 3H), 7.92 (d, J=2.40 Hz, 1H).

Step B: Preparation of 2-(7-(4-(1H-Pyrazol-1-yl)benzyloxy)-2,3-dihydro-1H-pyrrolo[1,2-a]indol-1-yl)acetic acid From tert-Butyl 2-(7-(4-(1H-Pyrazol-1-yl)benzyloxy)-2,3-dihydro-1H-pyrrolo[1,2-a]indol-1-yl)acetate, the title compound was prepared as a solid using a similar method to the one described in Example 1.20, Step C. LCMS m/z=388.4 [M+H]$^+$; $^1$H NMR (400 MHz, DMSO-d$_6$) δ ppm 2.14-2.28 (m, 1H), 2.55 (dd, J=16.23, 8.02 Hz, 1H), 2.63-2.72 (m, 1H), 2.72-2.83 (m, 1H), 3.52-3.63 (m, 1H), 3.89-4.01 (m, 1H), 4.04-4.14 (m, 1H), 5.11 (s, 2H), 6.01 (s, 1H), 6.51-6.57 (m, 1H), 6.78 (dd, J=8.65, 2.34 Hz, 1H), 7.08 (d, J=2.27 Hz, 1H), 7.19 (d, J=8.84 Hz, 1H), 7.56 (d, J=8.59 Hz, 2H), 7.74 (d, J=1.77 Hz, 1H), 7.84 (d, J=8.59 Hz, 2H), 8.48 (d, J=2.53 Hz, 1H), 12.27 (bs, 1H).

Example 1.24

Preparation of 2-(7-(4-(Cyclopentyloxy)-3-(trifluoromethyl)benzyloxy)-2,3-dihydro-1H-pyrrolo[1,2-a]indol-1-yl)acetic Acid (Compound 25)

Step A: Preparation of tert-Butyl 2-(7-(4-(Cyclopentyloxy)-3-(trifluoromethyl)benzyloxy)-2,3-dihydro-1H-pyrrolo[1,2-a]indol-1-yl)acetate From 4-(chloromethyl)-1-(cyclopentyloxy)-2-(trifluoromethyl)benzene, the title compound was prepared as a solid using a similar method to the one described in Example 1.20, Step B. LCMS m/z=530.3 [M+H]$^+$; $^1$H NMR (400 MHz, CDCl$_3$) δ ppm 1.49 (s, 9H), 1.53 (bs, 2H), 1.63 (bs, 2H), 1.77-1.97 (m, 4H), 2.20-2.35 (m, 1H), 2.49 (dd, J=15.79, 8.46 Hz, 1H), 2.73 (dd, J=15.79, 6.44 Hz, 1H), 2.79-2.94 (m, 1H), 3.65-3.76 (m, 1H), 3.93-4.04 (m, 1H), 4.06-4.15 (m, 1H), 4.84-4.91 (m, 1H), 5.01 (s, 2H), 6.84 (dd, J=8.72, 2.27 Hz, 1H), 6.98 (d, J=8.46 Hz, 1H), 7.08-7.15 (m, 2H), 7.54 (dd, J=8.46, 1.89 Hz, 1H), 7.64 (d, J=1.64 Hz, 1H).

Step B: Preparation of 2-(7-(4-(Cyclopentyloxy)-3-(trifluoromethyl)benzyloxy)-2,3-dihydro-1H-pyrrolo[1,2-a]indol-1-yl)acetic Acid From tert-Butyl 2-(7-(4-(cyclopentyloxy)-3-(trifluoromethyl)benzyloxy)-2,3-dihydro-1H-pyrrolo[1,2-a]indol-1-yl)acetate, the title compound was prepared as a solid using a similar method to the one described in Example 1.20, Step C. LCMS m/z=474.6 [M+H]$^+$; $^1$H NMR (400 MHz, DMSO-d$_6$) δ ppm 1.54-1.78 (m, 6H), 1.84-1.96 (m, 2H), 2.15-2.27 (m, 1H), 2.51-2.59 (m, 1H), 2.64-2.72 (m, 1H), 2.72-2.82 (m, 1H), 3.52-3.63 (m, 1H), 3.90-4.01 (m, 1H), 4.05-4.14 (m, 1H), 4.98-5.03 (m, 1H), 5.05 (s, 2H), 6.01 (s, 1H), 6.75 (dd, J=8.72, 2.40 Hz, 1H), 7.06 (d, J=2.40 Hz, 1H), 7.18 (d, J=8.59 Hz, 1H), 7.25 (d, J=9.22 Hz, 1H), 7.64-7.70 (m, 2H), 12.27 (bs, 1H).

Example 1.25

Preparation of 2-(7-(4-Isopropoxy-3-(trifluoromethyl)benzyloxy)-2,3-dihydro-1H-pyrrolo[1,2-a]indol-1-yl)acetic Acid (Compound 28)

Step A: Preparation of Isopropyl 4-isopropoxy-3-(trifluoromethyl)benzoate

To a mixture of 4-hydroxy-3-(trifluoromethyl)benzoic acid (14.55 mmol) and cesium carbonate (43.7 mmol) in DMA (60 mL) was added 2-bromopropane (36.4 mmol). The reaction was stirred at 80° C. for 16 h. The mixture was filtered through celite and concentrated under vacuum. The residue was dissolved in EtOAc and washed with water, then brine, then dried over MgSO$_4$, and filtered. The solvent was removed under vacuum to give the title compound as a light yellow oil (13.1 mmol). $^1$H NMR (400 MHz, CDCl$_3$) δ ppm 1.36 (d, J=6.32 Hz, 6H), 1.39 (d, J=6.06 Hz, 6H), 4.72 (septet, J=6.06 Hz, 1H), 5.24 (septet, J=6.25 Hz, 1H), 7.00 (d, J=8.84 Hz, 1H), 7.26 (s, OH), 8.15 (dd, J=8.72, 2.15 Hz, 1H), 8.23 (d, J=2.15 Hz, 1H).

Step B: Preparation of (4-Isopropoxy-3-(trifluoromethyl)phenyl)methanol

To a cooled (–78° C.) solution of 4-isopropoxy-3-(trifluoromethyl)benzoate (13.1 mmol) in DCM (85 mL) under nitrogen was added 2.0 M solution of LAH (19.0 mmol) by a syringe. The reaction was allowed to return to room temperature and stirred for 16 h. The reaction was cooled to 0° C. and quenched with water (0.95 mL) and 10% NaOH (aq) (1.90 mL). The mixture was filtered through Celite®. The filtrate was concentrated under vacuum to give the title compound as an oil (11.27 mmol). $^1$H NMR (400 MHz, DMSO-d$_6$) δ ppm 1.27 (d, J=6.06 Hz, 6H), 4.46 (d, J=5.81 Hz, 2H), 4.75 (septet, J=6.02 Hz, 1H), 5.20 (t, J=5.75 Hz, 1H), 7.23 (d, J=8.46 Hz, 1H), 7.47-7.56 (m, 2H).

Step C: Preparation of 4-(Chloromethyl)-1-isopropoxy-2-(trifluoromethyl)benzene To a solution of (4-isopropoxy-3-(trifluoromethyl)phenyl)methanol (11.27 mmol) in toluene (20 mL) was added thionyl chloride (67.7 mmol). The reaction was stirred at 75° C. for 3 h. The mixture was diluted with hexanes, washed with water (twice), saturated NaHCO$_3$, dried over MgSO$_4$, and filtered. The solvent was removed under vacuum to give the title compound as an oil (10.4 mmol). $^1$H NMR (400 MHz, DMSO-d$_6$) δ ppm 1.29 (d, J=6.06 Hz, 6H), 4.75-4.85 (m, 3H), 7.30 (d, J=8.46 Hz, 1H), 7.63-7.70 (m, 2H).

Step D: Preparation of tert-Butyl 2-(7-(4-Isopropoxy-3-(trifluoromethyl)benzyloxy)-2,3-dihydro-1H-pyrrolo[1,2-a]indol-1-yl)acetate To a mixture of tert-butyl 2-(7-hydroxy-2,3-dihydro-1H-pyrrolo[1,2-a]indol-1-yl)acetate (1.86 mmol) and cesium carbonate (2.8 mmol) in DMA (7.45 mL) was added 4-(chloromethyl)-1-isopropoxy-2-(trifluoromethyl)benzene (1.96 mmol). The reaction was stirred at 80° C. for 16 h. The mixture was filtered through Celite®. The solvent was removed under vacuum. The residue was purified by silica gel column chromatography to give the title compound as a solid. LCMS m/z=504.2 [M+H]$^+$; $^1$H NMR (400 MHz, DMSO-d$_6$) δ ppm 1.28 (d, J=5.94 Hz, 6H), 1.44 (s, 9H), 2.14-2.25 (m, 1H), 2.51-2.58 (m, 1H), 2.59-2.67 (m, 1H), 2.71-2.81 (m, 1H), 3.57 (m, 1H), 3.91-3.99 (m, 1H), 4.06-4.13 (m, 1H), 4.72-4.83 (m, 1H), 5.05 (s, 2H), 5.99 (s, 1H), 6.75 (dd, J=8.72, 2.40 Hz, 1H), 7.07 (d, J=2.40 Hz, 1H), 7.18 (d, J=8.72 Hz, 1H), 7.28 (d, J=9.22 Hz, 1H), 7.62-7.68 (m, 2H).

Step E: Preparation of 2-(7-(4-Isopropoxy-3-(trifluoromethyl)benzyloxy)-2,3-dihydro-1H-pyrrolo[1,2-a]indol-1-yl)acetic Acid To a solution of tert-butyl 2-(7-(4-isopropoxy-3-(trifluoromethyl)benzyloxy)-2,3-dihydro-1H-pyrrolo[1,2-a]indol-1-yl)acetate (0.418 g, 0.830 mmol) in dioxanes (10 mL) was added 1.0 M solution of LiOH (aq, 2.5 mL). The reaction was stirred at 70° C. for 4 h and acidified with 1M HCl (aq) to pH 3.0. The mixture was extracted with EtOAc, dried over Na$_2$SO$_4$, filtered, and concentrated. The residue was purified by silica gel column chromatography to give the title compound as a yellow solid (137 mg). LCMS m/z=448.4 [M+H]$^+$; $^1$H NMR (400 MHz, DMSO-d$_6$) δ ppm 1.28 (d, J=5.94 Hz, 6H), 2.15-2.26 (m, 1H), 2.51-2.59 (m, 1H), 2.64-2.72 (m, 1H), 2.72-2.82 (m, 1H), 3.53-3.63 (m, 1H), 3.91-4.00 (m, 1H), 4.05-4.14 (m, 1H), 4.74-4.82 (m, 1H), 5.05 (s, 2H), 6.01 (s, 1H), 6.75 (dd, J=8.72, 2.40 Hz, 1H), 7.06 (d, J=2.27 Hz, 1H), 7.18 (d, J=8.84 Hz, 1H), 7.26-7.32 (m, 1H), 7.63-7.69 (m, 2H), 12.28 (bs, 1H).

Resolution Via Chiral HPLC.
Column: normal phase ChiralPak IA column, 20 mm ID×250 mm L, 5 μm particle size
Eluent: 10% IPA/hexanes with 0.1% TFA
Gradient: Isocratic
Flow: 12 mL/min
Detector: 280 nm
Retention Times: 1$^{st}$ enantiomer: 29.8 min; 2$^{nd}$ enantiomer: 33.1 min

Example 1.26

Preparation of 1$^{st}$ Enantiomer of 2-(9-Chloro-7-(4-isopropoxy-3-(trifluoromethyl)benzyloxy)-2,3-dihydro-1H-pyrrolo[1,2-a]indol-1-yl)acetic Acid (Compound 29)

To a solution of the 1$^{st}$ enantiomer (described as the enantiomer isolated and having the retention time of 29.8 min per the conditions reported in Example 1.25) of 2-(7-(4-isopropoxy-3-(trifluoromethyl)benzyloxy)-2,3-dihydro-1H-pyrrolo[1,2-a]indol-1-yl)acetic Acid (0.049 mmol) in DCM (0.5 mL) at 0° C. was added NCS (0.049 mmol). The reaction was stirred for 15 minutes. The mixture was diluted with DCM and washed with water (twice) and saturated sodium thiolsulfate (aq). The organics were dried over $Na_2SO_4$, filtered, and concentrated to give the title compound as a yellow solid. LCMS m/z=482.3 [M+H]$^+$; $^1$H NMR (400 MHz, DMSO-d$_6$) δ ppm 1.29 (d, J=6.06 Hz, 6H), 2.24-2.35 (m, 1H), 2.51-2.59 (m, 1H), 2.77-2.87 (m, 1H), 2.94 (dd, J=16.36, 4.11 Hz, 1H), 3.62-3.74 (m, 1H), 3.96-4.05 (m, 1H), 4.11-4.19 (m, 1H), 4.74-4.83 (m, 1H), 5.10 (s, 2H), 6.86 (dd, J=8.78, 2.34 Hz, 1H), 6.96 (d, J=2.40 Hz, 1H), 7.28 (d, J=8.72 Hz, 1H), 7.31 (s, 1H), 7.65-7.72 (m, 2H), 12.35 (bs, 1H).

Example 1.27

Preparation of 2$^{nd}$ Enantiomer of 2-(9-Chloro-7-(4-isopropoxy-3-(trifluoromethyl)benzyloxy)-2,3-dihydro-1H-pyrrolo[1,2-a]indol-1-yl)acetic Acid (Compound 29)

From the 2$^{nd}$ enantiomer (described as the enantiomer isolated and having the retention time of 33.1 min per the conditions reported in Example 1.25) of 2-(7-(4-isopropoxy-3-(trifluoromethyl)benzyloxy)-2,3-dihydro-1H-pyrrolo[1,2-a] indol-1-yl)acetic acid, the title compound was prepared as a solid using a similar method to the one described in Example 1.26. LCMS m/z=482.3 [M+H]$^+$; $^1$H NMR (400 MHz, CD$_3$CN) δ ppm 1.32 (d, J=6.06 Hz, 6H), 2.29-2.40 (m, 1H), 2.58 (dd, J=16.48, 9.66 Hz, 1H), 2.81-2.93 (m, 1H), 3.06 (dd, J=16.48, 4.23 Hz, 1H), 3.68-3.78 (m, 1H), 3.95-4.05 (m, 1H), 4.09-4.19 (m, 1H), 4.69-4.80 (m, 1H), 5.08 (s, 2H), 6.86 (dd, J=8.84, 2.40 Hz, 1H), 7.01 (d, J=2.40 Hz, 1H), 7.17 (d, J=8.59 Hz, 1H), 7.21 (d, J=8.72 Hz, 1H), 7.59-7.65 (m, 1H), 7.67 (s, 1H), 9.05 (bs, 1H).

Example 1.28

Preparation of 2-(7-(4-Isopropoxy-3-(trifluoromethyl)benzyloxy)-9-methyl-2,3-dihydro-1H-pyrrolo[1,2-a]indol-1-yl)acetic Acid (Compound 36)

Step A: Preparation of tert-Butyl 2-(9-iodo-7-(4-Isopropoxy-3-(trifluoromethyl)benzyloxy)-2,3-dihydro-1H-pyrrolo[1,2-a]indol-1-yl)acetate To a solution of tert-butyl 2-(7-(4-isopropoxy-3-(trifluoromethyl)benzyloxy)-2,3-dihydro-1H-pyrrolo[1,2-a]indol-1-yl)acetate (0.722 g, 1.434 mmol) in DCM (24 mL) at 0° C. was added NIS (1.434 mmol). After 5 minutes, the reaction was diluted with DCM and washed with water (twice) and saturated sodium thiolsulfate (aq). The organics were dried over $Na_2SO_4$, filtered, and concentrated to give the title compound as a light-brown solid. LCMS m/z=630.5 [M+H]$^+$; $^1$H NMR (400 MHz, DMSO-d$_6$) δ ppm 1.29 (d, J=6.06 Hz, 6H), 1.38 (s, 9H), 2.27-2.38 (m, 1H), 2.51-2.56 (m, 1H), 2.77-2.89 (m, 1H), 2.94 (dd, J=15.92, 3.41 Hz, 1H), 3.51-3.61 (m, 1H), 3.99-4.09 (m, 1H), 4.12-4.21 (m, 1H), 4.74-4.83 (m, 1H), 5.10 (s, 2H), 6.78 (d, J=2.27 Hz, 1H), 6.85 (dd, J=8.72, 2.40 Hz, 1H), 7.25 (d, J=8.84 Hz, 1H), 7.30 (d, J=8.34 Hz, 1H), 7.66-7.73 (m, 2H).

Step B: Preparation of tert-Butyl 2-(7-(4-Isopropoxy-3-(trifluoromethyl)benzyloxy)-9-methyl-2,3-dihydro-1H-pyrrolo[1,2-a]indol-1-yl)acetate To a solution of tert-butyl 2-(9-iodo-7-(4-isopropoxy-3-(trifluoromethyl)benzyloxy)-2,3-dihydro-1H-pyrrolo[1,2-a]indol-1-yl)acetate (0.778 g, 1.236 mmol) in THF (12.3 mL) under nitrogen was added 2 M solution of dimethylzinc (1.854 mL, 3.71 mmol), followed by bis(tri-t-butylphosphine)Pd(0) (0.057 g, 0.111 mmol). The reaction was stirred overnight, slowly quenched with saturated NaHCO$_3$, diluted with EtOAc, and filtered through Celite®. The organics were washed with water (twice), brine, dried over MgSO$_4$, and filtered. The solvent was removed under vacuum. The residue was purified by silica gel column chromatography to give the title compound as a solid (0.366 g). LCMS m/z=518.6 [M+H]$^+$; $^1$H NMR (400 MHz, DMSO-d$_6$) δ ppm 1.28 (d, J=5.94 Hz, 6H), 1.38 (s, 9H), 2.15 (s, 3H), 2.19-2.30 (m, 1H), 2.43-2.48 (m, 1H), 2.69-2.81 (m, 2H), 3.54-3.64 (m, 1H), 3.86-3.96 (m, 1H), 3.98-4.07 (m, 1H), 4.73-4.84 (m, 1H), 5.07 (s, 2H), 6.74 (dd, J=8.65, 2.34 Hz, 1H), 7.00 (d, J=2.27 Hz, 1H), 7.13 (d, J=8.72 Hz, 1H), 7.29 (d, J=9.35 Hz, 1H), 7.64-7.71 (m, 2H).

Step C: Preparation of 2-(7-(4-Isopropoxy-3-(trifluoromethyl)benzyloxy)-9-methyl-2,3-dihydro-1H-pyrrolo[1,2-a]indol-1-yl)acetic Acid To a solution of tert-butyl 2-(7-(4-isopropoxy-3-(trifluoromethyl)benzyloxy)-9-methyl-2,3-dihydro-1H-pyrrolo[1,2-a]indol-1-yl)acetate (0.366 g, 0.707 mmol) in dioxanes was added aq LiOH (3.0 mmol). The reaction was stirred at 75° C. for 16 h, diluted with EtOAc and washed with 1M HCl(aq), dried over MgSO$_4$, filtered, and concentrated. The residue was triturated with hexanes to give the title compound as a solid (0.313 g). LCMS m/z=462.4 [M+H]$^+$; $^1$H NMR (400 MHz, DMSO-d$_6$) δ ppm 1.28 (d, J=5.94 Hz, 6H), 2.15 (s, 3H), 2.19-2.29 (m, 1H), 2.42-2.48 (m, 1H), 2.69-2.82 (m, 2H), 3.57-3.65 (m, 1H), 3.86-3.97 (m, 1H), 3.97-4.08 (m, 1H), 4.73-4.84 (m, 1H), 5.07 (s, 2H), 6.74 (dd, J=8.72, 2.40 Hz, 1H), 7.01 (d, J=2.40 Hz, 1H), 7.13 (d, J=8.59 Hz, 1H), 7.29 (d, J=9.22 Hz, 1H), 7.64-7.72 (m, 2H), 12.26 (bs, 1H).

Resolution Via Chiral HPLC.
Column: normal phase ChiralPak IA column, 20 mm ID×250 mm L, 5 μm particle size
Eluent: 10% IPA/hexanes with 0.1% TFA=
Gradient: Isocratic
Flow: 10 mL/min
Detector: 280 nm
Retention Times: 1$^{st}$ enantiomer: 17.6 min; 2$^{nd}$ enantiomer: 20.7 min Example 1.29

Preparation of 1$^{St}$ Enantiomer of 2-(9-Chloro-7-(4-(cyclopropylmethoxy)-3-(trifluoromethyl)benzyloxy)-2,3-dihydro-1H-pyrrolo[1,2-a]indol-1-yl)acetic Acid (Compound 30)

From the enantiomer (described as the enantiomer isolated and having the retention time of 17.1 minutes per the conditions reported in Example 1.19) of 2-(7-(4-(cyclopropylmethoxy)-3-(trifluoromethyl)benzyloxy)-2,3-dihydro-1H-pyrrolo[1,2-a]indol-1-yl)acetic acid, the title compound was prepared as a solid using a similar method to the one described in Example 1.26. LCMS m/z=494.4 [M+H]$^+$; $^1$H NMR (400 MHz, CD$_3$CN) δ ppm 0.32-0.39 (m, 2H), 0.55-0.63 (m, 2H), 1.20-1.30 (m, 1H), 2.28-2.40 (m, 1H), 2.53-2.63 (m, 1H), 2.80-2.92 (m, 1H), 3.05 (dd, J=16.48, 4.23 Hz, 1H), 3.68-3.78 (m, 1H), 3.97 (d, J=6.69 Hz, 2H), 3.98-4.04 (m, 1H), 4.09-4.18 (m, 1H), 5.08 (s, 2H), 6.86 (dd, J=8.78, 2.46 Hz, 1H), 7.00 (d, J=2.40 Hz, 1H), 7.13 (d, J=8.59 Hz, 1H), 7.20 (d, J=8.84 Hz, 1H), 7.64 (d, J=8.46 Hz, 1H), 7.69 (d, J=1.89 Hz, 1H).

Example 1.30

Preparation of 2$^{nd}$ Enantiomer of 2-(9-Chloro-7-(4-(cyclopropylmethoxy)-3-(trifluoromethyl)benzyloxy)-2,3-dihydro-1H-pyrrolo[1,2-a]indol-1-yl)acetic Acid (Compound 30)

From the 2$^{nd}$ enantiomer (described as the enantiomer isolated and having the retention time of 18.8 minutes per the conditions reported in Example 1.19) of 2-(7-(4-(cyclopropylmethoxy)-3-(trifluoromethyl)benzyloxy)-2,3-dihydro-1H-pyrrolo[1,2-a]indol-1-yl)acetic acid, the title compound was prepared as a solid using a similar method to the one described in Example 1.26. LCMS m/z=494.5 [M+H]$^+$; $^1$H NMR (400 MHz, ACETONITRILE-d$_3$) δ ppm 0.32-0.39 (m, 2H), 0.55-0.62 (m, 2H), 1.20-1.30 (m, 1H), 2.29-2.39 (m, 1H), 2.53-2.62 (m, 1H), 2.81-2.92 (m, 1H), 3.05 (dd, J=16.55, 4.17 Hz, 1H), 3.68-3.77 (m, 1H), 3.97 (d, J=6.69 Hz, 2H), 3.98-4.04 (m, 1H), 4.10-4.18 (m, 1H), 5.08 (s, 2H), 6.86 (dd, J=8.84, 2.40 Hz, 1H), 7.00 (d, J=2.40 Hz, 1H), 7.13 (d, J=8.59 Hz, 1H), 7.20 (d, J=8.84 Hz, 1H), 7.63 (dd, J=8.40, 1.96 Hz, 1H), 7.69 (d, J=1.89 Hz, 1H).

Example 1.31

Preparation of 2-(7-(4-(Fluoromethoxy)-3-(trifluoromethyl)benzyloxy)-2,3-dihydro-1H-pyrrolo[1,2-a]indol-1-yl)acetic Acid (Compound 31)

Step A: Preparation of methyl 4-(Fluoromethoxy)-3-(trifluoromethyl)benzoate

To a cooled (−78° C.) mixture of methyl 4-hydroxy-3-(trifluoromethyl)benzoate (2.45 g, 11.13 mmol) and cesium carbonate (5.44 g, 16.7 mmol) in DMF in a pressure vessel was bubbled chlorofluoromethane (7.00 g, 102 mmol). The vessel was sealed and the reaction was stirred at room temperature for 120 h. The reaction was filtered through Celite®. The filtrate was diluted with EtOAc, washed with water (4 times), dried over MgSO$_4$, filtered and concentrated under vacuum to give the title compound as a solid (2.44 g). LCMS m/z=253.4 [M+H]$^+$; $^1$H NMR (400 MHz, DMSO-d$_6$) δ ppm 3.88 (s, 3H), 5.98-6.20 (d, J=52.5 Hz, 2H), 7.59 (d, J=8.84 Hz, 1H), 8.18 (d, J=2.02 Hz, 1H), 8.28 (dd, J=8.84, 2.15 Hz, 1H); $^{19}$F NMR (376 MHz, DMSO-d$_6$) δ ppm −153.52 (s, 1F), −61.08 (s, 3F).

Step B: Preparation of (4-(Fluoromethoxy)-3-(trifluoromethyl)phenyl)methanol To a cooled (−78° C.) solution of methyl 4-(fluoromethoxy)-3-(trifluoromethyl)benzoate (2.44 g, 9.68 mmol) in DCM under nitrogen was added 2.0 M LAH (4.84 mL, 9.68 mmol) by syringed. The reaction was stirred for 15 min. The reaction was quenched with water (0.484 mL) and 10% NaOH (0.968 mL). The mixture was filtered and concentrated to give the title compound as an oil (1.84 g). $^1$H NMR (400 MHz, DMSO-d$_6$) δ ppm 4.52 (d, J=5.68 Hz, 2H), 5.32 (t, J=5.75 Hz, 1H), 5.85-6.08 (d, J=53.44 Hz, 2H), 7.39 (d, J=8.46 Hz, 1H), 7.56-7.69 (m, 2H); $^1$H NMR (376 MHz, DMSO-d$_6$) δ ppm −151.41 (s, 1F), −60.26 (s, 3F).

Step C: Preparation of 4-(Chloromethyl)-1-(fluoromethoxy)-2-(trifluoromethyl)benzene (4-(Fluoromethoxy)-3-(trifluoromethyl)phenyl)methanol (1.84 g, 8.21 mmol) was dissolved in thionyl chloride (8.09 mL, 111 mmol) and stirred for 3 h. The reaction was taken up in hexanes and washed with water (twice), saturated NaHCO$_3$, and water. The organics were dried over MgSO$_4$, filtered and concentrated under vacuum to give the title compound as a solid (1.60 g). $^1$H NMR (400 MHz, DMSO-d$_6$) δ ppm 4.83 (s, 2H), 5.83-6.14 (d, J=53.1 Hz, 2H), 7.46 (d, J=8.46 Hz, 1H), 7.69-7.87 (m, 2H).

Step D: Preparation of tert-Butyl 2-(7-(4-(Fluoromethoxy)-3-(trifluoromethyl)benzyloxy)-2,3-dihydro-1H-pyrrolo[1,2-a]indol-1-yl)acetate From 4-(chloromethyl)-1-(fluoromethoxy)-2-(trifluoromethyl)benzene, the title compound was prepared as a solid using a similar method to the one described in Example 1.25, Step D. LCMS m/z=494.6 [M+H]$^+$; $^1$H NMR (400 MHz, CDCl$_3$) δ ppm 1.49 (s, 9H), 2.19-2.34 (m, 1H), 2.49 (dd, J=15.79, 8.34 Hz, 1H), 2.73 (dd, J=15.79, 6.44 Hz, 1H), 2.80-2.93 (m, 1H), 3.64-3.76 (m, 1H), 3.99 (bs, 1H), 4.06-4.15 (m, 1H), 5.07 (s, 2H), 5.68-5.81 (d, J=53.93 Hz, 2H), 6.08 (s, 1H), 6.84 (dd, J=8.72, 2.40 Hz, 1H), 7.08 (d, J=2.40 Hz, 1H), 7.13 (d, J=8.72 Hz, 1H), 7.27 (d, J=8.46 Hz, 1H), 7.63 (dd, J=8.34, 1.77 Hz, 1H), 7.73 (d, J=1.77 Hz, 1H).

Step E: Preparation of 2-(7-(4-(Fluoromethoxy)-3-(trifluoromethyl)benzyloxy)-2,3-dihydro-1H-pyrrolo[1,2-a]indol-1-yl)acetic acid From tert-Butyl 2-(7-(4-(Fluoromethoxy)-3-(trifluoromethyl)benzyloxy)-2,3-dihydro-1H-pyrrolo[1,2-a]indol-1-yl)acetate, the title compound was prepared as a solid using a similar method to the one described in Example 1.28, Step C. LCMS m/z=438.4 [M+H]$^+$; $^1$H NMR (400 MHz, DMSO-d$_6$) δ ppm 2.15-2.26 (m, 1H), 2.55 (dd, J=16.29, 7.96 Hz, 1H), 2.64-2.72 (m, 1H), 2.72-2.82 (m, 1H), 3.53-3.62 (m, 1H), 3.91-4.00 (m, 1H), 4.06-4.14 (m, 1H), 5.12 (s, 2H), 5.92-6.05 (d, J=53.28, 2H), 6.01 (s, 1H), 6.77 (dd, J=8.72, 2.40 Hz, 1H), 7.07 (d, J=2.40 Hz, 1H), 7.19 (d, J=8.59 Hz, 1H), 7.45 (d, J=9.22 Hz, 1H), 7.75-7.81 (m, 2H), 12.26 (bs, 1H).

Example 1.32

Preparation of 2-(9-Chloro-7-(4-(fluoromethoxy)-3-(trifluoromethyl)benzyloxy)-2,3-dihydro-1H-pyrrolo[1,2-a]indol-1-yl)acetic Acid (Compound 32)

From 2-(7-(4-(fluoromethoxy)-3-(trifluoromethyl)benzyloxy)-2,3-dihydro-1H-pyrrolo[1,2-a]indol-1-yl)acetic acid, the title compound was prepared as a solid using a similar method to the one described in Example 1.26. LCMS m/z=472.0 [M+H]$^+$; $^1$H NMR (400 MHz, DMSO-d$_6$) δ ppm 2.22-2.35 (m, 1H), 2.75-2.86 (m, 1H), 2.90 (dd, J=16.11, 3.98 Hz, 1H), 3.62-3.72 (m, 1H), 3.95-4.04 (m, 1H), 4.09-4.19 (m, 1H), 5.17 (s, 2H), 5.92-6.06 (d, J=53.27 Hz, 2H), 6.87 (dd, J=8.84, 2.40 Hz, 1H), 6.97 (d, J=2.40 Hz, 1H), 7.28 (d, J=8.84 Hz, 1H), 7.46 (d, J=8.34 Hz, 1H), 7.78-7.83 (m, 2H).

Example 1.33

Preparation of 2-(7-(4-Cyclopentyl-3-(trifluoromethyl)benzyloxy)-9-methyl-2,3-dihydro-1H-pyrrolo[1,2-a]indol-1-yl)acetic Acid (Compound 1)

Step A: Preparation of Methyl 2-(7-(4-Cyclopentyl-3-(trifluoromethyl)benzyloxy)-9-methyl-2,3-dihydro-1H-pyrrolo[1,2-a]indol-1-yl)acetate Methyl 2-(7-(4-cyclopentyl-3-(trifluoromethyl)benzyloxy)-9-iodo-2,3-dihydro-1H-pyrrolo[1,2-a]indol-1-yl)acetate (0.923 g, 1.54 mmol) was mostly dissolved in anhydrous THF (15.4 mL) to give a turbid suspension which was degassed with $N_2$ for about 15 min. Bis(tri-t-butylphosphine) Pd(0) (0.071 g, 0.139 mmol) and 2.0 M methylzinc chloride in THF (2.318 mL, 4.64 mmol) were added at 25° C. The reaction mixture was sealed and heated at 70° C. to give a dark suspension. After 2 h at 70° C., the reaction mixture was cooled to 25° C., quenched with $NaHCO_3$ (4 mL), stirred for 5 min, and filtered through a celite pad. The filtrate was diluted with MTBE, washed with $H_2O$ (twice), brine, and dried over $MgSO_4$. The solvent was evaporated in vacuo to give a solid. The solid was dissolved in DCM/hexanes (1:1) and purified by silica gel column chromatography to give the titled compound (0.582 g) as a white solid. LCMS m/z=486.5 $[M+H]^+$. $^1H$ NMR (400 MHz, $CDCl_3$) δ ppm 1.58-1.66 (m, 2H), 1.67-1.79 (m, 2H), 1.80-1.91 (m, 2H), 2.05-2.14 (m, 2H), 2.23 (s, 3H), 2.26-2.36 (m, 1H), 2.51 (dd, J=−15.92, 10.11 Hz, 1H), 2.82-2.90 (m, 1H), 2.94 (dd, J=15.79, 4.67 Hz, 1H), 3.32-3.43 (m, 1H), 3.73 (s, 3H), 3.75-3.80 (m, 1H), 3.92-4.01 (m, 1H), 4.02-4.10 (m, 1H), 5.09 (s, 2H), 6.86 (dd, J=8.72, 2.40 Hz, 1H), 7.04 (d, J=2.27 Hz, 1H), 7.10 (d, J=8.84 Hz, 1H), 7.47 (d, J=8.08 Hz, 1H), 7.61 (d, J=8.08 Hz, 1H), 7.71 (s, 1H).

Step B: Preparation of 2-(7-(4-Cyclopentyl-3-(trifluoromethyl)benzyloxy)-9-methyl-2,3-dihydro-1H-pyrrolo[1,2-a]indol-1-yl)acetic Acid Methyl 2-(7-(4-cyclopentyl-3-(trifluoromethyl)benzyloxy)-1,2,3,4-tetrahydrocyclopenta[b]indol-3-yl)acetate (0.579 g, 1.192 mmol) was dissolved in 1,4-dioxane (10.74 mL). Aqueous 1.0 M lithium hydroxide (3.58 mL, 3.58 mmol) was added at 25° C. to give a slightly turbid solution. The reaction mixture was stirred at 60° C. for 1 h and cooled to 25° C. The solvent was evaporated in vacuo at 25° C. to a volume of 4 mL and added 0.5 M citric acid (14 mL) and MTBE (75 mL). The mixture was shaken. The organic layer was separated, washed with $H_2O$ (2×20 mL), brine (20 mL), and dried over $MgSO_4$. The solvent was evaporated in vacuo to give the title compound (0.540 g) as white crystals. LCMS m/z=472.3 $[M+H]^+$; $^1H$ NMR (400 MHz, DMSO-$d_6$) δ ppm 1.55-1.73 (m, 4H), 1.79-1.90 (m, 2H), 2.01 (m, 2H), 2.15 (s, 3H), 2.19-2.29 (m, 1H), 2.40-2.48 (m, 1H), 2.70-2.82 (m, 2H), 3.20-3.28 (m, 1H), 3.60 (m, 1H), 3.92 (m, 1H), 4.03 (m, 1H), 5.14 (s, 2H), 6.76 (dd, J=8.72, 2.40 Hz, 1H), 7.02 (d, J=2.40 Hz, 1H), 7.14 (d, J=8.72 Hz, 1H), 7.63 (d, J=8.00 Hz, 1H), 7.68-7.76 (m, 2H), 12.26 (bs, 1H).
Resolution Via Chiral HPLC.
Column: normal phase ChiralPak IA column, 20 mm ID×250 mm L, 5 μm particle size
Eluent: 10% IPA/hexanes with 0.1% TFA
Gradient: Isocratic
Flow: 6 mL/min
Retention Times: $1^{st}$ enantiomer: 21.9 min; $2^{nd}$ enantiomer: 25.3 min Example 1.34

Preparation of 2-(7-(4-Cyclopentyl-3-(trifluoromethyl)benzyloxy)-9-(pyridin-2-yl)-2,3-dihydro-1H-pyrrolo[1,2-a]indol-1-yl)acetic Acid (Compound 16)

The $1^{st}$ enantiomer (described as the enantiomer isolated and having the retention time of 15 min per the conditions reported in Example 1.7) of 2-(7-(4-cyclopentyl-3-(trifluoromethyl)benzyloxy)-2,3-dihydro-1H-pyrrolo[1,2-a]indol-1-yl)acetic acid (0.100 g, 0.219 mmol) was dissolved in anhydrous DCM (2.2 mL) using a plastic vial. The reaction was cooled to 0° C., and N-fluoropyridinium triflate (0.073 g, 0.295 mmol) was added. The reaction was allowed to warm to 25° C. and after 4 h there was a dark solution. The reaction was diluted with EtOAc (40 mL), washed with water/brine (2×10 mL), brine (10 mL), and dried over $MgSO_4$. The solvent was evaporated in vacuo. The residue was purified by HPLC to give the titled compound (0.011 g) as a yellow solid. LCMS m/z=535.5 $[M+H]^+$; $^1H$ NMR (400 MHz, $CD_3CN$) δ ppm 1.54-1.78 (m, 4H), 1.79-1.92 (m, 2H), 2.05 (dd, J=9.92, 4.48 Hz, 2H), 2.43-2.53 (m, 2H), 2.57-2.73 (m, 2H), 3.29-3.41 (m, 1H), 4.09-4.28 (m, 3H), 5.17 (d, J=3.54 Hz, 2H), 6.99 (dd, J=8.84, 2.27 Hz, 1H), 7.34 (d, J=8.84 Hz, 1H), 7.44 (d, J=2.27 Hz, 1H), 7.53 (t, J=6.25 Hz, 1H), 7.56-7.61 (m, 1H), 7.64-7.69 (m, 1H), 7.73 (s, 1H), 7.90 (d, J=8.34 Hz, 1H), 8.23 (td, J=7.86, 1.58 Hz, 1H), 8.66 (d, J=4.42 Hz, 1H).

Example 1.35

Preparation of 2-(7-(4-Cyclopentyl-3-(trifluoromethyl)benzyloxy)-9-ethyl-2,3-dihydro-1H-pyrrolo[1,2-a]indol-1-yl)acetic Acid (Compound 15)

Step A: Preparation of tert-Butyl 2-(7-(4-Cyclopentyl-3-(trifluoromethyl)benzyloxy)-9-ethyl-2,3-dihydro-1H-pyrrolo[1,2-a]indol-1-yl)acetate To a solution of tert-butyl 2-(7-(4-cyclopentyl-3-(trifluoromethyl)benzyloxy)-9-iodo-2,3-dihydro-1H-pyrrolo[1,2-a]indol-1-yl)acetate (17 mg, 0.027 mmol) in THF (0.500 mL) in a 0.5-2.0 mL heavy-walled microwave sealed tube under $N_2$ was added diethylzinc (0.074 mL, 0.037 mmol) and bis(tri-t-butylphosphine)palladium(0) (1.223 mg, 2.393 μmol). The reaction was then heated to 70° C. for 2 h. The reaction mixture was quenched with saturated $NaHCO_3$, filtered by vacuum filtration through Celite®, and washed with EtOAc (2×5 mL). The filtrate was then extracted with EtOAc (3×5 mL). The organic layers were combined and washed with saturated NaCl (1×10 mL), dried (MgSO4), and filtered by vacuum filtration through a glass fiber paper. The solvent was removed under reduced pressure. The residue was purified by preparative TLC to give the title compound (6.6 mg) as an amber oil. LCMS m/z=542.6 $[M+H]^+$.

Step B: Preparation 2-(7-(4-Cyclopentyl-3-(trifluoromethyl)benzyloxy)-9-ethyl-2,3-dihydro-1H-pyrrolo[1,2-a]indol-1-yl)acetic Acid tert-Butyl 2-(7-(4-cyclopentyl-3-(trifluoromethyl)benzyloxy)-9-ethyl-2,3-dihydro-1H-pyrrolo[1,2-a]indol-1-yl)acetate (6.6 mg, 0.012 mmol) was added to a solution of 2-amino-3-mercaptopropanoic acid (1.476 mg, 0.012 mmol) in TFA (1 mL). The reaction was stirred at 23° C. for 15 min in a 20 mL sealed scintillation vial. The mixture was poured into about 4 mL of ice water. The precipitate was collected by vacuum filtration through a glass fiber paper, washed with n-hexane (3×5 mL), and dried (vacuum oven) to give the title compound (0.8 mg) as a tan solid. LCMS m/z=486.3 $[M+H]^+$; $^1H$ NMR (400 MHz, $CD_3CN$) δ ppm 1.09 (t, J=7.52 Hz, 3H), 1.48-1.59 (m, 2H), 1.60-1.69 (m, 2H), 1.74-1.82 (m, 2H), 1.93-2.00 (m, 2H), 2.17-2.27 (m, 1H), 2.39-2.49 (m, 1H), 2.55-2.63 (m, 2H), 2.66-2.81 (m, 2H), 3.21-3.32 (m, 1H), 3.54-3.63 (m, 1H), 3.82-3.89 (m, 1H), 3.92-4.00 (m, 1H), 5.05 (s, 2H), 6.70 (dd, J=8.72, 2.40 Hz, 1H), 6.96 (d, J=2.27 Hz, 1H), 7.03 (d, J=8.72 Hz, 1H), 7.49 (d, 1H), 7.57 (d, J=9.35 Hz, 1H), 7.64 (d, J=1.14 Hz, 1H), 8.95 (bs, 1H).

Example 1.36

Preparation of 2-(9-Chloro-7-(3-cyano-4-isopropoxybenzyloxy)-2,3-dihydro-1H-pyrrolo[1,2-a]indol-1-yl)acetic Acid (Compound 8)

Step A: Preparation of tert-Butyl 2-(7-(3-Cyano-4-isopropoxybenzyloxy)-2,3-dihydro-1H-pyrrolo[1,2-a]indol-1-yl)acetate tert-Butyl 2-(7-hydroxy-2,3-dihydro-1H-pyrrolo[1,2-a]indol-1-yl)acetate (0.287 g, 1.000 mmol), cesium carbonate (0.489 g, 1.500 mmol) and 5-(chloromethyl)-2-isopropoxybenzonitrile (0.315 g, 1.500 mmol) were taken up in DMF (2.0 mL) and heated to 60° C. for 16 h in a 20 mL sealed scintillation vial. The reaction was cooled down to room temperature and poured into water and extracted into ether (2×5 mL). The organic layers were combined and washed with water (3×5 mL), saturated NaCl (1×5 mL), dried over MgSO$_4$, and filtered by vacuum filtration through a glass fiber paper. The solvent was removed under reduced pressure. The residue was purified by silica gel column chromatography to give the title compound (0.301 g) as a light yellow solid. LCMS m/z=461.5 [M+H]$^+$.

Step B: Preparation of 2-(7-(3-Cyano-4-isopropoxybenzyloxy)-2,3-dihydro-1H-pyrrolo[1,2-a]indol-1-yl)acetic Acid A solution of 2-amino-3-mercaptopropanoic acid (0.229 g, 1.889 mmol) in TFA (3.15 mL) was made and added to tert-butyl 2-(7-(3-cyano-4-isopropoxybenzyloxy)-2,3-dihydro-1H-pyrrolo[1,2-a]indol-1-yl)acetate (0.290 g, 0.630 mmol) in a 20 mL sealed scintillation vial and stirred at 23° C. for 15 min. After 15 min the solution was poured into ice water and stirred for 30 minutes. The resulting precipitate was collected by vacuum filtration, washed with water (2×5 mL) and n-Hexane (3×5 mL), and dried (vacuum oven) to give the title compound (0.202 g) as an off-white solid. LCMS m/z=405.5 [M+H]$^+$.

Step C: Preparation of 2-(9-Chloro-7-(3-cyano-4-isopropoxybenzyloxy)-2,3-dihydro-1H-pyrrolo[1,2-a]indol-1-371)acetic Acid 2-(7-(3-Cyano-4-isopropoxybenzyloxy)-2,3-dihydro-1H-pyrrolo[1,2-a]indol-1-yl)acetic Acid (50 mg, 0.124 mmol) was dissolved in DCM (1 mL) and cooled to 0° C. NCS (16.51 mg, 0.124 mmol) was added and the reaction was stirred at 0° C. for 15 min in a 20 mL sealed scintillation vial. The mixture was diluted with DCM and washed with water (2×10 mL), Na$_2$S$_2$O$_3$ (aq) (2×10 mL), dried over MgSO$_4$, and filtered by vacuum filtration through a glass fiber paper. The solvent was removed under reduced pressure to give the title compound (50.1 mg) as a yellow solid. LCMS m/z=439.3 [M+H]$^+$; $^1$H NMR (400 MHz, DMSO-d$_6$) ppm 1.32 (d, J=6.06 Hz, 6H), 2.24-2.35 (m, 1H), 2.52-2.59 (m, 1H), 2.77-2.87 (m, 1H), 2.94 (dd, J=16.29, 4.04 Hz, 1H), 3.64-3.73 (m 1H), 3.96-4.07 (m, 1H), 4.10-4.20 (m, 1H), 4.79 (dt, J=12.09, 6.02 Hz, 1H), 5.07 (s, 2H), 6.86 (dd, J=8.72, 2.40 Hz, 1H), 6.96 (d, J=2.27 Hz, 1H), 7.29 (dd, J=8.84, 3.79 Hz, 2H), 7.72 (dd, J=8.78, 2.21 Hz, 1H), 7.79 (d, J=2.15 Hz, 1H), 12.35 (s, 1H).

Example 1.37

Preparation of 2-(2-(3,4-Diethoxybenzyloxy)-6,7,8,9-tetrahydropyrido[1,2-a]indol-9-yl)acetic Acid (Compound 47)

Step A: Preparation of Ethyl 2-(2-(3,4-Diethoxybenzyloxy)-6,7,8,9-tetrahydropyrido[1,2-a]indol-9-yl)acetate Ethyl 2-(2-hydroxy-6,7,8,9-tetrahydropyrido[1,2-a]indol-9-yl)acetate (0.100 g, 0.366 mmol), cesium carbonate (0.179 g, 0.549 mmol) and 4-(chloromethyl)-1,2-diethoxybenzene (0.118 g, 0.549 mmol) were taken up in DMA (2 mL) and heated to 60° C. for 16 h in a 20 mL sealed scintillation vial. The reaction was cooled down to room temperature and filtered by vacuum filtration through a glass fiber paper. The solvent was removed under reduced pressure. The residue was purified by silica gel column chromatography to give the title compound (0.103 g) as an off-white solid. LCMS m/z=452.3 [M+H]$^+$.

Step B: Preparation 2-(2-(3,4-Diethoxybenzyloxy)-6,7,8,9-tetrahydropyrido[1,2-a]indol-9-yl)acetic Acid To a solution of ethyl 2-(2-(3,4-diethoxybenzyloxy)-6,7,8,9-tetrahydropyrido[1,2-a]indol-9-yl)acetate (0.100 g, 0.221 mmol) in 1,4-dioxane (4 mL) was added 1.0 M LiOH (aq) (1.107 mL, 1.107 mmol). The reaction was stirred at 23° C. for 16 h in a 20 mL sealed scintillation vial. The mixture was poured into 1 M HCl and extracted with EtOAc (3×5 mL). The organic layers were combined, dried over MgSO$_4$, and filtered by vacuum filtration through a glass fiber paper. The solvent was removed under reduced pressure to give the title compound (0.0831 g) as a tan solid. LCMS m/z=424.3 [M+H]$^+$; $^1$H NMR (400 MHz, DMSO-d$_6$) δ ppm 1.27-1.36 (m, 6H), 1.49 (d, J=11.37 Hz, 1H), 1.87-1.95 (m, 1H), 1.99-2.07 (m, 1H), 2.07-2.16 (m, 1H), 2.40-2.49 (m, 1H), 2.77-2.87 (m, 1H), 3.24-3.35 (m, 1H), 3.73-3.84 (m, 1H), 3.96-4.06 (m, 4H), 4.07-4.16 (m, 1H), 4.96 (s, 2H), 6.14 (s, 1H), 6.76 (dd, J=8.78, 2.34 Hz, 1H), 6.88-6.96 (m, 2H), 7.01-7.07 (m, 2H), 7.21 (d, J=8.84 Hz, 1H), 12.27 (s, 1H).

Example 1.38

Preparation of 2-(7-(3-Cyano-4-isopropoxybenzyloxy)-9-methyl-2,3-dihydro-1H-pyrrolo[1,2-a]indol-1-yl)acetic Acid (Compound 26)

Step A: Preparation of tert-Butyl 2-(7-(3-Cyano-4-isopropoxybenzyloxy)-9-iodo-2,3-dihydro-1H-pyrrolo[1,2-a]indol-1-yl)acetate tert-Butyl 2-(7-(3-cyano-4-isopropoxybenzyloxy)-2,3-dihydro-1H-pyrrolo[1,2-a]indol-1-yl)acetate (0.576 g, 1.251 mmol) was dissolved in DCM (12.51 mL). The reaction mixture was cooled to 0° C., and NIS (0.295 g, 1.313 mmol) was added while stirring. After stirring at 0° C. for 50 min, the reaction mixture was diluted with MTBE (60 mL), washed with water (2×20 mL), 2 M sodium thiosulfate (2×12.5 mL), brine (10 mL), and dried over MgSO$_4$. The solvent was evaporated in vacuo to give the title compound as a light-yellow solid (0.723 g) without further purification. LCMS m/z=587.4 [M+H]$^+$; $^1$H NMR (400 MHz, CD$_3$CN) δ ppm 1.36 (d, J=6.06 Hz, 6H), 1.40 (s, 9H), 2.34-2.45 (m, 1H), 2.52 (dd, J=15.92, 9.85 Hz, 1H), 2.87 (dt, J=18.60, 8.45 Hz, 1H), 2.99 (dd, J=15.92, 3.54 Hz, 1H), 3.57-3.65 (m, 1H), 4.05 (m, 1H), 4.17 (m, 1H), 4.75 (dt, J=12.13, 6.06 Hz, 1H), 5.06 (s, 2H), 6.83-6.85 (m, 1H), 6.85-6.89 (m, 1H), 7.14 (d, J=8.72

Hz, 1H), 7.19 (d, J=8.72 Hz, 1H), 7.67 (dd, J=8.72, 2.15 Hz, 1H), 7.70 (d, J=2.15 Hz, 1H).

Step B: Preparation of tert-Butyl 2-(7-(3-Cyano-4-isopropoxybenzyloxy)-9-methyl-2,3-dihydro-1H-pyrrolo[1,2-a]indol-1-yl)acetate tert-Butyl 2-(7-(3-cyano-4-isopropoxybenzyloxy)-9-iodo-2,3-dihydro-1H-pyrrolo[1,2-a]indol-1-yl)acetate (0.717 g, 1.223 mmol) was dissolved in anhydrous THF (12.2 mL, 1.223 mmol). The solution was degassed with nitrogen for about 5 min using a syringe needle. Bis(tri-t-butylphosphine)Pd(0) (0.056 g, 0.110 mmol) and 2.0 M methylzinc chloride in THF (1.83 mL, 3.67 mmol) were added. The reaction vessel was purged with nitrogen, sealed, and heated at 70° C. After 2 h, the reaction mixture was cooled to 25° C. and slowly added saturated NaHCO$_3$ (5 mL). After stirring for about 5 min, the reaction was diluted with EtOAc (20 mL), filtered through a celite pad, and the celite pad was washed with EtOAc (3×20 mL). The organic layer was washed with water (2×20 mL), brine (10 mL), and dried over MgSO$_4$. The solvent was evaporated in vacuo and the residue was purified by silica gel column chromatography to give the title compound as an oil (0.470 g). LCMS m/z=475.4 [M+H]$^+$; $^1$H NMR (400 MHz, Acetonitrile-d$_3$) δ ppm 1.36 (d, J=5.94 Hz, 6H), 1.41 (s, 9H), 2.19 (s, 3H), 2.27-2.37 (m, 1H), 2.46 (dd, J=15.66, 9.22 Hz, 1H), 2.72-2.86 (m, 2H), 3.60-3.69 (m, 1H), 3.93 (m, 1H), 4.00-4.10 (m, 1H), 4.75 (dt, J=12.13, 6.06 Hz, 1H), 5.03 (s, 2H), 6.77 (dd, J=8.72, 2.40 Hz, 1H), 7.00 (d, J=2.40 Hz, 1H), 7.11 (d, J=8.72 Hz, 1H), 7.13 (d, J=8.72 Hz, 1H), 7.63-7.68 (m, 1H), 7.69 (d, J=2.27 Hz, 1H).

Step C: Preparation of 2-(7-(3-Cyano-4-isopropoxy-benzyloxy)-9-methyl-2,3-dihydro-1H-pyrrolo[1,2-a]indol-1-yl)acetic Acid To a pre-cooled flask containing tert-butyl 2-(7-(3-cyano-4-isopropoxybenzyloxy)-9-methyl-2,3-dihydro-1H-pyrrolo[1,2-a]indol-1-yl)acetate (0.308 g, 0.649 mmol) was added a pre-cooled solution of D/L-2-Amino-3-mercaptopropanoic acid (0.079 g, 0.649 mmol) in TFA (6.49 mL, 0.649 mmol) at 0° C. After stirring for 3 h at 0° C., ice-cold water (65 mL) was added. The resulting suspension was diluted with Et$_2$O (130 mL). The organic layer was separated, washed with water (2×30 mL), brine (30 mL), and dried over MgSO$_4$. The solvent was coevaporated with toluene (25 mL) in vacuo at 25° C. The residue was coevaporated with toluene (20 mL) again to give an oil. The oil was dissolved in DCM (5 mL) and coevaporated with hexanes (25 mL) to give the title compound as a grey solid (0.299 g). LCMS m/z=419.4 [M+H]$^+$; $^1$H NMR (400 MHz, DMSO-d$_6$) α ppm 1.32 (d, J=6.06 Hz, 6H), 2.16 (s, 3H), 2.19-2.29 (m, 1H), 2.47 (d, J=6.69 Hz, 1H), 2.70-2.82 (m, 2H), 3.54-3.65 (m, 1H), 3.92 (m, 1H), 4.03 (dt, J=8.05, 1.91 Hz, 1H), 4.79 (dt, J=12.13, 6.06 Hz, 1H), 5.04 (s, 2H), 6.74 (dd, J=8.72, 2.40 Hz, 1H), 7.00 (d, J=2.40 Hz, 1H), 7.13 (d, J=8.72 Hz, 1H), 7.28 (d, J=8.84 Hz, 1H), 7.72 (dd, J=8.78, 2.21 Hz, 1H), 7.78 (d, J=2.15 Hz, 1H), 12.27 (bs, 1H).
Resolution Via Chiral HPLC
Column: normal phase ChiralPak IA, 250×20 mm ID, 5 μm particle size
Eluent: 1% MeOH/DCM with 0.1% TFA
Gradient: Isocratic
Flow: 6 mL/minute
Detector: 280 nM
Retention Times: 1$^{st}$ enantiomer: 25 min; 2$^{nd}$ enantiomer: 28 min Example 1.39

Preparation of 2-(2-(4-Isopropoxy-3-(trifluoromethyl)benzyloxy)-6,7,8,9-tetrahydropyrido indol-9-yl)acetic Acid (Compound 45)

Step A: Preparation of Ethyl 2-(2-(4-Isopropoxy-3-(trifluoromethyl)benzyloxy)-6,7,8,9-tetrahydropyrido[1,2-a]indol-9-yl)acetate Ethyl 2-(2-hydroxy-6,7,8,9-tetrahydropyrido[1,2-a]indol-9-yl)acetate (0.107 g, 0.391 mmol) was dissolved in anhydrous DMF (3.91 mL, 0.391 mmol). Cesium carbonate (0.166 g, 0.509 mmol) was added followed by 4-(chloromethyl)-1-isopropoxy-2-(trifluoromethyl)benzene (0.122 mL, 0.587 mmol) to give a suspension. The reaction was heated at 50° C. for 5 h. The solvent was evaporated in vacuo to give a residue which was dissolved in EtOAc (50 mL) and water (20 mL). The organic layer was washed with water (20 mL), brine (20 mL), and dried over MgSO$_4$. The solvent was evaporated in vacuo to give an oil which was purified by silica gel column chromatography to give the title compound as an oil (0.154 g). LCMS m/z=490.4 [M+H]$^+$; $^1$H NMR (400 MHz, Acetonitrile-d$_3$) α ppm 1.24 (t, J=7.14 Hz, 3H), 1.32 (d, J=6.06 Hz, 6H), 1.50-1.64 (m, 1H), 2.1 (m, 3H), 2.55 (dd, J=15.73, 8.02 Hz, 1H), 2.86 (dd, J=15.66, 5.94 Hz, 1H), 3.33-3.47 (m, 1H), 3.79-3.88 (m, 1H), 4.06-4.21 (m, 3H), 4.74 (dt, J=12.09, 6.02 Hz, 1H), 5.04 (s, 2H), 6.13 (s, 1H), 6.81 (dd, J=8.78, 2.46 Hz, 1H), 7.04 (d, J=2.40 Hz, 1H), 7.16 (d, J=8.59 Hz, 1H), 7.19 (d, J=8.84 Hz, 1H), 7.62 (d, J=8.59 Hz, 1H), 7.66 (d, J=1.89 Hz, 1H).

Step B: Preparation of 2-(2-(4-Isopropoxy-3-(trifluoromethyl)benzyloxy)-6,7,8,9-tetrahydropyrido indol-9-yl)acetic Acid Ethyl 2-(2-(4-isopropoxy-3-(trifluoromethyl)benzyloxy)-6,7,8,9-tetrahydropyrido[1,2-a]indol-9-yl)acetate (0.147 g, 0.3 mmol) was dissolved in 1,4-dioxane (4.5 mL). LiOH (1.0 M, 1.501 mL) was added at 25° C. to give a slightly turbid solution. The reaction was heated at 50° C. for 2 h, cooled to 24° C., and acidified with 0.5 M citric acid (6.01 mL, 3.00 mmol). The mixture was diluted with EtOAc (50 mL), washed with water (2×10 mL), brine (10 mL), and dried over MgSO$_4$. The solvent was evaporated in vacuo to give an oil which was coevaporated with DCM and hexanes (excess) at 25° C. to give the title compound as an off-white solid (147 mg). LCMS m/z=462.1 [M+H]$^+$; $^1$H NMR (400 MHz, DMSO-d$_6$) δ ppm 1.28 (d, J=6.06 Hz, 6H), 1.39-1.57 (m, 1H), 1.83-2.20 (m, 3H), 2.40-2.48 (m, 2H), 2.84 (dd, J=15.85, 5.62 Hz, 1H), 3.73-3.86 (m, 1H), 4.11 (m., 1H), 4.78 (dt, J=12.16, 6.11 Hz, 1H), 5.06 (s, 2H), 6.15 (s, 1H), 6.78 (dd, J=8.72, 2.40 Hz, 1H), 7.05 (d, J=2.40 Hz, 1H), 7.23 (d, J=8.72 Hz, 1H), 7.29 (d, J=9.22 Hz, 1H), 7.63-7.70 (m, 2H), 12.27 (bs, 1H).
Resolution Via Chiral HPLC
Column: normal phase ChiralPak IA, 250×20 mm ID, 5 μm particle size
Eluent: 30% IPA/hexanes
Gradient: Isocratic
Flow: 6 mL/minute
Detector: 280 nM
Retention Times: 1$^{st}$ enantiomer: 35 min; 2$^{nd}$ enantiomer: 40 min

Example 1.40

Preparation of 2-(7-(3,4-Diethoxybenzyloxy)-2,3-dihydro-1H-pyrrolo[1,2-a]indol-1-yl)acetic Acid (Compound 38)

Step A: Preparation of tert-Butyl 2-(7-(3,4-Diethoxybenzyloxy)-2,3-dihydro-1H-pyrrolo[1,2-a]indol-1-yl)acetate tert-Butyl 2-(7-hydroxy-2,3-dihydro-1H-pyrrolo[1,2-a]indol-1-yl)acetate (0.150 g, 0.522 mmol), cesium carbonate (0.255 g, 0.783 mmol) and 4-(chloromethyl)-1,2-diethoxybenzene (0.168 g, 0.783 mmol) were taken up in DMA (2 mL) and heated to 60° C. for 16 h in a 20 mL sealed scintillation vial. The mixture was cooled down to room temperature and filtered by vacuum filtration through a glass fiber paper. The solvent was removed under reduced pressure. The residue was purified by silica gel column chromatography to give the title compound (173.1 mg).

Step B: Preparation of 2-(7-(3,4-Diethoxybenzyloxy)-2,3-dihydro-1H-pyrrolo[1,2-a]indol-1-yl)acetic Acid tert-Butyl 2-(7-(3,4-diethoxybenzyloxy)-2,3-dihydro-1H-pyrrolo[1,2-a]indol-1-yl)acetate (173.1 mg) was taken up in dioxane (4 mL) and 1.0 M aqueous LiOH (1.11 mL) was added. The reaction was stirred at 70° C. 16 h, and stirred at 80° C. for an additional 5 h. The mixture was cooled to room temperature and poured into a separatory funnel containing EtOAc and 1.0 M HCl. The water layer was removed and the EtOAc layer was washed with water. The organics were dried over sodium sulfate, filtered, and concentrated under reduced pressure to give title compound (131.4 mg). LCMS m/z=410.4 [M+H]$^+$; $^1$H NMR (400 MHz, CDCl$_3$) δ ppm 1.28-1.34 (m, 6H), 2.15-2.26 (m, 1H), 2.54 (dd, J=16.3, 7.9 Hz, 1H), 2.68 (dd, J=16.3, 6.7 Hz, 1H), 2.72-2.82 (m, 1H), 3.53-3.62 (m, 1H), 3.91-4.93 (m, 6H), 4.95 (s, 2H), 6.0 (s, 1H), 6.73 (dd, J=8.7, 2.4 Hz, 1H), 6.90-6.96 (m, 2H), 7.02-7.06 (m, 2H), 7.17 (d, J=9.0 Hz, 1H), 12.3 (bs, 1H).

Example 1.41

Preparation of 2-(7-(3-Cyano-4-isopropoxybenzyloxy)-8-methyl-2,3-dihydro-1H-pyrrolo[1,2-a]indol-1-yl)acetic Acid (Compound 41)

Step A: Preparation of Ethyl 4-Bromo-5-methoxy-1H-indole-2-carboxylate

To a suspension of ethyl 5-methoxy-1H-indole-2-carboxylate (5 g, 22.81 mmol) in acetic acid (100 mL) was added bromine (1.169 mL, 22.81 mmol) slowly at room temperature. The reaction mixture was stirred at room temperature for 2 days. The solid was filtered off, washed with acetic acid and hexanes, and dried to give the title compound as a white solid (6.8 g). LCMS m/z=298.6 [M+H]$^+$.

Step B: Preparation of Ethyl 5-Methoxy-4-methyl-1H-indole-2-carboxylate

To a reaction mixture of ethyl 4-bromo-5-methoxy-1H-indole-2-carboxylate (1 g, 3.35 mmol) and bis(tri-t-butylphosphine)palladium (0) (0.171 g, 0.335 mmol) in THF (10 mL) was added a 2 M solution of methylzinc(II) chloride in THF (5.03 mL, 10.06 mmol) at room temperature. The reaction was stirred at 65° C. for 2 h, cooled down, and added saturated aqueous NaHCO$_3$ solution. The solid was filtered off through celite and washed with ethyl acetate. The filtrate was extracted with ethyl acetate. The combined organics were dried over anhydrous Na$_2$SO$_4$ and concentrated. The residue was purified by silica gel column chromatography to give the title compound as white solid (712 mg). LCMS m/z=234.2 [M+H]$^+$; $^1$H NMR (400 MHz, CDCl$_3$) α ppm 1.42 (t, J=7.1 Hz, 3H), 2.44 (s, 3H), 3.87 (s, 3H), 4.41 (q, J=7.1 Hz, 2H), 7.05 (d, J=9.0 Hz, 1H), 7.19-7.24 (m, 2H), 8.81 (s, 1H).

Step C: Preparation of 7-Methoxy-8-methyl-2,3-dihydro-1H-pyrrolo[1,2-a]indol-1-one To a suspension of ethyl 5-methoxy-4-methyl-1H-indole-2-carboxylate (712 mg, 3.05 mmol) in toluene (10 mL) was added a 1 M solution of KOtBu in THF (3.97 mL, 3.97 mmol). The reaction mixture was stirred at room temperature for 5 min, methyl acrylate (825 μL, 9.15 mmol) was added. The reaction was stirred at reflux overnight and neutralized with 1 N HCl aqueous solution. The solid was collected and divided into three microwave vial. Each was added AcOH (8 mL) and H$_2$O (1 mL), and heated at 180° C. for 15 min under microwave irradiation. The solvent was evaporated and the residue was purified by silica gel column chromatography to give the title compound as a yellow solid (500 mg). LCMS m/z=216.2 [M+H]$^+$; $^1$H NMR (400 MHz, CDCl$_3$) δ ppm 2.45 (s, 3H), 3.21 (t, J=6.5 Hz, 2H), 3.68 (s, 3H), 4.40 (t, J=6.2 Hz, 2H), 6.98 (s, 1H), 7.13 (d, J=9.0 Hz, 1H), 7.23 (d, J=9.0 Hz, 1H).

Step D: Preparation of Ethyl 2-(7-Methoxy-8-methyl-2,3-dihydro-1H-pyrrolo[1,2-a]indol-1-ylidene)acetate To a solution of ethyl 2-(diethoxyphosphoryl)acetate (1.38 mL, 6.97 mmol) in DMF (2 mL) was added sodium hydride (60% dispersion in mineral oil) (279 mg, 6.97 mmol) at 0° C. The reaction mixture was stirred for 10 min, then 7-methoxy-8-methyl-2,3-dihydro-1H-pyrrolo[1,2-a]indol-1-one (500 mg, 2.323 mmol) in DMF (6 mL) was added. The reaction mixture was warmed to room temperature and stirred for 1 h, then heated at 60° C. for 1 h, cooled down, poured into saturated NH$_4$Cl aqueous solution, extracted with ethyl acetate. The combined organics were washed with water, dried over anhydrous Na$_2$SO$_4$, and concentrated. The residue was purified by silica gel column chromatography to give the title compound (361 mg). LCMS m/z=286.2 [M+H]$^+$.

Step E: Preparation of Ethyl 2-(7-Methoxy-8-methyl-2,3-dihydro-1H-pyrrolo[1,2-a]indol-1-yl)acetate Ethyl 2-(7-methoxy-8-methyl-2,3-dihydro-1H-pyrrolo[1,2-a]indol-1-ylidene)acetate (351 mg, 1.23 mmol) was dissolved in EtOAc (6 mL) and ethanol (6 mL), 10% Palladium on carbon (120 mg) was added. The reaction was degassed and charged with hydrogen, then stirred at room temperature overnight. The solid was filtered off. The filtrate was concentrated to give the title compound (320 mg) as an oil without further purification. LCMS m/z=288.2 [M+H]$^+$; $^1$H NMR (400 MHz, CDCl$_3$) δ ppm 1.32 (t, J=7.1 Hz, 3H), 2.25-2.32 (m, 1H), 2.40 (s, 3H), 2.58 (dd, J=16.0 and 8.6 Hz, 1H), 2.80-2.95 (m, 2H), 3.73-3.80 (m, 1H), 3.85 (s, 3H), 3.95-4.02 (m, 1H), 4.06-4.18 (m, 1H), 4.18-4.26 (m, 2H), 6.11 (s, 1H), 6.84 (d, J=8.6 Hz, 1H), 7.02 (d, J=8.6 Hz, 1H).

Step F: Preparation of Ethyl 2-(7-Hydroxy-8-methyl-2,3-dihydro-1H-pyrrolo[1,2-a]indol-1-yl)acetate To a stirred solution of ethyl 2-(7-methoxy-8-methyl-2,3-dihydro-1H-pyrrolo[1,2-a]indol-1-yl)acetate (320 mg, 1.114 mmol) in anhydrous DCM (8 mL) was added a 1M solution of boron tribromide in DCM (3341 µL, 3.34 mmol) at 0° C. under nitrogen protection. The reaction mixture was stirred at this temperature for 1 h, neutralized by addition of saturated NaHCO$_3$ solution. The organic layer was separated and washed with water and dried over anhydrous Na$_2$SO$_4$. The solvent was evaporated, and the residue was purified by column chromatography to give the title compound (200 mg) as a light yellow oil. LCMS m/z=274.3 [M+H]$^+$; $^1$H NMR (400 MHz, CDCl$_3$) δ ppm 1.32 (t, J=7.1 Hz, 3H), 2.25-2.32 (m, 1H), 2.40 (s, 3H), 2.58 (dd, J=16.0, 8.5 Hz, 1H), 2.82-2.90 (m, 2H), 3.73-3.80 (m, 1H), 3.95-4.02 (m, 1H), 4.05-4.13 (m, 1H), 4.20-4.27 (m, 2H), 4.58 (s, 1H), 6.09 (s, 1H), 6.69 (d, J=8.5 Hz, 1H), 6.95 (d, J=8.5 Hz, 1H).

Step G: Preparation of Ethyl 2-(7-(3-Cyano-4-isopropoxybenzyloxy)-8-methyl-2,3-dihydro-1H-pyrrolo[1,2-a]indol-1-yl)acetate To a solution of ethyl 2-(7-hydroxy-8-methyl-2,3-dihydro-1H-pyrrolo[1,2-a]indol-1-yl)acetate (100 mg, 0.366 mmol) in DMF (3 mL) was added cesium carbonate (155 mg, 0.476 mmol), followed by 5-(chloromethyl)-2-isopropoxybenzonitrile (100 mg, 0.476 mmol). The reaction mixture was heated at 65° C. for 15 h and cooled down. The solid was filtered and washed with ethyl acetate. The combined solvent was evaporated, and the residue was purified by column chromatography to give the title compound (130 mg) as a colorless oil. LCMS m/z=447.7 [M+H]$^+$; $^1$H NMR (400 ME-1z, CDCl$_3$) δ ppm 1.32 (t, J=7.1 Hz, 3H), 1.42 (d, J=6.0 Hz, 6H), 2.25-2.32 (m, 1H), 2.42 (s, 3H), 2.58 (dd, J=16.0, 8.4 Hz, 1H), 2.82-2.92 (m, 2H), 3.73-3.80 (m, 1H), 3.95-4.02 (m, 1H), 4.08-4.15 (m, 1H), 4.20-4.27 (m, 2H), 4.62-4.69 (m, 1H), 4.96 (s, 2H), 6.13 (s, 1H), 6.83 (d, J=8.7 Hz, 1H), 6.97 (d, J=8.7 Hz, 1H), 7.01 (d, J=8.7 Hz, 1H), 7.59 (dd, J=8.6, 2.2 Hz, 1H), 7.63 (d, J=2.1 Hz, 1H).

Step H: Preparation of 2-(7-(3-Cyano-4-isopropoxybenzyloxy)-8-methyl-2,3-dihydro-1H-pyrrolo[1,2-a]indol-1-yl)acetic Acid To a solution of ethyl 2-(7-(3-cyano-4-isopropoxybenzyloxy)-8-methyl-2,3-dihydro-1H-pyrrolo[1,2-a]indol-1-yl)acetate (130 mg, 0.291 mmol) in dioxane (2 mL) was added a 1 M LiOH aqueous solution (1.747 mL, 1.747 mmol). The reaction mixture was stirred at room temperature for 5 h, acidified to pH 3 with 0.5 M citric acid aqueous solution, and extracted with ethyl acetate. The combined organics were washed with water, dried over anhydrous Na$_2$SO$_4$, and concentrated to give the title compound as pink solid (110 mg). LCMS m/z=419.4 [M+H]$^+$; $^1$H NMR (400 MHz, CDCl$_3$) δ ppm 1.42 (d, J=6.0 Hz, 6H), 2.25-2.35 (m, 1H), 2.41 (s, 3H), 2.67 (dd, J=16.5, 8.5 Hz, 1H), 2.88-2.98 (m, 2H), 3.73-3.81 (m, 1H), 3.97-4.04 (m, 1H), 4.10-4.16 (m, 1H), 4.62-4.68 (m, 1H), 4.97 (s, 2H), 6.17 (s, 1H), 6.84 (d, J=8.7 Hz, 1H), 6.97 (d, J=8.7 Hz, 1H), 7.01 (d, J=8.7 Hz, 1H), 7.59 (dd, J=8.6, 2.2 Hz, 1H), 7.63 (d, J=2.2 Hz, 1H).
Resolution Via Chiral HPLC
Column: normal phase ChiralPak IA column, 20 mm ID×250 mm L, 5 µm particle size
Eluent: 30% IPA/hexanes with 0.1% TFA
Gradient: Isocratic
Flow: 6 mL/min
Detector: 280 nm
Retention time: 1$^{st}$ enantiomer: 22.3 min; 2$^{nd}$ enantiomer: 25.0 min Example 1.42

Preparation of 2-(9-Chloro-7-(3-cyano-4-isopropoxybenzyloxy)-8-methyl-2,3-dihydro-1H-pyrrolo[1,2-a]indol-1-yl)acetic Acid (Compound 42)

To a solution of 2-(7-(3-cyano-4-isopropoxybenzyloxy)-8-methyl-2,3-dihydro-1H-pyrrolo[1,2-a]indol-1-yl)acetic Acid (30 mg, 0.072 mmol) in DCM (2 mL) was added N-chlorosuccinimide (10.1 mg, 0.075 mmol) at 0° C. The reaction was stirred at that temperature for 40 min, diluted with DCM, washed with aqueous Na$_2$S$_2$O$_3$ solution and water, and dried over anhydrous Na$_2$SO$_4$. The solvent was evaporated, and the residue was passed through a silica gel column with 5% MeOH/DCM to give the title compound as beige solid (23 mg). LCMS m/z=453.3 [M+H]$^+$; $^1$H NMR (400 MHz, CDCl$_3$) δ ppm 1.41 (d, J=6.0 Hz, 6H), 2.29-2.38 (m, 1H), 2.58 (dd, J=16.7, 10.5 Hz, 1H), 2.66 (s, 3H), 2.88-2.98 (m, 1H), 3.33 (dd, J=16.7, 3.7 Hz, 1H), 3.76-3.84 (m, 1H), 3.90-3.98 (m, 1H), 4.05-4.13 (m, 1H), 4.62-4.68 (m, 1H), 4.94 (s, 2H), 6.84 (d, J=8.8 Hz, 1H), 6.95-6.98 (m, 2H), 7.56-7.62 (m, 2H).

Example 1.43

Preparation of 2-(7-(3-Cyano-4-isopropoxybenzyloxy)-9-(methylsulfonyl)-2,3-dihydro-1H-pyrrolo[1,2-a]indol-1-yl)acetic Acid (Compound 43)

Step A: Preparation of tert-Butyl 2-(7-(3-Cyano-4-isopropoxybenzyloxy)-9-(methylsulfonyl)-2,3-dihydro-1H-pyrrolo[1,2-a]indol-1-yl)acetate tert-Butyl 2-(7-(3-cyano-4-isopropoxybenzyloxy)-9-iodo-2,3-dihydro-1H-pyrrolo[1,2-a]indol-1-yl)acetate (100 mg, 0.171 mmol) in NMP (2 mL) was added copper(I) iodide (162 mg, 0.853 mmol) and sodium methanesulfinate (102 mg, 0.853 mmol). The reaction mixture was heated at 125° C. under nitrogen protection for 8 h. The solid was filtered and washed with ethyl acetate. The filtrate was washed with water and dried over anhydrous Na$_2$SO$_4$. The solvent was evaporated and the residue was purified by column chromatography to give the title compound (36 mg). LCMS m/z=539.6 [M+H]$^+$; $^1$H NMR (400 MHz, CDCl$_3$) δ ppm 1.36 (s, 9H), 1.40 (d, J=6.0 Hz, 6H), 2.46-2.55 (m, 1H), 2.74 (dd, J=16.0, 9.0 Hz, 1H), 2.88-2.98 (m, 1H), 3.12 (s, 3H), 3.08-3.14 (dd, J=16.0, 3.6 Hz, 1H), 3.95-4.02 (m, 1H), 4.05-4.20 (m, 2H), 4.62-4.69 (m, 1H), 5.03 (s, 2H), 6.95 (dd, J=8.8, 2.4 Hz, 1H), 6.98 (d, J=8.8 Hz, 1H), 7.20 (d, J=8.8 Hz, 1H), 7.41 (d, J=2.4 Hz, 1H), 7.59 (dd, J=8.7, 2.2 Hz, 1H), 7.65 (d, J=2.2 Hz, 1H), Step B: Preparation of 2-(7-(3-Cyano-4-isopropoxybenzyloxy)-9-(methylsulfonyl)-2,3-dihydro-1H-pyrrolo[1,2-a]indol-1-yl)acetic Acid D/L-Cysteine (40.5 mg, 0.334 mmol) was dissolved in TFA (1 mL) and cooled down to 0° C. The solution was added to a solution of tert-butyl 2-(7-(3-cyano-4-isopropoxybenzyloxy)-9-(methylsulfonyl)-2,3-dihydro-1H-pyrrolo[1,2-a]indol-1-yl)acetate (36 mg, 0.067 mmol) in DCM (1 mL) at 0° C. The reaction was stirred at this temperature for 1 h. Water was added, then ethyl acetate was added. The organic layer was separated, washed with water and brine, dried over anhydrous Na$_2$SO$_4$, and concentrated. The residue was purified by preparative HPLC. The combined fractions were partially concentrated in vacuo and diluted with ethyl acetate. The organic layer was separated, washed with water, and dried over anhydrous Na₂SO₄. The solvent was evaporated to give the title compound as white solid. LCMS m/z=483.3 [M+H]⁺; ¹H NMR (400 MHz, CDCl₃) δ ppm 1.41 (d, J=6.0 Hz, 6H), 2.46-2.55 (m, 1H), 2.84 (dd, J=16.7 and 9.5 Hz, 1H), 2.92-3.03 (m, 1H), 3.11 (s, 3H), 3.33 (dd, J=16.7, 3.4 Hz, 1H), 3.98-4.08 (m, 1H), 4.10-4.17 (m, 1H), 4.17-4.25 (m, 1H), 4.62-4.69 (m, 1H), 5.04 (s, 2H), 6.95-7.00 (m, 2H), 7.22 (d, J=8.8 Hz, 1H), 7.41 (d, J=2.4 Hz, 1H), 7.59 (dd, J=8.7, 2.2 Hz, 1H), 7.66 (d, J=2.2 Hz, 1H).

Example 1.44

Preparation of 2-(2-(3-Cyano-4-isopropoxybenzyloxy)-6,7,8,9-tetrahydropyrido[1,2-a]indol-9-yl)acetic Acid (Compound 44)

Step A: Preparation of 5-(Benzyloxy)-1-(4-ethoxy-4-oxobutyl)-1H-indole-2-carboxylate Ethyl 5-(benzyloxy)-1H-indole-2-carboxylate (10 g, 33.9 mmol) was dissolved in anhydrous DMF (100 mL), the solution was cooled to 0° C. and slowly added sodium hydride (60% dispersion in mineral oil) (1.80 g, 45.0 mmol). The reaction was stirred at 0° C. for 30 min. Tetrabutylammonium iodide (8.50 g, 23.02 mmol) was added at 0° C. followed by addition of ethyl 4-bromobutyrate (7.28 mL, 50.8 mmol). The reaction mixture was warmed to room temperature and stirred for 16 h. Saturated aqueous NH₄Cl was added. The mixture was extracted with ethyl acetate. The combined organics were washed with water, brine and dried over anhydrous MgSO₄. The solvent was evaporated, and the residue was purified by silica gel column chromatography to give the title compound as an amber oil (13.46 g). LCMS m/z=410.3 [M+H]⁺; ¹H NMR (400 MHz, CDCl₃) δ ppm 1.18 (t, J=7.2 Hz, 3H), 1.33 (t, J=7.1 Hz, 3H), 2.05 (t, J=7.2 Hz, 2H), 2.20-2.32 (m, 2H), 4.05 (q, J=7.2 Hz, 2H), 4.28 (q, J=7.2 Hz, 2H), 4.52 (t, J=7.3 Hz, 2H), 5.03 (s, 2H), 6.99-7.09 (m, 2H), 7.13 (s, 1H), 7.19 (s, 1H), 7.21-7.35 (m, 3H), 7.36-7.44 (m, 2H).

Step B: Preparation of Ethyl 2-(Benzyloxy)-9-hydroxy-6,7-dihydropyrido[1,2-a]indole-8-carboxylate To a solution of ethyl 5-(benzyloxy)-1-(4-ethoxy-4-oxobutyl)-1H-indole-2-carboxylate (1 g, 2.442 mmol) in THF was added a 1 M solution of KOtBu in THF (3.17 mL, 3.17 mmol) at 0° C. The reaction was stirred at that temperature for 2 h, poured into 1 N HCl aqueous solution, extracted with ethyl acetate. The combined organics were washed with water, dried over Na₂SO₄, and concentrated to give the title compound (850 mg) without further purification. LCMS m/z=364.3 [M+H]⁺.

Step C: Preparation of 2-(Benzyloxy)-7,8-dihydropyrido[1,2-a]indol-9(6H)-one

The reaction mixture of ethyl 2-(benzyloxy)-9-hydroxy-6,7-dihydropyrido[1,2-a]indole-8-carboxylate (1.22 g, 3.36 mmol) in acetic acid (36 mL) and H₂O (3 mL) was heated at 220° C. for 10 min under microwave irradiation. The solvent was removed in vacuo. The residue was purified by silica gel column chromatography to give the title compound (780 mg) as a yellow solid. LCMS m/z=292.3 [M+H]⁺; ¹H NMR (400 MHz, CDCl₃) δ ppm 2.38-2.45 (m, 2H), 2.73 (t, J=6.4 Hz, 2H), 4.23 (t, J=5.9 Hz, 2H), 5.11 (s, 2H), 7.15 (dd, J=8.9, 2.4 Hz, 1H), 7.18 (d, J=2.3 Hz, 1H), 7.22 (s, 1H), 7.25-7.30 (m, 1H), 7.30-7.35 (m, 1H), 7.36-7.42 (m, 2H), 7.45-7.50 (m, 2H).

Step D: Preparation of Ethyl 2-(2-(Benzyloxy)-7,8-dihydropyrido[1,2-a]indol-9(6H)-ylidene)acetate To a solution of ethyl 2-(diethoxyphosphoryl)acetate (3.11 mL, 15.65 mmol) in DMF (10 mL) was added sodium hydride (60% dispersion in mineral oil) (626 mg, 15.65 mmol) at 0° C. The reaction was slowly warmed to room temperature and stirred for 10 min. 2-(Benzyloxy)-7,8-dihydropyrido[1,2-a]indol-9(6H)-one (570 mg, 1.956 mmol) in DMF was added. The reaction was heated at 65° C. for 2 h, cooled down, poured into saturated NH₄Cl aqueous solution, and extracted with ethyl acetate. The combined organics were washed with water, dried over anhydrous Na₂SO₄, and concentrated. The residue was purified by silica gel column chromatography to give the title compound (608 mg). LCMS m/z=362.5 [M+H]⁺.

Step E: Preparation of Ethyl 2-(2-Hydroxy-6,7,8,9-tetrahydropyrido[1,2-a]indol-9-yl)acetate Ethyl 2-(2-(benzyloxy)-7,8-dihydropyrido[1,2-a]indol-9(6H)-ylidene)acetate (608 mg, 1.682 mmol) was dissolved in THF/MeOH (1:1) (4 mL). Ammonium formate (648 mg, 10.28 mmol) and palladium hydroxide (20 wt % Pd on carbon) (60 mg) was added under nitrogen protection. The reaction was heated at reflux for 5 h. The solid was filtered. The filtrate was concentrated, dissolved in ethyl acetate, washed with water, dried over anhydrous Na₂SO₄, and concentrated. The residue was purified by silica gel column chromatography to give the title compound (402 mg) as colorless oil. LCMS m/z=274.3 [M+H]⁺; ¹H NMR (400 MHz, CDCl₃) δ ppm 1.32 (t, J=7.1 Hz, 3H), 1.50-1.61 (m, 1H), 1.98-2.08 (m, 1H), 2.08-2.22 (m, 2H), 2.55 (dd, J=15.6 and 8.7 Hz, 1H), 2.94 (dd, J=15.6, 5.5 Hz, 1H), 3.44-3.52 (m, 1H), 3.80-3.88 (m, 1H), 4.07-4.13 (m, 1H), 4.24 (q, J=7.1 Hz, 2H), 4.95 (s, 1H), 6.12 (s, 1H), 6.74 (dd, J=8.6, 2.4 Hz, 1H), 6.95 (d, J=2.4 Hz, 1H), 7.10 (d, J=8.6 Hz, 1H).

Step F: Preparation of Ethyl 2-(2-(3-Cyano-4-isopropoxybenzyloxy)-6,7,8,9-tetrahydropyrido[1,2-a]indol-9-yl)acetate To a mixture of ethyl 2-(2-hydroxy-6,7,8,9-tetrahydropyrido[1,2-a]indol-9-yl)acetate (50 mg, 0.183 mmol) and cesium carbonate (89 mg, 0.274 mmol) in DMF (2 mL) was added 5-(chloromethyl)-2-isopropoxybenzonitrile (46 mg, 0.22 mmol). The reaction was heated at 75° C. for 5 h and cooled down. The solid was filtered and washed with ethyl acetate. The combined solvent was evaporated, and the residue was purified by silica gel column chromatography to give the title compound (70 mg). LCMS m/z=447.4 [M+H]⁺; ¹H NMR (400 MHz, CDCl₃) δ ppm 1.30 (t, J=7.1 Hz, 3H), 1.40 (d, J=6.1 Hz, 6H), 1.51-1.61 (m, 1H), 1.98-2.08 (m, 1H), 2.08-2.24 (m, 2H), 2.55 (dd, J=15.6, 8.6 Hz, 1H), 2.93 (dd, J=15.6, 5.4 Hz, 1H), 3.45-3.54 (m, 1H), 3.82-3.92 (m, 1H), 4.10-4.17 (m, 1H), 4.22 (q, J=7.1 Hz, 2H), 4.61-4.68 (m, 1H), 5.00 (s, 2H), 6.17 (s, 1H), 6.85 (dd, J=8.8, 2.4 Hz, 1H), 6.95 (d, J=8.8 Hz, 1H), 7.05 (d, J=2.4 Hz, 1H), 7.16 (d, J=8.7 Hz, 1H), 7.58 (dd, J=8.7, 2.2 Hz, 1H), 7.65 (d, J=2.2 Hz, 1H).

Step G: Preparation of 2-(2-(3-Cyano-4-isopropoxybenzyloxy)-6,7,8,9-tetrahydropyrido[1,2-a]indol-9-yl)acetic Acid To a solution of ethyl 2-(2-(3-cyano-4-isopropoxybenzyloxy)-6,7,8,9-tetrahydropyrido[1,2-a]indol-9-yl)acetate (70 mg, 0.157 mmol) in dioxane (1 mL) was added 1 M LiOH aqueous solution (0.627 mL, 0.627 mmol). The reaction was stirred at room temperature for 8 h, diluted with water, and acidified to pH 4 with 0.5 M aqueous citric acid solution. The light pink solid was collected to give the title compound (63 mg). LCMS m/z=419.4 [M+H]$^+$; $^1$H NMR (400 MHz, CDCl$_3$) 1.40 (d, J=6.1 Hz, 6H), 1.55-1.65 (m, 1H), 1.98-2.12 (m, 1H), 2.15-2.25 (m, 2H), 2.65 (dd, J=16.1, 8.6 Hz, 1H), 3.01 (dd, J=−16.1, 5.3 Hz, 1H), 3.45-3.54 (m, 1H), 3.85-3.92 (m, 1H), 4.12-4.18 (m, 1H), 4.61-4.68 (m, 1H), 5.01 (s, 2H), 6.22 (s, 1H), 6.86 (dd, J=8.8, 2.4 Hz, 1H), 6.96 (d, J=8.7 Hz, 1H), 7.06 (d, J=2.4 Hz, 1H), 7.17 (d, J=8.7 Hz, 1H), 7.58 (dd, J=8.7, 2.2 Hz, 1H), 7.65 (d, J=2.2 Hz, 1H).

Resolution Via Chiral HPLC

Column: normal phase ChiralPak IA column, 20 mm ID×250 mm L, 5 μm particle size

Eluent: 30% IPA/hexanes

Gradient: Isocratic

Flow: 12 mL/min

Detector: 280 nm

Retention time: 1$^{st}$ enantiomer: 25.1 min; 2$^{nd}$ enantiomer: 30.7 min

Example 1.45

Preparation of 2-(2-(4-Cyclopentyl-3-(trifluoromethyl)benzyloxy)-6,7,8,9-tetrahydropyrido[1,2-a]indol-9-yl)acetic Acid (Compound 46)

Step A: Preparation of Ethyl 2-(2-(4-Cyclopentyl-3-(trifluoromethyl)benzyloxy)-6,7,8,9-tetrahydropyrido[1,2-a]indol-9-yl)acetate To a mixture of ethyl 2-(2-hydroxy-6,7,8,9-tetrahydropyrido[1,2-a]indol-9-yl)acetate (107 mg, 0.391 mmol) and cesium carbonate (191 mg, 0.587 mmol) in DMF (2 mL) was added 4-(chloromethyl)-1-cyclopentyl-2-(trifluoromethyl)benzene (123 mg, 0.47 mmol). The reaction was heated at 75° C. for 5 h and cooled down. The solid was filtered and washed with ethyl acetate. The combined solvent was evaporated, and the residue was purified by silica gel column chromatography to give the title compound (143 mg). LCMS m/z=500.4 [M+H]$^+$; $^1$H NMR (400 MHz, CDCl$_3$) δ ppm 1.32 (t, J=7.1 Hz, 3H), 1.52-1.67 (m, 3H), 1.68-1.80 (m, 2H), 1.80-1.92 (m, 2H), 2.00-2.24 (m, 5H), 2.55 (dd, J=15.6 and 8.7 Hz, 1H), 2.95 (dd, J=15.6 and 5.4 Hz, 1H), 3.35-3.45 (m, 1H), 3.45-3.55 (m, 1H), 3.83-3.92 (m, 1H), 4.10-4.18 (m, 1H), 4.23 (q, J=7.1 Hz, 2H), 5.10 (s, 2H), 6.19 (s, 1H), 6.90 (dd, J=8.8 and 2.4 Hz, 1H), 7.10 (d, J=2.4 Hz, 1H), 7.17 (d, J=8.8 Hz, 1H), 7.48 (d, J=8.1 Hz, 1H), 7.60 (dd, J=8.1 and 1.3 Hz, 1H), 7.71 (d, J=1.4 Hz, 1H).

Step B: Preparation of 2-(2-(4-Cyclopentyl-3-(trifluoromethyl)benzyloxy)-6,7,8,9-tetrahydropyrido[1,2-a]indol-9-yl)acetic Acid To a solution of ethyl 2-(2-(4-cyclopentyl-3-(trifluoromethyl)benzyloxy)-6,7,8,9-tetrahydropyrido[1,2-a]indol-9-yl)acetate (143 mg, 0.286 mmol) in dioxane (1.5 mL) was added 1 M LiOH aqueous solution (1.15 mL, 1.145 mmol). The reaction mixture was stirred at 45° C. for 3 h. A portion of the solvent was removed in vacuo. The remaining mixture was diluted with water, acidified with 0.5 M aqueous citric acid to pH 4, and extracted with ethyl acetate. The combined organics were washed with water, dried over anhydrous Na$_2$SO$_4$, and concentrated to give the title compound (105 mg). LCMS m/z=472.3 [M+H]$^+$; $^1$H NMR (400 MHz, CDCl$_3$) δ ppm 1.54-1.66 (m, 3H), 1.67-1.80 (m, 2H), 1.80-1.92 (m, 2H), 2.00-2.24 (m, 5H), 2.64 (dd, J=16.1 and 8.7 Hz, 1H), 3.01 (dd, J=16.1 and 5.3 Hz, 1H), 3.33-3.42 (m, 1H), 3.45-3.55 (m, 1H), 3.85-3.94 (m, 1H), 4.12-4.18 (m, 1H), 5.08 (s, 2H), 6.22 (s, 1H), 6.90 (dd, J=8.8 and 2.4 Hz, 1H), 7.10 (d, J=2.4 Hz, 1H), 7.17 (d, J=8.8 Hz, 1H), 7.47 (d, J=8.1 Hz, 1H), 7.59 (d, J=8.1 Hz, 1H), 7.70 (s, 1H).

Example 1.46

Preparation of 2-(2-(3,5-Bis(trifluoromethyl)benzyloxy)-6,7,8,9-tetrahydropyrido[1,2-a]indol-9-yl)acetic Acid (Compound 48)

Step A: Preparation of Ethyl 2-(2-(3,5-Bis(trifluoromethyl)benzyloxy)-6,7,8,9-tetrahydropyrido[1,2-a]indol-9-yl)acetate To a mixture of ethyl 2-(2-hydroxy-6,7,8,9-tetrahydropyrido[1,2-a]indol-9-yl)acetate (95 mg, 0.348 mmol) and cesium carbonate (170 mg, 0.521 mmol) in DMF (2 mL) was added 1-(bromomethyl)-3,5-bis(trifluoromethyl)benzene (128 mg, 0.417 mmol). The reaction mixture was heated at 75° C. for 15 h and cooled down. The solid was filtered and washed with ethyl acetate. The combined solvent was evaporated, and the residue was purified by silica gel column chromatography to give the title compound (145 mg). LCMS m/z=500.2 [M+H]$^+$; $^1$H NMR (400 MHz, CDCl$_3$) δ ppm 1.30 (t, J=7.1 Hz, 3H), 1.51-1.61 (m, 1H), 2.00-2.10 (m, 1H), 2.10-2.24 (m, 2H), 2.55 (dd, J=15.6, 8.6 Hz, 1H), 2.93 (dd, J=15.6, 5.4 Hz, 1H), 3.45-3.54 (m, 1H), 3.85-3.94 (m, 1H), 4.10-4.17 (m, 1H), 4.22 (q, J=7.1 Hz, 2H), 5.19 (s, 2H), 6.18 (s, 1H), 6.90 (dd, J=8.8, 2.4 Hz, 1H), 7.09 (d, J=2.4 Hz, 1H), 7.18 (d, J=8.7 Hz, 1H), 7.83 (s, 1H), 7.94 (s, 2H).

Step B: Preparation of 2-(2-(3,5-Bis(trifluoromethyl)benzyloxy)-6,7,8,9-tetrahydropyrido[1,2-a]indol-9-yl)acetic Acid To a solution of ethyl 2-(2-(3,5-bis(trifluoromethyl)benzyloxy)-6,7,8,9-tetrahydropyrido[1,2-a]indol-9-yl)acetate (145 mg, 0.29 mmol) in dioxane (1.5 mL) was added 1 M LiOH aqueous solution (1.16 mL, 1.161 mmol). The reaction was stirred at room temperature for 8 h, diluted with water, and acidified to pH 4 with 0.5 M aqueous citric acid. The solid precipitate was collected to give the title compound (125 mg). LCMS m/z=471.8 [M+H]$^+$; $^1$H NMR (400 MHz, CDCl$_3$) δ ppm 1.55-1.65 (m, 1H), 2.00-2.10 (m, 1H), 2.17-2.26 (m, 2H), 2.65 (dd, J=−16.1, 8.5 Hz, 1H), 3.00 (dd, J=16.1, 5.4 Hz, 1H), 3.45-3.54 (m, 1H), 3.85-3.94 (m, 1H), 4.14-4.22 (m, 1H), 5.19 (s, 2H), 6.23 (s, 1H), 6.91 (dd, J=8.8, 2.4 Hz, 1H), 7.09 (d, J=2.4 Hz, 1H), 7.19 (d, J=−8.7 Hz, 1H), 7.83 (s, 1H), 7.94 (s, 2H).

Resolution Via Chiral HPLC

Column: normal phase Chiralcel OD, 500×50 mm ID

Eluent: 20% IPA/hexanes

Gradient: Isocratic

Flow: 60 mL/min

Detector: 280 nm

Retention time: 1$^{st}$ enantiomer: 29.0 min; 2$^{nd}$ enantiomer: 40.2 min

Example 1.47

Preparation of 2-(2-(3-Cyano-5-(trifluoromethoxy)benzyloxy)-6,7,8,9-tetrahydropyrido[1,2-a]indol-9-yl)acetic Acid (Compound 27)

Step A: Preparation of Ethyl 2-(2-(3-Cyano-5-(trifluoromethoxy)benzyloxy)-6,7,8,9-tetrahydropyrido[1,2-a]indol-9-yl)acetate To a mixture of ethyl 2-(2-hydroxy-6,7,8,9-tetrahydropyrido[1,2-a]indol-9-yl)acetate (75 mg, 0.274 mmol) and cesium carbonate (134 mg, 0.412 mmol) in DMF (2 mL) was added 3-(chloromethyl)-5-(trifluoromethoxy)benzonitrile (78 mg, 0.329 mmol). The reaction was heated at 75° C. for 15 h and cooled down. The solid was filtered and washed with ethyl acetate. The combined solvent was evaporated, and the residue was purified by silica gel column chromatography to give the title compound (108 mg). LCMS m/z=473.6 [M+H]$^+$; $^1$H NMR (400 MHz, CDCl$_3$) δ ppm 1.30 (t, J=7.1 Hz, 3H), 1.51-1.62 (m, 1H), 2.00-2.10 (m, 1H), 2.10-2.24 (m, 2H), 2.55 (dd, J=15.6, 8.6 Hz, 1H), 2.93 (dd, J=15.6, 5.5 Hz, 1H), 3.45-3.54 (m, 1H), 3.85-3.93 (m, 1H), 4.10-4.17 (m, 1H), 4.22 (q, J=7.1 Hz, 2H), 5.14 (s, 2H), 6.18 (s, 1H), 6.87 (dd, J=8.8, 2.4 Hz, 1H), 7.05 (d, J=2.4 Hz, 1H), 7.18 (d, J=8.8 Hz, 1H), 7.44 (s, 1H), 7.58 (s, 1H), 7.71 (s, 1H).

Step B: Preparation of 2-(2-(3-Cyano-5-(trifluoromethoxy)benzyloxy)-6,7,8,9-tetrahydropyrido[1,2-a]indol-9-yl)acetic Acid To a solution of ethyl 2-(2-(3-cyano-5-(trifluoromethoxy)benzyloxy)-6,7,8,9-tetrahydropyrido[1,2-a]indol-9-yl)acetate (108 mg, 0.229 mmol) in dioxane (1 mL) was added 1 M LiOH aqueous solution (0.914 mL, 0.914 mmol). The reaction was stirred at room temperature for 8 h, diluted with water, and acidified to pH 4 with 0.5 M aqueous citric acid. The solid precipitate was collected to give the title compound (90 mg). LCMS m/z=445.3 [M+H]$^+$; $^1$H NMR (400 MHz, CDCl$_3$) δ ppm 1.57-1.68 (m, 1H), 2.00-2.14 (m, 1H), 2.16-2.27 (m, 2H), 2.65 (dd, J=16.1, 8.5 Hz, 1H), 3.01 (dd, J=16.1, 5.4 Hz, 1H), 3.46-3.55 (m, 1H), 3.85-3.93 (m, 1H), 4.13-4.20 (m, 1H), 5.13 (s, 2H), 6.23 (s, 1H), 6.89 (dd, J=8.8, 2.4 Hz, 1H), 7.05 (d, J=2.4 Hz, 1H), 7.19 (d, J=8.8 Hz, 1H), 7.44 (s, 1H), 7.58 (s, 1H), 7.70 (s, 1H).

Resolution Via Chiral HPLC
Column: normal phase Chiralcel OD, 500×50 mm ID
Eluent: 45% IPA/hexanes
Gradient: Isocratic
Flow: 60 mL/min
Detector: 280 nm
Retention time: 1$^{st}$ enantiomer: 43.1 min; 2$^{nd}$ enantiomer: 55.2 min

Example 1.48

Preparation of 2-(7-(3-Cyano-4-cyclopentylbenzyloxy)-2,3-dihydro-1H-pyrrolo[1,2-a]indol-1-yl)acetic Acid (Compound 37)

Step A: Preparation of 5-(Chloromethyl)-2-cyclopentylbenzonitrile

2-Cyclopentylbenzonitrile (1.3 g, 7.59 mmol) was transferred into a 2-necked RB flask, fitted with an addition funnel and dry nitrogen inlet. The starting material was stirred and cooled to −22° C. (dry ice/IPA bath). Sulfuric acid (3.25 mL, 61.0 mmol) was added in drops. 1,3,5-Trioxane (0.877 mL, 11.39 mmol) was added in 3 batches (The batches were added fairly quickly, one after another). Almost immediately, chlorosulfonic acid (0.915 mL, 13.67 mmol) was added in drops. Then the reaction mixture (dark brown in color) was allowed to warm up to −7° C. (over approx 15 min). It was stirred at between 6.9° C. and −5° C. for 1.5 h. The reaction was quenched by slowly pouring into ice water. MTBE was added and the mixture was stirred well and filtered through Celite®. The Celite® bed was washed with MTBE and the aqueous acid layer was separated. The acid layer was extracted with MTBE. The combined MTBE layer was washed with water followed by saturated NaHCO$_3$ solution. The organic layer was washed with water until washings were neutral to pH paper. The organic layer was dried over anhydrous Na$_2$SO$_4$ and filtered. The solvent was removed under reduced pressure. The residue was purified by silica gel column chromatography to give the title compound.

Step B: Preparation of 2-(7-(3-Cyano-4-cyclopentylbenzyloxy)-2,3-dihydro-1H-pyrrolo[1,2-a]indol-1-yl)acetic Acid 5-(Chloromethyl)-2-cyclopentylbenzonitrile (38.2 mg, 0.174 mmol), tert-butyl 2-(7-hydroxy-2,3-dihydro-1H-pyrrolo[1,2-a]indol-1-yl)acetate (50 mg, 0.174 mmol), and K$_2$CO$_3$ (36.1 mg, 0.261 mmol) were dissolved in DMF and heated to 60° C. for 16 h. The reaction mixture was filtered through Celite® and purified by HPLC. The intermediate was isolated and dissolved in TFA (0.2 M) and added D/L-cysteine. After 15 min, the mixture was poured into water and extracted with DCM. The organic extract was concentrated to give the title compound. LCMS m/z=415.6 [M+H]$^+$; $^1$H NMR (400 MHz, CDCl$_3$) δ ppm 1.55-1.67 (m, 2H), 1.70-1.78 (m, 2H), 1.80-1.88 (m, 2H), 2.11-2.20 (m, 2H), 2.26-2.36 (m, 1H), 2.66 (dd, J=16.5, 8.6 Hz, 1H), 2.86-2.97 (m, 2H), 3.42 (quintet, J=8.6 Hz, 1H), 3.75 (quintet, J=7.3 Hz, 1H), 3.97-4.05 (m, 1H), 4.10-4.17 (m, 1H), 5.06 (s, 2H), 6.12 (s, 1H), 6.85 (dd, J=8.0, 2.0 Hz, 1H), 7.06 (d, J=2.0 Hz, 1H), 7.14 (d, J=8.8 Hz, 1H), 7.39 (d, J=8.2 Hz, 1H), 7.60 (d, J=8.3 Hz, 1H), 7.69 (s, 1H).

Example 1.49

Preparation of 2-(9-Chloro-7-(3-chloro-4-(1,3-difluoropropan-2-yloxy)benzyloxy)-2,3-dihydro-1H-pyrrolo[1,2-a]indol-1-yl)acetic Acid (Compound 40)

From tert-butyl 2-(7-(3-chloro-4-(1,3-difluoropropan-2-yloxy)benzyloxy)-2,3-dihydro-1H-pyrrolo[1,2-a]indol-1-yl)acetate, the title compound was prepared using a similar method to the one described in Example 1.28, Step A and Example 1.25, Step E. $^1$H NMR (400 MHz, CDCl$_3$) δ ppm 2.32-2.41 (m, 1H), 2.60 (dd, J=16.7, 10.3 Hz, 1H), 2.92-3.11 (m, 1H), 3.30 (dd, J=16.5, 3.9 Hz, 1H), 3.78-3.86 (m, 1H), 3.97-4.05 (m, 1H), 4.11-4.18 (m, 1H), 4.58-4.69 (m, 3H), 4.76-4.79 (m, 2H), 5.04 (s, 2H), 6.90 (dd, J=8.8, 2.4 Hz, 1H), 7.05 (d, J=2.4 Hz, 1H), 7.09 (d, J=8.4 Hz, 1H), 7.13 (d, J=8.8 Hz, 1H), 7.32 (dd, J=8.4, 1.9 Hz, 1H), 7.53 (d, J=1.9 Hz, 1H).

Example 1.50

Preparation of 2-(7-(3-Chloro-4-(1,3-difluoropropan-2-yloxy)benzyloxy)-2,3-dihydro-1H-pyrrolo[1,2-a]indol-1-yl)acetic Acid (Compound 39)

Step A: Preparation of Methyl 3-Chloro-4-(1,3-difluoropropan-2-yloxy)benzoate

To a solution of 1,3-difluoropropan-2-ol (2.57 g, 26.8 mmol) in THF (35 mL) was added methyl 3-chloro-4-hydroxybenzoate (2.00 g, 10.72 mmol), followed by triphenylphosphine (7.03 g, 26.8 mmol) and DIAD (5.21 mL, 26.8 mmol). The reaction was stirred overnight at room temperature, diluted with EtOAc and washed with brine. The organics were separated, washed with brine, dried over $MgSO_4$, filtered, and concentrated. The residue was purified by silica gel chromatography to give the title compound (3.743 g) as a clear oil. LCMS m/z=265.1 $[M+H]^+$.

Step B: Preparation of 3-Chloro-4-(1,3-difluoropropan-2-yloxy)benzoic Acid

To a solution of methyl 3-chloro-4-(1,3-difluoropropan-2-yloxy)benzoate (2.00 g, 7.56 mmol) in dioxane (15.11 mL) was added LiOH (1.0 M aq, 22.67 mL, 22.67 mmol). The reaction was stirred at 30° C. for 1.5 h in a 1 L round-bottomed flask. The reaction was cooled to room temperature and poured into 1 N HCl. A precipitate was formed and filtered by vacuum filtration to give the title compound (1.5 g) as a white solid. LCMS m/z=250.9 $[M+H]^+$.

Step C: Preparation of 2-Chloro-4-(chloromethyl)-1-(1,3-difluoropropan-2-yloxy)benzene To a solution of 3-chloro-4-(1,3-difluoropropan-2-yloxy) benzoic acid (1.5 g, 5.99 mmol) at 0° C. in a round bottomed flask was added borane-THF (9.88 mL of a 1.0 M soln in THF, 9.88 mmol) slowly over 5 min. The mixture was stirred at 0° C. for 30 min at which time the ice-bath was removed and the reaction was warmed up to room temp and stirred overnight. The mixture was poured slowly into saturated $NaHCO_3$ solution at 0° C. and extracted with EtOAc (3×200 mL). The organic layers were combined, dried over $MgSO_4$, and filtered by vacuum filtration through a glass fiber paper. The solvent was removed under reduced pressure. The solid was dissolved in toluene (9.13 mL) and thionyl chloride was added (1.999 mL, 27.4 mmol). After 15 min, the reaction mixture was poured into water at 0° C. and extracted into MTBE (2×100 mL). The organic layers were combined and washed with saturated $NaHCO_3$ solution (3×100 mL) (caution! gas evolves), dried over $MgSO_4$, filtered by vacuum filtration through a glass fiber paper and the solvent was removed under reduced pressure to give the title compound (0.75 g). $^1H$ NMR (400 MHz, $CDCl_3$) δ ppm 4.51 (s, 2H), 4.60-4.70 (m, 3H), 4.75-4.79 (m, 2H), 7.06 (d, J=8.4 Hz, 1H), 7.25 (dd, J=8.4, 2.2 Hz, 1H), 7.44 (d, J=2.3 Hz, 1H).

Step D: Preparation of 2-(7-(3-Chloro-4-(1,3-difluoropropan-2-yloxy)benzyloxy)-2,3-dihydro-1H-pyrrolo[1,2-a]indol-1-yl)acetic Acid From tert-butyl 2-(7-hydroxy-2,3-dihydro-1H-pyrrolo[1,2-a]indol-1-yl)acetate and 2-chloro-4-(chloromethyl)-1-(1,3-difluoropropan-2-yloxy)benzene, the title compound was prepared using a similar method to the one described in Example 1.48, Step B. LCMS m/z=450.1 $[M+H]^+$; $^1H$ NMR (400 MHz, $CDCl_3$) δ ppm 2.27-2.36 (m, 1H), 2.67 (dd, J=16.4, 8.4 Hz, 1H), 2.87-2.97 (m, 2H), 3.75 (quintet, J=7.4 Hz, 1H), 3.98-4.05 (m, 1H), 4.15 (ddd, J=9.9, 8.6, 4.1 Hz, 1H), 4.56-4.69 (m, 3H), 4.75-4.78 (m, 2H), 5.00 (s, 2H), 6.12 (s, 1H), 6.86 (dd, J=8.7, 2.4 Hz, 1H), 7.06-7.09 (m, 2H), 7.14 (d, J=8.7 Hz, 1H), 7.31 (dd, J=8.4, 2.1 Hz, 1H), 7.51 (d, dr=2.1 Hz, 1H).

Example 1.51

Preparation of 2-(7-(4-Methoxy-3-(trifluoromethyl) benzyloxy)-2,3-dihydro-1H-pyrrolo[1,2-a]indol-1-yl)acetic Acid (Compound 35)

From tert-butyl 2-(7-hydroxy-2,3-dihydro-1H-pyrrolo[1,2-a]indol-1-yl)acetate and 4-(chloromethyl)-1-methoxy-2-(trifluoromethyl)benzene, the title compound was prepared using a similar method to the one described in Example 1.48, Step B. LCMS m/z=420.1 $[M+H]^+$; $^1H$ NMR (400 MHz, $CDCl_3$) δ ppm 2.31-2.39 (m, 1H), 2.50 (dd, J=16.3, 9.9 Hz, 1H), 2.75 (dd, J=16.3, 4.4 Hz, 1H), 2.83-2.93 (m, 1H), 3.59-3.67 (m, 1H), 3.85 (s, 3H), 3.95-4.05 (m, 2H), 4.06-4.14 (m, 2H), 5.30 (s, 1H), 6.67-6.74 (m, 2H), 6.86 (d, J=8.6 Hz, 1H), 7.08 (d, J=8.5 Hz, 1H), 7.28 (d, J=2.0 Hz, 1H), 7.43 (d, J=2.0 Hz, 1H).

Example 1.52

Preparation of 2-(7-(3-Cyano-4-methoxybenzyloxy)-2,3-dihydro-1H-pyrrolo[1,2-a]indol-1-yl)acetic Acid (Compound 33)

From tert-butyl 2-(7-hydroxy-2,3-dihydro-1H-pyrrolo[1,2-a]indol-1-yl)acetate and 5-(chloromethyl)-2-methoxybenzonitrile, the title compound was prepared using a similar method to the one described in Example 1.16, Step A & B. LCMS m/z=377.4 $[M+H]^+$; $^1H$ NMR (400 MHz, $CDCl_3$) δ ppm 2.28-2.37 (m, 1H), 2.68 (dd, J=16.4, 8.3 Hz, 1H), 2.87-2.98 (m, 2H), 3.73-3.81 (m, 1H), 3.94 (s, 3H), 3.99-4.06 (m, 1H), 4.11-4.18 (m, 1H), 5.02 (s, 2H), 6.13 (s, 1H), 6.85 (dd, J=8.7, 2.4 Hz, 1H), 6.98 (d, J=8.6 Hz, 1H), 7.07 (d, J=2.3 Hz, 1H), 7.15 (d, J=8.7 Hz, 1H), 7.64 (dd, J=8.6, 2.1 Hz, 1H), 7.66 (d, J=2.0 Hz, 1H).

Resolution Via Chiral HPLC

Column: normal phase ChiralPak IA column, 20 mm ID×250 mm L, 5 μm particle size

Eluent: 30% IPA/hexanes

Gradient: Isocratic

Flow: 12 mL/min

Detector: 280 nm

Retention time: $1^{st}$ enantiomer: 9.6 min; $2^{nd}$ enantiomer: 18.9 min

Example 1.53

Preparation of $1^{st}$ Enantiomer of 2-(9-Chloro-7-(3-cyano-4-methoxybenzyloxy)-2,3-dihydro-1H-pyrrolo[1,2-a]indol-1-yl)acetic Acid (Compound 34)

From the $1^{st}$ enantiomer (described as the enantiomer isolated and having the retention time of 9.6 min per the conditions reported in Example 1.52) of 2-(7-(3-cyano-4-methoxybenzyloxy)-2,3-dihydro-1H-pyrrolo[1,2-a]indol-1-yl)acetic acid, the title compound was prepared using a similar method to the one described in Example 1.26. LCMS m/z=411.3 $[M+H]^+$; $^1H$ NMR (400 MHz, $CDCl_3$) δ ppm 2.32-2.41 (m, 1H), 2.61 (dd, J=16.8, 10.3 Hz, 1H), 2.93-3.01 (m, 1H), 3.31 (dd, J=16.8, 3.9 Hz, 1H), 3.78-3.86 (m, 1H), 3.94 (s, 3H), 3.99-4.04 (m, 1H), 4.12-4.19 (m, 1H), 5.05 (s, 2H), 6.88 (dd, J=8.8, 2.4 Hz, 1H), 6.98 (d, J=8.6 Hz, 1H), 7.03 (d, J=2.4 Hz, 1H), 7.13 (d, J=8.8 Hz, 1H), 7.64 (dd, J=8.6, 2.2 Hz, 1H), 7.68 (d, J=2.1 Hz, 1H).

Example 1.54

Preparation of 2$^{nd}$ Enantiomer of 2-(9-Chloro-7-(3-cyano-4-methoxybenzyloxy)-2,3-dihydro-1H-pyrrolo[1,2-a]indol-1-yl)acetic Acid (Compound 34)

From the 2$^{nd}$ enantiomer (described as the enantiomer isolated and having the retention time of 18.9 min per the conditions reported in Example 1.52) of 2-(7-(3-cyano-4-methoxybenzyloxy)-2,3-dihydro-1H-pyrrolo[1,2-a]indol-1-yl) acetic acid, the title compound was prepared using a similar method to the one described in Example 1.26. LCMS m/z=411.2 [M+H]$^+$; $^1$H NMR (400 MHz, CDCl$_3$) δ ppm 2.32-2.41 (m, 1H), 2.61 (dd, J=16.8, 10.3 Hz, 1H), 2.93-3.01 (m, 1H), 3.31 (dd, J=16.8, 3.9 Hz, 1H), 3.78-3.86 (m, 1H), 3.94 (s, 3H), 3.99-4.04 (m, 1H), 4.12-4.19 (m, 1H), 5.05 (s, 2H), 6.88 (dd, J=8.8, 2.4 Hz, 1H), 6.98 (d, J=8.6 Hz, 1H), 7.03 (d, J=2.4 Hz, 1H), 7.13 (d, J=8.8 Hz, 1H), 7.64 (dd, J=8.6, 2.2 Hz, 1H), 7.68 (d, J=2.1 Hz, 1H).

Example 2

Homogeneous Time-Resolved Fluorescence (HTRF®) Assay for Direct cAMP Measurement Compounds were screened for agonists of the S1P1 receptor (e.g., human S1P1 receptor) using the HTRF® assay for direct cAMP measurement (Gabriel et al., Assay and Drug Development Technologies, 1:291-303, 2003) and recombinant CHO-K1 cells stably transfected with S1P1. CHO-K1 cells were obtained from ATCC® (Manassas, Va.; Catalog #CCL-61). An agonist of the S1P1 receptor was detected in the HTRF® assay for direct cAMP measurement as a compound which decreased cAMP concentration. HTRF® assay also was used to determine EC$_{50}$ values for S1P1 receptor agonists.

Principle of the Assay: HTRF® assay kit was purchased from Cisbio-US, Inc. (Bedford, Mass.; Catalog #62AM4PEC). The HTRF® assay supported by the kit is a competitive immunoassay between endogenous cAMP produced by the CHO-K 1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard Curve: The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the Assay: The HTRF® assay was carried out using a two-step protocol essentially according to the kit manufacturer's instructions, in 20 μL total volume per well in 384-well plate format (ProxiPlates; PerkinElmer, Fremont, Calif.; catalog #6008280). To each of the experimental wells was transferred 1500 recombinant CHO-K1 cells in 5 μL phosphate buffered saline containing calcium chloride and magnesium chloride (PBS+; Invitrogen, Carlsbad, Calif.; catalog #14040) supplemented with IBMX (250 μM) and rolipram (20 μM) (phosphodiesterase inhibitors; Sigma-Aldrich, St. Louis, Mo.; catalog #15879 and catalog #R6520, respectively), followed by test compound in 5 μL compound buffer (PBS+ supplemented with 10 μL NKH477 (water-soluble forskolin derivative; SignaGen Laboratories, Gaithersburg, Md.; catalog #PKI-NKH477-010)) or 5 μL compound buffer. The plate was then incubated at room temperature for 1 h. To each well was then added 5 μL cAMP-d2 conjugate in lysis buffer and 5 μL Cryptate conjugate in lysis buffer according to the kit manufacturer's instructions. The plate was then further incubated at room temperature for 1 hour, after which the assay plate was read.

Assay Readout: HTRF® readout was accomplished using a PHERAstar (BMG LABTECH Inc., Durham, N.C.) or EnVision™ (PerkinElmer, Fremont Calif.) microplate reader.

Certain compounds of the present invention and their corresponding activity values are shown in Table B.

TABLE B

| Compound No. | EC$_{50}$ S1P1 (HTRF ®) |
| --- | --- |
| 4 | 321 pM |
| 6 | 239 pM |
| 10 | 11 pM |
| 11 | 5.2 nM |
| 14 | 6.3 nM |

Certain other compounds of the invention had activity values ranging from about 11 pM to about 6.3 nM in this assay.

Example 3

Cellular/Functional Ca$^{2+}$ Assay for Agonist Activity on S1P3 Receptor

A compound of the invention can be shown to have no or substantially no agonist activity on the S1P3 receptor by using in assay a human neuroblastoma cell line which endogenously expresses S1P3 (predominantly), S1P2 and S1P5 receptors, but not S1P1 or S1P4 receptors, based on mRNA analysis (Villullas et al., *J. Neurosci. Res.*, 73:215-226, 2003). Of these, S1P3 and S1P2 receptors respond to agonists, such as S1P, with an intracellular calcium increase. No or substantially no increase of intracellular calcium in response to a test compound is indicative of the test compound exhibiting no or substantially no agonist activity on the S1P3 receptor. Such an assay can be performed commercially, e.g. by Caliper LifeSciences (Hopkinton, Mass.).

Assay: The human neuroblastoma cells are washed and resuspended in physiological buffer. The cells are then loaded with dye that measures intracellular calcium. S1P is used as a reference agonist. After addition of S1P or a test compound, fluorescence is measured at 485 nm excitation/525 nm emission every 2 s for at least 60 s. Calcium ionophore A23187 is then added as an internal positive control.

Example 4

Effect of Compounds in Peripheral Lymphocyte Lowering (PLL) Assay

A compound of the invention can be shown to induce peripheral lymphocyte lowering (PLL).

A. Mouse PLL Assay.

Animals: Male BALB/c mice (Charles River Laboratories, Wilmington, Mass.) were housed four per cage and maintained in a humidity-controlled (40 to 60%) and temperature-controlled (68 to 72° F.) facility on a 12 h:12 h light/dark cycle (lights on at 6:30 am) with free access to food (Harlan Teklad, Orange, Calif., Rodent Diet 8604) and water. Mice were allowed one week of habituation to the animal facility before testing.

Figure 11:
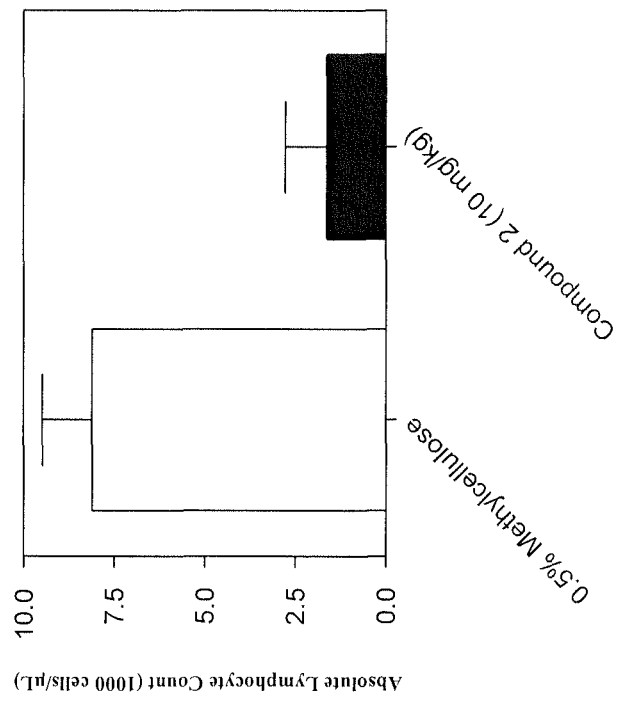
FIG. 11 shows the results of an experiment which measured the ability of Compound 2 to lower the absolute count of peripheral lymphocytes in mice compared to vehicle.

PLL Assay: Mice were given an oral dose of Compound 2 or dosing vehicle (0.5% methylcellulose) in a total volume of 10 mL/kg. Peripheral blood samples were collected at 5 hours post-dose. The mice were anesthetized with isoflurane and blood was collected via cardiac puncture. A complete cell count (CBC), including lymphocyte count, was obtained using a CELL-DYN® 3700 (Abbott Laboratories, Abbott Park, Ill.) instrument. Results are presented in FIG. 11, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIG. 11 that Compound 2 exhibited activity for inducing PBL lowering (lymphopenia) in the mouse.

B. Rat PLL Assay.

Animals: Male Sprague-Dawley rats (Charles River Laboratories, Hollister, Calif.) were housed and maintained in humidity (40 to 60%) and temperature (68 to 72° F.) controlled facility on a 12 h:12 h light/dark cycle (lights on at 6:30 am) with free access to food (Harlan Teklad, Orange, Calif., Rodent Diet 8604) and water. Rats were allowed (approximately) one week of habituation to the animal facility before testing.

Figure 12:
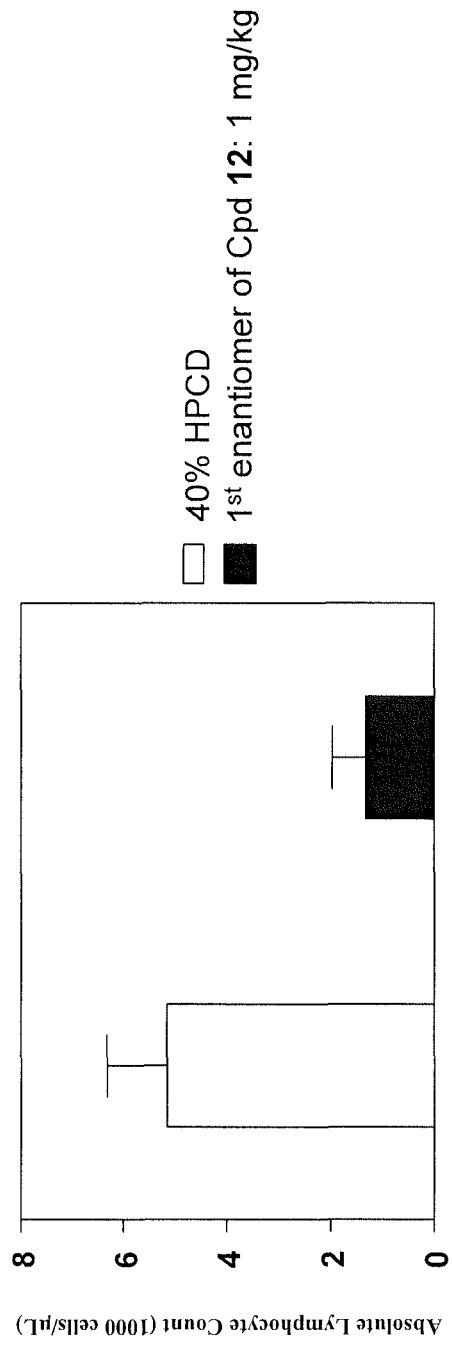
FIG. 12 shows the results of an experiment which measured the ability of the 1$^{st}$ enantiomer of Compound 12 (isolated after resolution of compound 12 by HPLC, with a retention time of 15 min per the conditions reported in Example 1.3) to lower the absolute count of peripheral lymphocytes in rats compared to vehicle.

PLL Assay: Rats were given a 1 mg/kg intravenous dose of the first enantiomer isolated after resolution of compound 12 by HPLC (retention time: 15 min per the conditions reported in Example 1.3), or dosing vehicle (40% hydroxypropylcyclodextrin (HPCD)) in a total volume of 1 mL/kg. Peripheral blood samples were collected at 5 h post-dose. Blood was collected via indwelling catheter. A complete cell count (CBC), including lymphocyte count, was obtained using a CELL-DYN® 3700 (Abbott Laboratories, Abbott Park, Ill.) instrument. Results are presented in FIG. 12, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIG. 12 that the first enantiomer isolated after resolution of compound 12 by HPLC exhibited activity for inducing PBL lowering (lymphopenia) in the rat.

Figure 13:
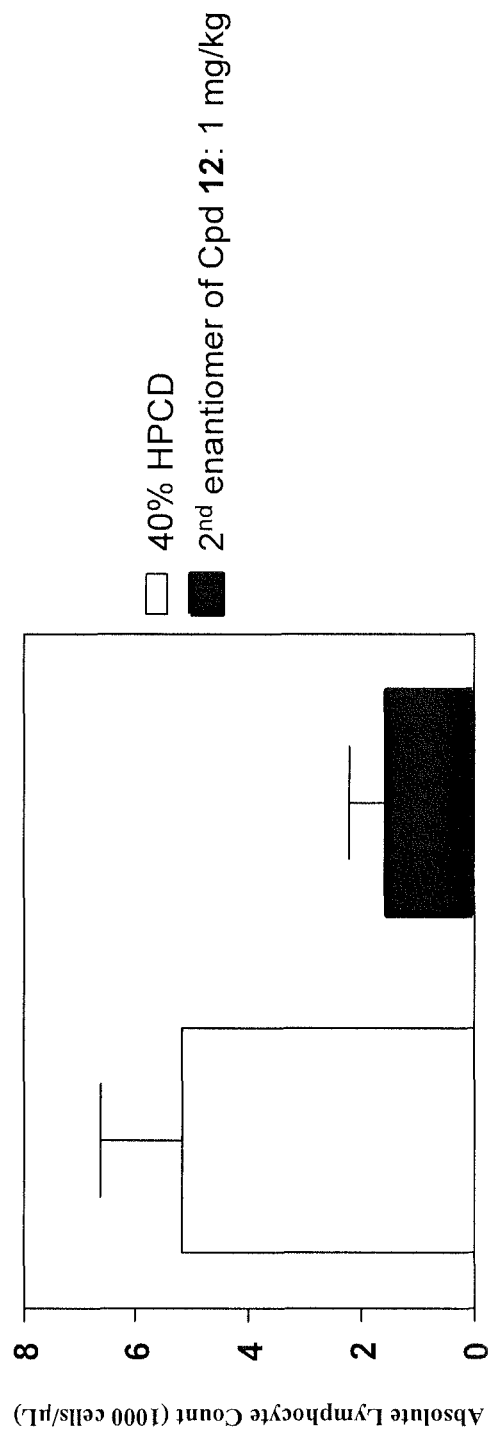
FIG. 13 shows the results of an experiment which measured the ability of the 2$^{nd}$ enantiomer of Compound 12 (isolated after resolution of compound 12 by HPLC, with a retention time of 18 min per the conditions reported in Example 1.3) to lower the absolute count of peripheral lymphocytes in rats compared to vehicle.

Similarly, rats were given a 1 mg/kg intravenous dose of the second enantiomer isolated after resolution of compound 12 by HPLC (retention time: 18 min per the conditions reported in Example 1.3), or dosing vehicle (40% hydroxypropylcyclodextrin (HPCD)) in a total volume of 1 mL/kg. Peripheral blood samples were collected at 5 h post-dose. Blood was collected via indwelling catheter. A complete cell count (CBC), including lymphocyte count, was obtained using a CELL-DYN® 3700 (Abbott Laboratories, Abbott Park, Ill.) instrument. Results are presented in FIG. 13, in which peripheral blood lymphocyte (PBL) count is shown for the 5 hour group. Reduction of the PBL count by the test compound in comparison with vehicle is indicative of the test compound exhibiting activity or inducing peripheral lymphocyte lowering. It is apparent from inspection of FIG. 13 that the second enantiomer isolated after resolution of compound 12 by HPLC exhibited activity for inducing PBL lowering (lymphopenia) in the rat.

Example 5

Effect of Compounds on Experimental Autoimmune Encephalomyelitis (EAE)

A compound of the invention can be shown to have therapeutic efficacy in multiple sclerosis by showing it to have therapeutic efficacy in experimental autoimmune encephalomyelitis (EAE), an animal model for multiple sclerosis. In certain exemplary well-established models, EAE is induced in rodents by injection of myelin oligodendrocyte glycoprotein (MOG) peptide, by injection of myelin basic protein (MBP) or by injection of proteolipid protein (PLP) peptide.

A. MOG-Induced EAE in Mice.

Animals: Female C57BL/6 mice (8 to 10 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan Teklad, Orange, Calif., Rodent Diet 8604) and water. Mice are allowed one week of habituation to the animal facility before testing.

Induction of EAE: Mice are immunized subcutaneously, 50 µL per hind flank, with a total of 100 µg $MOG_{35-55}$ peptide emulsified 1:1 with complete Freund's adjuvant containing 4 mg/mL heat-killed *Mycobacterium tuberculosis*. Mice also receive 200 ng pertussis toxin intraperitoneally on the day of immunization and 48 h later.

Clinical Scoring: Severity of disease symptoms is scored as follows (in increasing order of severity): 0=normal; 1=limp tail OR hind limb weakness; 2=limp tail AND limb weakness/weakness of 2 or more limbs; 3=severe limb weakness or single limb paralysis; 4=paralysis of 2 or more limbs; 5=death.

Drug Treatment: Mice are dosed orally, with vehicle or a test compound, once a day from day 3 until day 21. Dosing volume is 5 mL/kg. The test compound is dosed at, e.g., 1 mg/kg, 3 mg/kg, 10 mg/kg or 30 mg/kg. Mice are weighed daily. Mice are monitored daily from day 7 onward for disease symptoms. After the last dose on day 21, disease progression is monitored daily for 2 more weeks. Reduction of the severity of disease symptoms by the test compound in comparison with vehicle is indicative of the test compound exhibiting therapeutic efficacy in EAE.

B. PLP-Induced EAE in Mice.

Animals: Female SJL/J mice (8 to 10 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan-Teklad Western Res, Orange, Calif., Rodent Diet 8604) and water. Mice are allowed one week of habituation to the animal facility before testing.

Induction of EAE: Mice are immunized subcutaneously with 100 µg $PLP_{139-151}$ peptide emulsified 1:1 with complete Freund's adjuvant containing 4 mg/mL heat-killed *Mycobacterium tuberculosis*. Mice also receive 200 ng pertussis toxin intravenously on the day of immunization.

Clinical Scoring: Severity of disease symptoms is scored as follows (in increasing order of severity): 0=normal; 1=limp tail OR hind limb weakness; 2=limp tail AND limb weakness/weakness of 2 or more limbs; 3=severe limb weakness or single limb paralysis; 4=paralysis of 2 or more limbs; 5=death.

Drug Treatment: Mice are dosed orally, with vehicle or a test compound, once a day from day 3 until day 21. Dosing volume is 5 ml/kg. The test compound is dosed at, e.g., 1 mg/kg, 3 mg/kg, 10 mg/kg or 30 mg/kg. Mice are weighed daily. Mice are monitored daily from day 7 onward for disease symptoms. After the last dose on day 21, disease progression is monitored daily for two more weeks.

C. MBP-Induced EAE in Rats.

Animals: Male Lewis rats (325-375 g at start of study) (Harlan, San Diego, Calif.) are housed two per cage and maintained in a humidity-controlled (30-70%) and temperature-controlled (20-22° C.) facility on a 12 h:12 h light/dark cycle (lights on at 6:30 A.M.) with free access to food (Harlan-Teklad Western Res., Orange, Calif., Rodent Diet 8604) and water. Rats are allowed one week of habituation to the animal facility before testing. During the study, rats are weighed daily prior to clinical scoring at 11 am.

Induction of EAE: Myelin basic protein (MBP; guinea pig) is dissolved in sterile saline at a concentration of 1 mg/ml, and then emulsified 1:1 with complete Freund's adjuvant (1 mg/ml). 50 µL of this emulsion is administered by intraplantar (ipl) injection into both hind paws of each rat, for a total injected volume of 100 µL per rat and a total dose of 50 µg of MBP per rat.

Clinical Scoring: Severity of disease symptoms is scored daily after body weighing and before drug dosing. Severity of disease symptoms is scored as follows (in increasing order of severity): 0=normal; 1=tail OR limb weakness; 2=tail AND limb weakness; 3=severe hind limb weakness or single limb paralysis; 4=loss of tail tone and paralysis of 2 or more limbs; 5=death.

Drug Treatment: Rats are dosed orally, with vehicle or a test compound, 1 hour prior to MBP injection on day 0 and daily thereafter, after clinical scoring, for the duration of the study. Dosing volume is 5 mL/kg. The test compound is dosed at, e.g., 1 mg/kg, 3 mg/kg, 10 mg/kg or 30 mg/kg. Reduction of the severity of disease symptoms by the test compound in comparison with vehicle is indicative of the test compound exhibiting therapeutic efficacy in EAE.

Example 6

Effect of Compounds on Type I Diabetes

A compound of the invention can be shown to have therapeutic efficacy in type I diabetes using an animal model for type I diabetes, such as cyclophosphamide-induced type I diabetes in mice.

Animals: Baseline blood glucose measurements are taken from 9-10 week old female NOD/Ltj mice (Jackson Laboratory, Bar Harbor, Me.) to ensure that they are normoglycemic (blood glucose is 80-120 mg/dL) prior to initiation of the experiment. Blood glucose is measured from tail bleeds using a OneTouch® Ultra® meter and test strips (LifeScan, Milpitas, Calif.).

Cyclophosphamide Induction of Type I Diabetes: On day 0 and day 14, normoglycemic NOD mice are injected intraperitoneally with 4 mg cyclophosphamide monohydrate (200 mg/kg) dissolved in 0.9% saline. If mice are diabetic (blood glucose is >250 mg/dL), they are not given a booster dose of cyclophosphamide on day 14.

Drug Treatment: Mice are dosed orally, with vehicle or test compound, once a day from day 0 until day 25. Compounds are suspended in 0.5% methyl cellulose vehicle using a sonicator to ensure uniform suspension. Mice are weighed twice weekly and are dosed according to weight. Dosing volume is 5 mL/kg. The test compound is dosed at, e.g., 1 mg/kg, 3 mg/kg, 10 mg/kg or 30 mg/kg. Blood glucose is measured twice weekly. After dosing is completed at day 25, the mice continue to be monitored and blood glucose measurements are taken once a week for 3 weeks. Promotion of normoglycemia by the test compound in comparison with vehicle is indicative of the test compound exhibiting therapeutic efficacy in type I diabetes.

Example 7

Allograft Survival

A compound of the invention can be shown to have therapeutic efficacy in prolonging allograft survival by showing it to have therapeutic efficacy in prolonging, e.g., survival of a skin allograft in an animal model.

Animals: Female Balbc/mice (6 to 7 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan Teklad, Orange, Calif., Rodent Diet 8604) and water. Female C57BL/6 mice (8 to 10 weeks of age at start of study) (Jackson Laboratory, Bar Harbor, Me.) are similarly housed and maintained. Mice are allowed one week of habituation to the animal facility before testing.

Skin Allograft: Balbc/J and C57BL/6 mice are used as donors and recipients, respectively, in a model of skin allograft transplantation. Donor Balbc/J mice are anesthetized, and 0.5 cm—diameter full thickness areas of abdominal skin are surgically removed. Skin grafts harvested from the Balbc/J mice are sutured onto the dorsum of anesthetized recipient C57BL/6 mice. Sutured allografts are covered with Vaseline gauze and Bolster dressing for 7 days. The allografted mice are divided into 8 groups of 8 mice each.

Clinical Scoring: Skin allografts are inspected and digital images recorded daily until rejection, which is defined as the first day on which more than 80% of the graft is necrotic. Histological analysis of the rejected graft is carried out on hematoxylin and eosin (H&E)-stained sections. In an optional related study, on post-transplantation day 5 isolated lymphocytes from peripheral lymph nodes and spleen are counted and characterized for activation markers (e.g., T-cell activation markers) by flow cytometry. Also on day 5, grafts are removed from transplanted recipients, cut into small fragments, digested with collagenase and sedimented over Ficoll-Paque (Pharmacia Biotech, Uppsala, Sweden) to isolate graft-infiltrating lymphocytes, which are counted and characterized for activation markers (e.g., T-cell activation markers) by flow cytometry. Histological analysis of the graft on day 5 can be carried out on hematoxylin and eosin (H&E)-stained sections.

Drug Treatment: Mice are dosed orally, with vehicle or test compound, once a day from the day of transplantation until the end of the study, e.g. until day 14, 21 or 28. Dosing volume is 5 mL/kg. The test compound is dosed at, e.g., 1 mg/kg, 3 mg/kg, 10 mg/kg or 30 mg/kg. Delay of time of rejection of the skin allograft by the test compound in comparison with vehicle is indicative of the test compound exhibiting therapeutic efficacy in prolonging skin allograft survival.

Example 8

Effect of Compounds on Colitis

A compound of the invention can be shown to have therapeutic efficacy in colitis using an animal model for colitis. Suitable animal models are known in the art (Boismenu et al., *J. Leukoc. Biol.*, 67:267-278, 2000). A first exemplary animal model for colitis is trinitrobenzenesulfonic acid (TNBS)-induced colitis, which presents clinical and histopathological findings that resemble those in Crohn's disease (Neurath et al., *J. Exp. Med.*, 182:1281-1290, 1995; Boismenu et al., *J. Leukoc. Biol.*, 67:267-278, 2000). A second exemplary animal model for colitis is dextran sulfate sodium (DSS)-induced colitis, which presents clinical and histopathological findings that resemble those in ulcerative colitis (Okayasu et al., *Gastroenterology,* 98:694-702, 1990; Boismenu et al., *J. Leukoc. Biol.,* 67:267-278, 2000). Compounds can be commercially tested for efficacy in at least DSS-induced colitis and TNBS-induced colitis, e.g. by the Jackson Laboratory (Bar Harbor, Me.).

A. Mouse Model for Colitis.

Animals: Male BALB/c mice (6 weeks of age at start of study) (Jackson Laboratory, Bar Harbor, Me.) are housed four per cage and maintained in a humidity-controlled (40-60%) and temperature-controlled (68-72° F.) facility on a 12 h:12 h light/dark cycle (lights on at 6:30 am) with free access to food (Harlan Teklad, Orange Calif., Rodent Diet 8604) and water. Mice are allowed one week of habituation to the animal facility before testing.

TNBS Induction of Colitis: Mice are weighed for baseline body weights and fasted later that day beginning at 6:15 pm just prior to lights-out (day 0). Body weights are taken again the following morning (day 1) at approximately 7:30 am. Mice are anesthetized with isoflurane prior to induction of colitis. Colitis is induced in the mice by intracolonic injection of about 150 mg/kg TNBS in 50% ethanol (in a volume of 150 µL) using an intubation needle (22 g, 1.5 in) inserted completely into the anus with the mouse held by the tail in a vertical position. The mouse is held vertically for 30 additional seconds to allow thorough absorption and minimize leakage, after which the mouse is returned to its cage. Mice are then fed, following the preceding approximately 14 hour of fasting. Each morning thereafter, the mice are weighed. In control experiments, mice receive 50% ethanol alone using the same protocol.

Drug Treatment: Drug treatment begins on day 2. Mice are dosed orally, with vehicle or a test compound, once a day from day 2 until the conclusion of the experiment on, e.g., day 7, 14 or 21. Dosing volume is 5 mL/kg. The test compound is dosed at, e.g., 1 mg/kg, 3 mg/kg, 10 mg/kg or 30 mg/kg.

Clinical Scoring: Upon conclusion of the experiment, colons are extracted and measured. Mice are euthanized with $CO_2$ and colon is removed from anus to cecum. Excised colon is measured for entire length, length from anus to end of inflamed area and length of inflamed (affected) area. After measurements, colon is cleared of excrement by flushing with saline and then cut open to clear more thoroughly. Colon is then weighed and preserved in neutral buffered formalin (NBF; 10% formalin, pH 6.7-7.0). The colon tissue is embedded in paraffin and processed for hematoxylin and eosin (H & E)-stained sections. Severity of disease symptoms is scored histologically from the stained sections as follows: 0=no evidence of inflammation; 1=low level of leukocyte infiltration with infiltration seen in <10% of high-power fields AND no structural changes; 2=moderate leukocyte infiltration with infiltration seen in 10% to 25% of high-power fields AND crypt elongation AND bowel wall thickening that does not extend beyond the mucosal layer AND no ulcerations; 3=high level of leukocyte infiltration seen in 25% to 50% of high-power fields AND crypt elongation AND infiltration beyond the mucosal layer AND thickening of the bowel wall AND superficial ulcerations; 4=marked degree of transmural leukocyte infiltration seen in >50% of high-power fields AND elongated and distorted crypts AND bowel wall thickening AND extensive ulcerations. Reduction of the severity of the disease symptoms by the test compound in comparison with vehicle is indicative of the test compound exhibiting therapeutic efficacy in colitis.

B. Rat Model for Colitis.

Animals: Male Wistar rats (175-200 g at start of study) (Charles River Laboratories, Wilmington, Mass.) are housed two per cage and maintained in a humidity-controlled (40-60%) and temperature-controlled (68-72° F.) facility on a 12 h:12 h light/dark cycle (lights on at 6:30 am) with free access to food (Harlan Teklad, Orange Calif., Rodent Diet 8604) and water. Rats are allowed one week of habituation to the animal facility before testing.

TNBS Induction of Colitis: Rats are weighed for baseline body weights and fasted later that day beginning at 6:15 pm just prior to lights-out (day 0). Body weights are taken again the following morning (day 1) at approximately 7:30 am. Rats are anesthetized with isoflurane prior to induction of colitis. Colitis is induced in the rats by intracolonic injection of about 60 mg/kg TNBS in 50% ethanol (in a volume of 500 µL) using a fabricated intubation needle (7.5 Fr umbilical catheter and 14 g hub) inserted 8 cm into the anus with the rat held by the tail in a vertical position. The rat is held vertically for 30 additional s to allow thorough absorption and minimize leakage, after which the rat is returned to its cage. Rats are then fed, following the preceding approximately 14 h of fasting. Each morning thereafter, the rats are weighed. In control experiments, rats receive 50% ethanol alone using the same protocol.

Drug Treatment: Drug treatment begins on day 2. Rats are dosed orally, with vehicle or test compound, once a day from day 2 until the conclusion of the experiment on, e.g., day 7, 14 or 21. Dosing volume is 5 mL/kg. Test compound is dosed at, e.g., 1 mg/kg, 3 mg/kg, 10 mg/kg or 30 mg/kg.

Clinical Scoring: Upon conclusion of the experiment, colons are extracted and measured. Rats are euthanized with $CO_2$ and colon is removed from anus to cecum. Excised colon is measured for entire length, length from anus to end of inflamed area, and length of inflamed (affected) area. After measurements, colon is cleared of excrement by flushing with saline and then cut open to clear more thoroughly. Colon is then weighed and preserved in neutral buffered formalin (NBF; 10% formalin, pH 6.7-7.0). The colon tissue is embedded in paraffin and processed for hematoxylin and eosin (H & E)-stained sections. Severity of disease symptoms is scored histologically from the stained sections as follows: 0=no evidence of inflammation; 1=low level of leukocyte infiltration with infiltration seen in <10% of high-power fields AND no structural changes; 2=moderate leukocyte infiltration with infiltration seen in 10% to 25% of high-power fields AND crypt elongation AND bowel wall thickening that does not extend beyond the mucosal layer AND no ulcerations; 3=high level of leukocyte infiltration seen in 25% to 50% of high-power fields AND crypt elongation AND infiltration beyond the mucosal layer AND thickening of the bowel wall AND superficial ulcerations; 4=marked degree of transmural leukocyte infiltration seen in >50% of high-power fields AND elongated and distorted crypts AND bowel wall thickening AND extensive ulcerations. Reduction of the severity of the disease symptoms by the test compound in comparison with vehicle is indicative of the test compound exhibiting therapeutic efficacy in colitis.

Example 9

Effects of Compounds on Cardiac Telemetry in the Rat

Animals: Male Sprague-Dawley rats (250-300 g at time of surgery) are implanted by Charles River Laboratories (Wilmington, Mass.) with cardiac transmitting devices (Data Sciences PhysioTel C50-PXT) into the peritoneal space, with a pressure-sensing catheter inserted into the descending aorta. Rats are allowed at least one week to recover. Rats are housed in individual cages and maintained in a humidity-controlled (30-70%) and temperature-controlled (20-22° C.) facility on a 12 h:12 h light/dark cycle (lights on at 7:00 am) with free access to food (Harlan-Teklad, Orange, Calif., Rodent Diet 8604) and water. Rats are allowed one week of habituation to the animal facility before testing.

Measurement of Cardiovascular Parameters: The implanted transmitting devices transmit continuous measurements of blood pressure (systolic, diastolic, mean arterial, pulse), heart rate, body temperature, and motor activity in freely moving conscious animals. These data are transmitted via radiofrequency to a computer which bin the data into 1 min averages using DataSciences ART software. Telemetry recording takes place over a 21-h period, starting at noon and continuing until 9:00 am the following day. A maximum of eight rats are tested at a time, and the same eight rats are utilized for all treatment groups in a within-subject design.

Drug Treatment: Rats are injected orally with vehicle or compound at 1:00 pm. A full study (vehicle+3 doses) requires four separate testing sessions, which occur on Mondays-Tuesdays and Thursdays-Fridays. During each of the testing sessions, the eight rats are divided into four treatment groups such that each group comprises N=2 for any given session. Rats are re-tested in subsequent testing sessions in a crossover design such that by the end of the four sessions, all animals receive all treatments in a pseudo-random order, and each group comprises N=8.

Exemplary Bradycardia Assay: It is expressly contemplated that the rats can be used to show that a compound of the invention has no or substantially no activity for bradycardia. By way of illustration and not limitation, the rats are administered vehicle or a test compound and heart rate is then measured over a 120 min period. No or substantially no reduction of heart rate in response to the test compound in comparison with vehicle is indicative of the test compound exhibiting no or substantially no activity for bradycardia.

Example 10

Effect of Compounds on Arthritis

Female Lewis rats were used in this study. Acclimated animals were anesthetized with isoflurane and given the first collagen injection (day 0). On day 6, they were anesthetized again for the second collagen injection. Collagen was prepared by making a 4 mg/mL solution in 0.01 N acetic acid. Equal volumes of collagen and incomplete Freund's adjuvant were emulsified by hand mixing until a bead of this material held its form when placed in water. Each animal received 300 µL of the mixture each time, spread over 3 subcutaneous sites on the back.

Treatment (p.o., q.d., 5 mL/kg dosing volume) began on day 0 and continued through day 16 with vehicle or compounds given at 24 h intervals. Rats were weighed on days 0, 3, 6 and 9 through 17 and caliper measurements of the ankles taken on days 9 through 17.

Figure 14:
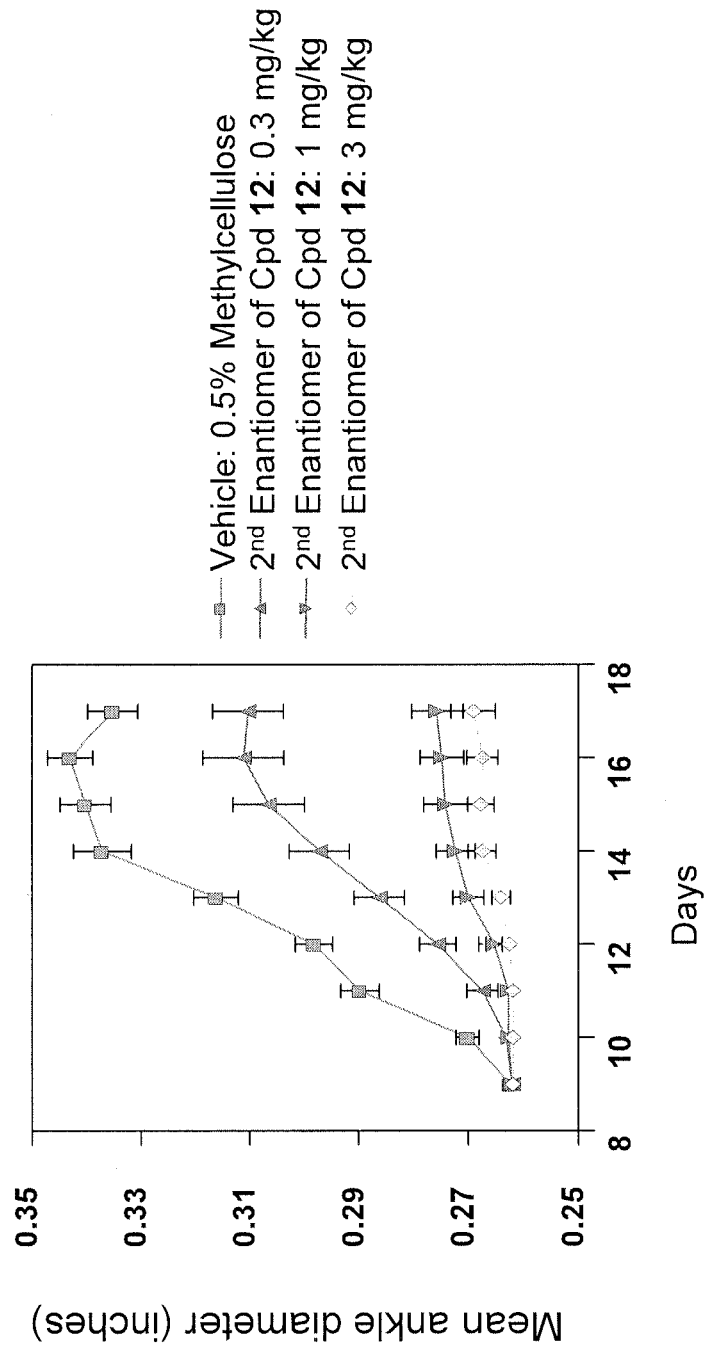
FIG. 14 shows the results of an experiment which measured the ability of three different doses of the 2$^{nd}$ enantiomer of Compound 12 (isolated after resolution of compound 12 by HPLC, with a retention time of 18 min per the conditions reported in Example 1.3) to reduce the mean ankle diameter in rats compared to vehicle.

The second enantiomer isolated after resolution of compound 12 by HPLC (retention time: 18 min per the conditions reported in Example 1.3), was dosed at 0.3, 1 and 3 mg/kg. It is apparent from inspection of FIG. 14 that the second enantiomer isolated after resolution of compound 12 by HPLC exhibited activity for reducing mean ankle diameter in the rat. A reduction in mean ankle diameter in the treated animal compared to vehicle only treated animals is an indication that compound 12 exhibits therapeutic efficacy in the collagen-induced arthritis assay.

Those skilled in the art will recognize that various modifications, additions, substitutions and variations to the illustrative examples set forth herein can be made without departing from the spirit of the invention and are, therefore, considered within the scope of the invention. All documents referenced above, including, but not limited to, printed publications and provisional and regular patent applications, are incorporated herein by reference in their entirety.

What is claimed is:

1. A method for treating an S1P1 receptor-associated disorder in an individual comprising administering to said individual in need thereof a therapeutically effective amount of a compound selected from 2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof, wherein said disorder is selected from the group consisting of psoriasis, rheumatoid arthritis, psoriatic arthritis, inflammatory bowel disease, Crohn's disease, transplant rejection, multiple sclerosis, biliary cirrhosis, systemic lupus erythematosus, ulcerative colitis, type I diabetes, hypertensive nephropathy, glomerulosclerosis, myocardial ischemia-reperfusion injury, and acne.

2. A method according to claim 1, wherein the compound is selected from (R)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

3. A method according to claim 1, wherein the compound is selected from (S)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

4. A method according to claim 1, wherein said disorder is multiple sclerosis.

5. A method according to claim 4, wherein the compound is selected from (R)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

6. A method according to claim 4, wherein the compound is selected from (S)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

7. A pharmaceutical composition comprising a compound selected from 2-(9-chloro-7-(4-isopropoxy-3-(trifluoromethyl)benzyloxy)-2,3-dihydro-1H-pyrrolo[1,2-a]indol-1-yl) acetic acid and pharmaceutically acceptable salts, solvates, and hydrates thereof and a pharmaceutically acceptable carrier.

8. The pharmaceutical composition of claim 7, wherein the compound is selected from (R)-2-(9-chloro-7-(4-isopropoxy-3-(trifluoromethyl)benzyloxy)-2,3-dihydro-1H-pyrrolo [1,2-a]indol-1-yl)acetic acid and pharmaceutically acceptable salts, solvates, and hydrates thereof.

9. The pharmaceutical composition of claim 7, wherein the compound is selected from (S)-2-(9-chloro-7-(4-isopropoxy-3-(trifluoromethyl)benzyloxy)-2,3-dihydro-1H-pyrrolo [1,2-a]indol-1-yl)acetic acid and pharmaceutically acceptable salts, solvates, and hydrates thereof.

10. A process for preparing the composition of claim 7, comprising admixing a compound selected from 2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof; and a pharmaceutically acceptable carrier.

11. A process for preparing the composition of claim 8, comprising admixing a compound selected from (R)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof; and a pharmaceutically acceptable carrier.

12. A process for preparing the composition of claim 9, comprising admixing a compound selected from (S)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof; and a pharmaceutically acceptable carrier.

13. A method according to claim 1, wherein said disorder is biliary cirrhosis.

14. A method according to claim 13, wherein the compound is selected from (R)-2-(9-chloro-7-(4-isopropoxy-3-(trifluoromethyl)benzyloxy)-2,3-dihydro-1H-pyrrolo [1,2-a]indol-1-yl)acetic acid and pharmaceutically acceptable salts, solvates, and hydrates thereof.

15. A method according to claim 13, wherein the compound is selected from (S)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

16. A method according to claim 1, wherein said disorder is psoriasis.

17. A method according to claim 16, wherein the compound is selected from (R)-2-(9-chloro-7-(4-isopropoxy-3-(trifluoromethyl)benzyloxy)-2,3-dihydro-1H-pyrrolo [1,2-a]indol-1-yl)acetic acid and pharmaceutically acceptable salts, solvates, and hydrates thereof.

18. A method according to claim 16, wherein the compound is selected from (S)-2-(9 -chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

19. A method according to claim 1, wherein said disorder is rheumatoid arthritis.

20. A method according to claim 19, wherein the compound is selected from (R)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

21. A method according to claim 19, wherein the compound is selected from (S)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

22. A method according to claim 1, wherein said disorder is psoriatic arthritis.

23. A method according to claim 22, wherein the compound is selected from (R)-2-(9-chloro-7-(4-isopropoxy-3-(trifluoromethyl)benzyloxy)-2,3-dihydro-1H-pyrrolo [1,2-a]indol-1-yl)acetic acid and pharmaceutically acceptable salts, solvates, and hydrates thereof.

24. A method according to claim 22, wherein the compound is selected from (S)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

25. A method according to claim 1, wherein said disorder is inflammatory bowel disease.

26. A method according to claim 25, wherein the compound is selected from (R)-2-(9-chloro-7-(4-isopropoxy-3-(trifluoromethyl)benzyloxy)-2,3-dihydro-1H-pyrrolo [1,2-a]indol-1-yl)acetic acid and pharmaceutically acceptable salts, solvates, and hydrates thereof.

27. A method according to claim 25, wherein the compound is selected from (S)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

28. A method according to claim 1, wherein said disorder is Crohn's disease.

29. A method according to claim 28, wherein the compound is selected from (R)-2-(9-chloro-7-(4-isopropoxy-3-(trifluoromethyl)benzyloxy)-2,3-dihydro-1H-pyrrolo [1,2-a]indol-1-yl)acetic acid and pharmaceutically acceptable salts, solvates, and hydrates thereof.

30. A method according to claim 28, wherein the compound is selected from (S)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

31. A method according to claim 1, wherein said disorder is ulcerative colitis.

32. A method according to claim 31, wherein the compound is selected from (R)-2-(9-chloro-7-(4-isopropoxy-3-(trifluoromethyl)benzyloxy)-2,3-dihydro-1H-pyrrolo[1,2-a]indol -1-yl)acetic acid and pharmaceutically acceptable salts, solvates, and hydrates thereof.

33. A method according to claim 31, wherein the compound is selected from (S)-2-(9-chloro-7-(4-isopropoxy-3-(trifluoromethyl)benzyloxy)-2,3-dihydro-1H-pyrrolo[1,2-a]indol-1-yl)acetic acid and pharmaceutically acceptable salts, solvates, and hydrates thereof.

\* \* \* \* \*